US008691209B2

(12) United States Patent
Bachmann et al.

(10) Patent No.: US 8,691,209 B2
(45) Date of Patent: *Apr. 8, 2014

(54) PACKAGING OF IMMUNOSTIMULATORY SUBSTANCES INTO VIRUS-LIKE PARTICLES: METHOD OF PREPARATION AND USE

(75) Inventors: Martin F. Bachmann, Winterthur (CH); Tazio Storni, Viganello (CH); Patrik Maurer, Winterthur (CH); Alain Tissot, Zürich (CH); Katrin Schwarz, Schlieren (CH); Edwin Meijerink, Zürich (CH); Gerd Lipowsky, Zürich (CH); Paul Pumpens, Riga (LV); Indulis Cielens, Riga (LV); Regina Renhofa, Riga (LV)

(73) Assignee: Cytos Biotechnology AG, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/294,006

(22) Filed: Nov. 10, 2011

(65) Prior Publication Data

US 2012/0301499 A1    Nov. 29, 2012

Related U.S. Application Data

(63) Continuation of application No. 10/244,065, filed on Sep. 16, 2002, now abandoned.

(60) Provisional application No. 60/318,994, filed on Sep. 14, 2001, provisional application No. 60/374,145, filed on Apr. 22, 2002.

(51) Int. Cl.
*A01N 63/00* (2006.01)
*C12N 1/20* (2006.01)
*C12N 7/00* (2006.01)

(52) U.S. Cl.
USPC ............... 424/93.2; 435/235.1; 435/252.1

(58) Field of Classification Search
None
See application file for complete search history.

(56) References Cited

U.S. PATENT DOCUMENTS

| | | |
|---|---|---|
| 4,722,840 A | 2/1988 | Valenzuela et al. |
| 4,918,166 A | 4/1990 | Kingsman et al. |
| 5,057,540 A | 10/1991 | Kensil et al. |
| 5,071,651 A | 12/1991 | Sabara et al. |
| 5,334,394 A | 8/1994 | Kossovsky et al. |
| 5,374,426 A | 12/1994 | Sabara et al. |
| 5,698,424 A | 12/1997 | Mastico et al. |
| 5,780,448 A | 7/1998 | Davis |
| 5,871,747 A | 2/1999 | Gengoux-Sedlik et al. |
| 5,904,925 A | 5/1999 | Exner |
| 5,935,821 A | 8/1999 | Chatterjee et al. |
| 5,939,598 A | 8/1999 | Kucherlapati et al. |
| 5,962,636 A | 10/1999 | Bachmaier et al. |
| 5,989,868 A | 11/1999 | Harrison et al. |
| 6,159,728 A | 12/2000 | Stockley et al. |
| 6,194,388 B1 | 2/2001 | Krieg et al. |
| 6,207,646 B1 | 3/2001 | Krieg et al. |
| 6,231,864 B1 | 5/2001 | Birkett |
| 6,239,116 B1 | 5/2001 | Krieg et al. |
| 6,326,200 B1 | 12/2001 | Valmori et al. |
| 6,339,068 B1 | 1/2002 | Krieg et al. |
| 6,406,705 B1 | 6/2002 | Davis et al. |
| 6,429,199 B1 | 8/2002 | Krieg et al. |
| 6,541,438 B1 | 4/2003 | Smets et al. |
| 6,653,292 B1 | 11/2003 | Krieg et al. |
| 6,719,978 B2 | 4/2004 | Schiller et al. |
| 6,727,230 B1 | 4/2004 | Hutcherson et al. |
| 6,927,278 B1 * | 8/2005 | Diamond ............. 530/300 |
| 6,949,520 B1 | 9/2005 | Hartmann et al. |
| 7,094,409 B2 | 8/2006 | Bachmann et al. |
| 7,115,266 B2 | 10/2006 | Bachmann |
| 7,128,911 B2 | 10/2006 | Bachmann et al. |
| 7,264,810 B2 | 9/2007 | Renner et al. |
| 7,271,156 B2 | 9/2007 | Krieg et al. |
| 7,279,165 B2 | 10/2007 | Bachmann et al. |
| 7,320,793 B2 | 1/2008 | Renner et al. |

(Continued)

FOREIGN PATENT DOCUMENTS

| | | |
|---|---|---|
| CA | 2 457 804 A1 | 12/2003 |
| DE | 2 034 118 | 1/1972 |

(Continued)

OTHER PUBLICATIONS

Hajek and Friesen. Proteolytic Processing and Assembly of gag and gag-pol Proteins of TED, a Baculovirus-Associated Retrotransposon of the Gypsy Family. Journal of Virology, Nov. 1998, p. 8718-8724.*
Angeletti, RH, "Design of useful peptide antigens.", J Biomol Tech, 1999, pp. 2-10, vol. 10, Issue 1, The Association of Biomolecular Resource Facilities, US.
Bachmann, MF, et al., "The influence of antigen organization on B cell responsiveness.", Science , 1993, pp. 1448-1451, vol. 262, Issue 5138, AAAS, US.
Barnes, WM, "PCR amplification of up to 35-kb DNA with high fidelity and high yield from lambda bacteriophage templates.", Proc Natl Acad Sci USA, 1994, pp. 2216-2220, vol. 91, Issue 6, National Academy of Sciences, US.
Blanchart, J-S, et al., "A new generation of Melan-A/MART-1 peptides that fulfill both increased immunogenicity and high resistance to biodegradation: implication for molecular anti-melanoma immunotherapy.", J Immunol, 2001, pp. 5852-5861, vol. 167, Issue 10, The American Association of Immunologists, US.

(Continued)

Primary Examiner — Michelle S Horning
(74) Attorney, Agent, or Firm — Fanelli Haag & Kilger PLLC

(57) ABSTRACT

The invention relates to the finding that virus like particles (VLPs) can be loaded with immunostimulatory substances, in particular with DNA oligonucleotides containing non-methylated C and G (CpGs). Such CpG-VLPs are dramatically more immunogenic than their CpG-free counterparts and induce enhanced B and T cell responses. The immune response against antigens optionally coupled, fused or attached otherwise to the VLPs is similarly enhanced as the immune response against the VLP itself. In addition, the T cell responses against both the VLPs and antigens are especially directed to the Th1 type. Antigens attached to CpG-loaded VLPs may therefore be ideal vaccines for prophylactic or therapeutic vaccination against allergies, tumors and other self-molecules and chronic viral diseases.

33 Claims, 60 Drawing Sheets

(56) References Cited

U.S. PATENT DOCUMENTS

| | | | |
|---|---|---|---|
| 7,494,656 | B2 | 2/2009 | Bachmann et al. |
| 7,517,520 | B2 * | 4/2009 | Manolova et al. ............ 424/93.2 |
| 7,537,767 | B2 * | 5/2009 | Bachmann et al. ......... 424/185.1 |
| 7,666,408 | B2 | 2/2010 | Bachmann |
| 7,767,212 | B2 | 8/2010 | Bachmann et al. |
| 7,785,873 | B2 | 8/2010 | Bachmann et al. |
| 7,959,928 | B2 | 6/2011 | Bachmann et al. |
| 2001/0044416 | A1 | 11/2001 | McCluskie et al. |
| 2002/0081295 | A1 | 6/2002 | Schiller et al. |
| 2003/0026782 | A1 | 2/2003 | Krieg et al. |
| 2003/0050263 | A1 | 3/2003 | Krieg et al. |
| 2003/0050268 | A1 | 3/2003 | Krieg et al. |
| 2003/0060440 | A1 | 3/2003 | Klinman et al. |
| 2003/0087848 | A1 | 5/2003 | Bratzler et al. |
| 2003/0091593 | A1 | 5/2003 | Bachmann et al. |
| 2003/0091599 | A1 | 5/2003 | Davis et al. |
| 2003/0099668 | A1 | 5/2003 | Bachmann et al. |
| 2003/0219459 | A1 | 11/2003 | Bachmann et al. |
| 2003/0224010 | A1 | 12/2003 | Davis et al. |
| 2004/0005338 | A1 | 1/2004 | Bachmann et al. |
| 2004/0030118 | A1 | 2/2004 | Wagner et al. |
| 2004/0234512 | A1 | 11/2004 | Wagner et al. |
| 2004/0235777 | A1 | 11/2004 | Wagner et al. |
| 2004/0235778 | A1 | 11/2004 | Wagner et al. |
| 2005/0043529 | A1 | 2/2005 | Davis et al. |
| 2006/0204475 | A1 | 9/2006 | Bachmann et al. |
| 2006/0210588 | A1 | 9/2006 | Bachmann et al. |
| 2006/0251623 | A1 | 11/2006 | Bachmann et al. |
| 2006/0251677 | A1 | 11/2006 | Bachmann et al. |
| 2007/0184068 | A1 | 8/2007 | Renner et al. |
| 2008/0292652 | A1 | 11/2008 | Bachmann et al. |
| 2009/0246215 | A1 | 10/2009 | Bachmann et al. |
| 2011/0027220 | A1 | 2/2011 | Bachmann et al. |
| 2011/0045013 | A1 | 2/2011 | Bachmann et al. |
| 2011/0091411 | A1 | 4/2011 | Bachmann et al. |
| 2011/0212122 | A1 | 9/2011 | Bachmann et al. |
| 2011/0262472 | A1 | 10/2011 | Bachmann et al. |
| 2011/0293649 | A1 * | 12/2011 | Bachmann et al. ......... 424/186.1 |
| 2011/0305723 | A1 | 12/2011 | Renner et al. |

FOREIGN PATENT DOCUMENTS

| | | |
|---|---|---|
| EP | 0 201 416 B1 | 4/1991 |
| EP | 0 468 520 A2 | 1/1992 |
| EP | 0 421 635 B1 | 7/1995 |
| EP | 0 772 619 B1 | 5/1997 |
| EP | 0 855 184 A1 | 7/1998 |
| JP | 2001-151698 A | 6/2001 |
| WO | WO 90/15878 A1 | 12/1990 |
| WO | WO 92/11291 | 7/1992 |
| WO | WO 92/13081 | 8/1992 |
| WO | WO 93/00434 A1 | 1/1993 |
| WO | WO 94/02499 A1 | 2/1994 |
| WO | WO 94/15585 | 7/1994 |
| WO | WO 95/26204 A1 | 10/1995 |
| WO | WO 96/02555 A1 | 2/1996 |
| WO | WO 96/30523 | 10/1996 |
| WO | WO 96/30523 A2 | 10/1996 |
| WO | WO 96/40162 A1 | 12/1996 |
| WO | WO 97/26883 A1 | 7/1997 |
| WO | WO 97/28259 A1 | 8/1997 |
| WO | WO 98/15631 | 4/1998 |
| WO | WO 98/16247 | 4/1998 |
| WO | WO 98/18810 A1 | 5/1998 |
| WO | WO 98/33517 A1 | 8/1998 |
| WO | WO 98/37919 A1 | 9/1998 |
| WO | WO 98/40100 A1 | 9/1998 |
| WO | WO 98/49195 A1 | 11/1998 |
| WO | WO 98/50071 A1 | 11/1998 |
| WO | WO 98/52581 A1 | 11/1998 |
| WO | WO 98/55495 A1 | 12/1998 |
| WO | WO 99/07839 A2 | 2/1999 |
| WO | WO 99/11275 A2 | 3/1999 |
| WO | WO 99/28478 A1 | 6/1999 |
| WO | WO 99/29723 A1 | 6/1999 |
| WO | WO 99/51259 A2 | 10/1999 |
| WO | WO 99/57289 A2 | 11/1999 |
| WO | WO 99/58118 A2 | 11/1999 |
| WO | WO 00/00462 A1 | 1/2000 |
| WO | WO 00/06588 A1 | 2/2000 |
| WO | WO 00/09159 A1 | 2/2000 |
| WO | WO 00/14217 A2 | 3/2000 |
| WO | WO 00/23955 | 4/2000 |
| WO | WO 00/23955 A1 | 4/2000 |
| WO | WO 00/32227 | 6/2000 |
| WO | WO 00/32227 A2 | 6/2000 |
| WO | WO 00/37610 A2 | 6/2000 |
| WO | WO 00/39304 A2 | 6/2000 |
| WO | WO 00/46365 * | 8/2000 ............. C12N 15/11 |
| WO | WO 00/46365 A1 | 8/2000 |
| WO | WO 00/50006 A2 | 8/2000 |
| WO | WO 00/50461 A1 | 8/2000 |
| WO | WO 00/54803 A2 | 9/2000 |
| WO | WO 00/62800 A2 | 10/2000 |
| WO | WO 01/00232 A2 | 1/2001 |
| WO | WO 01/12223 A2 | 2/2001 |
| WO | WO 01/16320 A1 | 3/2001 |
| WO | WO 01/22972 A2 | 4/2001 |
| WO | WO 01/22990 A2 | 4/2001 |
| WO | WO 01/26681 A2 | 4/2001 |
| WO | WO 01/35991 A2 | 5/2001 |
| WO | WO 01/38358 A2 | 5/2001 |
| WO | WO 01/51083 A2 | 7/2001 |
| WO | WO 01/54720 A1 | 8/2001 |
| WO | WO 01/56603 A1 | 8/2001 |
| WO | WO 01/58478 A1 | 8/2001 |
| WO | WO 01/62275 A1 | 8/2001 |
| WO | WO 01/77158 A1 | 10/2001 |
| WO | WO 01/85208 A2 | 11/2001 |
| WO | WO 01/98333 A2 | 12/2001 |
| WO | WO 02/10416 A1 | 2/2002 |
| WO | WO 02/14478 A2 | 2/2002 |
| WO | WO 02/26209 A2 | 4/2002 |
| WO | WO 02/32450 A2 | 4/2002 |
| WO | WO 02/053141 A2 | 7/2002 |
| WO | WO 02/056905 A2 | 7/2002 |
| WO | WO 02/056907 A2 | 7/2002 |
| WO | WO 03/024480 A2 | 3/2003 |
| WO | WO 03/024481 A2 | 3/2003 |
| WO | WO 03/030656 A2 | 4/2003 |
| WO | WO 03/031466 A2 | 4/2003 |
| WO | WO 03/039225 A2 | 5/2003 |
| WO | WO 03/040164 A2 | 5/2003 |
| WO | WO 03/040308 A2 | 5/2003 |
| WO | WO 03/045431 A2 | 6/2003 |
| WO | WO 03/059386 A2 | 7/2003 |
| WO | WO 03/103570 A2 | 12/2003 |
| WO | WO 2004/000351 A1 | 12/2003 |

OTHER PUBLICATIONS

Braun, H. et al., "Oligonucleotide and plasmid DNA packaging into polyoma VP1 virus-like particles expressed in *Escherichia coli*.", Biotechnol Appl Biochem, 1999, pp. 31-43, vol. 29, Portland Press Ltd, GB.

Del Prete, G, "Human Th1 and Th2 lymphocytes: their role in the pathophysiology of atopy.", Allergy, 1992, pp. 450-455, vol. 47, Issue 5, Munksgaard, Copenhagen.

Dullforce, P, et al., "Enhancement of T cell-independent immune responses in vivo by CD40 antibodies.", Nat Med, 1998, pp. 88-91, vol. 4, Issue 1, Nature Publishing Group, GB.

Golmohammadi, R, et al., "The refined structure of bacteriophage MS2 at 2.8 A resolution.", J Mol Biol, 1993, pp. 620-639, vol. 234, Issue 3, Academic Press Ltd, GB.

Greenstone, Iil, et al., "Chimeric papillomavirus virus-like particles elicit antitumor immunity against the E7 oncoprotein in an HPV16 tumor model.", Proc Natl Acad Sci USA, 1998, pp. 1800-1805, vol. 95, Issue 4, National Academy of Sciences, US.

Gursel, I, et al., "Sterically stabilized cationic liposomes improve the uptake and immunostimulatory activity of CpG oligonucleotides.", J Immunol, 2001, pp. 3324-3328, vol. 167, Issue 6, The American Association of Immunologists, US.

(56) References Cited

OTHER PUBLICATIONS

Häcker, H, et al., "CpG-DNA-specific activation of antigen-presenting cells requires stress kinase activity and is preceded by non-specific endocytosis and endosomal maturation.", EMBO J, 1998, pp. 6230-6240, vol. 17, Issue 21, Oxford University Press, GB.

Hallsworth, MP, et al., "Selective enhancement of GM-CSF, TNF-alpha, IL-1 beta and IL-8 production by monocytes and macrophages of asthmatic subjects.", Eur Respir J, 1994, pp. 1096-1102, vol. 7, Issue 6, ERS Journals Ltd, GB.

Hartmann, G, et al., "Mechanism and function of a newly identified CpG DNA motif in human primary B cells.", J Immunol, 2000, pp. 944-953, vol. 164, Issue 2, The American Association of Immunologists, US.

Heal, KG, et al., "Expression and immunogenicity of a liver stage malaria epitope presendted as a foreign peptide on the surface of RNA-free MS2 bacteriophage capsids", Vaccine, 2000, pp. 251-258, vol. 18, Elsevier Science Ltd., GB.

Holt, PG, et al.,"Supression of IgE responses following inhalation of antigen", Immunol Today, 1987, pp. 14-18, vol. 8, Elsevier Science Publishers BV, NL.

Hsu, C-H, et al., "Inhibition of specific IgE response in vivo by allergen-gene transfer.", Int Immunol, 1996, pp. 1405-1411, vol. 8, Issue 9, Oxford University Press, GB.

Jegerlehner, A, et al., "Carrier induced epitopic suppression of antibody responses induced by virus-like particles is a dynamic phenomenon caused by carrier-specific antibodies.", Vaccine, 2010, pp. 5503-5512, vol. 28, Issue 33, Elsevier Ltd., GB.

Joseph, A, et al., "Liposomal immunostimulatory DNA sequence (ISS-ODN): an efficient parenteral and mucosal adjuvant for influenza and hepatitis B vaccines.", Vaccine, 2002, pp. 3342-3354, vol. 20, Issue 27-28, Elsevier Science Ltd., GB.

Kimura, Y, et al., "Binding of oligoguanylate to scavenger receptors is required for oligonucleotides to augment NK cell activity and induce IFN.", J Biochem, 1994, pp. 991-994, vol. 116, Issue 5, Oxford University Press, GB.

Kline, JN, et al., "Immune Redirection by CpG Oligonucleotides: Conversion of a Th2 Response to a Th1 Response in a Murine Model of Asthma", Journal of Investigative Medicine, 1997, pp. 282A-283A, vol. 45, Issue 3, American Federation for Medical Research, US.

Krieg, AM, et al., "A role for endogenous retroviral sequences in the regulation of lymphocyte activation.", J Immunol, 1989, pp. 2448-2451, vol. 143, Issue 8, The American Association of Immunologists, US.

Krieg, AM, et al., "B Cell Activation Induced by Oligodeoxynucleotides (ODN) or DNA Containing Un-Methylated CpG Motifs", ACR Poster Session—Inflammatory Mediators and Phagocytic Cell Function, 1994, pp. S379, Association for Consumer Research, US.

Krieg, AM, "Immune Stimulation by CpG DNA", Antisense & Nucleic Acid Drug Development, 1999, vol. 9, pp. 429-431, Mary Ann Liebert, Inc., US.

Kuramoto, E, et al., "Changes of host cell infiltration into Meth A fibrosarcoma tumor during the course of regression induced by injections of a BCG nucleic acid fraction.", Int J Immunopharmacol, 1992, pp. 773-782, vol. 14, Issue 5, International Society for Immunopharmacology, GB.

Le Gal, F-A, et al., "Lipopeptide-base melanoma cancer vaccine induced a strong MART-27-35-cytotoxic T lymphocyte response in a preclinal study.", Int J Cancer, 2002, pp. 221-227, vol. 98, Issue 2, Wiley-Liss Inc., The International Union Against Cancer, US.

Leong, DLY, et al., "Antigenic Competition Between and Endotoxic Adjuvant and a Protein Antigen.", Infect Immun, 1971, pp. 308-317, vol. 3, Issue 2, American Society for Microbiology, US.

Li, X-M, et al., "Mucosal IFN-gamma gene transfer inhibits pulmonary allergic responses in mice.", J Immunol, 1996, pp. 3216-3219, vol. 157, Issue 8, The American Association of Immunologists, US.

Livingston, PO, et al., "Serological response of melanoma patients receiving melanoma cell vaccines. I. Autologous cultured melanoma cells.", Int J Cancer, 1982, pp. 413-422, vol. 30, Issue 4, International Union Against Cancer, US.

Mastico, RA, et al., "Multiple presentation of foreign peptides on the surface of an RNA-free spherical bacteriophage capsid.", J Gen Virol, 1993, pp. 541-548, vol. 74, Society for General Microbiology, GB.

McPeck, M, et al., "Aerosol delivery during continuous nebulization.", Chest, 1997, pp. 1200-1205, vol. 111, Issue 5, The American College of Chest Physicians, US.

Miconnet, I, et al., "CpG are efficient adjuvants for specific CTL induction against tumor antigen-derived peptide.", J Immunol, 2002, pp. 1212-1218, vol. 168, Issue 3, The American Association of Immunologists, US.

Minenkova, OO, et al., "Design of specific immunogens using filamentous phage as the carrier.", Gene, 1993, pp. 85-88, vol. 128, Issue 1, Elsevier Science Publishers BV, NL.

Miyamura, K, et al., "Parvovirus particles as platforms for protein presentation.", Proc Natl Acad Sci USA, 1994, pp. 8507-8511, vol. 91, Issue 18, National Academy of Sciences, US.

Mobley, JL, et al., "Cytokine networks in allergic lung inflammation: an opportunity for drug intervention.", Expert Opin Investig Drugs, 1997, pp. 1-6, vol. 6, Issue 1, Ashley Publications Ltd, GB.

Murray, K, et al., "The core antigen of hepatitis B virus as a carrier for immunogenic peptides.", Biol Chem, 1999, pp. 277-283, vol. 380, Issue 3, Walter de Gruyter, DE/US.

Nyce, JW, "Respirable antisense oligonucleotides as novel therapeutic agents for asthma and other pulmonary diseases.", Expert Opin Investig Drugs, 1997, pp. 1149-1156, vol. 6, Issue 9, Ashley Publications Ltd, GB.

Nyce, JW, et al., "DNA antisense therapy for asthma in an animal model.", Nature, 1997, pp. 721-725, vol. 385, Issue 6618, Nature Publishing Group, GB.

Pisetsky, DS, et al., "Stimulation of Murine Lymphocyte Proliferation by a Phosphorothioate Oligonucleotide with antisense activity for herpes simplex Virus", Life Sciences, 1993, pp. 101-107, vol. 54, Pergamon Press, US.

Pumpens, P, et al., "Artificial Genes for Chimeric Virus-Like Particles. In: Artificial DNA—Methods and Applications, Y.E. Khudyakov and H.A. Fields (eds)", Artificial DNA—Methods and Applications, 2003, pp. 249-327, CRC Press, US.

Raz, E, et al., "Intradermal gene immunization: the possible role of DNA uptake in the induction of cellular immunity to viruses.", Proc Natl Acad Sci USA, 1994, pp. 9519-9523, vol. 91, Issue 20, National Academy of Sciences, US.

Reynolds, SR, et al., "Stimulation of CD8+ T cell responses to MAGE-3 and Melan A/MART-1 by immunization to polyvalent melanoma vaccine.", Int J Cancer, 1997, pp. 972-976, vol. 72, Issue 6, Wiley-Liss Inc, The International Union Against Cancer, US.

Romero, P, et al.,"Antigenicity and immunogenicity of Melan-A/MART-1 derived peptides as targets for tumor reactive CTL in human melanoma.", Immunol Rev, 2002, pp. 81-96, vol. 188, Blackwell Munksgaard, DK.

Ruedl, C, et al., "Cross-presentation of virus-like particles by skin-derived CD8(−) dendritic cells: a dispensable role for TAP.", Eur J Immunol, 2002, pp. 818-825, vol. 32, Issue 3, Wiley-VCH Verlag GmbH, DE.

Schödel, F, et al., "Hybrid hepatitis B virus core antigen as a vacccine carrier moiety: I. presentation of foreign epitopes.", J Biotechnol, 1996, pp. 91-96, vol. 44, Issue 1-3, Elsevier Science VB, NL.

Shi, W, et al., "Papillomavirus pseudovirus: a novel vaccine to induce mucosal and systemic cytotoxic T-lymphocyte responses.", J Virol, 2001, pp. 10139-10148, vol. 75, Issue 21, American Society for Microbiology, US.

Stoll, E, et al., "Revised amino acid sequence of Qbeta coat protein between positions 1 and 60.", J Biol Chem, 1977, pp. 990-993, vol. 252, Issue 3, American Society for Biochemistry and Molecular Biology, US.

Street, M, et al., "Differences in the effectiveness of delivery of B- and CTL-epitopes incorporated into the hepatitis B core antigen (HBcAg) c/e1-region.", Arch Virol, 1999, pp. 1322-1343, vol. 144, Issue 7, Springer Verlag, AT.

(56) References Cited

OTHER PUBLICATIONS

Tindle, RW, et al., "Chimeric hepatitis B core antigen particles containing B- and Th-epitopes of human papillomavirus type 16 E7 protein induce specific antibody and T-helper responses in immunised mice.", Virology, 1994, pp. 547-557, vol. 200, Issue 2, Acacemic Press Inc, US.

Tokanuga, T, et al., "Synthetic oligonucleotides with particular base sequences from the cDNA encoding proteins of *Mycobacterium bovis* BCG induce interferons and activate natural killer cells.", Microbiol Immunol, 1992, pp. 55-66, vol. 36, Issue 1, Wiley-Blackwell, AU.

Touze, A, et al., "In vitro gene transfer using human papillomavirus-like particles.", Nucleic Acids Res, 1998, pp. 1317-1323, vol. 26, Issue 5, Oxford University Press, GB.

Uhlmann, E, et al., "Antisense Oligonucleotides: A New Therapeutic Principle", Chemical Reviews, 1990, pp. 544-548, vol. 90, Issue 4, American Chemical Society, US.

Valmori, D, et al., "Enhanced generation of specific tumor-reactive CTL in vitro by selected Melan-A/MART-1 immunodominant peptide analogues.", J Immunol, 1998, pp. 1750-1758, vol. 160, Issue 4, The American Association of Immunologists, US.

Valmori, D, et al., "Induction of potent antitumor CTL responses by recombinant vaccinia encoding a melan-A peptide analogue.", J Immunol, 2000, pp. 1125-1131, vol. 164, Issue 2, The American Association of Immunologists, US.

Vogel, FR, et al., "A compendium of vaccine adjuvants and excipients.", Pharm Biotechnol, 1995, pp. 141-228, vol. 6, Plenum Press, US.

Wang, F, et al., "Phase I trial of a MART-1 peptide vaccine with incomplete Freund's adjuvant for resected high-risk melanoma.", Clin Cancer Res, 1999, pp. 2756-2765, vol. 5, Issue 10, American Association for Cancer Research, US.

Winter, G, et al., "Cloning of influenza cDNA into M13: the sequence of the RNA segment encoding the A/PR/8/34 matrix protein.", Nucleic Acids Res, 1980, pp. 1965-1974, vol. 8, Issue 9, IRL Press Limited, GB.

Wong, S, "Table of Contents in: Chemistry of protein conjugation and cross-linking", 1991, CRC Press Inc, US.

Woodberry, T, et al., "Immunogenicity of a human immunodeficiency virus (HIV) polytope vaccine containing multiple HLA A2 HIV CD8(+) cytotoxic T-cell epitopes.", J Virol, 1999, pp. 5320-5325, vol. 73, Issue 7, American Society for Microbiology, US.

Yamamoto, S, et al., "In vitro augmentation of natural killer cell activity and production of interferon-alpha/beta and -gamma with deoxyribonucleic acid fraction from *Mycobacterium bovis* BCG.", Jpn J Cancer Res, 1988, pp. 866-873, vol. 79, Issue 7, Japanese Cancer Association, JP.

Yssel, H, et al., "T cell activation-inducing epitopes of the house dust mite allergen Der p I. Proliferation and lymphokine production patterns by Der p I-specific CD4+ T cell clones.", J Immunol, 1992, pp. 738-745, vol. 148, Issue 3, The American Association of Immunologists, US.

Zarour, HM, et al.,"Melan-A/MART-1(51-73) represents an immunogenic HLA-DR4-restricted epitope recognized by melanoma-reactive CD4(+) T cells.", Proc Natl Acad Sci USA, 2000, pp. 400-405, vol. 97, Issue 1, National Academy of Sciences, US.

Zebede, SL, et al., "Influenza A virus M2 protein: monoclonal antibody restriction of virus growth and detection of M2 in virions.", J Virol, 1988, pp. 2762-2772, vol. 62, Issue 8, American Society for Microbiology, US.

U.S. Appl. No. 08/593,554, inventor Carson, D.A., et al., filed Jan. 30, 1996. (Not Published—Abandoned).

English language Abstract of German Patent Publication No. DE 2 034 118, European Patent Office, espacenet database—Worldwide, (2012).

Adams, S.E.,et al.,"The expression of hybrid HIV:Ty virus-like particles in yeast". Nature. Sep. 3-9, 1987;329(6134):68-70, Nature Publishing Group.

Adhin, MR. et al., "Nucleotide sequence from the ssRNA bacteriophage JP34 resolves the discrepancy between serological and biophysical classification". Virology. May 1989;170(1):238-42, Academic Press Inc.

Ahmed, R., et al., "T4+ T helper cell function in vivo: differential requirement for induction of antiviral cytotoxic T-cell and antibody responses". J. Virol. Jun. 1988;62(6):2102-6, American Society for Microbiology.

Albert, M. L., et al., "Immature dendritic cells phagocytose apoptotic cells via alphavbeta5 and CD36, and cross-present antigens to cytotoxic T Lymphocytes," J. Exp. Med. Oct. 5, 1998;188(7):1359-68, The Rockefellerr University Press.

Albert, M. L., et al., "Dendritic cells acquire antigen from apoptotic cells and induce class I-restricted CTLs," Nature. Mar. 5, 1998;392(6671):86-9, Nature Publishing Group.

Bachmann & Zinkernagel, "Neutralizing antiviral B cell responses", Annu. Rev. Immunol. 1997;15:235-70, Annual Reviews Inc.

Bachmann & Zinkernagel, "The influence of virus structure on antibody responses and virus serotype formation", Immunol. Today. Dec. 1996;17(12):553-558, Elsevier Science Ltd.

Bachmann et al., "Distinct roles for LFA-1 and CD28 during activation of naive T cells: adhesion versus costimulation", Immunity. Oct. 1997;7(4):549-57, Cell Press.

Bachmann et al., "Four types of Ca2+ signals in naive CD8+ cytotoxic T cells after stimulation with T cell agonists, partial agonists and antagonists", Eur. J. Immunol. Dec. 1997;27(12):3414-9, Wiley-VCH Verlag GmbH, D-69451 Weinheim.

Bachmann et al., "Functional maturation of an antiviral cytotoxic T-cell response",J. Virol. Aug. 1997;71(8):5764-8, American Society for Microbiology.

Bachmann et al., "Peptide-induced T cell receptor down-regulation on naive T cells predicts agonist/partial agonist properties and strictly correlates with T cell activation", Eur. J. Immunol. Sep. 1997;27(9):2195-203, Wiley-VCH Verlag GmbH, D-69451 Weinheim.

Bachmann et al., "Dendritic cells process exogenous viral proteins and virus-like particles for class I presentation to CD8+ cytotoxic T lymphocytes", Eur. J. Immunol. Nov. 1996;26(11):2595-600, Wiley-VCH Verlag GmbH, D-69451.

Bachmann et al., "Evaluation of lymphocytic choriomeningitis virus-specific cytotoxic T cell responses", Immunology Methods Manual 1997: 1921-1933, Academic Press Ltd.

Bachmann et al., "TRANCE, a tumor necrosis factor family member critical for CD40 ligand-independent T helper cell activation",J. Exp. Med. Apr. 5, 1999;189(7):1025-31. The Rockefeller University Press.

Bachmann et al., "Immune responses in the absence of costimulation: viruses know the trick", J. Immunol. Dec. 1, 1998;161(11):5791-4, The American Association of Immunologists.

Banchereau, J., and R.M. Steinman, "Dendritic cells and the control of immunity". Nature . Mar. 19, 1998;392(6673):245-52. Review, Nature Publishing Group.

Battegay, M., et al., "Antiviral immune responses of mice lacking MHC class II or its associated invariant chain", Cell Immunol. Jan. 10, 1996;167(1):115-21, Elsevier Science.

Beaucage, S.I., and Caruthers, M.H., "Deoxynucleoside Phosphoramidites—A new class of key intermediates for Deoxypolynucleotide Synthesis", Tet. Let. 1981 22:1859-1862, Pergamon Press Ltd.

Bennett, S.R.M., et al., "Induction of a CD8+ cytotoxic T lymphocyte response by cross-priming requires cognate CD4+ T cell help", J. Exp. Med. Jul. 7, 1997;186(1):65-70 The Rockefeller University Press.

Bennett, S.R.M., et al., "Help for cytotoxic-T-cell responses is mediated by CD40 signalling", Nature. Jun. 4, 1998;393(6684):478-80, Nature Publishing Group.

Berman, et al., "Protection of chimpanzees from infection by HIV-1 after vaccination with recombinant glycoprotein gp120 but not gp160", Nature. Jun. 14, 1990; 345(6276):622-5, Nature Publishing Group.

Boeke, J.D., and Sandmeyer, S.B., "Chapter 4: Yeast Transposable Elements," in *The Molecular and Cellular Biology of the Yeast Saccharomyces: Genome Dynamics, Protein Synthesis, and Energetics*,

(56) References Cited

OTHER PUBLICATIONS vol. 1, Broach, J.R., et al., eds., Cold Spring Harbor Laboratory Press, Cold Spring Harbor, NY, pp. 193-261 (1991).

Borisova et al., "Hybrid hepatitis B virus nucleocapsid bearing an immunodominant region from hepatitis B virus surface antigen", *J. Virol.* Jun. 1993;67(6):3696-701, American Society for Microbiology.

Borrow, P., et al.,"CD40L-deficient mice show deficits in antiviral immunity and have an impaired memory CD8+ CTL response", *J. Exp. Med.* May 1, 1996;183(5):2129-42, The Rockefeller University Press.

Brändle et al., "The shared tumor-specific antigen encoded by mouse Gene P1A is a target nor only fpr cytolytic T lymphocytes but also for tumor rejection", 1998, *Eur. J. Immunol.* 28:4010-4019, Wiley-VCH Verlag GmbH, D-69451.

Buller, R. et al., "Induction of cytotoxic T-cell responses in vivo in the absence of CD4 helper cells", *Nature* Jul. 2-8, 1987;328(6125):77-9, Nature Publishing Group.

Carlson et al., "Vaccine protection of *Rhesus macaques* against simian immunodeficiency virus infection", *AIDS Res.Hum. Retroviruses.* Nov. 1990;6(11):1239-46.

Cella, M., et al., "Origin, maturation and antigen presenting function of dendritic cells", *Curr. Opin. Immunol.* Feb. 1997;9(1):10-6. Review, Current Biology Ltd.

Chackerian, B. et al., "Induction of autoantibodies to mouse CCR5 with recominant papillomavirus particles", *Proc. Natl. Acad. Sci. U S A.* Mar. 2, 1999;96(5):2373-2378, National Academy Press.

Clarke et al., "Presentation and immunogenicity of viral epitopes on the surface of hybrid hepatitis B virus core particles produced in bacteria", *J. Gen. Virol.* May 1990;71 (Pt 5): 1109-17, Cambridge University Press.

Cohen, et al., "CD4+ T-cells from mice immunized to syn*Gene*ic sarcomas recognize distinct, non-shared tumor antigens", *Cancer Res.* Feb. 15, 1994;54(4):1055-1058, The American Association for Cancer Research.

DeClercq, E., "Interferon Induction by Polynucleotides, Modified Polynucleotides, and Polycarboxylates", *Methods in Enzymology* 1981;78:227-236, Academic Press.

Desrosiers et al., "Vaccine protection against simian immunodeficiency virus infection", *Proc. Natl. Acad. Sci. USA.* Aug. 1989;86(16):6353-7, National Academy Press.

Diehl, L., et al., "CD40 activation in vivo overcomes peptide-induced peripheral cytotoxic T-lymphocyte tolerance and augments anti-tumor vaccine efficacy", Nat. Med. Jul. 1999;5(7):774-9, Nature Publishing Company.

Eckhardt et al., "Hepatitis B virus core antigen has two nuclear localization sequences in the arginine-rich carboxyl terminus", *J. Virol.* Feb. 1991;65(2):575-82, American Society for Microbiology.

Ehl, S., et al., "Viral and bacterial infections interfere with peripheral tolerance induction and activate CD8+ T cells to cause immunopathology", *J Exp. Med.* Mar. 2, 1998;187(5):763-74, The Rockefeller University Press.

Emr, S.D., "Heterologous *Gene* expression in yeast", *Methods Enzymol.* 1990;185:231-3, Academic Press.

Engleman, E.G., "Dendrtic cells: potential role in cancer therapy", *Cytotechnology.* 1997;25(1-3):1-8, Kluwer Academic Publishers.

Fehr, T., et al., "Role of repetitive antigen patterns for induction of antibodies against antibodies", *J. Exp. Med.* May 19, 1997;185(10):1785-92, The Rockefeller University Press.

Foy, T.M., et al., "Immune Regulation by CD40 and Its Ligand GP39", *Annu. Rev. Immunol.* 1996 14: 591-617, Annual Reviews Inc.

Froehler et al., "Synthesis of DNA via deoxynucleoside H-phosphonate intermediates", *Nucl. Acids. Res.* 1986 14: 5399-5407, Oxford University Press.

Gaffney et al., "Large-Scale Oligonucleotide Synthesis by the H-Phosphonate Method", *Tet. Let.* 1988 29: 2619-2622, Pergamon Press.

Garegg et al., "Nucleoside H-Phosphonates. IV. Automated solid phase synthesis of oligoribonucleotides by the hydrogenphosphonate approach", *Tet. Let.* 27:4055-4058 (1986), Pergamon Journals Ltd.

Garza, K.M., et al., "Role of antigen-presenting cells in mediating tolerance and autoimmunity", *J. Exp. Med.* Jun. 5, 2000;191(11):2021-7, The Rockefeller University Press.

Geysen et al., "Use of peptide synthesis to probe viral antigens for epitopes to a resolution of a single amino acid", *Proc. Natl. Acad. Sci. U S A.* Jul. 1984;81(13):3998-4002, National Academy Press.

Gluckman, J.C., "In vitro *Gene*ration of human dendritic cells and cell therapy", *Cytokines Cell Mol Ther.* Sep. 1997;3(3):187-96, Martin Dunitz Ltd.

Golmohammadi, R. et al., "The crystal structure of bacteriophage Q beta at 3.5 A resolution", *Structure.* May 15, 1996;4(5):543-54, Current Biology Ltd.

Guerder, S., ad P. Matzinger, "A fail-safe mechanism for maintaining self-tolerance", *J. Exp. Med.* Aug. 1, 1992;176(2):553-64, The Rockefeller University Press.

Harding, C.V. and Song, R., "Phagocytic processing of exogenous particulate antigens by macrophages for presentation by class I MIIC molecules", *J. Immunol.* Dec . 1, 1994;153(11):4925-33, Elsevier/North-Holland Biomedical Press.

Ho et al., "Site-directed muta*Gene*sis by overlap extension using the polymerase chain reaction", *Gene.* Apr. 15, 1989;77(1):51-9, Elsevier.

Husmann, L.A., and M.J. Bevan, "Cooperation between helper T cells and cytotoxic T lymphocyte precursors", *Ann. NY. Acad. Sci.* 1988;532:158-69, New York Academy of Sciences.

Huston et al., "Protein engineering of single-chain Fv analogs and fusion proteins", *Methods Enzymol.* 1991;203:46-88, Macmillan Publishers Ltd.

Jiang, X., et al., "Norwalk Virus Cloning and Characterization", *Science* 250:1580-1583 1990, Americar Association for the Advancement of Science.

Kang, Y.C., et al.,"Development of HIV/AIDS vaccine using chimeric gag-env virus-like particles", *Biol. Chem.* Mar. 1999;380(3):353-64, High Wire Press.

Kastelein, RA. et al., "Effect of the sequences upstream from the ribosome-binding site on the yield of protein from the cloned *Gene* for phage MS2 coat protein", *Gene.* Sep. 1983;23(3):245-54, Elsevier.

Klovins, J., et al., "Nucleotide sequence of a ssRNA phage from Acinetobacter: kinship to coliphages", *J Gen. Virol.* Jun. 2002;83(Pt 6):1523-33, Cambridge University Press.

Kovacsovics-Bankowski, M., et al., "Efficient major histocompatibility complex class I presentation of exogenous antigen upon phagocytosis by macrophages", *Proc. Natl. Acad. Sci. U S A.* Jun. 1, 1993;90(11):4942-6, National Academy Press.

Kozlovska, T.M., et al., "Recombinant RNA phage Q beta capsid particles synthesized and self-assembled in *Escherichia coli*", *Gene.* Dec. 27, 1993;137(1):133-137, Elsevier.

Kozlovska, T.M., et al., "RNA phage Q beta coat protein as a carrier for foreign epitopes", *Intervirology.* 1996;39(1-2):9-15, S. Karger AG, Basel.

Kozlovskaya, T.M. et al. "Formation of capsid-like structures as a result of the expression of a cloned envelope protein gene from RNA-containing bacteriophage fr", *Dokl. Akad. Nauk. SSSR* 287: 452-455, Erivan Akademiia Nauk Armianskoi SSR (1986).

Kratz, P.A., et al., "Native display of complete foreign protein domains on the surface of hepatitis B virus capsids", *Proc. Natl. Acad. Sci. U S A.* Mar. 2, 1999;96(5):1915-20, National Academy Press.

Kündig et al., "Fibroblasts as efficient antigen-presenting cells in lymphoid organs", *Science.* Jun. 2, 1995;268(5215):1343-7, American Association for the Advancement of Science.

Kündig, T.M., et al.,"Duration of TCR stimulation determines costimulatory requirement of T cells", *Immunity.* Jul. 1996;5(1):41-52, Cell Press.

Leist, T.P., et al., "Functional analysis of T lymphocyte subsets in antiviral host defense", *J. Immunol.* Apr. 1, 1987;138(7):2278-81, The American Association of Immunologists.

Leist, T.P., et al., "Impaired Generation of anti-viral cytotoxicity against lymphocytic choriomeningitis and vaccinia virus in mice treated with CD4-specific monoclonal antibody", Scand. *J. Immunol.* Dec. 1989;30(6):679-86, Blackwell Publishing.

(56) References Cited

OTHER PUBLICATIONS

Levy, H.B., "Induction of interferon in vivo and in vitro by polynucleotides and derivatives, and preparation of derivatives", *Methods of Enzymol.* 1981;78(Pt A):242-51, Academic Press.

Lim F. et al., "The RNA-binding site of bacteriophage Qbeta coat protein", *J. Biol. Chem.* Dec. 13, 1996;271(50):31839-45, The American Society for Biochemistry and Molecular Biology Inc.

Matsui, S.M., et al., "The isolation and characterization of a Norwalk virus-specific cDNA", *J. Clin. Invest.* Apr. 1991;87(4):1456-61, High Wire Press.

Maxwell, J.R., et al., CD40 activation boosts T cell immunity in vivo by enhancing T cell clonal expansion and delaying peripheral T cell deletion, *J. Immunol.* Feb. 15, 1999;162(4):2024-34, The American Association of Immunologists.

Medzhitov, R. and Janeway, C.A., Jr., Innate immunity: the virtues of a nonclonal system of recognition, *Cell.* Oct. 31, 1997;91(3):295-8, Cell Press.

Murphey-Corb et al., "A formalin-inactivated whole SIV vaccine confers protection in macaques", *Science.* Dec. 8, 1989;246(4935):1293-7, American Association for the Advancement of Science.

NCBI Entrez, GenBank Report, Accession No. VCBPM2, from Min Jou, W. et al. (Jan. 2001).

NCBI Entrez, GenBank Report, Accession No. AAC06250, from Beekwilder, M.J. et al. (Mar. 2002).

NCBI Entrez, GenBank Report, Accession No. AAC14699, from Beekwilder, M.J. et al. (Apr. 1998).

NCBI Entrez, GenBank Report, Accession No. AAC14704, from Beekwilder, M.J. et al. (Apr. 1998).

NCBI Entrez, GenBank Report, Accession No. P03611, from Weber, K. et al. (Nov. 1997).

NCBI Entrez, GenBank Report, Accession No. VCBPFR, from Wittmann-Liebold, B. et al. (Jul. 1999).

NCBI Entrez, GenBank Report, Accession No. CAA30374, from Inokuchi, Y. et al. (Feb. 1999).

NCBI Entrez, GenBank Report, Accession No. NP_040754, from Inokuchi, Y. et al. (Dec. 2002).

NCBI Entrez, GenBank Report, Accession No. VCBPR7, from Willis, M.C. et al. (Apr. 1996).

NCBI Entrez, GenBank Report, Accession No. AAA16663, from Kozlovska, T.M. et al. (Mar. 1994).

NCBI Entrez, GenBank Report, Accession No. NP_695026, from Jacobson, A.B.. et al. (Apr. 1988).

NCBI Entrez, GenBank Report, Accession No. VCBPQB, from Maita, T. et al. (Dec. 1993).

Nestle et al., "Vaccination of melanoma patients with peptide- or tumor lysate-pulsed dendritic cells", *Nat. Med.* Mar. 1998;4(3):328-32, Nature Publishing Company.

Neirynck, S. et al., "A universal influenza A vaccine based on the extracellular domain of the M2 protein", *Nat. Med.* Oct. 1999;5(10):1157-63, Nature Publishing Company.

Ni, CZ., et al., "Crystal structure of the coat protein from the GA bacteriophage: model of the unassembled dimer", *Protein Sci.* Dec. 1996;5(12):2485-93, Cambridge University Press.

Ohashi et al., "Ablation of 'tolerance' and induction of diabetes by virus infection in viral antigen transgenic mice", *Cell.* Apr. 19, 1991;65(2):305-17, Cell Press.

Ossendorp, F., et al., Specific T helper cell requirement for optimal induction of cytotoxic T lymphocytes against major histocompatibility complex class II negative tumors, *J. Exp. Med.* Mar. 2, 1998;187(5):693-702, The Rockefeller University Press.

Pedersen et al., "Isolation of a T-lymphotropic virus from domestic cats with an immunodeficiency-like syndrome", *Science.* Feb. 13, 1987;235(4790):790-3, American Association for the Advancement of Science.

Pircher, H.P. et al., "Tolerance induction in double specific T-cell receptor transgenic mice varies with antigen", *Nature.* Nov. 30, 1989;342(6249):559-61, Nature Publishing Group.

Preikschat, P., et al., "Expression, assembly competence and antigenic properties of hepatitis B virus core *Gene* deletion variants from infected liver cells", *J. Gen. Virol.* Jul. 1999;80 ( Pt 7):1777-88, Cambridge University Press.

Priano, C. et al., A complete plasmid-based complementation system for RNA coliphage Q beta: three proteins of bacteriophages Q beta (group III) and SP (group IV) can be interchanged, *J. Mol. Biol.* Jun. 2, 1995;249(2):283-97, Academic Press.

Pumpens, P. and Grens, E., "HBV core particles as a carrier for B cell/T cell epitopes", *Intervirology.* 2001;44(2-3):98-114, 2001 S. Karger AG, Basel.

Pushko P. et al., "Analysis of RNA phage fr coat protein assembly by insertion, deletion and substitution muta*Genesis*", *Protein Eng.* Nov. 1993;6(8):883-91, Oxford University Press.

Renkvist et al., "A listing of human tumor antigens recognized by T cells", *Cancer Immunol. Immunother.* Mar. 2001;50(1):3-15, Springer Verlag.

Ridge, J.P., et al., "A conditioned dendritic cell can be a temporal bridge between a CD4+ T-helper and a T-killer cell". *Nature.* Jun. 4, 1998;393(6684):474-8, Nature Publishing Company.

Roth, J.F., "The yeast Ty virus-like particles", *Yeast.* Jun. 30, 2000;16(9):785-95, John Wiley & Sons Ltd.

Rueda, P. et al., "Minor displacements in the insertion site provoke major differences in the induction of antibody responses by chimeric parvovirus-like particles", *Virology.* Oct. 10, 1999;263(1):89-99, Academic Press.

Ruedl, C., et al., "CD8(+) T cells mediate CD40-independent maturation of dendritic cells in vivo", *J. Exp. Med.* Jun. 21, 1999;189(12):1875-84, The Rockefeller University Press.

Sallusto, F., and A. Ianzavecchia, "Efficient presentation of soluble antigen by cultured human dendritic cells is maintained by granulocyte/macrophage colony-stimulating factor plus interleukin 4 and downregulated by tumor necrosis factor alpha", *J. Exp. Med.* Apr. 1, 1994;179(4):1109-18, The Rockefeller University Press.

Salunke D.M., et al, "Self-assembly of purified polyomavirus capsid protein VP1", *Cell.* Sep. 12, 1986;46(6):895-904, Cell Press.

Sasnauskas K, et al., "Yeast cells allow high-level expression and formation of polyomavirus-like particles", *Biol Chem.* Mar. 1999;380(3):381-6, Walter de Gruyter.

Sasnauskas K. et al., 3rd International Workshop "Virus-like particles as vaccines." Berlin, Sep. 26-29, 2001.

Schoenenberger, S.P., et al., "T-cell help for cytotoxic T lymphocytes is mediated by CD40-CD40L interactions", *Nature* 393:480 (1998), Nature Publishing Group.

Smiley B,K., et al., "Enhanced readthrough of opal (UGA) stop codons and production of *Mycoplasma pneumoniae* P1 epitopes in *Escherichia coli*", *Gene.* Nov. 30, 1993;134(1):33-40, Elsevier.

Sotomayor, E.M., et al., "Conversion of tumor-specific CD4+ T-cell tolerance to T-cell priming through in vivo ligation of CD40", *Nat. Med.* Jul. 1999;5(7):780-7, Nature Publishing Company.

Speiser et al., "Self antigens expressed by solid tumors do not efficiently stimulate naive or activated T cells: implications for immunotherapy", *J. Exp. Med.* Aug. 29, 1997;186(5):645-53, The Rockefeller University Press.

Steinman, R.M., "Dendritic cells and immune-based therapies", *Exp. Hematol.* Jul. 1996;24(8):859-62, Elsevier.

Stott et al., "Preliminary report: protection of cynomolgus macaques against simian immunodeficiency virus by fixed infected-cell vaccine", *Lancet.* Dec. 22-29, 1990;336(8730):1538-41, Lancet's Press.

Studier et al., "Use of T7 RNA polymerase to direct expression of clones Genes", *Methods Enzymol.* 1990;185:60-89, Macmillan Publishers Ltd.

Taylor, K.M., et al., "Position-dependent processing of peptides presented on the surface of cowpea mosaic virus", *Biol Chem.* Mar. 1999;380(3):387-92, The American Society for Biochemistry and Molecular Biology Inc.

Tissot et al., "Characterizing the functionality of recombinant T-cell receptors in vitro: a pMHC tetramer based approach", *J Immunol Methods.* Mar. 6, 2000;236(1-2):147-65, Elsevier Science.

Torrence, P.F., "Preparation of a synthetic polynucleotide interferon inducer", *Methods Enzymol.* 1981;78(Pt A):326-31, Macmillan Publishers Ltd.

(56) References Cited

OTHER PUBLICATIONS

Touzé A., et al., "*Gene* transfer using human polyomavirus BK virus-like particles expressed in insect cells", *J Gen Virol.* Dec. 2001;82(Pt 12):3005-9, Cambridge University Press.

Townsend A. & Bodmer H., "Antigen recognition by class I-restricted T lymphocytes", *Annu. Rev. Immunol.* 1989;7:601-24, Annual Reviews Inc.

Tripp, R.A., et al., "Characteristics of the influenza virus-specific CD8+ T cell response in mice homozygous for disruption of the H-2¹Ab Gene", *J. Immunol.* Sep. 15, 1995;155(6):2955-9, The American Association of Immunologists.

Twomey, et al., "Structure and immunogenicity of experimental foot-and-mouth disease and poliomyelitis vaccines", *Vaccine.* Nov. 1995;13(16):1603-10, Elsevier Science Ltd.

Van Schooten, W., et al., "Biological properties of dendritic cells: implications to their use in the treatment of cancer", *Mol. Med. Today.* Jun. 1997;3(6):254-60, Elsevier Science Ltd.

Vella, A.T., et al., "Lipopolysaccharide interferes with the induction of peripheral T cell death", *Immunity.* Mar. 1995;2(3):261-70, Cell Press.

Warnes, et al., "Expression of the measles virus nucleoprotein *Gene* in *Escherichia coli* and assembly of nucleocapsid-like structures", *Gene.* Jul. 28, 1996;160(2):173-8, Elsevier.

Weigle, W.O., "Analysis of autoimmunity through experimental models of thyroiditis and allergic encephalomyelitis", *Adv. Immunol.* 1980;30:159-273, Academic Press Inc.

Whitmire, J.K., et al., "CD40 ligand-deficient mice *Gene*rate a normal primary cytotoxic T-lymphocyte response but a defective humoral response to a viral infection", *J. Virol.* Dec. 1996;70(12):8375-81, American Society for Microbiology.

Witherell, GW. & Uhlenbeck, "Specific RNA binding by Q beta coat protein", *Biochemistry.* Jan. 10, 1989;28(1):71-6, American Chemical Socie.

Yuan et al., "Subtype-independent immature secretion and subtype-dependent replication deficiency of a highly frequent, naturally occurring mutation of human hepatitis B virus core antigen", *J Virol.* Dec. 1999;73(12):10122-8, American Society for Microbiology.

Yuasa et al. "Isolation and Some Characteristics of an Agent Inducing Anemia in Chicks", *Avian. Dis.* 23:366-385 1979.

Zhou et al., "Cys residues of the hepatitis B virus capsid protein are not essential for the assembly of viral core particles but can influence their stability", *J. Virol.* Sep. 1992;66(9):5393-8, American Society for Microbiology.

Kozlovskaya, T.M., et al., "Formation of capsid-like structures as a result of the expression of a cloned envelope protein gene from RNA-containing bacteriophage fr," STNEasy, Accession No. 1986:219892, CAplus English abstract (1986) (Document AT20).

Dialog File 351, Accession No. 4796523, Derwent World Patents Index English language abstract for EP 0 201 416 B1 (Document AN3).

Bachmann, M.F. and Zinkernagel, R.M., "The influence of virus structure on antibody responses and virus serotype formation," *Immunol. Today 17*:553-558, Elsevier Science Publishers (1996).

Brown, W.L., et al., "RNA Bacteriophage Capsid-Mediated Drug Delivery and Epitope Presentation," *Intervirology 45*:371-380, S. Karger AG Basel (Jan. 2002).

Chackerian, B., et al., "Induction of autoantibodies to mouse CCR5 with recombinant papillomavirus particles," *Proc. Natl. Acad. Sci. USA 96*:2373-2378, National Academy of Sciences (1999).

Fehr, T., et al., "T cell-independent type I antibody response against B cell epitopes expressed repetitively on recombinant virus particles," *Proc. Natl. Acad. Sci. USA 95*:9477-9481, National Academy of Science (1998).

Fitchen, J., et al., "Plant virus expressing hybrid coat protein with added murine epitope elicits autoantibody response," *Vaccine 13*:1051-1057, Elsevier Science Ltd. (1995).

Gerber, S., et al., "Human Papillomavirus Virus-Like Particles are Efficient Oral Immunogens when Coadministered with *Escherichia coli* Heat-Labile Entertoxin Mutant R192G or CpG DNA," *J. Virol. 75*:4752-4760, American Society for Microbiology (May 2001).

Ioannou, X.P., et al., "CpG-containing oligodeoxynucleotides, in combination with conventional adjuvants, enhance the magnitude and change the bias of the immune responses to a herpesvirus glycoprotein," *Vaccine 21*:127-137, Elsevier Science Ltd. (Nov. 2002).

Jegerlehner, A., et al., "A molecular assembly system that renders antigens of choice highly repetitive for induction of protective B cell responses," *Vaccine 20*:3104-3112, Elsevier Science Ltd. (Aug. 2002).

Kaisho, T. and Akira, S., "Toll-like receptors as adjuvant receptors," *Biochim. Biophys. Acta 1589*:1-13, Elsevier Science (Feb. 2002).

Klovins, J., et al., "Nucleotide sequence of a ssRNA phage from *Acinetobacter*: kinship to coliphages," *J. Gen. Virol. 83*:1523-1533, Society for General Microbiology (Jun. 2002).

Kozlovska, T.M., et al., "RNA Phage Qβ Coat Protein as a Carrier for Foreign Epitopes," *Intervirology 39*:9-15, S. Karger AG Basel (1996).

Kozlovska, T.M., et al., "Recombinant RNA phage Qβ capsid particles synthesized and self-assembled in *Escherichia coli,*" *Gene 137*:133-137, Elsevier Science Publishers (1993).

Kratz, P.A., et al., "Native display of complete foreign protein domains on the surface of hepatitis B virus capsids," *Proc. Natl. Acad. Sci. USA 96*:1915-1920 (1999).

Lechner, F., et al., "Virus-Like Particles as a Modular System for Novel Vaccines," *Intervirology 45*:212-217, S. Karger AG Basel (Jan. 2002).

Li, Y., et al., "Vaccination Against Angiogenesis-Associated Antigens: A Novel Cancer Immunotherapy Strategy," *Curr. Mol. Med 3*:773-779, Bentham Science Publishers Ltd. (Dec. 2003).

Moss, R.B., et al., "In vitro immune function after vaccination with an inactivated, gp120-depleted HIV-1 antigen with immunostimulatory oligodeoxynucleotides," *Vaccine* 18:1081-1087, Elsevier Science (Jan. 2000).

Neirynck, S., et al., "A universal influenza A vaccine based on the extracellular domain of the M2 protein," *Nat. Med. 5*:1157-1163, Nature Publishing Company (1999).

Nieland, J.D., et al., "Chimeric Papillomavirus Virus-like Particles Induce a Murine Self-Antigen-Specific Protective and Therapeutic Antitumor Immune Response," *J. Cell. Biochem. 73*:145-152, Wiley-Liss Inc. (1999).

Slepushkin, V.A., et al., "Protection of mice against influenza A virus challenge by vaccination with baculovirus-expressed M2 protein," *Vaccine 13*:1399-1402, Elsevier Science Ltd. (1995).

Storni, T., et al., "Critical Role for Activation of Antigen-Presenting Cells in Priming of Cytotoxic T Cell Responses After Vaccination with Virus-Like Particles," *J. Immunol. 168*:2880-2886, The American Association of Immunologists (Mar. 2002).

Vasiljeva, I., et al., "Masaic Qβ coats as a new presentation model," *FEBS Lett. 431*:7-11, Elsevier Science B.V. (1998).

Witte, L., et al., "Monoclonal antibodies targeting the VEGF receptor-2 (Flk1/KDR) as an anti-angiogenic therapeutic strategy," *Cancer Metastasis Rev. 17*:155-161, Kluwer Academic Publishers (1998).

Allison (1994) Int J Technol Assess Health Care 10(1):107-20—Adjuvants and Immune Enhancement.

Azuma (1992) Vaccine 10(14):1000-6—Synthetic immunoadjuvants: application to non-specific host stimulation and potentiation of vaccine immunogenicity.

Ballas et al. (1996) J Immunol 157(5):1840-5—Induction of NK Activity in Murine and Human Cells by CpG Motifs in Oligodeoxynucleotides and Bacterial DNA.

Bartholomé et al. (1999) J Interferon Cytokine Res 19(5):471-8—IFN-62 Interferes with the Differenatiation of Dendritic Cells from Peripheral Blood Mononuclear Cells: Selective Inhibition of CD40-Dependent Interleukin-12 Secretion.

Bird (1987) TIG 3(12):342-347—CpG islands as gene markers in the vertebrate nucleus.

Blackwell and Krieg (Apr. 2003) J Immunol 170(8):4061-8—CpG-A-Induced Monocyte IFN-Gamma-Inducible Protein-10 Production Is Regulated by Plasmacytoid Dendritic Cell-Derived IFN-α[1].

Branda et al. (1993) Biochem Pharmacol 45(10):2037-43—Immune Stimulation by an Antisense Oligomer Complementary to the *rev* Gene of HIV-1.

(56) References Cited

OTHER PUBLICATIONS

Branda et al. (1996) J Lab Clin Med 128(3):329-38—Amplification of antibody production by phosphorothioate oligodeoxynucleotides.
Buonaguro et al. (Jan. 2001) Antiviral Res 49(1):35-47—High efficient production of Pr55$^{gag}$ virus-like particles expressing multiple HIV-1 epitopes, including a gp120 protein derived from an Ugandan HIV-1 isolate of subtype A.
Cella et al. (1999) Nat Med 5(8):919-23—Plasmacytoid monocytes migrate to inflamed lymph nodes and produce large amounts of type I interferon.
Cella et al. (1999) J Exp Med 189(5):821-9—Maturation, Activation, and Protection of Dendritic Cells Induced by Double-stranded RNA.
Choi and Rao (Sep. 2000) Virology 275(2):249-57—Packaging of Tobacco Mosaic Virus Subgenomic RNAs by Brome Mosaic Virus Coat Protein Exhibits RNA Controlled Polymorphism.
Choi et al. (Jan. 2002) Proc Natl Acad Sci U S A 99(2):655-60—tRNA elements mediate the assembly of an icosahedral RNA virus.
Clark et al. (Nov. 2001) J Gen Virol 82(Pt 11):2791-7—Immunity against both polyomavirus VP1 and a transgene product induced following intranasal delivery of VP1 pseudocapsid-DNA complexes.
Cooper et al. (Aug. 2004) Vaccine 22(23-24):3136-43—Safety and immunogenicity of CPG 7909 injection as an adjuvant to Fluarix influenza vaccine.
Dalpke et al. (May 2002) Immunology 106(1):102-12—Phosphodiester CpG oligonucleotides as adjuvants: polyguanosine runs enhance cellular uptake and improve immunostimulative activity of phosphodiester CpG oligonucleotides in vitro and in vivo.
Francois et al. (1988) Clin Immunol Immunopathol 48(3):297-306—Examination of the Inhibitory and Stimulatory Effects of IFN-$\alpha$, -$\beta$, and -$\gamma$ on Human B-cell Proliferation Induced by Various B-cell Mitogens.
Gavett et al. (1995) J Exp Med 182(5)-36—Interleukin 12 Inhibits Antigen-induced Airway Hyperresponsiveness, Inflammation, and Th2 Cytokine Expression in Mice.
Gilbert et al. (1997) Nat Biotechnol 15(12):1280-4—A protein particle vaccine containing multiple malaria epitopes.
Gilkeson et al. (1989) J Immunol 142(5):1482-6—Induction of Anti-double Stranded DNA Antibodies in Normal Mice by Immunization with Bacterial DNA.
Goeckeritz et al. (1999) Int Immunol 11(10):1693-700—Multivalent cross-linking of membrane Ig sensitizes murine B cells to a broader spectrum of CpG-containing oligodeoxynucleotide motifs, including their methylated counterparts, for stimulation of proliferation and Ig secretion.
Guschlbauer et al. (1990) J Biomol Struct Dyn 8(3):491-511—Four-Stranded Nucleic Acid Structures 25 Years Later: From Guanosine Gels to Telomer DNA.
Halperin et al. (Jun. 2003) Vaccine 21(19-20):2461-7—A phase I study of the safety and immunogenicity of recombinant hepatitis B surface antigen co-administered with an immunostimulatory phosphorothioate oligonucleotide adjuvant.
Halpern et al. (1996) Cell Immunol 167(1):72-8—Bacterial DNA Induces Murine Interferon-gamma Production by Stimulation of Interleukin-12 and Tumor Necrosis Factor-$\alpha$.
Hartmann et al. (1999) Proc Natl Acad Sci U S A 96(16):9305-10—CpG DNA: a potent signal for growth, activation, and maturation of human dendritic cells.
Heath (1994) Cancer Biother 9(1):1-6—Cytokines and the Rational Choice of Immunological Adjuvants.
Holt (1994) Lancet 344(8920):456-8—A potential vaccine strategy for asthma and allied atopic diseases during early childhood.
Hsu et al. (1996) Nat Med 2(5):540-4—Immunoprophylaxis of allergen-induced immunoglobulin E synthesis and airway hyperresponsiveness in vivo by genetic immunization.
Iho et al. (1999) J Immunol 163(7):3642-52—Oligodeoxynucleotides Containing Palindrome Sequences with Internal 5'-CpG-3' Act Directly on Human NK and Activated T Cells to Induce IFN-$\gamma$ Production In Vitro.
Jiang et al. (1999) Vaccine 17(7-8):1005-13—Heterotypic protection from rotavirus infection in mice vaccinated with virus-like particles.
Jiang et al. (1999) Hum Gene Ther 10(16):2627-36—A Genetically Engineered Spleen Necrosis Virus-Derived Vector That Displays the HIV Type 1 Glycoprotein 120 Envelope Peptide.
Kataoka et al. (1992) Jpn J Cancer Res 83(3):244-7—Antitumor Activity of Synthetic Oligonucleotides with Sequences from cDNA Encoding Proteins of *Mycobacterium bovis* BCG.
Kerkmann (May 2003) J Immunol 170(9):4464-74—Activation with CpG-A and CpG-B Oligonucleotides Reveals Two Distinct Regulatory Pathways of Type I IFN Synthesis in Human Plasmacytoid Dendritic Cells.
Kline et al. (1996) J. Invest Med 44(7):380A—Cpg Motif Oligonucleotides are Effective in Prevention of Eosinophilic Inflammation in a Murine Model of Asthma.
Kline et al. (1998) J Immunol 160(6):2555-9—Modulation of Airway Inflammation by CpG Oligodeoxynucleotides in a Murine Model of Asthma.
Kline et al. (Feb. 2002) Am J Physiol Lung Cell Mol Physiol 283(1):L170-9—Treatment of established asthma in a murine model using CpG oligodeoxynucleotides.
Klinman (Apr. 2004) Nat Rev Immunol 4(4):249-58—Immunotherapeutic uses of CpG Oligodeoxynucleotides.
Klinman et al. (1996) Proc Natl Acad Sci U S A 93(7):2879-83—CpG motifs present in bacteria DNA rapidly induce lymphocytes to secrete interleukin 6, interleukin 12, and interferon $\gamma$.
Klinman et al. (Jun. 2000) Drug News Perspect 13(5):289-96—Immunotherapeutic Applications of CpG-Containing Oligodeoxynucleotides.
Klinman et al. (Jan. 2004) Vaccine 22(21-22):2881-6—CpG oligonucleotides improve the protective immune response induced by the anthrax vaccination of *Rhesus macaques*.
Krieg (1999) Biochim Biophys Acta 1489(1):107-16—Mechanisms and applications of immune stimulatory CpG oligodeoxynucleotides.
Krieg (Apr. 2002) Annu Rev Immunol 20:709-60—CpG Motifs in Bacterial DNA and Their Immune Effects.
Krieg and Davis (Feb. 2001) Curr Opin Mol Ther 3(1):15-24—Enhancing vaccines with immune stimulatory CpG DNA.
Krieg et al. (1995) Nature 374(6522):546-9—CpG motifs in bacterial DNA trigger direct B-cell activation.
Krieg et al. (1996) Antisense Nucleic Acid Drug Dev 6(2):133-9—Oligodeoxynucleotide Modifications Determine the Magnitude of B Cell Stimulation CpG Motifs.
Krug (Jul. 2001) Eur J Immunol 31(7):2154-63—Identification of CpG oligonucleotide sequences with high induction of IFN-$\alpha/\beta$ in plasmacytoid dendritic cells.
Krug et al. (Apr. 2003) J Immunol 170(7):3468-77—CpG-A Oligonucleotides Induce a Monocyte-Derived Dendritic Cell-Like Phenotype That Preferentially Activates CD8 T Cells.
Kuramoto et al. (1992) Jpn J Cancer Res 83(11):1128-31—Oligonucleotide Sequences Required for Natural Killer Cell Activation.
Kuramoto et al. (1992) Cancer Immunol Immunother 34(5):283-8—Induction of T-cell mediated immunity against MethA fibrosarcoma by intratumoral injections of a *Bacillus calmette-Guérin* nucleic acid fraction.
Lee et al. (Oct. 2000) J Immunol 165(7):3631-9—Effects of a Hexameric Deoxyriboguanosine Run Conjugation into CpG Oligodeoxynucleotides on Their Immunostimulatory Potentials.
Leibl et al. (1998) Vaccine 16(4):340-5—Adjuvant/carrier activity of inactivated tick-borne encephalitis virus.
Liljas et al. (1994) J Mol Biol 244(3):279-90—Crystal Structure of Bacteriophage fr Capsids at 3.5 Å Resolution.
Liu et al. (1998) Blood 92(10):3730-6—Immunostimulatory CpG Oligodeoxynucleotides Enhance the Immune Response to Vaccine Strategies Involving Granulocyte-Macrophage Colony-Stimulating Factor.
Lotz et al. (1987) J Rheumatol 14(1):42-5—Effects of Recombinant Human Interferons on Rheumatoid Arthritis B Lymphocytes Activated by Epstein-Barr Virus.
Luo et al. (1998) Virology 240(2):316-25—Induction of V3-Specific Cytotoxic T Lymphocyte Responses by HIV gag Particles Carrying Multiple Immunodominant V3 Epitopes of gp120.

(56) References Cited

OTHER PUBLICATIONS

Mahon (Jul. 2001) Curr Med Chem 8(9):1057-75—The Rational Design of Vaccine Adjuvants for Mucosal and Neonatal Immunization.
Martin (1993) AIDS 7(10):1315-23—Immunization of human HIV-seronegative volunteers with recombinant p17/p24:Ty virus-like particles elicits HIV-1 p24-specific cellular and humoral immune responses.
McIntyre et al. (1993) Antisense Res Dev 3(4):309-22—A Sense Phosphorothioate Oligonucleotide Directed to the Initiation Codon of Transcription Factor NF-$_\kappa$ B P65 Causes Sequence-Specific Immune Stimulation.
Merritt and Johnson (1965) J Immunol 940( ):416-22—Studies on the Adjuvant Action of Bacterial Endotoxins on Antibody Formation. Vi. Enhancement of Antibody Formation by Nucleic Acids.
Messina et al. (1991) J Immunol 147(6):1759-64—Stimulation of In Vitro Murine Lymphocyte Proliferation by Bacterial DNA.
Messina et al. (1993) Cell Immunol 147(1):148-57—The influence of DNA Structure on the in Vitro Stimulation of Murine Lymphocytes by Natural and Synthetic Polynucleotide Antigens.
Mojcik et al. (1993) Clin Immunol Immunopathol 67(2):130-6—Administration of a Phosphorothioate Oligonucleotide Antisense to Murine Endogenous Retroviral MCF Env Causes Immune Effects in Vivo in a Sequence-Specific Manner.
Nohria and Rubin (1994) Biotherapy 7(3-4):261-9—Cytokines as potential vaccine adjuvants.
Notka et al. (Sep. 2000) Vaccine 18:291-301—Accelerated clearance of SHIV in rhesus monkeys by virus-like particle vaccines is dependent on induction of neutralizing antibodies.
Oxenius et al. (1999) J Virol 73(5):4120-6—CpG-Containing Oligonucleotides are Efficient Adjuvants for Induction of Protective Antiviral Immune Responses with T-Cell Peptide Vaccines.
Pisetsky et al. (1993) Mol Biol Rep 18(3):217-21—Stimulation of in vitro proliferation of murine lymphocytes by synthetic oligodeoxynucleotides.
Pisetsky et al. (1994) Life Sci 54(2):101-7—Stimulation of Murine Lymphocyte Proliferation by a Phosphorothioate Oligonucleotide With Antisense Activity for Herpes Simplex Virus.
Raz (1997) Springer Semin Immunopathol 19(2):131-7—Introduction: gene vaccination, current concepts and future directions.
Raz et al. (1996) Proc Natl Acad Sci U S A 93(10):5141-5—Preferential induction of a Th$_1$ immune response and inhibition of specific IgE antibody formation by plasmid DNA immunization.
Saiki et al. (1988) Vaccine 6(3):238-44—Induction of tumoricidal macrophages and production of cytokines by synthetic muramyl dipeptide analogues.
Sato et al. (1996) Science 273(5273):352-4—Immunostimulatory DNA Sequences Necessary for Effective Intradermal Gene Immunization.
Schwarz et al. (Jun. 2003) Eur J Immunol 33(6):1465-70—Role of Toll-like receptors in costimulating cytotoxic T cell responses.
Siegal et al. (1999) Science 284(5421):1835-7—The nature of the Principal Type 1 Interferon-Producing Cells in Human Blood.
Takauji et al. (Nov. 2002) J Leukoc Biol 72(5):1011-9—CpG-DNA-induced IFN-α production involves p38 MAPK-dependent STAT1 phosphorylation in human plasmacytoid dendritic cell precursors.
Tars et al. (1997) J Mol Biol 271(5):759-73—The Crystal Structure of Bacteriophage GA and a Comparison of Bacteriophages Belonging to the Major Groups of *Escherichia coli* Leviviruses.
Torrence (1981) Methods Enzymol 78(Pt A):326-31—Preparation of a synthetic Polynucleotide Interferon Inducer.
Uhlmann and Vollmer (Mar. 2003) Curr Opin Drug Discov Devel 6(2):204-17—Recent advances in the development of immunostimulatory oligonucleotides.
van Ojik et al. (1999) pp. 157-158—Phase I/II study with CpG 7909 as adjuvant to vaccination with MAGE-3 protein in patients with MAGE-3 positive tumors.
Verthelyi et al. (Feb. 2001) J Immunol 166(4):2372-7—Human Peripheral Blood Cells Differentially Recognize and Respond to Two Distinct CPG Motifs.
Verthelyi et al. (Apr. 2004) AIDS 18(7):1003-8—CpG oligodeoxynucleotides improve the response to hepatitis B immunization in healthy and SIV-infected *Rhesus macaques*.
Vrtala et al. (1998) J Immunol 160(12):6137-44—Immunization with Purified Natural and Recombinant Allergens Induces Mouse Igg1 Antibodies That Recognize Similar Epitopes as Human Ige and Inhibit the Human Ige-Allergen Interaction and Allergen-Induced Basophil Derangulation.
Weiner (2000) pp. 1-9—Declaration in support of U.S. Appl. No. 09/286,098.
Weiner et al. (1997) Proc Natl Acad Sci U S A 94(20):10833-7—Immunostimulatory oligodeoxynucleotides containing the CpG motif are effective as immune adjuvants in tumor antigen immunization.
Weyermann et al. (Dec. 2004) J Control Release 100(3):411-23—Comparison of antisense oligonucleotide drug delivery systems.
Yamamoto et al. (1992) J Immunol 148(12):4072-6—Unique Palindromic Sequences in Synthetic Oligonucleotides Are Required to Induce IFN [Correction of INF] and Augment IFN-Mediated [Correction of INF] Natural Killer Activity.
Yamamoto et al. (1994) Antisense Res Dev 4(2):119-22—Ability of Oligonucleotides with Certain Palindromes to Induce Interferon Production and Augment Natural Killer Cell Activity Is Associated with Their Base Length.
Yamamoto et al. (1994) Jpn J Cancer Res 85(8):775-9—Synthetic Oligonucleotides with Certain Palindromes Stimulate Interferon Production of Human Peripheral Blood Lymphocytes in Vitro.
Yamamoto (1994) Microbiol Immunol 38(10):831-6—Lipofection of Synthetic Oligodeoxyribonucleotide Having a Palindromic Sequence of AACGTT to Murine Splenocytes Enhances Interferon Production and Natural Killer Activity.
Yamamoto et al. (Jan. 2000) Springer Semin Immunopathol 22(1-2):11-9—The discovery of immunostimulatory DNA sequence.
Yu et al. (Sep. 2002) Biochem Biophys Res Commun 297(1):83-90—Potent CpG oligonucleotides containing phosphodiester linkages: in vitro and in vivo immunostimulatory properties.
Zlotnick et al. (Nov. 2000) Virology 277(2):450-6—Mechanism of Capsid Assembly for an Icosahedral Plant Virus.
U.S. Appl. No. 60/156,147, filed Sep. 27, 1999.
Brazolot Millan, C., et al., "CpG DNA can induce strong Th1 humoral and cell-mediated immune responses against hepatitis B surface antigen in young mice," *Proc. Natl. Acad. Sci. USA* 95:15553-15558, National Academy of Sciences, US (1998).
Chackerian, B., et al., "Conjugation of a self-antigen to pappillomavirus-like particles allows for efficient induction of protective autoantibodies," *J. Clin. Invest.* 108:415-423, The American Society for Clinical Investigation, US (Aug. 2001).
Chu, R.S., et al., "CpG oligodeoxynucleotides act as adjuvants that switch on T helper 1 (Th1) Immunity," *J. Exp. Med.* 186:1623-1631, The Rockefeller University Press, US (1997).
Davis, H.L., et al. "CpG DNA is a potent enhancer of specific immunity in mice immunized with recombinant hepatitis B surface antigen," *J. Immunol.* 160:870-876, The American Assoc. of Immunologists, US (1998).
Goldmann, C., et al., "Molecular cloning and expression of major structural protein VP1 of the human polyomavirus JC virus: formation of virus-like particles useful for immunological and therapeutic studies," *J. Virol.* 73:4465-4469, American Society for Microbiology, US (1999).
Goldmann, C., et al., "Packaging of small molecules into VP1-virus-like particles of the human polyomavirus JC virus," *J. Virol. Methods* 90:85-90, Elsevier Science B.V., Netherlands (Oct. 2000).
Hill, A.V.S., et al., "DNA-based vaccines for malaria: a heterologous prime-boost immunisation strategy," (Proceedings of a conference titled "Development and clinical progress of DNA vaccines," held at the Paul-Ehrlich-Institut, Langen, Germany, Oct. 6-8, 1999) *Dev. Biol.* (Basel) 104:171-179, Karger, Switzerland (Aug. 2000).
Horner, A.A., et al., "Immunostimulatory DNA is a potent mucosal adjuvant," *Cell. Immunol.* 190:77-82, Academic Press, US (1998).
Kalams, S.A. and Walker, B.D., "The critical need for CD4 help in maintaining effective cytotoxic T lymphocyte responses," *J. Exp. Med.* 188:2199-2204, The Rockefeller University Press, US (1998).

(56) References Cited

OTHER PUBLICATIONS

Klenerman, P. and Zinkernagel, R.M., "Original antigenic sin impairs cytotoxic T lymphocyte responses to viruses bearing variant epitopes," *Nature* 394:482-485, Macmillan Publishers Ltd., UK (1998).

Klinman, D.M., "Therapeutic applications of CpG-containing oligodeoxynucleotides," *Antisense & Nucleic Acid Drug Dev.* 8:181-184, Mary Ann Liebert, Inc., US (1998).

Klinman, D M , et al., "CpG motifs as immune adjuvants," *Vaccine* 17:19-25, Elsevier Science Ltd., Netherlands (1999).

Krieg, A.M., "Direct immunologic activities of CpG DNA and implications for gene therapy," *J. Gene Med.* 1:56-63, John Wiley & Sons, Ltd., UK (1999).

Krieg, A.M., et al., "The role of CpG dinucleotides in DNA vaccines," *Trends Microbiol.* 6:23-27, Elsevier Science Ltd., Netherlands (1998).

Lenz, P., et al., "Papillomavirus-like particles induce acute activation of dendritic cells," *J. Immunol.* 166:5346-5355, The American Assoc. of Immunologists, US (May 2001).

McCluskie, M.J. and Davis, H.L., "Cutting edge: CpG DNA is a potent enhancer of systemic and mucosal immune responses against hepatitis B surface antigen with intranasal administration to mice," *J. Immunol.* 166:4463-4466, The American Assoc. of Immunologists, US (1998).

McCluskie, M.J. and Davis, H.L., "Novel strategies using DNA for the induction of mucosal immunity," *Crit. Rev. in Immunol.* 19:303-329, Begell House, Inc., US (1999).

Roman, M., et al., "Immunostimulatory DNA sequences function as T helper-1-promoting adjuvants," *Nat. Med.* 3:849-854, Nature Publishing Group, UK (1997).

Scott, D., et al., "Immunogenicity of biotinylated hapten-avidin complexes," *Mol. Immunol.* 21:1055-1060, Pergamon Press Ltd., US (1984).

Sedlik, C., et al., "Recombinant parvovirus-like particles as an antigen carrier: a novel nonreplicative exogenous antigen to elicit protective antiviral cytotoxic T cells," *Proc. Natl. Acad. Sci. USA* 94:7503-7508, National Academy of Sciences, US (1997).

Stacey, K.J. and Blackwell, J.M., "Immunostimulatory DNA as an adjuvant in vaccination against *Leishmania major*," *Infect. Immun.* 67:3719-3726, American Society for Microbiology, US (1999).

Wagner, R., et al., "Construction, expression, and immunogenicity of chimeric HIV-1 virus-like particles," *Virology* 220:128-140, Academic Press, Inc., US (1996).

Patent Abstract of Japan, English language Abstract of Japanese Patent Publication No. 2001-151698 A, published Jun. 5, 2001.

Co-pending, U.S. Appl. No. 13/038,272, inventors Bachmann, M.F., et al., filed Mar. 1, 2011 (Not Published).

Attwood, T. K., "The Babel of Bioinformatics," *Science* 290(5491):471-473, American Association for the Advancement of Science, United States (2000).

Baker, D., and Sali, A., "Protein Structure Predication and Structural Genomics," *Science* 294(5540):93-96, American Association for the Advancement of Science, United States (2001).

Hoffmann, T. K., et al., "T cells specific for HPV16 E7 epitopes in patients with squamous cell carcinoma of the oropharynx," *Int. J. Cancer* 118(8):1984-1991, Wiley-Liss, Inc., United States (2006).

Powell, A. T., et al., "Studies on spin labeled ribonucleic acids encapsulated by viral proteins," *Nucleic Acids Research* 5(11):3977-3992, Information Retrieval Limited, United Kingdom (1978).

Singh, M., and O'Hagan, D., "Advances in vaccine adjuvants," *Nature Biotechnology* 17:1075-1081, Nature America Inc., United States (1999).

Storni, T., et al., "Nonmethylated CG Motifs Packaged into Virus-Like Particles Induce Protective Cytotoxic T Cell Responses in the Absence of Systemic Side Effects," *The Journal of Immunology* 172(3):1777-1785, The American Association of Immunologists, United States (2004).

\* cited by examiner

5'   TCCATGACGTTCCTGAATAAT   3'

Fig.1A 1    atggacattg accctataa agaatttgga gctactgtgg agttactctc gttttgcct tctgacttct ttccttccgt cagagatctc ctagacaccg
     M  D  I  D  P  Y  K  E  F  G  A  T  V  E  L  L  S  F  L  P  S  D  F  F  P  S  V  R  D  L  L  D  T 101  cctcagctct gtatcgagaa gccttagagt ctcctgagca ttgctcacct caccatactg agccattctc tgctggggg aattgatgac
     A  S  A  L  Y  R  E  A  L  E  S  P  E  H  C  S  P  H  H  T  A  L  R  Q  A  I  L  C  W  G  E  L  M 201  tctagctacc tggtgggta ataatttgga agatccagca tccaggatc tagtagtcaa ttatgttaat actaacatgg gtttaaagat caggcaacta
     T  L  A  T  W  V  G  N  N  L  E  D  P  A  S  R  D  L  V  V  N  Y  V  N  T  N  M  G  L  K  I  R  Q  L 301  ttgtggtttc atatatcttg ccttactttt ggaagagaga ctgtacttga atatttggtc tctttcgag tgtggattcg gaggcagtc cctagaagac cctagagaga cccagagaaga
     L  W  F  H  I  S  C  L  T  F  G  R  E  T  V  L  E  Y  L  V  S  F  G  V  W  I  R  T  P  P  A  Y  R 401  caccaaatgc ccctatctta tcaacacttc cgaaactac tgttgttaga cgacggacc gaggcagtc cctagaaga agaactccct cgcctgcag
     P  P  N  A  P  I  L  S  T  L  P  E  T  T  V  V  R  R  R  D  R  G  R  S  P  R  R  R  T  P  S  P  R 501  acgcagatct caatgccgc gtcgagaag atctccaatct cggaatctc aatgtcttct cggaaatctc aatgtcttct gtttacaact tgctaccat gtaa
     R  R  R  S  Q  S  P  R  R  R  R  R  S  Q  S  R  E  S  Q  C  L  L  K  A  V  Y  N  F  A  T  M  -

Fig.1B amino acid sequence of the BKV AS VP1 protein (GI:332779)

MAPTKRKGECPGAAPKKPKEPVQVPKLLIKGGVEVLEVKTGVDAIT
EVECFLNPEMGDPDDNLRGYSQHLSAENAFESDSPDRKMLPCYSTA
RIPLPNLNEDLTCGNLLMWEAVTVKTEVIGITSMLNLHAGSQKVHE
NGGGKPVQGSNFHFFAVGGDPLEMQGVLMNYRTKYPQGTITPKNPT
AQSQVMNTDHKAYLDKNNAYPVECWIPDPSRNENTRYFGTYTGGEN
VPPVLHVTNTATTVLLDEQGVGPLCKADSLYVSAADICGLFTNSSG
TQQWRGLARYFKIRLRKRSVKNPYPISFLLSDLINRRTQKVDGQPM
YGMESQVEEVRVFDGTEQLPGDPDMIRYIDRQGQLQTKMV

Fig.10 nucleic acid sequence of the 246 bp DNA fragment

```
  1 GGCGGTGGTG TCAGATCTAC AATGATCGTC ATCACCTTGG TGATGCTGAA
 51 GAAGAAACAG TACACATCCA TTCATCATGG TGTGGTGGAG GTTGACGCCG
101 CTGTCACCCC AGAGGAGCGC CACCTGTCCA AGATGCAGCA GAACGGCTAC
151 GAAAATCCAA CCTACAAGTT CTTTGAGCAG ATGCAGAACG CTAGCTATCC
201 ATACGATGTC CCTGATTACG CCTAACGCGA ATTCGCCAGC ACAGTG
```

Fig.11

| OD 50% titer | BKV | BKV plus 0.3 nmol CpG(pt) | BKV plus 20 nmol CpG(pt) | BKV / 0.3 nmol CpG(pt) |
|---|---|---|---|---|
| IgG1 | 1015 | 823 | <40 | 340 |
| Stdev | 470 | 412 | 0 | 241 |
| IgG2a | 1190 | 1142 | 4193 | 2596 |
| Stdev | 406 | 1219 | 1137 | 1232 |

Cy(CpG)20

CyCyCy

CyCpG

CyOpA

+ CyOpA

+ CyCpG$_{20}$OpA

+ CyCpG$_{20}$

+ CyCyCy

+ CpG$_{20}$OpA

+ tRNA

"intact" capsids
from *E.coli* w/o any nucleic acid recombinant reassembled

Fig. 49

SEQUENCE LISTING

```
<160> NUMBER OF SEQ ID NOS: 136

<210> SEQ ID NO 1
<211> LENGTH: 594
<212> TYPE: DNA
<213> ORGANISM: artificial sequence
<220> FEATURE:
<223> OTHER INFORMATION: chemically synthesized

<400> SEQUENCE: 1
atggacattg acccttataa agaatttgga gctactgtgg agttactctc gtttttgcct      60
tctgacttct ttccttccgt cagagatctc ctagacaccg cctcagctct gtatcgagaa     120
gccttagagt ctcctgagca ttgctcacct caccatactg cactcaggca agccattctc     180
tgctgggggg aattgatgac tctagctacc tgggtgggta ataatttgga agatccagca     240
tccagggatc tagtagtcaa ttatgttaat actaacatgg gtttaaagat caggcaacta     300
ttgtggtttc atatatcttg ccttactttt ggaagagaga ctgtacttga atatttggtc     360
```

```
tctttcggag tgtggattcg cactcctcca gcctatagac caccaaatgc ccctatctta    420
tcaacacttc cggaaactac tgttgttaga cgacgggacc gaggcaggtc ccctagaaga    480
agaactccct cgcctcgcag acgcagatct caatcgccgc gtcgcagaag atctcaatct    540
cgggaatctc aatgtcttct ccttaaagct gtttacaact tcgctaccat gtaa          594
```

<210> SEQ ID NO 2
<211> LENGTH: 197
<212> TYPE: PRT
<213> ORGANISM: artificial sequence
<220> FEATURE:
<223> OTHER INFORMATION: chemically synthesized

<400> SEQUENCE: 2

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys Leu Leu Leu Lys Ala Val Tyr
            180                 185                 190

Asn Phe Ala Thr Met
        195
```

<210> SEQ ID NO 3
<211> LENGTH: 362
<212> TYPE: PRT
<213> ORGANISM: Unknown
<220> FEATURE:
<223> OTHER INFORMATION: BK Polyomavirus capsid protein VP1

<400> SEQUENCE: 3

```
Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asp Asn Leu Arg
    50                  55                  60

Gly Tyr Ser Gln His Leu Ser Ala Glu Asn Ala Phe Glu Ser Asp Ser
```

```
                65                  70                  75                  80
Pro Asp Arg Lys Met Leu Pro Cys Tyr Ser Thr Ala Arg Ile Pro Leu
                    85                  90                  95

Pro Asn Leu Asn Glu Asp Leu Thr Cys Gly Asn Leu Leu Met Trp Glu
                100                 105                 110

Ala Val Thr Val Lys Thr Glu Val Ile Gly Ile Thr Ser Met Leu Asn
            115                 120                 125

Leu His Ala Gly Ser Gln Lys Val His Glu Asn Gly Gly Lys Pro
        130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
                180                 185                 190

Asp His Lys Ala Tyr Leu Asp Lys Asn Ala Tyr Pro Val Glu Cys
        195                 200                 205

Trp Ile Pro Asp Pro Ser Arg Asn Glu Asn Thr Arg Tyr Phe Gly Thr
        210                 215                 220

Tyr Thr Gly Gly Glu Asn Val Pro Pro Val Leu His Val Thr Asn Thr
225                 230                 235                 240

Ala Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
        260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
        290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
                340                 345                 350

Arg Gln Gly Gln Leu Gln Thr Lys Met Val
        355                 360

<210> SEQ ID NO 4
<211> LENGTH: 246
<212> TYPE: DNA
<213> ORGANISM: artificial sequence
<220> FEATURE:
<223> OTHER INFORMATION: chemically synthesized

<400> SEQUENCE: 4
ggcggtggtg tcagatctac aatgatcgtc atcaccttgg tgatgctgaa gaagaaacag      60
tacacatcca ttcatcatgg tgtggtggag gttgacgccg ctgtcacccc agaggagcgc     120
cacctgtcca agatgcagca gaacggctac gaaaatccaa cctacaagtt ctttgagcag     180
atgcagaacg ctagctatcc atacgatgtc cctgattacg cctaacgcga attcgccagc     240
acagtg                                                                246

<210> SEQ ID NO 5
<211> LENGTH: 57
<212> TYPE: DNA
```

```
-continued

<213> ORGANISM: Unknown
<220> FEATURE:
<223> OTHER INFORMATION: bacteriophage AP205

<400> SEQUENCE: 5
tctagaattt tctgcgcacc catcccgggt ggcgcccaaa gtgaggaaaa tcacatg     57

<210> SEQ ID NO 6
<211> LENGTH: 35
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (21)..(25)
<223> OTHER INFORMATION: Shine Delgarno Sequence

<400> SEQUENCE: 6
tctagattaa cccaacgcgt aggagtcagg ccatg                              35

<210> SEQ ID NO 7
<211> LENGTH: 10
<212> TYPE: PRT
<213> ORGANISM: artificial sequence
<220> FEATURE:
<223> OTHER INFORMATION: chemically synthesized

<400> SEQUENCE: 7

Cys Gly Asp Lys Thr His Thr Ser Pro Pro
1               5                   10

<210> SEQ ID NO 8
<211> LENGTH: 10
<212> TYPE: PRT
<213> ORGANISM: artificial sequence
<220> FEATURE:
<223> OTHER INFORMATION: chemically synthesized

<400> SEQUENCE: 8

Asp Lys Thr His Thr Ser Pro Pro Cys Gly
1               5                   10

<210> SEQ ID NO 9
<211> LENGTH: 17
<212> TYPE: PRT
<213> ORGANISM: artificial sequence
<220> FEATURE:
<223> OTHER INFORMATION: chemically synthesized

<400> SEQUENCE: 9

Cys Gly Gly Pro Lys Pro Ser Thr Pro Pro Gly Ser Ser Gly Gly Ala
1               5                   10                  15
Pro

<210> SEQ ID NO 10
<211> LENGTH: 132
<212> TYPE: PRT
<213> ORGANISM: Unknown
<220> FEATURE:
<223> OTHER INFORMATION: Bacteriophage Q-beta

<400> SEQUENCE: 10

Ala Lys Leu Glu Thr Val Thr Leu Gly Asn Ile Gly Lys Asp Gly Lys
1               5                   10                  15
Gln Thr Leu Val Leu Asn Pro Arg Gly Val Asn Pro Thr Asn Gly Val
                20                  25                  30
```

```
Ala Ser Leu Ser Gln Ala Gly Ala Val Pro Ala Leu Glu Lys Arg Val
         35                  40                  45

Thr Val Ser Val Ser Gln Pro Ser Arg Asn Arg Lys Asn Tyr Lys Val
 50                  55                  60

Gln Val Lys Ile Gln Asn Pro Thr Ala Cys Thr Ala Asn Gly Ser Cys
 65                  70                  75                  80

Asp Pro Ser Val Thr Arg Gln Ala Tyr Ala Asp Val Thr Phe Ser Phe
                 85                  90                  95

Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
            115                 120                 125

Asn Pro Ala Tyr
            130

<210> SEQ ID NO 11
<211> LENGTH: 328
<212> TYPE: PRT
<213> ORGANISM: Unknown
<220> FEATURE:
<223> OTHER INFORMATION: Bacteriophage Q-beta

<400> SEQUENCE: 11

Met Ala Lys Leu Glu Thr Val Thr Leu Gly Asn Ile Gly Lys Asp Gly
 1               5                  10                  15

Lys Gln Thr Leu Val Leu Asn Pro Arg Gly Val Asn Pro Thr Asn Gly
             20                  25                  30

Val Ala Ser Leu Ser Gln Ala Gly Ala Val Pro Ala Leu Glu Lys Arg
         35                  40                  45

Val Thr Val Ser Val Ser Gln Pro Ser Arg Asn Arg Lys Asn Tyr Lys
     50                  55                  60

Val Gln Val Lys Ile Gln Asn Pro Thr Ala Cys Thr Ala Asn Gly Ser
 65                  70                  75                  80

Cys Asp Pro Ser Val Thr Arg Gln Ala Tyr Ala Asp Val Thr Phe Ser
                 85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
            115                 120                 125

Leu Asn Pro Ala Tyr Trp Leu Leu Ile Ala Gly Gly Gly Ser Gly Ser
            130                 135                 140

Lys Pro Asp Pro Val Ile Pro Asp Pro Ile Asp Pro Pro Gly
145                 150                 155                 160

Thr Gly Lys Tyr Thr Cys Pro Phe Ala Ile Trp Ser Leu Glu Glu Val
                165                 170                 175

Tyr Glu Pro Pro Thr Lys Asn Arg Pro Trp Pro Ile Tyr Asn Ala Val
                180                 185                 190

Glu Leu Gln Pro Arg Glu Phe Asp Val Ala Leu Lys Asp Leu Leu Gly
            195                 200                 205

Asn Thr Lys Trp Arg Asp Trp Asp Ser Arg Leu Ser Tyr Thr Thr Phe
            210                 215                 220

Arg Gly Cys Arg Gly Asn Gly Tyr Ile Asp Leu Asp Ala Thr Tyr Leu
225                 230                 235                 240

Ala Thr Asp Gln Ala Met Arg Asp Gln Lys Tyr Asp Ile Arg Glu Gly
                245                 250                 255
```

```
Lys Lys Pro Gly Ala Phe Gly Asn Ile Glu Arg Phe Ile Tyr Leu Lys
            260                 265                 270

Ser Ile Asn Ala Tyr Cys Ser Leu Ser Asp Ile Ala Ala Tyr His Ala
            275                 280                 285

Asp Gly Val Ile Val Gly Phe Trp Arg Asp Pro Ser Ser Gly Gly Ala
            290                 295                 300

Ile Pro Phe Asp Phe Thr Lys Phe Asp Lys Thr Lys Cys Pro Ile Gln
305                 310                 315                 320

Ala Val Ile Val Val Pro Arg Ala
                325

<210> SEQ ID NO 12
<211> LENGTH: 129
<212> TYPE: PRT
<213> ORGANISM: Unknown
<220> FEATURE:
<223> OTHER INFORMATION: Bacteriophage R17

<400> SEQUENCE: 12

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 13
<211> LENGTH: 130
<212> TYPE: PRT
<213> ORGANISM: Unknown
<220> FEATURE:
<223> OTHER INFORMATION: Bacteriophage fr

<400> SEQUENCE: 13

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
```

```
                    100                 105                 110
Phe Lys Thr Gly Asn Pro Ile Ala Thr Ala Ile Ala Ala Asn Ser Gly
        115                 120                 125

Ile Tyr
    130

<210> SEQ ID NO 14
<211> LENGTH: 130
<212> TYPE: PRT
<213> ORGANISM: Unknown
<220> FEATURE:
<223> OTHER INFORMATION: Bacteriophage GA

<400> SEQUENCE: 14

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 15
<211> LENGTH: 132
<212> TYPE: PRT
<213> ORGANISM: Unknown
<220> FEATURE:
<223> OTHER INFORMATION: Bacteriophage SP

<400> SEQUENCE: 15

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
```

130

<210> SEQ ID NO 16
<211> LENGTH: 329
<212> TYPE: PRT
<213> ORGANISM: Unknown
<220> FEATURE:
<223> OTHER INFORMATION: Bacteriophage SP

<400> SEQUENCE: 16

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
    50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Leu Val Ala Ser Ser Gly Gly Gly Asp
    130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Asp Tyr Asp
    210                 215                 220

Ile Ala Asn Arg Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
                325

<210> SEQ ID NO 17
<211> LENGTH: 130
<212> TYPE: PRT
<213> ORGANISM: Unknown

```
<220> FEATURE:
<223> OTHER INFORMATION: Bacteriophage MS2

<400> SEQUENCE: 17

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 18
<211> LENGTH: 133
<212> TYPE: PRT
<213> ORGANISM: Unknown
<220> FEATURE:
<223> OTHER INFORMATION: Bacteriophage M11

<400> SEQUENCE: 18

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
                20                  25                  30

Val Ala Ala Leu Ser Glu Ala Gly Ala Val Pro Ala Leu Glu Lys Arg
            35                  40                  45

Val Thr Ile Ser Val Ser Gln Pro Ser Arg Asn Arg Lys Asn Tyr Lys
50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125

Leu Asn Pro Ala Tyr
    130

<210> SEQ ID NO 19
<211> LENGTH: 133
<212> TYPE: PRT
<213> ORGANISM: Unknown
<220> FEATURE:
<223> OTHER INFORMATION: Bacteriophage MX1

<400> SEQUENCE: 19

Met Ala Lys Leu Gln Ala Ile Thr Leu Ser Gly Ile Gly Lys Asn Gly
```

```
            1               5              10              15
Asp Val Thr Leu Asn Leu Asn Pro Arg Gly Val Asn Pro Thr Asn Gly
                20              25              30

Val Ala Ala Leu Ser Glu Ala Gly Ala Val Pro Ala Leu Glu Lys Arg
                35              40              45

Val Thr Ile Ser Val Ser Gln Pro Ser Arg Asn Arg Lys Asn Tyr Lys
                50              55              60

Val Gln Val Lys Ile Gln Asn Pro Thr Ser Cys Thr Ala Ser Gly Thr
 65              70              75              80

Cys Asp Pro Ser Val Thr Arg Ser Ala Tyr Ala Asp Val Thr Phe Ser
                85              90              95

Phe Thr Gln Tyr Ser Thr Asp Glu Glu Arg Ala Leu Val Arg Thr Glu
                100             105             110

Leu Lys Ala Leu Leu Ala Asp Pro Met Leu Ile Asp Ala Ile Asp Asn
                115             120             125

Leu Asn Pro Ala Tyr
                130

<210> SEQ ID NO 20
<211> LENGTH: 330
<212> TYPE: PRT
<213> ORGANISM: Unknown
<220> FEATURE:
<223> OTHER INFORMATION: Bacteriophage NL95

<400> SEQUENCE: 20

Met Ala Lys Leu Asn Lys Val Thr Leu Thr Gly Ile Gly Lys Ala Gly
 1               5              10              15

Asn Gln Thr Leu Thr Leu Thr Pro Arg Gly Val Asn Pro Thr Asn Gly
                20              25              30

Val Ala Ser Leu Ser Glu Ala Gly Ala Val Pro Ala Leu Glu Lys Arg
                35              40              45

Val Thr Val Ser Val Ala Gln Pro Ser Arg Asn Arg Lys Asn Tyr Lys
                50              55              60

Val Gln Ile Lys Leu Gln Asn Pro Thr Ala Cys Thr Lys Asp Ala Cys
 65              70              75              80

Asp Pro Ser Val Thr Arg Ser Gly Ser Arg Asp Val Thr Leu Ser Phe
                85              90              95

Thr Ser Tyr Ser Thr Glu Arg Glu Arg Ala Leu Ile Arg Thr Glu Leu
                100             105             110

Ala Ala Leu Leu Lys Asp Asp Leu Ile Val Asp Ala Ile Asp Asn Leu
                115             120             125

Asn Pro Ala Tyr Trp Ala Ala Leu Leu Ala Ala Ser Pro Gly Gly Gly
                130             135             140

Asn Asn Pro Tyr Pro Gly Val Pro Asp Ser Pro Asn Val Lys Pro Pro
145             150             155             160

Gly Gly Thr Gly Thr Tyr Arg Cys Pro Phe Ala Cys Tyr Arg Arg Gly
                165             170             175

Glu Leu Ile Thr Glu Ala Lys Asp Gly Ala Cys Ala Leu Tyr Ala Cys
                180             185             190

Gly Ser Glu Ala Leu Val Glu Phe Glu Tyr Ala Leu Glu Asp Phe Leu
                195             200             205

Gly Asn Glu Phe Trp Arg Asn Trp Asp Gly Arg Leu Ser Lys Tyr Asp
                210             215             220

Ile Glu Thr His Arg Arg Cys Arg Gly Asn Gly Tyr Val Asp Leu Asp
225             230             235             240
```

```
Ala Ser Val Met Gln Ser Asp Glu Tyr Val Leu Ser Gly Ala Tyr Asp
            245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
            275                 280                 285

Tyr Arg Ser Tyr Gly Met Val Ile Gly Phe Trp Thr Asp Ser Lys Ser
            290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
            325                 330

<210> SEQ ID NO 21
<211> LENGTH: 129
<212> TYPE: PRT
<213> ORGANISM: Unknown
<220> FEATURE:
<223> OTHER INFORMATION: Bacteriophage f2

<400> SEQUENCE: 21

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 22
<211> LENGTH: 128
<212> TYPE: PRT
<213> ORGANISM: Unknown
<220> FEATURE:
<223> OTHER INFORMATION: Bacteriophage PP7

<400> SEQUENCE: 22

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80
```

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 23
<211> LENGTH: 132
<212> TYPE: PRT
<213> ORGANISM: Unknown
<220> FEATURE:
<223> OTHER INFORMATION: Bacteriophage Q-beta

<400> SEQUENCE: 23

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 24
<211> LENGTH: 132
<212> TYPE: PRT
<213> ORGANISM: Unknown
<220> FEATURE:
<223> OTHER INFORMATION: Bacteriophage Q-beta

<400> SEQUENCE: 24

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 25
<211> LENGTH: 132
<212> TYPE: PRT
<213> ORGANISM: Unknown
<220> FEATURE:
<223> OTHER INFORMATION: Bacteriophage Q-beta

<400> SEQUENCE: 25

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 26
<211> LENGTH: 132
<212> TYPE: PRT
<213> ORGANISM: Unknown
<220> FEATURE:
<223> OTHER INFORMATION: Bacteriophage Q-beta

<400> SEQUENCE: 26

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 27
<211> LENGTH: 132

```
<212> TYPE: PRT
<213> ORGANISM: Unknown
<220> FEATURE:
<223> OTHER INFORMATION: Bacteriophage Q-beta

<400> SEQUENCE: 27

Ala Arg Leu Glu Thr Val Thr Leu Gly Asn Ile Gly Lys Asp Gly
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
    130

<210> SEQ ID NO 28
<211> LENGTH: 184
<212> TYPE: PRT
<213> ORGANISM: Hepatitis B virus

<400> SEQUENCE: 28

Met Asp Ile Asp Pro Tyr Glu Phe Gly Ala Thr Val Glu Leu Leu Ser
1               5                   10                  15

Phe Leu Pro Ser Asp Phe Phe Pro Ser Val Arg Asp Leu Leu Asp Thr
            20                  25                  30

Ala Ser Ala Leu Tyr Arg Glu Ala Leu Glu Ser Pro Glu His Cys Ser
            35                  40                  45

Pro His His Thr Ala Leu Arg Gln Ala Ile Leu Cys Trp Gly Glu Leu
    50                  55                  60

Met Thr Leu Ala Thr Trp Val Gly Asn Asn Leu Glu Asp Pro Ala Ser
65                  70                  75                  80

Arg Asp Leu Val Val Asn Tyr Val Asn Thr Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
            115                 120                 125

Pro Ala Tyr Arg Pro Pro Asn Ala Pro Ile Leu Ser Thr Leu Pro Glu
    130                 135                 140

Thr Thr Val Val Arg Arg Arg Asp Arg Gly Arg Ser Pro Arg Arg Arg
145                 150                 155                 160

Thr Pro Ser Pro Arg Arg Arg Ser Gln Ser Pro Arg Arg Arg Arg
                165                 170                 175

Ser Gln Ser Arg Glu Ser Gln Cys
            180

<210> SEQ ID NO 29
```

```
<211> LENGTH: 183
<212> TYPE: PRT
<213> ORGANISM: Hepatitis B virus

<400> SEQUENCE: 29

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180

<210> SEQ ID NO 30
<211> LENGTH: 183
<212> TYPE: PRT
<213> ORGANISM: Hepatitis B virus

<400> SEQUENCE: 30

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Thr Asn Ala Pro Ile Leu Ser Thr Leu Pro
    130                 135                 140

Glu Thr Cys Val Ile Arg Arg Arg Gly Arg Ser Pro Arg Arg Arg Thr
145                 150                 155                 160
```

```
Pro Ser Pro Arg Arg Arg Ser Gln Ser Pro Arg Arg Arg Ser
                165                 170                 175

Gln Ser Arg Gly Ser Gln Cys
        180

<210> SEQ ID NO 31
<211> LENGTH: 212
<212> TYPE: PRT
<213> ORGANISM: Hepatitis B virus

<400> SEQUENCE: 31

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 32
<211> LENGTH: 212
<212> TYPE: PRT
<213> ORGANISM: Hepatitis B virus

<400> SEQUENCE: 32

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
```

```
                    85                  90                  95
Leu Ala Thr Trp Val Gly Gly Asn Leu Glu Asp Pro Ile Ser Arg Asp
                100                 105                 110

Leu Val Val Ser Tyr Val Asn Thr Asn Met Gly Leu Lys Phe Arg Gln
                115                 120                 125

Leu Leu Trp Phe His Ile Ser Cys Leu Thr Phe Gly Arg Glu Thr Val
                130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Arg
                195                 200                 205

Glu Ser Gln Cys
            210

<210> SEQ ID NO 33
<211> LENGTH: 183
<212> TYPE: PRT
<213> ORGANISM: Hepatitis B virus

<400> SEQUENCE: 33

Met Asp Ile Asp Pro Tyr Lys Glu Phe Gly Ala Thr Val Glu Leu Leu
1               5                   10                  15

Ser Phe Leu Pro Thr Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 34
<211> LENGTH: 212
<212> TYPE: PRT
<213> ORGANISM: Hepatitis B virus

<400> SEQUENCE: 34

Met Gln Leu Phe His Leu Cys Leu Ile Ile Ser Cys Ser Cys Pro Thr
1               5                   10                  15
```

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
            85                  90                  95

Leu Ala Thr Trp Val Gly Gly Asn Leu Glu Asp Pro Val Ser Arg Asp
        100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
        195                 200                 205

Glu Ser Gln Cys
    210

<210> SEQ ID NO 35
<211> LENGTH: 212
<212> TYPE: PRT
<213> ORGANISM: Hepatitis B virus

<400> SEQUENCE: 35

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
            85                  90                  95

Leu Ala Thr Trp Val Gly Gly Asn Leu Glu Asp Pro Val Ser Arg Asp
        100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

```
Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 36
<211> LENGTH: 212
<212> TYPE: PRT
<213> ORGANISM: Hepatitis B virus

<400> SEQUENCE: 36

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro Gln
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 37
<211> LENGTH: 212
<212> TYPE: PRT
<213> ORGANISM: Hepatitis B virus

<400> SEQUENCE: 37

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60
```

```
Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Lys Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
                195                 200                 205

Gly Ser Gln Cys
        210

<210> SEQ ID NO 38
<211> LENGTH: 183
<212> TYPE: PRT
<213> ORGANISM: Hepatitis B virus

<400> SEQUENCE: 38

Met Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
                 20                  25                  30

Thr Ala Ser Ala Leu Phe Arg Asp Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Gly Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Asp Thr Val Ile Glu Tyr Leu Val Ser Phe Gly Val Trp Ile Arg Thr
        115                 120                 125

Pro Pro Ala Tyr Arg Pro Ser Asn Ala Pro Ile Leu Ser Thr Leu Pro
130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 39
<211> LENGTH: 183
<212> TYPE: PRT
<213> ORGANISM: Hepatitis B virus
```

<400> SEQUENCE: 39

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Arg Ser
                165                 170                 175

Gln Ser Arg Glu Ser Gln Cys
            180
```

<210> SEQ ID NO 40
<211> LENGTH: 212
<212> TYPE: PRT
<213> ORGANISM: Hepatitis B virus

<400> SEQUENCE: 40

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg His Ala Ile Leu Cys Trp Gly Asp Leu Arg Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Tyr Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
```

```
            180                 185                 190
Arg Arg Arg Arg Ser Gln Ser Pro Arg Arg Arg Ser Gln Ser Arg
            195                 200                 205

Glu Ser Gln Cys
        210

<210> SEQ ID NO 41
<211> LENGTH: 212
<212> TYPE: PRT
<213> ORGANISM: Hepatitis B virus

<400> SEQUENCE: 41

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Phe Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Ala Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Gln Ala
145                 150                 155                 160

Tyr Arg Pro Pro Asn Ala Pro Ile Leu Ser Thr Leu Pro Glu Thr Cys
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 42
<211> LENGTH: 183
<212> TYPE: PRT
<213> ORGANISM: Artificial Sequence
<220> FEATURE:
<223> OTHER INFORMATION: chemically synthesized

<400> SEQUENCE: 42

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60
```

```
Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 43
<211> LENGTH: 212
<212> TYPE: PRT
<213> ORGANISM: Hepatitis B virus

<400> SEQUENCE: 43

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Ser
            85                  90                  95

Leu Ala Thr Trp Val Gly Val Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 44
<211> LENGTH: 183
<212> TYPE: PRT
<213> ORGANISM: Hepatitis B virus
```

<400> SEQUENCE: 44

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 45
<211> LENGTH: 183
<212> TYPE: PRT
<213> ORGANISM: Hepatitis B virus

<400> SEQUENCE: 45

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
```

<210> SEQ ID NO 46
<211> LENGTH: 183
<212> TYPE: PRT
<213> ORGANISM: Hepatitis B virus

<400> SEQUENCE: 46

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Ala Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Thr Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 47
<211> LENGTH: 212
<212> TYPE: PRT
<213> ORGANISM: Hepatitis B virus

<400> SEQUENCE: 47

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

```
Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
        195                 200                 205

Glu Ser Gln Cys
    210

<210> SEQ ID NO 48
<211> LENGTH: 212
<212> TYPE: PRT
<213> ORGANISM: Hepatitis B virus

<400> SEQUENCE: 48

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
        195                 200                 205

Glu Ser Gln Cys
    210

<210> SEQ ID NO 49
<211> LENGTH: 212
<212> TYPE: PRT
<213> ORGANISM: Hepatitis B virus

<400> SEQUENCE: 49

Met Gln Leu Phe His Leu Cys Leu Ile Ile Ser Cys Thr Cys Pro Thr
1               5                   10                  15

Val Gln Ala Ser Lys Leu Cys Leu Gly Trp Leu Trp Gly Met Asp Ile
            20                  25                  30
```

```
Asp Pro Tyr Lys Gln Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
                100                 105                 110

Leu Val Val Ser Tyr Val Asn Thr Asn Met Gly Leu Lys Phe Arg Gln
                115                 120                 125

Leu Leu Trp Phe His Ile Ser Cys Leu Thr Phe Gly Arg Glu Thr Val
        130                 135                 140

Ile Glu Tyr Leu Val Ala Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Arg
                195                 200                 205

Glu Ser Gln Cys
        210

<210> SEQ ID NO 50
<211> LENGTH: 212
<212> TYPE: PRT
<213> ORGANISM: Hepatitis B virus

<400> SEQUENCE: 50

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
                20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
 50                  55                  60

Ala Leu Tyr Arg Glu Ala Phe Glu Cys Ser Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Gly Asn Leu Glu Asp Pro Ile Ser Arg Asp
                100                 105                 110

Leu Val Val Ser Tyr Val Asn Thr Asn Met Gly Leu Lys Phe Arg Gln
                115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190
```

```
Arg Arg Arg Arg Ser Gln Ser Pro Arg Arg Arg Ser Gln Ser Arg
        195                 200                 205

Glu Ser Gln Cys
    210

<210> SEQ ID NO 51
<211> LENGTH: 212
<212> TYPE: PRT
<213> ORGANISM: Hepatitis B virus
<220> FEATURE:
<221> NAME/KEY: MISC_FEATURE
<222> LOCATION: (28)..(28)
<223> OTHER INFORMATION: Xaa can be any amino acid

<400> SEQUENCE: 51

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Xaa Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65              70                  75                  80

His Thr Ala Leu Arg Gln Ala Ile Leu Cys Trp Gly Asp Leu Ile Thr
            85                  90                  95

Leu Ser Thr Trp Val Gly Gly Asn Leu Glu Asp Pro Thr Ser Arg Asp
        100                 105                 110

Leu Val Val Ser Tyr Val Asn Thr Asn Met Gly Leu Lys Phe Arg Gln
    115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
            165                 170                 175

Val Val Arg Arg Arg Gly Arg Ser Pro Arg Arg Arg Thr Pro Ser Pro
        180                 185                 190

Arg Arg Arg Arg Ser Gln Ser Pro Arg Arg Arg Thr Gln Ser Arg
    195                 200                 205

Glu Ser Gln Cys
    210

<210> SEQ ID NO 52
<211> LENGTH: 212
<212> TYPE: PRT
<213> ORGANISM: Hepatitis B virus

<400> SEQUENCE: 52

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60
```

```
Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
            210

<210> SEQ ID NO 53
<211> LENGTH: 212
<212> TYPE: PRT
<213> ORGANISM: Hepatitis B virus

<400> SEQUENCE: 53

Met Gln Leu Phe His Leu Cys Leu Ile Ile Ser Cys Ser Cys Pro Thr
  1               5                  10                  15

Val Gln Ala Ser Lys Leu Cys Leu Gly Trp Leu Trp Gly Met Asp Ile
                 20                  25                  30

Asp Pro Tyr Lys Glu Phe Gly Ala Thr Val Glu Leu Leu Ser Phe Leu
             35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Cys Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
            210
```

<210> SEQ ID NO 54
<211> LENGTH: 212
<212> TYPE: PRT
<213> ORGANISM: Hepatitis B virus

<400> SEQUENCE: 54

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Pro Gln Cys
    210
```

<210> SEQ ID NO 55
<211> LENGTH: 212
<212> TYPE: PRT
<213> ORGANISM: Hepatitis B virus

<400> SEQUENCE: 55

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Ser Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
```

```
            115                 120                 125
Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
    210

<210> SEQ ID NO 56
<211> LENGTH: 212
<212> TYPE: PRT
<213> ORGANISM: Hepatitis B virus

<400> SEQUENCE: 56

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Leu Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
    210

<210> SEQ ID NO 57
<211> LENGTH: 212
<212> TYPE: PRT
<213> ORGANISM: Hepatitis B virus

<400> SEQUENCE: 57

Met Gln Leu Phe His Leu Cys Leu Ile Ile Ser Cys Ser Cys Pro Thr
1               5                   10                  15
```

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
            85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Lys Gln
            115                 120                 125

Leu Leu Trp Phe His Ile Ser Cys Leu Thr Phe Gly Arg Glu Thr Val
            130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
210

<210> SEQ ID NO 58
<211> LENGTH: 212
<212> TYPE: PRT
<213> ORGANISM: Hepatitis B virus

<400> SEQUENCE: 58

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
            85                  90                  95

Leu Ala Thr Trp Val Gly Thr Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
            130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

```
Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 59
<211> LENGTH: 183
<212> TYPE: PRT
<213> ORGANISM: Hepatitis B virus

<400> SEQUENCE: 59

Met Asp Ile Asp Pro Tyr Lys Glu Phe Gly Ala Ser Met Glu Leu Leu
1               5                   10                  15

Ser Phe Leu Pro Ser Asp Phe Tyr Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Thr Pro His His Thr Ala Leu Arg Gln Ala Ile Leu Cys Trp Gly Glu
    50                  55                  60

Leu Met Thr Leu Ala Thr Trp Val Gly Gly Asn Leu Gln Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Val Ser Cys Leu Thr Phe Gly Arg
            100                 105                 110

Glu Thr Val Val Glu Tyr Leu Val Ser Phe Gly Val Trp Ile Arg Thr
        115                 120                 125

Pro Gln Ala Tyr Arg Pro Pro Asn Ala Pro Ile Leu Ser Thr Leu Pro
    130                 135                 140

Glu Thr Cys Val Val Arg Arg Gly Arg Ser Pro Arg Arg Arg Thr
145                 150                 155                 160

Pro Ser Pro Arg Arg Arg Ser Gln Ser Pro Arg Arg Arg Arg Ser
                165                 170                 175

Gln Ser Arg Glu Ser Gln Cys
            180

<210> SEQ ID NO 60
<211> LENGTH: 183
<212> TYPE: PRT
<213> ORGANISM: Hepatitis B virus

<400> SEQUENCE: 60

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg His Val Phe Leu Cys Trp Gly Asp
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95
```

```
Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 61
<211> LENGTH: 212
<212> TYPE: PRT
<213> ORGANISM: Hepatitis B virus

<400> SEQUENCE: 61

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Thr Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 62
<211> LENGTH: 212
<212> TYPE: PRT
<213> ORGANISM: Hepatitis B virus

<400> SEQUENCE: 62

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
```

```
                    20                  25                  30
Asp Pro Tyr Lys Glu Phe Gly Ala Thr Val Glu Leu Leu Ser Phe Leu
            35                  40                  45

Pro Ser Asp Phe Phe Pro Ser Val Arg Asp Leu Leu Asp Thr Ala Ser
        50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Ile Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 63
<211> LENGTH: 183
<212> TYPE: PRT
<213> ORGANISM: Hepatitis B virus

<400> SEQUENCE: 63

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Val
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Ala Arg Arg Arg Ser Gln Ser Pro Arg Arg Arg Arg Ser
                165                 170                 175

Gln Ser Arg Glu Ser Gln Cys
```

<210> SEQ ID NO 64
<211> LENGTH: 213
<212> TYPE: PRT
<213> ORGANISM: Hepatitis B virus

<400> SEQUENCE: 64

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Asn
                85                  90                  95

Leu Ala Thr Trp Val Gly Gly Asn Leu Glu Asp Pro Val Ser Arg Asp
            100                 105                 110

Leu Val Val Gly Tyr Val Asn Thr Thr Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Pro Arg Arg Arg Arg Ser Gln Ser Pro Arg Arg Arg Ser Gln Ser
        195                 200                 205

Arg Glu Ser Gln Cys
    210

<210> SEQ ID NO 65
<211> LENGTH: 183
<212> TYPE: PRT
<213> ORGANISM: Hepatitis B virus

<400> SEQUENCE: 65

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

```
Glu Thr Val Ile Glu Tyr Leu Val Ser Phe Gly Val Trp Ile Arg Thr
            115                 120                 125
Pro Pro Ala Tyr Arg Pro Pro Asn Ala Pro Ile Leu Ser Thr Leu Pro
        130                 135                 140
Glu Thr Thr Val Val Arg Arg Arg Gly Arg Thr Pro Arg Arg Arg Thr
145                 150                 155                 160
Pro Ser Pro Arg Arg Arg Arg Ser Gln Ser Pro Arg Arg Arg Arg Ser
                165                 170                 175
Gln Ser Arg Glu Ser Gln Cys
            180

<210> SEQ ID NO 66
<211> LENGTH: 212
<212> TYPE: PRT
<213> ORGANISM: Hepatitis B virus

<400> SEQUENCE: 66

Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
            20                  25                  30
Asp Pro Tyr Lys Glu Phe Gly Ala Thr Val Glu Leu Leu Ser Phe Leu
        35                  40                  45
Pro Ser Asp Phe Phe Pro Ser Val Arg Ala Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg Gln Ala Ile Leu Cys Trp Gly Glu Leu Met Thr
                85                  90                  95
Leu Ala Thr Trp Val Gly Val Asn Leu Glu Asp Pro Ala Ser Arg Asp
            100                 105                 110
Leu Val Val Ser Tyr Val Asn Thr Asn Met Gly Leu Lys Phe Arg Gln
        115                 120                 125
Ile Leu Trp Phe His Ile Ser Cys Leu Thr Phe Gly Arg Glu Thr Val
    130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Ser Gln Ser Arg
        195                 200                 205
Glu Ser Gln Cys
    210

<210> SEQ ID NO 67
<211> LENGTH: 212
<212> TYPE: PRT
<213> ORGANISM: Hepatitis B virus

<400> SEQUENCE: 67

Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
            20                  25                  30
```

```
Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Thr
                 85                  90                  95

Leu Ala Thr Trp Val Gly Val Asn Leu Glu Asp Pro Ala Thr Arg Asp
                100                 105                 110

Leu Val Val Ser Tyr Val Asn Thr Asn Val Gly Leu Lys Phe Arg Gln
            115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
        210

<210> SEQ ID NO 68
<211> LENGTH: 212
<212> TYPE: PRT
<213> ORGANISM: Hepatitis B virus

<400> SEQUENCE: 68

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Arg Ile Leu Cys Trp Gly Glu Leu Met Thr
                 85                  90                  95

Leu Ala Thr Trp Val Gly Val Asn Leu Glu Asp Pro Ala Ser Arg Asp
                100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190
```

Arg Arg Arg Arg Ser Gln Ser Pro Arg Arg Thr Arg Ser Gln Ser Arg
            195                 200                 205

Glu Ser Gln Cys
    210

<210> SEQ ID NO 69
<211> LENGTH: 212
<212> TYPE: PRT
<213> ORGANISM: Hepatitis B virus

<400> SEQUENCE: 69

Met Gln Leu Phe His Leu Cys Leu Val Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Asn Asn Leu Glu Asp Pro Ala Ser Arg Asp
            100                 105                 110

Leu Val Val Asn Tyr Val Asn Thr Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 70
<211> LENGTH: 212
<212> TYPE: PRT
<213> ORGANISM: Hepatitis B virus

<400> SEQUENCE: 70

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Ala Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr

```
                    85                  90                  95
Leu Ala Thr Trp Val Gly Val Asn Leu Glu Asp Pro Ala Ser Arg Asp
                100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
        195                 200                 205

Glu Ser Gln Cys
    210

<210> SEQ ID NO 71
<211> LENGTH: 183
<212> TYPE: PRT
<213> ORGANISM: Hepatitis B virus

<400> SEQUENCE: 71

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 72
<211> LENGTH: 183
<212> TYPE: PRT
<213> ORGANISM: Hepatitis B virus

<400> SEQUENCE: 72

Met Asp Ile Asp Pro Tyr Lys Glu Phe Gly Ala Thr Val Glu Leu Leu
1               5                   10                  15
```

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Gly Arg Ser Pro Arg Arg Arg Thr
145                 150                 155                 160

Pro Ser Pro Arg Arg Arg Ser Gln Ser Pro Arg Arg Arg Ser
            165                 170                 175

Gln Ser Arg Gly Ser Gln Cys
            180

<210> SEQ ID NO 73
<211> LENGTH: 188
<212> TYPE: PRT
<213> ORGANISM: Hepatitis B virus

<400> SEQUENCE: 73

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
            165                 170                 175

Arg Arg Arg Arg Ser Gln Ser Pro Ser Thr Asn Cys
            180                 185

<210> SEQ ID NO 74

```
<211> LENGTH: 217
<212> TYPE: PRT
<213> ORGANISM: Hepatitis B virus

<400> SEQUENCE: 74

Met Tyr Leu Phe His Leu Cys Leu Val Phe Ala Cys Val Pro Cys Pro
1               5                   10                  15

Thr Val Gln Ala Ser Lys Leu Cys Leu Gly Trp Leu Trp Asp Met Asp
                20                  25                  30

Ile Asp Pro Tyr Lys Glu Phe Gly Ser Ser Tyr Gln Leu Leu Asn Phe
            35                  40                  45

Leu Pro Leu Asp Phe Phe Pro Asp Leu Asn Ala Leu Val Asp Thr Ala
        50                  55                  60

Ala Ala Leu Tyr Glu Glu Glu Leu Thr Gly Arg Glu His Cys Ser Pro
65                  70                  75                  80

His His Thr Ala Ile Arg Gln Ala Leu Val Cys Trp Glu Glu Leu Thr
                85                  90                  95

Arg Leu Ile Thr Trp Met Ser Glu Asn Thr Thr Glu Glu Val Arg Arg
            100                 105                 110

Ile Ile Val Asp His Val Asn Asn Thr Trp Gly Leu Lys Val Arg Gln
        115                 120                 125

Thr Leu Trp Phe His Leu Ser Cys Leu Thr Phe Gly Gln His Thr Val
    130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
            180                 185                 190

Arg Thr Pro Ser Pro Arg Arg Arg Ser Gln Ser Pro Arg Arg Arg
                195                 200                 205

Arg Ser Gln Ser Pro Ala Ser Asn Cys
        210                 215

<210> SEQ ID NO 75
<211> LENGTH: 262
<212> TYPE: PRT
<213> ORGANISM: Hepatitis B virus

<400> SEQUENCE: 75

Met Asp Val Asn Ala Ser Arg Ala Leu Ala Asn Val Tyr Asp Leu Pro
1               5                   10                  15

Asp Asp Phe Phe Pro Lys Ile Glu Asp Leu Val Arg Asp Ala Lys Asp
                20                  25                  30

Ala Leu Glu Pro Tyr Trp Lys Ser Asp Ser Ile Lys Lys His Val Leu
            35                  40                  45

Ile Ala Thr His Phe Val Asp Leu Ile Glu Asp Phe Trp Gln Thr Thr
        50                  55                  60

Gln Gly Met His Glu Ile Ala Glu Ala Ile Arg Ala Val Ile Pro Pro
65                  70                  75                  80

Thr Thr Ala Pro Val Pro Ser Gly Tyr Leu Ile Gln His Asp Glu Ala
                85                  90                  95

Glu Glu Ile Pro Leu Gly Asp Leu Phe Lys Gln Glu Glu Arg Ile
            100                 105                 110

Val Ser Phe Gln Pro Asp Tyr Pro Ile Thr Ala Arg Ile His Ala His
        115                 120                 125
```

```
Leu Lys Ala Tyr Ala Lys Ile Asn Glu Glu Ser Leu Asp Arg Ala Arg
        130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
                180                 185                 190

Ile Gln Val Ala Gln Gly Gly Arg Lys Thr Ser Thr Ala Thr Arg Lys
                195                 200                 205

Pro Arg Gly Leu Glu Pro Arg Arg Lys Val Lys Thr Thr Val Val
        210                 215                 220

Tyr Gly Arg Arg Arg Ser Lys Ser Arg Glu Arg Arg Ala Ser Ser Pro
225                 230                 235                 240

Gln Arg Ala Gly Ser Pro Leu Pro Arg Ser Ser Ser His His Arg
                245                 250                 255

Ser Pro Ser Pro Arg Lys
                260

<210> SEQ ID NO 76
<211> LENGTH: 305
<212> TYPE: PRT
<213> ORGANISM: Hepatitis B virus

<400> SEQUENCE: 76

Met Trp Asp Leu Arg Leu His Pro Ser Pro Phe Gly Ala Ala Cys Gln
1               5                   10                  15

Gly Ile Phe Thr Ser Ser Leu Leu Phe Leu Val Thr Val Pro Leu
                20                  25                  30

Val Cys Thr Ile Val Tyr Asp Ser Cys Leu Cys Met Asp Ile Asn Ala
                35                  40                  45

Ser Arg Ala Leu Ala Asn Val Tyr Asp Leu Pro Asp Asp Phe Phe Pro
        50                  55                  60

Lys Ile Asp Asp Leu Val Arg Asp Ala Lys Asp Ala Leu Glu Pro Tyr
65                  70                  75                  80

Trp Arg Asn Asp Ser Ile Lys Lys His Val Leu Ile Ala Thr His Phe
                85                  90                  95

Val Asp Leu Ile Glu Asp Phe Trp Gln Thr Thr Gln Gly Met His Glu
                100                 105                 110

Ile Ala Glu Ala Leu Arg Ala Ile Ile Pro Ala Thr Thr Ala Pro Val
                115                 120                 125

Pro Gln Gly Phe Leu Val Gln His Glu Glu Ala Glu Glu Ile Pro Leu
        130                 135                 140

Gly Glu Leu Phe Arg Tyr Gln Glu Glu Arg Leu Thr Asn Phe Gln Pro
145                 150                 155                 160

Asp Tyr Pro Val Thr Ala Arg Ile His Ala His Leu Lys Ala Tyr Ala
                165                 170                 175

Lys Ile Asn Glu Glu Ser Leu Asp Arg Ala Arg Arg Leu Leu Trp Trp
                180                 185                 190

His Tyr Asn Cys Leu Leu Trp Gly Glu Pro Asn Val Thr Asn Tyr Ile
                195                 200                 205

Ser Arg Leu Arg Thr Trp Leu Ser Thr Pro Glu Lys Tyr Arg Gly Lys
        210                 215                 220

Asp Ala Pro Thr Ile Glu Ala Ile Thr Arg Pro Ile Gln Val Ala Gln
225                 230                 235                 240
```

-continued

```
Gly Gly Arg Asn Lys Thr Gln Gly Val Arg Lys Ser Arg Gly Leu Glu
            245                 250                 255

Pro Arg Arg Arg Val Lys Thr Thr Ile Val Tyr Gly Arg Arg
        260                 265                 270

Ser Lys Ser Arg Glu Arg Arg Ala Pro Thr Pro Gln Arg Ala Gly Ser
        275                 280                 285

Pro Leu Pro Arg Thr Ser Arg Asp His His Arg Ser Pro Ser Pro Arg
    290                 295                 300

Glu
305

<210> SEQ ID NO 77
<211> LENGTH: 185
<212> TYPE: PRT
<213> ORGANISM: Hepatitis B virus

<400> SEQUENCE: 77

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 78
<211> LENGTH: 152
<212> TYPE: PRT
<213> ORGANISM: Hepatitis B virus

<400> SEQUENCE: 78

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
```

```
            65                  70                  75                  80
Lys Gly Gly Ser Arg Asp Leu Val Val Ser Tyr Val Asn Thr Asn Val
                85                  90                  95
Gly Leu Lys Phe Arg Gln Leu Leu Trp Phe His Ile Ser Cys Leu Thr
            100                 105                 110
Phe Gly Arg Glu Thr Val Leu Glu Tyr Leu Val Ser Phe Gly Val Trp
            115                 120                 125
Ile Arg Thr Pro Pro Ala Tyr Arg Pro Pro Asn Ala Pro Ile Leu Ser
        130                 135                 140
Thr Leu Pro Glu Thr Thr Val Val
145                 150

<210> SEQ ID NO 79
<211> LENGTH: 3635
<212> TYPE: DNA
<213> ORGANISM: artificial sequence
<220> FEATURE:
<223> OTHER INFORMATION: chemically synthesized

<400> SEQUENCE: 79
cgagctcgcc cctggcttat cgaaattaat acgactcact atagggagac cggaattcga      60
gctcgcccgg ggatcctcta gaattttctg cgcacccatc ccgggtggcg cccaaagtga     120
ggaaaatcac atggcaaata agccaatgca accgatcaca tctacagcaa ataaaattgt     180
gtggtcggat ccaactcgtt tatcaactac attttcagca agtctgttac gccaacgtgt     240
taagttggt atagccgaac tgaataatgt ttcaggtcaa tatgtatctg tttataagcg     300
tcctgcacct aaaccggaag gttgtgcaga tgcctgtgtc attatgccga tgaaaaacca     360
atccattcgc acagtgattt cagggtcagc cgaaaacttg ctaccttaa aagcagaatg      420
ggaaactcac aaacgtaacg ttgacacact cttcgcgagc ggcaacgccg gtttgggttt     480
ccttgaccct actgcggcta tcgtatcgtc tgatactact gcttaagctt gtattctata     540
gtgtcaccta atcgtatgt gtatgataca taaggttatg tattaattgt agccgcgttc      600
taacgacaat atgtacaagc ctaattgtgt agcatctggc ttactgaagc agacccatc      660
atctctctcg taaactgccg tcagagtcgg tttggttgga cgaaccttct gagtttctgg     720
taacgccgtt ccgcacccgg gaaatggtca ccgaaccaat cagcagggtc atcgctagcc     780
agatcctcta cgccggacgc atcgtggccg gcatcaccgg cgcacacagt gcggttgctg     840
gcgcctatat cgccgacatc accgatgggg aagatcgggc tcgccacttc gggctcatga     900
gcgcttgttt cggcgtgggt atggtggcag gccccgtggc cggggactg ttgggcgcca      960
tctccttgca tgcaccattc cttgcggcgg cggtgcttca acggcctcaa cctactactg    1020
ggctgcttcc taatgcagga gtcgcataag ggagagcgtc gatatggtgc actctcagta    1080
caatctgctc tgatgccgca tagttaagcc aactccgcta tcgctacgtg actgggtcat    1140
ggctgcgccc cgacacccgc caacacccgc tgacgcgccc tgacgggctt gtctgctccc    1200
ggcatccgct tacagacaag ctgtgaccgt ctccgggagc tgcatgtgtc agaggttttc    1260
accgtcatca ccgaaacgcg cgaggcagct tgaagacgaa agggcctcgt gatacgccta    1320
tttttatagg ttaatgtcat gataataatg gtttcttaga cgtcaggtgg cacttttcgg    1380
ggaaatgtgc gcggaacccc tatttgttta ttttctaaa tacattcaaa tatgtatccg     1440
ctcatgagac aataaccctg ataaatgctt caataatatt gaaaaaggaa gagtatgagt    1500
attcaacatt tccgtgtcgc ccttattccc ttttttgcgg catttgcct tcctgttttt     1560
gctcacccag aaacgctggt gaaagtaaaa gatgctgaag atcagttggg tgcacgagtg    1620
```

```
ggttacatcg aactggatct caacagcggt aagatccttg agagttttcg ccccgaagaa    1680
cgttttccaa tgatgagcac tttttaaagtt ctgctatgtg gcgcggtatt atcccgtatt    1740
gacgccgggc aagagcaact cggtcgccgc atacactatt ctcagaatga cttggttgag    1800
tactcaccag tcacagaaaa gcatcttacg gatggcatga cagtaagaga attatgcagt    1860
gctgccataa ccatgagtga taacactgcg gccaacttac ttctgacaac gatcggagga    1920
ccgaaggagc taaccgcttt tttgcacaac atggggggatc atgtaactcg ccttgatcgt    1980
tgggaaccgg agctgaatga agccatacca aacgacgagc gtgacaccac gatgcctgta    2040
gcaatggcaa caacgttgcg caaactatta actggcgaac tacttactct agcttcccgg    2100
caacaattaa tagactggat ggaggcggat aaagttgcag gaccacttct gcgctcggcc    2160
cttccggctg gctggtttat tgctgataaa tctggagccg tgagcgtgg gtctcgcggt    2220
atcattgcag cactggggcc agatggtaag ccctcccgta tcgtagttat ctacacgacg    2280
gggagtcagg caactatgga tgaacgaaat agacagatcg ctgagatagg tgcctcactg    2340
attaagcatt ggtaactgtc agaccaagtt tactcatata tactttagat tgatttaaaa    2400
cttcattttt aatttaaaag gatctaggtg aagatccttt tgataatct catgaccaaa    2460
atcccttaac gtgagttttc gttccactga gcgtcagacc ccgtagaaaa gatcaaagga    2520
tcttcttgag atcctttttt tctgcgcgta atctgctgct tgcaaacaaa aaaaccaccg    2580
ctaccagcgg tggtttgttt gccggatcaa gagctaccaa ctcttttttcc gaaggtaact    2640
ggcttcagca gagcgcagat accaaatact gtccttctag tgtagccgta gttaggccac    2700
cacttcaaga actctgtagc accgcctaca tacctcgctc tgctaatcct gttaccagtg    2760
gctgctgcca gtggcgataa gtcgtgtctt accgggttgg actcaagacg atagttaccg    2820
gataaggcgc agcggtcggg ctgaacgggg ggttcgtgca cacagcccag cttggagcga    2880
acgacctaca ccgaactgag atacctacag cgcgagcatt gagaaagcgc cacgcttccc    2940
gaagggagaa aggcggacag gtatccggta agcggcaggg tcggaacagg agagcgcacg    3000
agggagcttc caggggggaaa cgcctggtat ctttatagtc ctgtcgggtt tcgccacctc    3060
tgacttgagc gtcgattttt gtgatgctcg tcagggggggc ggagcctatg gaaaaacgcc    3120
agcaacgcgg ccttttttacg gttcctggcc ttttgctggc cttttgctca catgttcttt    3180
cctgcgttat ccccctgattc tgtggataac cgtattaccg cctttgagtg agctgatacc    3240
gctcgccgca gccgaacgac gagcgcagcg agtcagtgag cgaggaagcg gaagagcgcc    3300
caatacgcaa accgcctctc cccgcgcgtt ggccgattca ttaatgcagc tgtggtgtca    3360
tggtcggtga tcgccagggt gccgacgcgc atctcgactg catggtgcac caatgcttct    3420
ggcgtcaggc agccatcgga agctgtggta tggccgtgca ggtcgtaaat cactgcataa    3480
ttcgtgtcgc tcaaggcgca ctcccgttct ggataatgtt ttttgcgccg acatcataac    3540
ggttctggca aatattctga aatgagctgt tgacaattaa tcatcgaact agttaactag    3600
tacgcaagtt cacgtaaaaa gggtatcgcg gaatt                                3635
```

<210> SEQ ID NO 80
<211> LENGTH: 131
<212> TYPE: PRT
<213> ORGANISM: Unknown
<220> FEATURE:
<223> OTHER INFORMATION: Bacteriophage AP205

<400> SEQUENCE: 80

Met Ala Asn Lys Pro Met Gln Pro Ile Thr Ser Thr Ala Asn Lys Ile

```
                1               5                  10                 15
Val Trp Ser Asp Pro Thr Arg Leu Ser Thr Thr Phe Ser Ala Ser Leu
                   20                  25                 30

Leu Arg Gln Arg Val Lys Val Gly Ile Ala Glu Leu Asn Asn Val Ser
                   35                  40                 45

Gly Gln Tyr Val Ser Val Tyr Lys Arg Pro Ala Pro Lys Pro Glu Gly
                   50                  55                 60

Cys Ala Asp Ala Cys Val Ile Met Pro Asn Glu Asn Gln Ser Ile Arg
 65                70                  75                      80

Thr Val Ile Ser Gly Ser Ala Glu Asn Leu Ala Thr Leu Lys Ala Glu
                       85                  90                 95

Trp Glu Thr His Lys Arg Asn Val Asp Thr Leu Phe Ala Ser Gly Asn
                  100                 105                110

Ala Gly Leu Gly Phe Leu Asp Pro Thr Ala Ala Ile Val Ser Ser Asp
                  115                 120                125

Thr Thr Ala
     130

<210> SEQ ID NO 81
<211> LENGTH: 131
<212> TYPE: PRT
<213> ORGANISM: Unknown
<220> FEATURE:
<223> OTHER INFORMATION: Bacteriophage AP205

<400> SEQUENCE: 81

Met Ala Asn Lys Thr Met Gln Pro Ile Thr Ser Thr Ala Asn Lys Ile
 1               5                  10                 15

Val Trp Ser Asp Pro Thr Arg Leu Ser Thr Thr Phe Ser Ala Ser Leu
                   20                  25                 30

Leu Arg Gln Arg Val Lys Val Gly Ile Ala Glu Leu Asn Asn Val Ser
                   35                  40                 45

Gly Gln Tyr Val Ser Val Tyr Lys Arg Pro Ala Pro Lys Pro Glu Gly
                   50                  55                 60

Cys Ala Asp Ala Cys Val Ile Met Pro Asn Glu Asn Gln Ser Ile Arg
 65                70                  75                      80

Thr Val Ile Ser Gly Ser Ala Glu Asn Leu Ala Thr Leu Lys Ala Glu
                       85                  90                 95

Trp Glu Thr His Lys Arg Asn Val Asp Thr Leu Phe Ala Ser Gly Asn
                  100                 105                110

Ala Gly Leu Gly Phe Leu Asp Pro Thr Ala Ala Ile Val Ser Ser Asp
                  115                 120                125

Thr Thr Ala
     130

<210> SEQ ID NO 82
<211> LENGTH: 3607
<212> TYPE: DNA
<213> ORGANISM: artificial Sequence
<220> FEATURE:
<223> OTHER INFORMATION: chemically synthesized

<400> SEQUENCE: 82
cgagctcgcc cctggcttat cgaaattaat acgactcact atagggagac cggaattcga      60
gctcgcccgg ggatcctcta gattaaccca acgcgtagga gtcaggccat ggcaaataag     120
acaatgcaac cgatcacatc tacagcaaat aaaattgtgt ggtcggatcc aactcgttta     180
tcaactacat tttcagcaag tctgttacgc caacgtgtta agttggtat agccgaactg     240
```

-continued

```
aataatgttt caggtcaata tgtatctgtt tataagcgtc ctgcacctaa accgaaggtc    300
agatgcctgt gtcattatgc cgaatgaaaa ccaatccatt cgcacagtga tttcagggtc    360
agccgaaaac ttggctacct taaaagcaga atgggaaact cacaaacgta acgttgacac    420
actcttcgcg agcggcaacg ccggtttggg tttccttgac cctactgcgg ctatcgtatc    480
gtctgatact actgcttaag cttgtattct atagtgtcac ctaaatcgta tgtgtatgat    540
acataaggtt atgtattaat ggtagccgcg ttctaacgac aatatgtaca agcctaattg    600
tgtagcatct ggcttactga agcagaccct atcatctctc tcgtaaactg ccgtcagagt    660
cggttgggtt ggacagacct ctgagtttct ggtaacgccg ttccgcaccc cggaaatggt    720
caccgaacca ttcagcaggg tcatcgctag ccagatcctc tacgccggac gcatcgtggc    780
ccgcatcacc ggcgccacag gtgcggtgct ggcgcctata tcgccgacat caccgatggg    840
gaagatcggg ctcgccactt cgggctcatg atcgctggtt ccgcctggg tatggtggca    900 ggccccgtgg cccgggggac tgttgggcgc catctccttg catgcaccat tccttgcggc    960
ggcggtgctc aacggcctca acctactact gggctgcttc ctaatgcagg agtcgcataa   1020
gggagagcgt cgatatggtg cactctcagt acaatctgct ctgatgccgc atagttaagc   1080
caactccgct atcgctacgt gactgggtca tggctgcgcc ccgacacccg ccaacacccg   1140
ctgacgcgcc ctgacgggct tgtctgcttc cggcatccgc ttacagacaa gctgtgaccg   1200
tctccgggag ctgcatgtgt cagaggtttt caccgtcatc accgaaacgc gcgaggcagc   1260
ttgaagacga aagggcctcg tgatacgcct atttttatag gttaatgtca tgataataat   1320
ggtttcttag acgtcaggtg gcacttttcg gggaaatgtg cgcggacccc ctattggttt   1380 attttttctaa atacattcaa atatgtatcc gctcatgaga caataaccct gataaatgct   1440
tcaataatat tgaaaaagga agagtatgag tattcaacat ttccgtgtcg cccttattcc   1500
cttttttgcg gcattttgcc ttcctgtttt tgctcaccca gaaacgctgg tgaaagtaaa   1560
agatgctgaa gatcagttgg gtgcacgagt gggttacatc gaactggatc tcaacagcgg   1620
taagatcctt gagagttttc gccccgaaga acgttttcca tgatgagca cttttaaagt   1680 tctgctatgt gtcgcggtat tatcccgtat tgacgccggg caagagcaac tcggtcgccg   1740
catacactat tctcagaatg acttggtggt acctaccagt cacagaaaag catcttacgg   1800
atggcatgac agtaagagaa ttatgcagtg ctgccataac catgagtgat aacactgcgg   1860
ccaacttact tctgacaacg atcggaggac cgaaggagct aaccgctttt ttgcacaaca   1920
tgggggatca tgtaactcgc cttgatcgtt gggaaccgga gctgaatgaa gccataccaa   1980
acgacgagcg tgacaccacg atgcctgtac gaacggcaac aacgttgcgc aaactattaa   2040
ctggcgaact acttactcta gcttcccggc aacaattaat agactggatg gaggcggata   2100
aagttgcagg accacttctg cgctcggccc ttccggctgg ctggtttatt gctgataaat   2160
ctggagccgg tgagcgtggg tctcgcggta tcattgcagc actggggcca gatggtaagc   2220
cctcccgtat cgtagttatc tacacgacgg ggagtcaggc aactatggat gaacgaaata   2280
gacagatcgc tgagataggt gcctcactga ttaagcattg gtaactgtca gaccaagttt   2340
actcatatat actttagatt gatttaaaac ttcatttta atttaaaagg atctaggtga   2400
agatcctttt tgataatctc atgaccaaaa tcccttaacg tgagttttcg ttccactgag   2460
cggtcagacc ccgtagaaag atcaaaggat cttcttgaga tcctttttt ctgcgcgtaa   2520 tctgctgctt gcaaacaaaa aaaccaccgc taccagcggt ggtttgtttg ccggatcaag   2580
agctaccaac tctttttccg aaggtaactg gcttcagcag agcgcagata ccaaatactg   2640
```

```
tccttctagt gtagccgtag ttaggccacc acttcaagaa ctctgtagca ccgcctacat   2700
acctcgctct gctaatcctg ttaccagtgg ctgctgccag tggcgataag tcgtgtctta   2760
ccgggttgga ctcaagacga taggtaccgg ataaggcgca gcggtcgggc tgaacggggg   2820
gttcgtgcac acagcccagc ttggagcgaa cgacctacac cgaactgaga tacctacagc   2880
gcgagcattg agaaagcgcc acgcttcccg aagggagaaa ggcggacagg tatccggtaa   2940
gcggcagggt cggaacaaga gagcgcacga gggagcttcc aggggaaac gcctggtatc    3000 tttatagtcc tgtcgggttt cgccacctct gacttgagcg tcgatttttg tgatgctcgt   3060
caggggggcg gagcctatgg aaaaacgcca gcaacgcggc cttttacgg ttcctggcct    3120 ttggctggcc ttttgctcac atgttctttc ctgcgttatc ccctgattct gtggataacc   3180
gtattaccgc ctttgagtga gctgataccg ctcgccgcag ccgaacgacc gacggcgcag   3240
cgagtcagtg agcgaggaag cggaagagcg cccaatacgc aaaccgcctc tccccgcgcg   3300
ttggccgatt cattaatgca gctgtggtgt catggtcggt gatcgccagg gtgccgacgc   3360
gcatctcgac tgcatggtgc accaatgctt ctggcgtcag gcagccatcg aagctgtgg    3420 tatgccgtg caggtcgtaa atcactgcat aattcgtgtc gctcaaggcg cactcccgtt    3480
ctggataatg tttttgcgg cgacatcata acggttctgg caaatattct gaaatgagct    3540
ggtgacaatt aatcatcgaa ctagttaact agtacgcaag ttcacgtaaa aagggtatcg   3600
cggaatt                                                             3607
```

<210> SEQ ID NO 83
<211> LENGTH: 18
<212> TYPE: PRT
<213> ORGANISM: artificial sequence
<220> FEATURE:
<223> OTHER INFORMATION: chemically synthesized

<400> SEQUENCE: 83

Pro Lys Pro Ser Thr Pro Pro Gly Ser Ser Gly Gly Ala Pro Gly Gly
1               5                   10                  15

Cys Gly

<210> SEQ ID NO 84
<211> LENGTH: 6
<212> TYPE: PRT
<213> ORGANISM: artificial sequence
<220> FEATURE:
<223> OTHER INFORMATION: chemically synthesized

<400> SEQUENCE: 84

Gly Cys Gly Gly Gly Gly
1               5

<210> SEQ ID NO 85
<211> LENGTH: 6
<212> TYPE: PRT
<213> ORGANISM: artificial sequence
<220> FEATURE:
<223> OTHER INFORMATION: chemically synthesized

<400> SEQUENCE: 85

Gly Gly Gly Gly Cys Gly
1               5

<210> SEQ ID NO 86
<211> LENGTH: 6
<212> TYPE: PRT

```
<213> ORGANISM: artificial sequence
<220> FEATURE:
<223> OTHER INFORMATION: chemically synthesized

<400> SEQUENCE: 86

Cys Gly Lys Lys Gly Gly
1               5

<210> SEQ ID NO 87
<211> LENGTH: 6
<212> TYPE: PRT
<213> ORGANISM: artificial sequence
<220> FEATURE:
<223> OTHER INFORMATION: chemically synthesized

<400> SEQUENCE: 87

Cys Gly Asp Glu Gly Gly
1               5

<210> SEQ ID NO 88
<211> LENGTH: 6
<212> TYPE: PRT
<213> ORGANISM: artificial sequence
<220> FEATURE:
<223> OTHER INFORMATION: chemically synthetized

<400> SEQUENCE: 88

Gly Gly Lys Lys Gly Cys
1               5

<210> SEQ ID NO 89
<211> LENGTH: 6
<212> TYPE: PRT
<213> ORGANISM: artificial sequence
<220> FEATURE:
<223> OTHER INFORMATION: chemically synthesized

<400> SEQUENCE: 89

Gly Gly Glu Asp Gly Cys
1               5

<210> SEQ ID NO 90
<211> LENGTH: 9
<212> TYPE: PRT
<213> ORGANISM: Homo sapiens

<400> SEQUENCE: 90

Lys Thr Trp Gly Gln Tyr Trp Gln Val
1               5

<210> SEQ ID NO 91
<211> LENGTH: 9
<212> TYPE: PRT
<213> ORGANISM: Homo sapiens

<400> SEQUENCE: 91

Ile Thr Asp Gln Val Pro Phe Ser Val
1               5

<210> SEQ ID NO 92
<211> LENGTH: 9
<212> TYPE: PRT
<213> ORGANISM: Homo sapiens

<400> SEQUENCE: 92

Tyr Leu Glu Pro Gly Pro Val Thr Ala
1               5
```

```
<210> SEQ ID NO 93
<211> LENGTH: 10
<212> TYPE: PRT
<213> ORGANISM: Homo sapiens

<400> SEQUENCE: 93

Leu Leu Asp Gly Thr Ala Thr Leu Arg Leu
1               5                   10

<210> SEQ ID NO 94
<211> LENGTH: 10
<212> TYPE: PRT
<213> ORGANISM: Homo sapiens

<400> SEQUENCE: 94

Val Leu Tyr Arg Tyr Gly Ser Phe Ser Val
1               5                   10

<210> SEQ ID NO 95
<211> LENGTH: 9
<212> TYPE: PRT
<213> ORGANISM: Homo sapiens

<400> SEQUENCE: 95

Ala Ala Gly Ile Gly Ile Leu Thr Val
1               5

<210> SEQ ID NO 96
<211> LENGTH: 9
<212> TYPE: PRT
<213> ORGANISM: Homo sapiens

<400> SEQUENCE: 96

Ile Leu Thr Val Ile Leu Gly Val Leu
1               5

<210> SEQ ID NO 97
<211> LENGTH: 9
<212> TYPE: PRT
<213> ORGANISM: Homo sapiens

<400> SEQUENCE: 97

Met Leu Leu Ala Val Leu Tyr Cys Leu
1               5

<210> SEQ ID NO 98
<211> LENGTH: 9
<212> TYPE: PRT
<213> ORGANISM: Homo sapiens

<400> SEQUENCE: 98

Tyr Met Asp Gly Thr Met Ser Gln Val
1               5

<210> SEQ ID NO 99
<211> LENGTH: 9
<212> TYPE: PRT
<213> ORGANISM: Homo sapiens

<400> SEQUENCE: 99

Val Leu Pro Asp Val Phe Ile Arg Cys
1               5

<210> SEQ ID NO 100
```

```
<210> SEQ ID NO 100
<211> LENGTH: 9
<212> TYPE: PRT
<213> ORGANISM: Homo sapiens

<400> SEQUENCE: 100

Phe Leu Trp Gly Pro Arg Ala Leu Val
1               5

<210> SEQ ID NO 101
<211> LENGTH: 9
<212> TYPE: PRT
<213> ORGANISM: Homo sapiens

<400> SEQUENCE: 101

Tyr Leu Ser Gly Ala Asn Leu Asn Leu
1               5

<210> SEQ ID NO 102
<211> LENGTH: 9
<212> TYPE: PRT
<213> ORGANISM: Homo sapiens

<400> SEQUENCE: 102

Ser Thr Pro Pro Pro Gly Thr Arg Val
1               5

<210> SEQ ID NO 103
<211> LENGTH: 9
<212> TYPE: PRT
<213> ORGANISM: Homo sapiens

<400> SEQUENCE: 103

Leu Leu Gly Arg Asn Ser Phe Glu Val
1               5

<210> SEQ ID NO 104
<211> LENGTH: 9
<212> TYPE: PRT
<213> ORGANISM: Homo sapiens

<400> SEQUENCE: 104

Lys Ile Phe Gly Ser Leu Ala Phe Leu
1               5

<210> SEQ ID NO 105
<211> LENGTH: 9
<212> TYPE: PRT
<213> ORGANISM: Homo sapiens

<400> SEQUENCE: 105

Ile Ile Ser Ala Val Val Gly Ile Leu
1               5

<210> SEQ ID NO 106
<211> LENGTH: 8
<212> TYPE: PRT
<213> ORGANISM: Homo sapiens

<400> SEQUENCE: 106

Thr Leu Gly Ile Val Cys Pro Ile
1               5

<210> SEQ ID NO 107
<211> LENGTH: 9
<212> TYPE: PRT
<213> ORGANISM: lymphocytic choriomeningitis virus
```

<400> SEQUENCE: 107

Lys Ala Val Tyr Asn Phe Ala Thr Met
1               5

<210> SEQ ID NO 108
<211> LENGTH: 9
<212> TYPE: PRT
<213> ORGANISM: artificial sequence
<220> FEATURE:
<223> OTHER INFORMATION: chemically synthesized

<400> SEQUENCE: 108

Leu Pro Tyr Leu Gly Trp Leu Val Phe
1               5

<210> SEQ ID NO 109
<211> LENGTH: 21
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(21)
<223> OTHER INFORMATION: phosphorothioate bound

<400> SEQUENCE: 109
tccatgacgt tcctgaataa t                                      21

<210> SEQ ID NO 110
<211> LENGTH: 21
<212> TYPE: DNA
<213> ORGANISM: artificial sequence
<220> FEATURE:
<223> OTHER INFORMATION: chemically synthesized

<400> SEQUENCE: 110
tccatgacgt tcctgaataa t                                      21

<210> SEQ ID NO 111
<211> LENGTH: 20
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(20)
<223> OTHER INFORMATION: phosphorothioate bound

<400> SEQUENCE: 111
tccatgacgt tcctgacgtt                                        20

<210> SEQ ID NO 112
<211> LENGTH: 20
<212> TYPE: DNA
<213> ORGANISM: artificial sequence
<220> FEATURE:
<223> OTHER INFORMATION: chemically synthesized

<400> SEQUENCE: 112
tccatgacgt tcctgacgtt                                        20

<210> SEQ ID NO 113
<211> LENGTH: 19
<212> TYPE: DNA
<213> ORGANISM: artificial sequence

```
<220> FEATURE:
<223> OTHER INFORMATION: chemically synthesized
<220> FEATURE:
<221> NAME/KEY: misc_feature
<222> LOCATION: (1)..(2)
<223> OTHER INFORMATION: phosphorothioate bound
<220> FEATURE:
<221> NAME/KEY: misc_feature
<222> LOCATION: (15)..(19)
<223> OTHER INFORMATION: phosphorothioate bound

<400> SEQUENCE: 113
ggggtcaacg ttgaggggg                                                   19

<210> SEQ ID NO 114
<211> LENGTH: 19
<212> TYPE: DNA
<213> ORGANISM: artificial sequence
<220> FEATURE:
<223> OTHER INFORMATION: chemically synthesized

<400> SEQUENCE: 114
ggggtcaacg ttgaggggg                                                   19

<210> SEQ ID NO 115
<211> LENGTH: 21
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(21)
<223> OTHER INFORMATION: phosphorothioate bound

<400> SEQUENCE: 115
attattcagg aacgtcatgg a                                                21

<210> SEQ ID NO 116
<211> LENGTH: 30
<212> TYPE: DNA
<213> ORGANISM: artificial sequence
<220> FEATURE:
<223> OTHER INFORMATION: chemically synthesized

<400> SEQUENCE: 116
gggggggggg gacgatcgtc gggggggggg                                       30

<210> SEQ ID NO 117
<211> LENGTH: 30
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(30)
<223> OTHER INFORMATION: phosphorothioate bound

<400> SEQUENCE: 117
gggggggggg gacgatcgtc gggggggggg                                       30

<210> SEQ ID NO 118
<211> LENGTH: 62
<212> TYPE: DNA
<213> ORGANISM: artificial sequence
<220> FEATURE:
<223> OTHER INFORMATION: chemically synthesized

<400> SEQUENCE: 118
```

```
cgcgcgcgcg cgcgcgcgcg cgcgcgcgcg cgcgcgcgcg aaatgcatgt caaagacagc    60
at                                                                  62

<210> SEQ ID NO 119
<211> LENGTH: 61
<212> TYPE: DNA
<213> ORGANISM: artificial sequence
<220> FEATURE:
<223> OTHER INFORMATION: chemically synthesized

<400> SEQUENCE: 119
tccatgacgt tcctgaataa tcgcgcgcgc gcgcgcgcgc gcgcgcgcgc gcgcgcgcgc    60
g                                                                   61

<210> SEQ ID NO 120
<211> LENGTH: 83
<212> TYPE: DNA
<213> ORGANISM: artificial sequence
<220> FEATURE:
<223> OTHER INFORMATION: chemically synthesized

<400> SEQUENCE: 120
tccatgacgt tcctgaataa tcgcgcgcgc gcgcgcgcgc gcgcgcgcgc gcgcgcgcgc    60
gaaatgcatg tcaaagacag cat                                           83

<210> SEQ ID NO 121
<211> LENGTH: 43
<212> TYPE: DNA
<213> ORGANISM: artificial sequence
<220> FEATURE:
<223> OTHER INFORMATION: chemically synthesized

<400> SEQUENCE: 121
tccatgacgt tcctgaataa taaatgcatg tcaaagacag cat                     43

<210> SEQ ID NO 122
<211> LENGTH: 63
<212> TYPE: DNA
<213> ORGANISM: artificial sequence
<220> FEATURE:
<223> OTHER INFORMATION: chemically synthesized

<400> SEQUENCE: 122
tccatgacgt tcctgaataa ttccatgacg ttcctgaata attccatgac gttcctgaat    60
aat                                                                 63

<210> SEQ ID NO 123
<211> LENGTH: 150
<212> TYPE: DNA
<213> ORGANISM: artificial sequence
<220> FEATURE:
<223> OTHER INFORMATION: chemically synthesized

<400> SEQUENCE: 123
tccatgacgt tcctgaataa ttccatgacg ttcctgaata attccatgac gttcctgaat    60
aattggatga cgttggtgaa taattccatg acgttcctga ataattccat gacgttcctg   120
aataattcca tgacgttcct gaataattcc                                   150

<210> SEQ ID NO 124
<211> LENGTH: 253
<212> TYPE: DNA
<213> ORGANISM: artificial sequence
```

```
<220> FEATURE:
<223> OTHER INFORMATION: chemically synthesized

<400> SEQUENCE: 124
ctagaactag tggatccccc gggctgcagg aattcgattc atgacttcct gaataattcc    60
atgacgttgg tgaataattc catgacgttc ctgaataatt ccatgacgtt cctgaataat   120
tccatgacgt tcctgaataa ttccatgacg ttcctgaata attccatgac gttcctgaat   180
aattccatga cgttcctgaa taattccatg acgttcctga aaattccaat caagcttatc   240
gataccgtcg acc                                                      253

<210> SEQ ID NO 125
<211> LENGTH: 12
<212> TYPE: PRT
<213> ORGANISM: artificial sequence
<220> FEATURE:
<223> OTHER INFORMATION: chemically synthesized

<400> SEQUENCE: 125

Cys Gly Gly Lys Ala Val Tyr Asn Phe Ala Thr Met
1               5                   10

<210> SEQ ID NO 126
<211> LENGTH: 12
<212> TYPE: PRT
<213> ORGANISM: artificial sequence
<220> FEATURE:
<223> OTHER INFORMATION: chemically synthesized

<400> SEQUENCE: 126

Lys Ala Val Tyr Asn Phe Ala Thr Met Gly Gly Cys
1               5                   10

<210> SEQ ID NO 127
<211> LENGTH: 9
<212> TYPE: PRT
<213> ORGANISM: artificial sequence
<220> FEATURE:
<223> OTHER INFORMATION: chemically synthesized
<220> FEATURE:
<221> NAME/KEY: REPEAT
<222> LOCATION: (1)..(1)
<223> OTHER INFORMATION: can be absent or repeated up to 5 times
<220> FEATURE:
<221> NAME/KEY: REPEAT
<222> LOCATION: (3)..(3)
<223> OTHER INFORMATION: can be absent or repeated up to 10 times
<220> FEATURE:
<221> NAME/KEY: REPEAT
<222> LOCATION: (4)..(4)
<223> OTHER INFORMATION: can be absent or repeated up to 2 times
<220> FEATURE:
<221> NAME/KEY: REPEAT
<222> LOCATION: (5)..(9)
<223> OTHER INFORMATION: can be absent or repeated up to 3 times

<400> SEQUENCE: 127

Gly Cys Gly Ser Gly Gly Gly Gly Ser
1               5

<210> SEQ ID NO 128
<211> LENGTH: 10
<212> TYPE: PRT
<213> ORGANISM: artificial sequence
<220> FEATURE:
<223> OTHER INFORMATION: chemically synthesized
<220> FEATURE:
<221> NAME/KEY: REPEAT
<222> LOCATION: (1)..(1)
```

```
<223> OTHER INFORMATION: can be absent or repeated up to 10 times
<220> FEATURE:
<221> NAME/KEY: REPEAT
<222> LOCATION: (2)..(2)
<223> OTHER INFORMATION: can be absent or repeated up to 2 times
<220> FEATURE:
<221> NAME/KEY: REPEAT
<222> LOCATION: (3)..(7)
<223> OTHER INFORMATION: can be absent or repeated up to 3 times
<220> FEATURE:
<221> NAME/KEY: REPEAT
<222> LOCATION: (8)..(8)
<223> OTHER INFORMATION: can be absent or repeated up to 8 times
<220> FEATURE:
<221> NAME/KEY: REPEAT
<222> LOCATION: (10)..(10)
<223> OTHER INFORMATION: can be absent or repeated up to 5 times

<400> SEQUENCE: 128

Gly Ser Gly Gly Gly Gly Ser Gly Cys Gly
1               5                   10

<210> SEQ ID NO 129
<211> LENGTH: 10
<212> TYPE: PRT
<213> ORGANISM: artificial sequence
<220> FEATURE:
<223> OTHER INFORMATION: chemically synthesized

<400> SEQUENCE: 129

Gly Gly Gly Gly Ser Gly Gly Gly Gly Ser
1               5                   10

<210> SEQ ID NO 130
<211> LENGTH: 3
<212> TYPE: PRT
<213> ORGANISM: artificial sequence
<220> FEATURE:
<223> OTHER INFORMATION: chemically synthesized

<400> SEQUENCE: 130

Cys Gly Gly
1

<210> SEQ ID NO 131
<211> LENGTH: 3
<212> TYPE: PRT
<213> ORGANISM: artificial sequence
<220> FEATURE:
<223> OTHER INFORMATION: chemically synthetized
<220> FEATURE:
<221> NAME/KEY: REPEAT
<222> LOCATION: (1)..(1)
<223> OTHER INFORMATION: can be absent or repeated 1 to 5 times
<220> FEATURE:
<221> NAME/KEY: REPEAT
<222> LOCATION: (3)..(3)
<223> OTHER INFORMATION: can be absent or repeated 1 to 12 times

<400> SEQUENCE: 131

Gly Cys Gly
1

<210> SEQ ID NO 132
<211> LENGTH: 3
<212> TYPE: PRT
<213> ORGANISM: artificial sequence
<220> FEATURE:
<223> OTHER INFORMATION: chemically synthesized
<220> FEATURE:
<221> NAME/KEY: REPEAT
<222> LOCATION: (1)..(1)
```

```
<223> OTHER INFORMATION: can be absent or repeated 1 to 12 times
<220> FEATURE:
<221> NAME/KEY: REPEAT
<222> LOCATION: (3)..(3)
<223> OTHER INFORMATION: can be absent or repeated 1 to 5 times

<400> SEQUENCE: 132

Gly Cys Gly
1

<210> SEQ ID NO 133
<211> LENGTH: 5
<212> TYPE: PRT
<213> ORGANISM: artificial sequence
<220> FEATURE:
<223> OTHER INFORMATION: chemically synthesized
<220> FEATURE:
<221> NAME/KEY: REPEAT
<222> LOCATION: (1)..(5)
<223> OTHER INFORMATION: can be repeated n times

<400> SEQUENCE: 133

Gly Gly Gly Gly Ser
1               5

<210> SEQ ID NO 134
<211> LENGTH: 4
<212> TYPE: PRT
<213> ORGANISM: artificial sequence
<220> FEATURE:
<223> OTHER INFORMATION: chemically synthesized

<400> SEQUENCE: 134

Gly Gly Cys Gly
1

<210> SEQ ID NO 135
<211> LENGTH: 3
<212> TYPE: PRT
<213> ORGANISM: artificial sequence
<220> FEATURE:
<223> OTHER INFORMATION: chemically synthesized

<400> SEQUENCE: 135

Gly Gly Cys
1

<210> SEQ ID NO 136
<211> LENGTH: 3
<212> TYPE: PRT
<213> ORGANISM: artificial sequence
<220> FEATURE:
<223> OTHER INFORMATION: chemically synthesized
<220> FEATURE:
<221> NAME/KEY: MISC_FEATURE
<222> LOCATION: (3)..(3)
<223> OTHER INFORMATION: residue 3 is amidated

<400> SEQUENCE: 136

Gly Gly Cys
1
```

PACKAGING OF IMMUNOSTIMULATORY SUBSTANCES INTO VIRUS-LIKE PARTICLES: METHOD OF PREPARATION AND USE

CROSS-REFERENCE TO RELATED APPLICATIONS

This application is a continuation of U.S. application Ser. No. 10/244,065, filed Sep. 16, 2002, now abandoned, which claims the benefit of U.S. Provisional Application No. 60/318,994, filed Sep. 14, 2001, and U.S. Provisional Application No. 60/374,145, filed Apr. 22, 2002, each of which is hereby incorporated by reference in its entirety.

REFERENCE TO SEQUENCE LISTING SUBMITTED ELECTRONICALLY

The content of the electronically submitted substitute sequence listing, file name: 1700_0220004SEQ IDListing.ascii.txt; Size: 151,531 bytes; and Date of Creation: Jun. 22, 2012, filed herewith, is incorporated herein by reference in its entirety.

BACKGROUND OF THE INVENTION

1. Field of the Invention

The present invention is related to the fields of vaccinology, immunology and medicine. The invention provides compositions and methods for enhancing immunological responses against virus-like particles (VLPs) or against antigens coupled, fused or attached otherwise to VLPs by packaging immunostimulatory substances, in particular immunostimulatory nucleic acids, and even more particular oligonucleotides containing at least one non-methylated CpG sequence, into the VLPs. The invention can be used to induce strong and sustained T cell responses particularly useful for the treatment of tumors and chronic viral diseases as well as allergies and other chronic diseases.

2. Related Art

The essence of the immune system is built on two separate foundation pillars: one is specific or adaptive immunity which is characterized by relatively slow response-kinetics and the ability to remember; the other is non-specific or innate immunity exhibiting rapid response-kinetics but lacking memory. Lymphocytes are the key players of the adaptive immune system. Each lymphocyte expresses antigen-receptors of unique specificity. Upon recognizing an antigen via the receptor, lymphocytes proliferate and develop effector function. Few lymphocytes exhibit specificity for a given antigen or pathogen, and massive proliferation is usually required before an effector response can be measured—hence, the slow kinetics of the adaptive immune system. Since a significant proportion of the expanded lymphocytes survive and may maintain some effector function following elimination of the antigen, the adaptive immune system reacts faster when encountering the antigen a second time. This is the basis of its ability to remember.

In contrast to the situation with lymphocytes, where specificity for a pathogen is confined to few cells that must expand to gain function, the cells and molecules of the innate immune system are usually present in massive numbers and recognize a limited number of invariant features associated with pathogens (Medzhitov, R. and Janeway, C. A., Jr., Cell 91:295-298 (1997)). Examples of such patterns include lipopolysaccharides (LPS), non-methylated CG-rich DNA (CpG) or double stranded RNA, which are specific for bacterial and viral infections, respectively.

Most research in immunology has focused on the adaptive immune system and only recently has the innate immune system entered the focus of interest. Historically, the adaptive and innate immune system were treated and analyzed as two separate entities that had little in common. Such was the disparity that few researchers wondered why antigens were much more immunogenic for the specific immune system when applied with adjuvants that stimulated innate immunity (Sotomayor, E. M., et al., Nat. Med. 5:780 (1999); Diehl, L., et al., Nat. Med. 5:774 (1999); Weigle, W. O., Adv. Immunol. 30:159 (1980)). However, the answer posed by this question is critical to the understanding of the immune system and for comprehending the balance between protective immunity and autoimmunity.

Rationalized manipulation of the innate immune system and in particular activation of APCs involved in T cell priming to deliberately induce a self-specific T cell response provides a means for T cell-based tumor-therapy. Accordingly, the focus of most current therapies is on the use of activated dendritic cells (DCs) as antigen-carriers for the induction of sustained T cell responses (Nestle et al., Nat. Med. 4:328 (1998)). Similarly, in vivo activators of the innate immune system, such as CpGs or anti-CD40 antibodies, are applied together with tumor cells in order to enhance their immunogenicity (Sotomayor, E. M., et al., Nat. Med. 5:780 (1999); Diehl, L., et al., Nat. Med. 5:774 (1999)).

Generalized activation of APCs by factors that stimulate innate immunity may often be the cause for triggering self-specific lymphocytes and autoimmunity. Activation may result in enhanced expression of costimulatory molecules or cytokines such as IL-12 or IFNα. This view is compatible with the observation that administration of LPS together with thyroid extracts is able to overcome tolerance and trigger autoimmune thyroiditis (Weigle, W. O., Adv. Immunol. 30:159 (1980)). Moreover, in a transgenic mouse model, it was recently shown that administration of self-peptide alone failed to cause auto-immunity unless APCs were activated by a separate pathway (Garza, K. M., et al., J. Exp. Med. 191:2021 (2000)). The link between innate immunity and autoimmune disease is further underscored by the observation that LPS, viral infections or generalized activation of APCs delays or prevents the establishment of peripheral tolerance (Vella, A. T., et al., Immunity 2:261 (1995); Ehl, S., et al., J. Exp. Med. 187:763 (1998); Maxwell, J. R., et al., J. Immunol. 162:2024 (1999)). In this way, innate immunity not only enhances the activation of self-specific lymphocytes but also inhibits their subsequent elimination. These findings may extend to tumor biology and the control of chronic viral diseases.

Induction of cytotoxic T lymphocyte (CTL) responses after immunization with minor histocompatibility antigens, such as the HY-antigen, requires the presence of T helper cells (Th cells) (Husmann, L. A., and M. J. Bevan, Ann. NY. Acad. Sci. 532:158 (1988); Guerder, S., and P. Matzinger, J. Exp. Med. 176:553 (1992)). CTL-responses induced by cross-priming, i.e. by priming with exogenous antigens that reached the class I pathway, have also been shown to require the presence of Th cells (Bennett, S. R. M., et al., J. Exp. Med. 186:65 (1997)). These observations have important consequences for tumor therapy where T help may be critical for the induction of protective CTL responses by tumor cells (Ossendorp, F., et al., J. Exp. Med. 187:693 (1998)).

An important effector molecule on activated Th cells is the CD40-ligand (CD40L) interacting with CD40 on B cells, macrophages and dendritic cells (DCs) (Foy, T. M., et al., *Annu. Rev. Immunol.* 14:591 (1996)). Triggering of CD40 on B cells is essential for isotype switching and the generation of B cell memory (Foy, T. M., et al., *Ann. Rev. Immunol.* 14:591 (1996)). More recently, it was shown that stimulation of CD40 on macrophages and DCs leads to their activation and maturation (Cella, M., et al., *Curr. Opin. Immunol.* 9:10 (1997); Banchereau, J., and R. M. Steinman *Nature* 392:245 (1998)). Specifically, DCs upregulate costimulatory molecules and produce cytokines such as IL-12 upon activation. Interestingly, this CD40L-mediated maturation of DCs seems to be responsible for the helper effect on CTL responses. In fact, it has recently been shown that CD40-triggering by Th cells renders DCs able to initiate a CTL-response (Ridge, J. P., et al., *Nature* 393:474 (1998); Bennett, S. R. M., et al., *Nature* 393:478 (1998); Schoenenberger, S. P., et al., *Nature* 393:480 (1998)). This is consistent with the earlier observation that Th cells have to recognize their ligands on the same APC as the CTLs, indicating that a cognate interaction is required (Bennett, S. R. M., et al., *J. Exp. Med.* 186:65 (1997)). Thus CD40L-mediated stimulation by Th cells leads to the activation of DCs, which subsequently are able to prime CTL-responses. In the human, type I interferons, in particular interferon $\alpha$ and $\beta$ may be equally important as IL-12.

In contrast to these Th-dependent CTL responses, viruses are often able to induce protective CTL-responses in the absence of T help (for review, see (Bachmann, M. F., et al., *J. Immunol.* 161:5791 (1998)). Specifically, lymphocytic choriomeningitis virus (LCMV) (Leist, T. P., et al., *J. Immunol.* 138:2278 (1987); Ahmed, R., et al., *J. Virol.* 62:2102 (1988); Battegay, M., et al., *Cell Immunol.* 167:115 (1996); Borrow, P., et al., *J. Exp. Med.* 183:2129 (1996); Whitmire, J. K., et al., *J. Virol.* 70:8375 (1996)), vesicular stomatitis virus (VSV) (Kündig, T. M., et al., *Immunity* 5:41 (1996)), influenza virus (Tripp, R. A., et al., *J. Immunol.* 155:2955 (1995)), vaccinia virus (Leist, T. P., et al., *Scand. J. Immunol.* 30:679 (1989)) and ectromelia virus (Buller, R., et al., *Nature* 328:77 (1987)) were able to prime CTL-responses in mice depleted of $CD4^+$ T cells or deficient for the expression of class II or CD40. The mechanism for this Th cell independent CTL-priming by viruses is presently not understood. Moreover, most viruses do not stimulate completely Th cell independent CTL-responses, but virus-specific CTL-activity is reduced in Th-cell deficient mice. Thus, Th cells may enhance anti-viral CTL-responses but the mechanism of this help is not fully understood yet. DCs have recently been shown to present influenza derived antigens by cross-priming (Albert, M. L., et al., *J. Exp. Med.* 188:1359 (1998); Albert, M. L., et al., *Nature* 392:86 (1998)). It is therefore possible that, similarly as shown for minor histocompatibility antigens and tumor antigens (Ridge, J. P., et al., *Nature* 393:474 (1998); Bennett, S. R. M., et al., *Nature* 393:478 (1998); Schoenenberger, S. P., et al., *Nature* 393:480 (1998)), Th cells may assist induction of CTLs via CD40 triggering on DCs. Thus, stimulation of CD40 using CD40L or anti-CD40 antibodies may enhance CTL induction after stimulation with viruses or tumor cells.

However, although CD40L is an important activator of DCs, there seem to be additional molecules that can stimulate maturation and activation of DCs during immune responses. In fact, CD40 is not measurably involved in the induction of CTLs specific for LCMV or VSV (Ruedl, C., et al., *J. Exp. Med.* 189:1875 (1999)). Thus, although VSV-specific CTL responses are partly dependent upon the presence of $CD4^+$ T cells (Kündig, T. M., et al., *Immunity* 5:41 (1996)), this helper effect is not mediated by CD40L. Candidates for effector molecules triggering maturation of DCs during immune responses include Trance and TNF$\alpha$ (Bachmann, M. F., et al., *J. Exp. Med.* 189:1025 (1999); Sallusto, F., and A. Lanzavecchia, *J Exp Med* 179:1109 (1994)).

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen.

Unlike isolated proteins, viruses induce prompt and efficient immune responses in the absence of any adjuvants both with and without T-cell help (Bachmann & Zinkernagel, *Ann. Rev. Immunol.* 15:235-270 (1997)). Although viruses often consist of few proteins, they are able to trigger much stronger immune responses than their isolated components. For B cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann & Zinkernagel, *Immunol. Today* 17:553-558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann & Zinkernagel, *Ann. Rev. Immunol.* 15:235-270 (1997)). Viral structure is even linked to the generation of anti-antibodies in autoimmune disease and as a part of the natural response to pathogens (see Fehr, T., et al., *J. Exp. Med.* 185:1785-1792 (1997)). Thus, antigens on viral particles that are organized in an ordered and repetitive array are highly immunogenic since they can directly activate B cells.

In addition to strong B cell responses, viral particles are also able to induce the generation of a cytotoxic T cell response, another crucial arm of the immune system. These cytotoxic T cells are particularly important for the elimination of non-cytopathic viruses such as HIV or Hepatitis B virus and for the eradication of tumors. Cytotoxic T cells do not recognize native antigens but rather recognize their degradation products in association with MHC class I molecules (Townsend & Bodmer, *Ann. Rev. Immunol.* 7:601-624 (1989)). Macrophages and dendritic cells are able to take up and process exogenous viral particles (but not their soluble, isolated components) and present the generated degradation product to cytotoxic T cells, leading to their activation and proliferation (Kovacsovics-Bankowski et al., *Proc. Natl. Acad. Sci. USA* 90:4942-4946 (1993); Bachmann et al., *Eur. J. Immunol.* 26:2595-2600 (1996)).

Viral particles as antigens exhibit two advantages over their isolated components: (1) due to their highly repetitive surface structure, they are able to directly activate B cells, leading to high antibody titers and long-lasting B cell memory; and (2) viral particles, but not soluble proteins, have the potential to induce a cytotoxic T cell response, even if the viruses are non-infectious and adjuvants are absent.

Several new vaccine strategies exploit the inherent immunogenicity of viruses. Some of these approaches focus on the particulate nature of the virus particle; for example see Harding, C. V. and Song, R., (*J. Immunology* 153:4925 (1994)), which discloses a vaccine consisting of latex beads and antigen; Kovacsovics-Bankowski, M., et al. (*Proc. Natl. Acad. Sci. USA* 90:4942-4946 (1993)), which discloses a vaccine consisting of iron oxide beads and antigen; U.S. Pat. No. 5,334,394 to Kossovsky, N., et al., which discloses core particles coated with antigen; U.S. Pat. No. 5,871,747, which discloses synthetic polymer particles carrying on the surface one or more proteins covalently bonded thereto; and a core particle with a non-covalently bound coating, which at least partially covers the surface of said core particle, and at least one biologically active agent in contact with said coated core particle (see, e.g., WO 94/15585).

In a further development, virus-like particles (VLPs) are being exploited in the area of vaccine production because of both their structural properties and their non-infectious nature. VLPs are supermolecular structures built in a symmetric manner from many protein molecules of one or more types. They lack the viral genome and, therefore, are noninfectious. VLPs can often be produced in large quantities by heterologous expression and can be easily be purified.

In addition, DNA rich in non-methylated CG motifs (CpG), as present in bacteria and most non-vertebrates, exhibits a potent stimulatory activity on B cells, dendritic cells and other APC's in vitro as well as in vivo. Although bacterial DNA is immunostimulatory across many vertebrate species, the individual CpG motifs may differ. In fact, CpG motifs that stimulate mouse immune cells may not necessarily stimulate human immune cells and vice versa.

Although DNA oligomers rich in CpG motifs can exhibit immunostimulatory capacity, their efficiency is often limited, since they are unstable in vitro and in vivo. Thus, they exhibit unfavorable pharmacokinetics. In order to render CpG-oligonucleotides more potent, it is therefore usually necessary to stabilize them by introducing phosphorothioate modifications of the phosphate backbone.

A second limitation for the use of CpG-oligonucleotides to stimulate immune responses is their lack of specificity, since all APC's and B cells in contact with CpG-oligonucleotides become stimulated. Thus, the efficiency and specificity of CpG-oligonucleotides may be improved by stabilizing them or packaging them in a way that restricts cellular activation to those cells that also present the relevant antigen.

In addition, immunostimulatory CpG-oligodeoxynucleotides induce strong side effects by causing extramedullary hemopoiesis accompanied by splenomegaly and lymphadenopathy in mice (Sparwasser et al., *J. Immunol.* (1999), 162: 2368-74 and Example 18).

VLPs have been shown to be efficiently presented on MHC class I molecules as they, presumably after uptake by macropinocytosis, are efficiently processed and crossprimed onto MHC class I. The mechanism of crosspriming is not clear to date, but TAP-dependent and TAP-independent pathways have been proposed.

There have been remarkable advances made in vaccination strategies recently, yet there remains a need for improvement on existing strategies. In particular, there remains a need in the art for the development of new and improved vaccines that promote a strong CTL immune response and anti-pathogenic protection as efficiently as natural pathogens in the absence of generalized activation of APCs and other cells.

SUMMARY OF THE INVENTION

This invention is based on the surprising finding that immunostimulatory substances such as DNA oligonucleotides can be packaged into VLPs which renders them more immunogenic. Unexpectedly, the nucleic acids and oligonucleotides, respectively, present in VLPs can be replaced specifically by the immunostimulatory substances and DNA-oligonucleotides containing CpG motifs, respectively. Surprisingly, these packaged immunostimulatory substances, in particular immunostimulatory nucleic acids such as unmethylated CpG-containing oligonucleotides retained their immunostimulatory capacity without widespread activation of the innate immune system. The compositions comprising VLP's and the immunostimulatory substances in accordance with the present invention, and in particular the CpG-VLPs are dramatically more immunogenic than their CpG-free counterparts and induce enhanced B and T cell responses. The immune response against antigens optionally coupled, fused or attached otherwise to the VLPs is similarly enhanced as the immune response against the VLP itself. In addition, the T cell responses against both the VLPs and antigens are especially directed to the Th1 type. Antigens attached to CpG-loaded VLPs may therefore be ideal vaccines for prophylactic or therapeutic vaccination against allergies, tumors and other self-molecules and chronic viral diseases.

In a first embodiment, the invention provides a composition for enhancing an immune response in an animal comprising a virus-like particle and an immunostimulatory substance, preferably an immunostimulatory nucleic acid, an even more preferably an unmethylated CpG-containing oligonucleotide, where the substance, nucleic acid or oligonucleotide is coupled, fused, or otherwise attached to or enclosed by, i.e., bound, to the virus-like particle. In another embodiment, the composition further comprises an antigen bound to the virus-like particle.

In a preferred embodiment of the invention, the immunostimulatory nucleic acids, in particular the unmethylated CpG-containing oligonucleotides are stabilized by phosphorothioate modifications of the phosphate backbone. In another preferred embodiment, the immunostimulatory nucleic acids, in particular the unmethylated CpG-containing oligonucleotides are packaged into the VLPs by digestion of RNA within the VLPs and simultaneous addition of the DNA oligonucleotides containing CpGs of choice. In an equally preferred embodiment, the VLPs can be disassembled before they are reassembled in the presence of CpGs.

In a further preferred embodiment, the immunostimulatory nucleic acids do not contain CpG motifs but nevertheless exhibit immunostimulatory activities. Such nucleic acids are described in WO 01/22972. All sequences described therein are hereby incorporated by way of reference.

In a further preferred embodiment, the virus-like particle is a recombinant virus-like particle. Also preferred, the virus-like particle is free of a lipoprotein envelope. Preferably, the recombinant virus-like particle comprises, or alternatively consists of, recombinant proteins of Hepatitis B virus, BK virus or other human Polyoma virus, measles virus, Sindbis virus, Rotavirus, Foot-and-Mouth-Disease virus, Retrovirus, Norwalk virus or human Papilloma virus, RNA-phages, Qβ-phage, GA-phage, fr-phage and Ty. In a specific embodiment, the virus-like particle comprises, or alternatively consists of, one or more different Hepatitis B virus core (capsid) proteins (HBcAgs).

In a further preferred embodiment, the virus-like particle comprises recombinant proteins, or fragments thereof, of a RNA-phage. Preferred RNA-phages are Qβ-phage, AP 205-phage, GA-phage, fr-phage In another embodiment, the antigen is a recombinant antigen. In yet another embodiment, the antigen can be selected from the group consisting of: (1) a polypeptide suited to induce an immune response against cancer cells; (2) a polypeptide suited to induce an immune response against infectious diseases; (3) a polypeptide suited to induce an immune response against allergens; (4) a polypeptide suited to induce an improved response against self-antigens; and (5) a polypeptide suited to induce an immune response in farm animals or pets.

In yet another embodiment, the antigen can be selected from the group consisting of: (1) an organic molecule suited to induce an immune response against cancer cells; (2) an organic molecule suited to induce an immune response against infectious diseases; (3) an organic molecule suited to induce an immune response against allergens; (4) an organic molecule suited to induce an improved response against self-antigens; (5) an organic molecule suited to induce an immune response in farm animals or pets; and (6) an organic molecule suited to induce a response against a drug, a hormone or a toxic compound.

In a particular embodiment, the antigen comprises, or alternatively consists of, a cytotoxic T cell epitope. In a related embodiment, the virus-like particle comprises the Hepatitis B virus core protein and the cytotoxic T cell epitope is fused to the C-terminus of said Hepatitis B virus core protein. In one embodiment, they are fused by a leucine linking sequence.

In another aspect of the invention, there is provided a method of enhancing an immune response in a human or other animal species comprising introducing into the animal a composition comprising a virus-like particle and immunostimulatory substance, preferably an immunostimulatory nucleic acid, an even more preferably an unmethylated CpG-containing oligonucleotide where the substance, preferably the nucleic acid, and even more preferably the oligonucleotide is bound (i.e. coupled, attached or enclosed) to the virus-like particle. In a further embodiment, the composition further comprises an antigen bound to the virus-like particle.

In yet another embodiment of the invention, the composition is introduced into an animal subcutaneously, intramuscularly, intranasally, intradermally, intravenously or directly into a lymph node. In an equally preferred embodiment, the immune enhancing composition is applied locally, near a tumor or local viral reservoir against which one would like to vaccinate.

In a preferred aspect of the invention, the immune response is a T cell response, and the T cell response against the antigen is enhanced. In a specific embodiment, the T cell response is a cytotoxic T cell response, and the cytotoxic T cell response against the antigen is enhanced.

The present invention also relates to a vaccine comprising an immunologically effective amount of the immune enhancing composition of the present invention together with a pharmaceutically acceptable diluent, carrier or excipient. In a preferred embodiment, the vaccine further comprises at least one adjuvant, such as incomplete Freund's adjuvant. The invention also provides a method of immunizing and/or treating an animal comprising administering to the animal an immunologically effective amount of the disclosed vaccine.

In a preferred embodiment of the invention, the immunostimulatory substance-containing VLPs, preferably the immunostimulatory nucleic acid-containing VLP's, an even more preferably the unmethylated CpG-containing oligonucicotide VLPs are used for vaccination of animals or humans against the VLP itself or against antigens coupled, fused or attached otherwise to the VLP. The modified VLPs can be used to vaccinate against tumors, viral diseases, self-molecules and self antigens, respectively, or non-peptidic small molecules, for example. The vaccination can be for prophylactic or therapeutic purposes, or both. Also, the modified VLPs can be used to vaccinate against allergies in order to induce immune-deviation.

In the majority of cases, the desired immune response will be directed against antigens coupled, fused or attached otherwise to the immunostimulatory substance-containing VLPs, preferably the immunostimulatory nucleic acid-containing VLP's, an even more preferably the unmethylated CpG-containing oligonucleotide VLPs. The antigens can be peptides, proteins, domains, carbohydrates or small molecules such as, for example, steroid hormones or drugs, such as nicotine. Under some conditions, the desired immune response can be directed against the VLP itself. This latter application will be used in cases where the VLP originates from a virus against which one would like to vaccinate.

The route of injection is preferably subcutaneous or intramuscular, but it would also be possible to apply the CpG-containing VLPs intradermally, intranasally, intravenously or directly into the lymph node. In an equally preferred embodiment, the CpG-containing antigen-coupled or free VLPs are applied locally, near a tumor or local viral reservoir against which one would like to vaccinate.

It is to be understood that both the foregoing general description and the following detailed description are exemplary and explanatory only and are intended to provide further explanation of the invention as claimed.

BRIEF DESCRIPTION OF THE DRAWINGS/FIGURES

FIG. 1 shows the DNA sequence of the CpG-oligonucleotide (SEQ ID NO:109) (A) and the DNA sequence (SEQ ID NO:1) and the corresponding protein sequence (SEQ ID NO:2) of the peptide p33-containing VLP derived from hepatitis B core (B). The nonameric p33 epitope is genetically fused to the C-terminus of the hepatitis B core protein at position 185 via a three leucine linking sequence.

FIG. 2 shows the structure of the p33-VLPs as assessed by electron microscopy (A) and SDS PAGE (B). Recombinantly produced wild-type VLPs (composed of HBcAg [aa 1-185] monomers) and p33-VLPs were loaded onto a Sephacryl S-400 gel filtration column (Amersham Pharmacia Biotechnology AG) for purification. Pooled fractions were loaded onto a Hydroxyapatite column. Flow through (which contains purified HBc capsids) was collected and loaded onto a reducing SDS-PAGE gel for monomer molecular weight analysis (B).

FIG. 3 shows p33-VLPs in a native agarose gel electrophoresis (1% agarose) after control incubation or after digestion with RNase A upon staining with ethidium bromide (A) or Coomassie blue (B) in order to assess for the presence of RNA or protein. Recombinantly produced p33-VLPs were diluted at a final concentration of 0.5 ug/ul protein in PBS buffer and incubated in the absence (lane 1) or presence (lane 2) of RNase A (100 ug/ml) (Sigma, Division of Fluka AG, Switzerland) for 2 h at 37° C. The samples were subsequently complemented with 6-fold concentrated DNA-loading buffer (MBS Fermentas GmbH, Heidelberg, Germany) and run for 30 min at 100 volts in a 1% native agarose gel. The Gene Ruler marker (MBS Fermentas GmbH, Heidelberg, Germany) was used as reference for p33-VLPs migration velocity (lane M). Arrows are indicating the presence of RNA packaged in p33-VLPs (A) or p33-VLP capsids themselves (B). Identical results were obtained in 3 independent experiments.

FIG. 4 shows p33-VLPs in a native agarose gel electrophoresis (1% agarose) after control incubation or after digestion with RNase A in the presence of buffer only or CpG-containing DNA-oligomers upon staining with ethidium bromide (A) or Coomassie blue (B) in order to assess for the presence of RNA/DNA or protein. Recombinant p33-VLPs were diluted at a final concentration of 0.5 ug/ul protein in PBS buffer and incubated in the absence (lane 1) or presence (lane 2 and 3) of RNase A (100 ug/ml) (Sigma, Division of Fluka AG, Switzerland) for 2 h at 37° C. 5 nmol CpG-oligonucleotides (containing phosphorothioate modification of the backbone) were added to sample 3 before RNase A digestion. The Gene Ruler marker (MBS Fermentas GmbH, Heidelberg, Germany) was used as reference for p33-VLPs migration velocity (lane M). Arrows are indicating the presence of RNA or CpG-oligonucleotides in p33-VLPs (A) or p33-VLPs capsids themselves (B). Identical results were obtained when CpG oligonucleotides with phosphodiester bonds were used for co-incubation of VLPs with RNase A.

FIG. 5 shows p33-VLPs in a native agarose gel electrophoresis (1% agarose) before and after digestion with RNase A in the presence of CpG-containing DNA-oligomers and subsequent dialysis (for the elimination of VLP-unbound CpG DNA) upon staining with ethidium bromide (A) or Coomassie blue (B) in order to assess for the presence of DNA or protein. Recombinant p33-VLPs were diluted at a final concentration of 0.5 ug/ul protein in PBS buffer and incubated in absence (lane 1) or in presence (lanes 2 to 5) of RNase A (100 ug/ml) (Sigma, Division of Fluka AG, Switzerland) for 2 h at 37° C. 50 nmol CpG-oligonucleotides (containing phosphorothioate modification of the phosphate backbone: lanes 2 and 3, containing phosphodiester bonds: lanes 4 and 5) were added to VLPs before RNase A digestion. Treated samples were extensively dialysed for 24 hours against PBS (4500-fold dilution) with a 300 kDa MWCO dialysis membrane (Spectrum Medical Industries Inc., Houston, USA) to eliminate the in excess DNA (lanes 3 and 5). The Gene Ruler marker (MBS Fermentas GmbH, Heidelberg, Germany) was used as reference for p33-VLPs migration velocity (lane M). Arrows are indicating the presence of RNA or CpG-oligonucleotides in p33-VLPs (A) or p33-VLP capsids themselves (B).

FIG. 6 shows p33-VLPs in a native agarose gel electrophoresis (1% agarose) after control incubation or after digestion with RNase A where CpG-containing oligonucleotides were added only after completing the RNA digestion upon staining with ethidium bromide (A) or Coomassie blue (B) in order to assess for the presence of RNA/DNA or protein. Recombinant p33-VLPs were diluted at a final concentration of 0.5 ug/ul protein in PBS buffer and incubated in the absence (lane 1) or presence (lane 2 and 3) of RNase A (100 ug/ml) (Sigma, Division of Fluka AG, Switzerland) for 2 h at 37° C. 5 nmol CpG-oligonucleotides (containing phosphorothioate modification of the phosphate backbone) were added to sample 3 only after the RNase A digestion. The Gene Ruler marker (MBS Fermentas GmbH, Heidelberg, Germany) was used as reference for p33-VLPs migration velocity (lane M). Arrows are indicating the presence of RNA or CpG-oligonucleotides in p33-VLPs (A) or p33-VLP capsids themselves (B). Identical results were obtained when CpG oligonucleotides with phosphodiester bonds were used for reassembly of VLPs.

FIG. 7 shows that p33-VLPs packaged with CpG-oligonucleotides (containing phosphorothioate modification of the phosphate backbone), are effective at inducing viral protection. Mice were subcutaneously primed with 100 μg p33-VLP alone, mixed with 20 nmol CpG-oligonucleotide (p33-VLP+CpG) or p33-VLP packaged with CpG-oligonucleotide after dialysis of free CpG-oligonucleotide (p33-VLP/CpG). Untreated naïve mice served as negative control. Twenty-one days later, mice were challenged with LCMV (200 pfu, intravenously) and viral titers were assessed in the spleens 5 days later as described in Bachmann, M. F., "Evaluation of lymphocytic choriomeningitis virus-specific cytotoxic T cell responses," in *Immunology Methods Manual*, Lefkowitz, I., ed., Academic Press Ltd., New York, N.Y. (1997) p. 1921.

FIG. 8 shows that p33-VLPs packaged with CpG-oligonucleotide (containing phosphodiester bonds) are effective at inducing viral protection. Mice were subcutaneously primed with 100 μg p33-VLP alone, mixed with 20 nmol CpG-oligonucleotides (p33-VLP+CpG) or p33-VLPs packaged with CpG-oligonucleotides after dialysis of free CpG-oligonucleotides) (p33-VLP/CpG). Untreated naïve mice served as negative control. Twenty-one days later, mice were challenged with LCMV (200 pfu, intravenously) and viral titers were assessed in the spleens 5 days later as described in Bachmann, M. F., "Evaluation of lymphocytic choriomeningitis virus-specific cytotoxic T cell responses," in *Immunology Methods Manual*, Lefkowitz, I., ed., Academic Press Ltd., New York, N.Y. (1997) p. 1921.

FIG. 9 shows that mice treated with CpG-oligonucleotides alone are not protected from viral infection. Mice were subcutaneously primed with 20 nmol CpG-oligonucleotides (CpG), or left untreated as negative control (naive). Twenty-one days later, mice were challenged with LCMV (200 pfu, intravenously) and viral titers were assessed in the spleens 5 days later as described in Bachmann, M. F., "Evaluation of lymphocytic choriomeningitis virus-specific cytotoxic T cell responses," in *Immunology Methods Manual*, Lefkowitz, I., ed., Academic Press Ltd., New York, N.Y. (1997) p. 1921.

FIG. 10 shows the amino acid sequence of the BKV (AS) VP1 protein (GI:332779, SEQ ID NO:3). This sequence was expressed in yeast to produce BKV capsids (Sasnauskas K. et al., *J. Biol Chem* 380(3):381 (1999); K. et al., *Generation of recombinant virus-like particles of different polyomaviruses in yeast*. 3$^{rd}$ International Workshop "Virus-like particles as vaccines" Berlin, (2001)).

FIG. 11 shows the DNA sequence of the 246 bp double stranded DNA fragment (SEQ ID NO:4) used for packaging and stabilization of BKV VLPs.

FIG. 12 shows BKV VLPs (15 μg) in a native 0.8% agarose gel electrophoresis after control incubation or after digestion with RNase A and subsequent incubation with fluorescent phosphorothioate (pt) CpG-oligonucleotides. UV excitation leads to detection of DNA in an ethidium bromide stained gel (A) and to fluorescence of CpG-FAM oligomers in the absence of ethidium bromide (B). Lane 1: BKV VLPs untreated; lane 2: BKV VLPs RNase A treated; lane 3: BKV VLPs RNase A treated with CpG(pt)-FAM; lane 4: BKV VLPs RNase A treated with CpG(pt)-FAM plus DNaseI treatment; lane M: Gene Ruler 1 kb DNA ladder (MBI Fermentas GmbH, Heidelberg, Germany). Arrows are indicating the presence of RNA or CpG-FAM oligomers in BKV VLPs.

FIG. 13 shows BKV VLPs (15 μg) in a native 0.8% agarose gel electrophoresis after control incubation or after digestion with RNase A and subsequent incubation with double stranded (ds) DNA (246 bp) upon staining with ethidium bromide (A) or Coomassie Blue (B). Lane 1: BKV VLPs untreated; lane 2: BKV VLPs RNase A treated; lane 3: BKV VLPs treated with RNase A and incubated with ds DNA; lane M: Gene Ruler 1 kb DNA ladder (MBI Fermentas GmbH, Heidelberg, Germany). Arrows indicate the presence of RNA or ds DNA in BKV VLPs.

FIG. 14 shows BKV VLPs (15 μg) in a native 0.8% agarose gel electrophoresis after control incubation or after digestion with RNase A and subsequent incubation with CpG-oligonucleotides (with phosphate- or with phosphorothioate (pt) backbone) upon staining with ethidium bromide (A) or Coomassie Blue (B). Lane 1: BKV VLPs stock (PBS/50% glycerol); lane 2: BKV VLPs untreated (PBS buffer); lane 3: BKV VLPs RNase A treated; lane 4: BKV VLPs RNase A treated post-dialysis; lane 5: BKV VLPs RNase A treated with CpG-oligonucleotides; lane 6: BKV VLPs RNase A treated with CpG(pt)-oligomers; lane 7: BKV VLPs RNase A treated with CpG(pt)-oligomers post-dialysis; lane M: Gene Ruler 1 kb DNA ladder (MBI Fermentas GmbH, Heidelberg, Germany). Arrows indicate the presence of RNA or CpG-oligonucleotides in BKV VLPs.

FIG. 15 shows mouse IgG1 and IgG2a OD50% antibody titers to BKV VLPs on day 14 after immunization with BKV VLPs and phosphorothioate (pt) CpG-oligonucleotides. Lane 1: RNase treated BKV VLPs; lane 2: RNase treated BKV VLPs in combination with 0.3 nmol CpG(pt)-oligomer; lane 3: RNase treated BKV VLPs in combination with 20 nmol CpG(pt)-oligomer; lane 4: RNase treated BKV VLPs containing 0.3 nmol CpG(pt)-oligomer.

FIG. 16 shows p33-VLPs in a native agarose gel electrophoresis (1% agarose) after control incubation or after digestion with RNase A where linear double-stranded DNA (350 base pairs long) was added only after completing the RNA digestion upon staining with ethidium bromide (A) or Coomassie blue (B) in order to assess for the presence of RNA/DNA or protein. Recombinant p33-VLPs were diluted at a final concentration of 0.5 ug/ul protein in PBS buffer and incubated in the absence (lane 1) or presence (lanes 2, 3 and 4) of RNase A (100 ug/ml) (Sigma, Division of Fluka AG, Switzerland) for 2 h at 37° C. Linear double-stranded DNA of 350 bp in length was added to sample 3 and 4 only after the RNase A digestion to a final concentration of 100 ng/ml and incubated for 3 hours at 37° C. Sample 4 was further digested with DNase I (50 IU/ml)(Sigma, Division of Fluka AG, Switzerland) for additional 3 hours at 37° C. The Gene Ruler marker (MBS Fermentas GmbH, Heidelberg, Germany) was used as reference for p33-VLPs migration velocity (lane M). Arrows are indicating the presence of RNA/dsDNA free or enclosed in p33-VLPs (A) and p33-VLPs (B).

FIG. 49 shows different immunostimulatory nucleic acids packaged in VLP fused to antigen result in a potent antigen-specific CTL response and virus protection.

DETAILED DESCRIPTION OF THE INVENTION

Figure 2A:
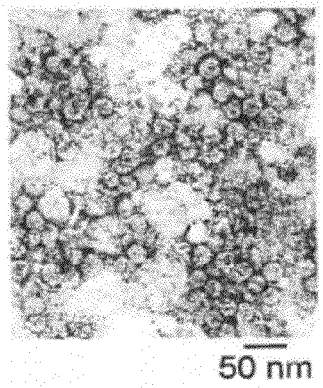

Unless defined otherwise, all technical and scientific terms used herein have the same meanings as commonly understood by one of ordinary skill in the art to which this invention

1. DEFINITIONS

Amino acid linker: An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occurring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1-C6 alkyl-, cycloalkyl (C5,C6), aryl or heteroaryl moiety. However, in addition to an amino acid linker, a linker comprising preferably a C1-C6 alkyl-, cycloalkyl-(C5,C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Animal: As used herein, the term "animal" is meant to include, for example, humans, sheep, horses, cattle, pigs, dogs, cats, rats, mice, mammals, birds, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds and mammals. Preferably, the antibodies are human, murine, rabbit, goat, guinea pig, camel, horse or chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598 by Kucherlapati et al.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens.

A "microbial antigen" as used herein is an antigen of a microorganism and includes, but is not limited to, infectious virus, infectious bacteria, parasites and infectious fungi. Such antigens include the intact microorganism as well as natural isolates and fragments or derivatives thereof and also synthetic or recombinant compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to the skilled artisan.

Examples of infectious viruses that have been found in humans include but are not limited to: Retroviridae (e.g. human immunodeficiency viruses, such as HIV-1 (also referred to as HTLV-III, LAV or HTLV-III/LAV, or HIV-III); and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to, *Pasteurella* species, Staphylococci species and *Streptococcus* species. Gram negative bacteria include, but are not limited to, *Escherichia coli, Pseudomonas* species, and *Salmonella* species. Specific examples of infectious bacteria include but are not limited to: *Helicobacter pyloris, Borelia burgdorferi, Legionella pneumophilia, Mycobacteria* sps. (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers,*

*Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia, Actinomyces israelii* and *Chlamydia*.

Examples of infectious fungi include: *Cryptococcus neoformans, Histoplasma capsulatum, Coccidioides immitis, Blastomyces dermatitidis, Chlamydia trachomatis* and *Candida albicans*. Other infectious organisms (i.e., protists) include: *Plasmodium* such as *Plasmodium falciparum, Plasmodium malariae, Plasmodium ovale, Plasmodium vivax, Toxoplasma gondii* and *Shistosoma*.

Other medically relevant microorganisms have been descried extensively in the literature, e.g., see C. G. A. Thomas, "Medical Microbiology", Bailliere Tindall, Great Britain 1983, the entire contents of which is hereby incorporated by reference.

The compositions and methods of the invention are also useful for treating cancer by stimulating an antigen-specific immune response against a cancer antigen. A "tumor antigen" as used herein is a compound, such as a peptide, associated with a tumor or cancer and which is capable of provoking an immune response. In particular, the compound is capable of provoking an immune response when presented in the context of an MHC molecule. Tumor antigens can be prepared from cancer cells either by preparing crude extracts of cancer cells, for example, as described in Cohen, et al., *Cancer Research*, 54:1055 (1994), by partially purifying the antigens, by recombinant technology or by de novo synthesis of known antigens. Tumor antigens include antigens that are antigenic portions of or are a whole tumor or cancer polypeptide. Such antigens can be isolated or prepared recombinantly or by any other means known in the art. Cancers or tumors include, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors.

Antigen presenting cell: As used herein, the term "antigen presenting cell" is meant to refer to a heterogenous population of leucocytes or bone marrow derived cells which possess an immunostimulatory capacity. For example, these cells are capable of generating peptides bound to MHC molecules that can be recognized by T cells. The term is synonymous with the term "accessory cell" and includes, for example, Langerhans' cells, interdigitating cells, B cells, macrophages and dendritic cells. Under some conditions, epithetral cells, endothelial cells and other, non-bone marrow derived cells may also serve as antigen presenting cells.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

Attachment Site, First: As used herein, the phrase "first attachment site" refers to an element of non-natural or natural origin, to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the virus-like particle. Multiple first attachment sites are present on the surface of virus-like particle typically in a repetitive configuration.

Attachment Site, Second: As used herein, the phrase "second attachment site" refers to an element associated with the antigen or antigenic determinant to which the first attachment site located on the surface of the virus-like particle may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Bound: As used herein, the term "bound" refers to binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term also includes the enclosement, or partial enclosement, of a substance. The term "bound" is broader than and includes terms such as "coupled," "fused," "enclosed", "packaged" and "attached." For example, the immunostimulatory substance such as the unmethylated CpG-containing oligonucicotide can be enclosed by the VLP without the existence of an actual binding, neither covalently nor non-covalently.

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Coupled: As used herein, the term "coupled" refers to attachment by covalent bonds or by strong non-covalent interactions. Any method normally used by those skilled in the art for the coupling of biologically active materials can be used in the present invention.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

CpG: As used herein, the term "CpG" refers to an oligonucleotide which contains an unmethylated cytosine, guanine dinucleotide sequence (e.g. "CpG DNA" or DNA containing a cytosine followed by guanosine and linked by a phosphate bond) and stimulates/activates, e.g. has a mitogenic effect on, or induces or increases cytokine expression by, a vertebrate cell. For example, CpGs can be useful in activating B cells, NK cells and antigen-presenting cells, such as monocytes, dendritic cells and macrophages, and T cells. The CpGs can include nucleotide analogs such as analogs containing phosphorothioester bonds and can be double-stranded or single-stranded. Generally, double-stranded molecules are more stable in vivo, while single-stranded molecules have increased immune activity.

Epitope: As used herein, the term "epitope" refers to portions of a polypeptide having antigenic or immunogenic activity in an animal, preferably a mammal, and most preferably in a human. An "immunogenic epitope," as used herein, is defined as a portion of a polypeptide that elicits an antibody response or induces a T-cell response in an animal, as determined by any method known in the art. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic. Antigenic epitopes can also be T-cell epitopes, in which case they can be bound immunospecifically by a T-cell receptor within the context of an MHC molecule.

An epitope can comprise 3 amino acids in a spatial conformation which is unique to the epitope. Generally, an epitope consists of at least about 5 such amino acids, and more usually, consists of at least about 8-10 such amino acids. If the epitope is an organic molecule, it may be as small as Nitrophenyl.

Immune response: As used herein, the term "immune response" refers to a humoral immune response and/or cellular immune response leading to the activation or proliferation of B- and/or T-lymphocytes. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant.

Immunization: As used herein, the terms "immunize" or "immunization" or related terms refer to conferring the ability to mount a substantial immune response (comprising antibodies or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

Immunostimulatory nucleic acid: As used herein, the term immunostimulatory nucleic acid refers to a nucleic acid capable of inducing and/or enhancing an immune response. Immunostimulatory nucleic acids, as used herein, comprise ribonucleic acids and in particular deoxyribonucleic acids. Preferably, immunostimulatory nucleic acids contain at least one CpG motif e.g. a CG dinucleotide in which the C is unmethylated. The CG dinucleotide can be part of a palindromic sequence or can be encompassed within a non-palindromic sequence. Immunostimulatory nucleic acids not containing CpG motifs as described above encompass, by way of example, nucleic acids lacking CpG dinucleotides, as well as nucleic acids containing CG motifs with a methylated CG dinucleotide. The term "immunostimulatory nucleic acid" as used herein should also refer to nucleic acids that contain modified bases such as 4-bromo-cytosine.

Immunostimulatory substance: As used herein, the term "immunostimulatory substance" refers to a substance capable of inducing and/or enhancing an immune response. Immunostimulatory substances, as used herein, include, but are not limited to, toll-like receptor activating substances and substances inducing cytokine secretion. Toll-like receptor activating substances include, but are not limited to, immunostimulatory nucleic acids, peptideoglycans, lipopolysaccharides, lipoteichonic acids, imidazoquinoline compounds, flagellins, lipoproteins, and immunostimulatory organic substances such as taxol.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 0.5 to 30 nanometers, more preferably 5 to 15 nanometers.

Oligonucleotide: As used herein, the terms "oligonucleotide" or "oligomer" refer to a nucleic acid sequence comprising 2 or more nucleotides, generally at least about 6 nucleotides to about 100,000 nucleotides, preferably about 6 to about 2000 nucleotides, and more preferably about 6 to about 300 nucleotides, even more preferably about 20 to about 300 nucleotides, and even more preferably about 20 to about 100 nucleotides. The terms "oligonucleotide" or "oligomer" also refer to a nucleic acid sequence comprising more than 100 to about 2000 nucleotides, preferably more than 100 to about 1000 nucleotides, and more preferably more than 100 to about 500 nucleotides. "Oligonucleotide" also generally refers to any polyribonucleotide or polydeoxyribonucleotide, which may be unmodified RNA or DNA or modified RNA or DNA. "Oligonucleotide" includes, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "oligonucleotide" refers to triple-stranded regions comprising RNA or DNA or both RNA and DNA. Further, an oligonucleotide can be synthetic, genomic or recombinant, e.g., λ-DNA, cosmid DNA, artificial bacterial chromosome, yeast artificial chromosome and filamentous phage such as M13.

The term "oligonucleotide" also includes DNAs or RNAs containing one or more modified bases and DNAs or RNAs with backbones modified for stability or for other reasons. For example, suitable nucleotide modifications/analogs include peptide nucleic acid, inosin, tritylated bases, phosphorothioates, alkylphosphorothioates, 5-nitroindole deoxyribofuranosyl, 5-methyldeoxycytosine and 5,6-dihydro-5,6-dihydroxydeoxythymidine. A variety of modifications have been made to DNA and RNA; thus, "oligonucleotide" embraces chemically, enzymatically or metabolically modified forms of polynucleotides as typically found in nature, as well as the chemical forms of DNA and RNA characteristic of viruses and cells. Other nucleotide analogs/modifications will be evident to those skilled in the art.

Packaged: The term "packaged" as used herein refers to the state of an immunostimulatory substance, in particular an immunostimulatory nucleic acid in relation to the VLP. The term "packaged" as used herein includes binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term also includes the enclosement, or partial enclosement, of a substance. The term "packaged" includes terms such as "coupled, "enclosed" and "attached." For example, the immunostimulatory substance such as the unmethylated CpG-containing oligonucleotide can be enclosed by the VLP without the existence of an actual binding, neither covalently nor non-covalently. In preferred embodiments, in particular, if immunostimulatory nucleic acids are the immunostimulatory substances, the term "packaged" indicates that the nucleic acid in a packaged state is not accessible to DNAse or RNAse hydrolysis. In preferred embodiments, the immunostimulatory nucleic acid is packaged inside the VLP capsids, most preferably in a non-covalent manner.

The compositions of the invention can be combined, optionally, with a pharmaceutically-acceptable carrier. The term "pharmaceutically-acceptable carrier" as used herein means one or more compatible solid or liquid fillers, diluents or encapsulating substances which are suitable for administration into a human or other animal. The term "carrier" denotes an organic or inorganic ingredient, natural or synthetic, with which the active ingredient is combined to facilitate the application.

Organic molecule: As used herein, the term "organic molecule" refers to any chemical entity of natural or synthetic origin. In particular the term "organic molecule" as used herein encompasses, for example, any molecule being a member of the group of nucleotides, lipids, carbohydrates, polysaccharides, lipopolysaccharides, steroids, alkaloids, terpenes and fatty acids, being either of natural or synthetic origin. In particular, the term "organic molecule" encompasses molecules such as nicotine, cocaine, heroin or other pharmacologically active molecules contained in drugs of abuse. In general an organic molecule contains or is modified to contain a chemical functionality allowing its coupling, binding or other method of attachment to the virus-like particle in accordance with the invention.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis.

A substance which "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}Cr$ release assay, with and without the substance. The amount of the substance at which the CTL lytic activity is enhanced as compared to the CTL lytic activity without the substance is said to be an amount sufficient to enhance the immune response of the animal to the antigen. In a preferred embodiment, the immune response in enhanced by a factor of at least about 2, more preferably by a factor of about 3 or more. The amount of cytokines secreted may also be altered.

Effective Amount: As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Self antigen: As used herein, the term "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology two self-molecules as defined above (>95%, preferably >97%, more preferably >99%) may also be considered self. In a further preferred embodiment of the present invention, the antigen is a self antigen. Very preferred embodiments of self-antigens useful for the present invention are described WO 02/056905, the disclosures of which are herewith incorporated by reference in its entirety.

Treatment: As used herein, the terms "treatment", "treat", "treated" or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

Vaccine: As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response including, but not limited to, the production of antibodies, cytokines and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include incomplete Freund's adjuvant, aluminum hydroxide and modified muramyldipeptide. The term "adjuvant" as used herein also refers to typically specific stimulators of the immune response which when combined with the vaccine of the present invention provide for an even more enhanced and typically specific immune response. Examples include, but limited to, GM-CSF, IL-2, IL-12, IFNα. Further examples are within the knowledge of the person skilled in the art.

Virus-like particle: As used herein, the term "virus-like particle" refers to a structure resembling a virus particle but which has not been demonstrated to be pathogenic. Typically, a virus-like particle in accordance with the invention does not carry genetic information encoding for the proteins of the virus-like particle. In general, virus-like particles lack the viral genome and, therefore, are noninfectious. Also, virus-like particles can often be produced in large quantities by heterologous expression and can be easily purified. Some virus-like particles may contain nucleic acid distinct from their genome. As indicated, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (generated by expression of a Qβ CP gene containing, for example, a TAA stop codon precluding any expression of the longer A1 protein through suppression, see Kozlovska, T. M., et al., *Intervirology* 39: 9-15 (1996)), or additionally contain A1 protein subunits in the capsid assembly.

The term "virus particle" as used herein refers to the morphological form of a virus. In some virus types it comprises a genome surrounded by a protein capsid; others have additional structures (e.g., envelopes, tails, etc.).

Non-enveloped viral particles are made up of a proteinaceous capsid that surrounds and protects the viral genome. Enveloped viruses also have a capsid structure surrounding the genetic material of the virus but, in addition, have a lipid bilayer envelope that surrounds the capsid. In a preferred embodiment of the invention, the VLP's are free of a lipoprotein envelope or a lipoprotein-containing envelope. In a further preferred embodiment, the VLP's are free of an envelope altogether.

One, a, or an: When the terms "one," "a," or "an" are used in this disclosure, they mean "at least one" or "one or more," unless otherwise indicated.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, $2^{nd}$ edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," *Meth. Enzymol.* 128, Academic Press San Diego (1990); Scopes, R. K., "Protein Purification Principles and Practice," $3^{rd}$ ed., Springer-Verlag, New York (1994)) are also adequately described in the literature, all of which are incorporated herein by reference.

2. COMPOSITIONS AND METHODS FOR ENHANCING AN IMMUNE RESPONSE

The disclosed invention provides compositions and methods for enhancing an immune response against one or more antigens in an animal. Compositions of the invention comprise, or alternatively consist of, a virus-like particle and an immunostimulatory substance, preferably an immunostimulatory nucleic acid, and even more preferably an unmethylated CpG-containing oligonucleotide where the an immunostimulatory substance, the immunostimulatory nucleic acid or the oligonucleotide is bound to the virus-like particle. Furthermore, the invention conveniently enables the practitioner to construct such a composition for various treatment and/or prophylactic prevention purposes, which include the prevention and/or treatment of infectious diseases, as well as chronic infectious diseases, and the prevention and/or treatment of cancers, for example.

Virus-like particles in the context of the present application refer to structures resembling a virus particle but which are not pathogenic. In general, virus-like particles lack the viral genome and, therefore, are noninfectious. Also, virus-like particles can be produced in large quantities by heterologous expression and can be easily purified.

In a preferred embodiment, the virus-like particle is a recombinant virus-like particle. The skilled artisan can produce VLPs using recombinant DNA technology and virus coding sequences which are readily available to the public. For example, the coding sequence of a virus envelope or core protein can be engineered for expression in a baculovirus expression vector using a commercially available baculovirus vector, under the regulatory control of a virus promoter, with appropriate modifications of the sequence to allow functional linkage of the coding sequence to the regulatory sequence. The coding sequence of a virus envelope or core protein can also be engineered for expression in a bacterial expression vector, for example.

Examples of VLPs include, but are not limited to, the capsid proteins of Hepatitis B virus (Ulrich, et al., *Virus Res.* 50:141-182 (1998)), measles virus (Warnes, et al., *Gene* 160: 173-178 (1995)), Sindbis virus, rotavirus (U.S. Pat. Nos. 5,071,651 and 5,374,426), foot-and-mouth-disease virus (Twomey, et al., *Vaccine* 13:1603-1610, (1995)), Norwalk virus (Jiang, X., et al., *Science* 250:1580-1583 (1990); Matsui, S. M., et al., *J. Clin. Invest.* 87:1456-1461 (1991)), the retroviral GAG protein (PCT Patent Appl. No. WO 96/30523), the retrotransposon Ty protein p1, the surface protein of Hepatitis B virus (WO 92/11291), human papilloma virus (WO 98/15631), human polyoma virus (Sasnauskas K., et al., *Biol. Chem.* 380(3):381-386 (1999); Sasnauskas K., et al., *Generation of recombinant virus-like particles of different polyomaviruses in yeast.* 3rd International Workshop "Virus-like particles as vaccines." Berlin, Sep. 26-29, 2001), RNA phages, Ty, fr-phage, GA-phage, AP 205-phage and, in particular, Qβ-phage.

As will be readily apparent to those skilled in the art, the VLP of the invention is not limited to any specific form. The particle can be synthesized chemically or through a biological process, which can be natural or non-natural. By way of example, this type of embodiment includes a virus-like particle or a recombinant form thereof. In a more specific embodiment, the VLP can comprise, or alternatively consist of, recombinant polypeptides of Rotavirus; recombinant polypeptides of Norwalk virus; recombinant polypeptides of Alphavirus; recombinant proteins which form bacterial pili or pilus-like structures; recombinant polypeptides of Foot and Mouth Disease virus; recombinant polypeptides of measles virus, recombinant polypeptides of Sindbis virus, recombinant polypeptides of Retrovirus; recombinant polypeptides of Hepatitis B virus (e.g., a HBcAg); recombinant polypeptides of Tobacco mosaic virus; recombinant polypeptides of Flock House Virus; recombinant polypeptides of human Papillomavirus; recombinant polypeptides of Polyoma virus and, in particular, recombinant polypeptides of human Polyoma virus, and in particular recombinant polypeptides of BK virus; recombinant polypeptides of bacteriophages, recombinant polypeptides of RNA phages; recombinant polypeptides of Ty; recombinant polypeptides of fr-phage, recombinant polypeptides of GA-phage, recombinant polypeptides of AP 205-phage and, in particular, recombinant polypeptides of Qβ-phage. The virus-like particle can further comprise, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; and l) bacteriophage PP7.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr.

In a further preferred embodiment of the present invention, the recombinant proteins comprise, or alternatively consist essentially of, or alternatively consist of coat proteins of RNA phages.

RNA-phage coat proteins forming capsids or VLPs, or fragments of the bacteriophage coat proteins compatible with self-assembly into a capsid or a VLP, are, therefore, further preferred embodiments of the present invention. Bacteriophage Qβ coat proteins, for example, can be expressed recombinantly in *E. coli*. Further, upon such expression these proteins spontaneously form capsids. Additionally, these capsids form a structure with an inherent repetitive organization.

Specific preferred examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein), bacteriophage R17 (SEQ ID NO:12; PIR Accession No. VCBPR7), bacteriophage fr (SEQ ID NO:13; PIR Accession No. VCBPFR), bacteriophage GA (SEQ ID NO:14; GenBank Accession No. NP-040754), bacteriophage SP (SEQ ID NO:15; GenBank Accession No. CAA30374 referring to SP CP and SEQ ID NO: 16; Accession No. referring to SP A1 protein), bacteriophage MS2 (SEQ ID NO:17; PIR Accession No. VCBPM2), bacteriophage M11 (SEQ ID NO:18; GenBank Accession No. AAC06250), bacteriophage MX1 (SEQ ID NO:19; GenBank Accession No. AAC14699), bacteriophage NL95 (SEQ ID NO:20; GenBank Accession No. AAC14704), bacteriophage f2 (SEQ ID NO: 21; GenBank Accession No. P03611), bacteriophage PP7 (SEQ ID NO: 22). Furthermore, the A1 protein of bacteriophage Qβ or C-terminal truncated forms missing as much as 100, 150 or 180 amino acids from its C-terminus may be incorporated in a capsid assembly of Qβ coat proteins. Generally, the percentage of Qβ A1 protein relative to Qβ CP in the capsid assembly will be limited, in order to ensure capsid formation.

Qβ coat protein has also been found to self-assemble into capsids when expressed in *E. coli* (Kozlovska T M. et al., *GENE* 137: 133-137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., *Structure* 4: 543-5554 (1996)) leading to a remarkable stability of the capsid of Qβ coat protein. Capsids or VLPs made from recombinant Qβ coat protein may contain, however, subunits not linked via disulfide links to other subunits within the capsid, or incompletely linked. Thus, upon loading recombinant Qβ capsid on non-reducing SDS-PAGE, bands corresponding to monomeric Qβ coat protein as well as bands corresponding to the hexamer or pentamer of Qβ coat protein are visible. Incompletely disulfide-linked subunits could appear as dimer, trimer or even tetramer bands in non-reducing SDS-PAGE. Qβ capsid protein also shows unusual resistance to organic solvents and denaturing agents. Surprisingly, we have observed that DMSO and acetonitrile concentrations as high as 30%, and Guanidinium concentrations as high as 1 M do not affect the stability of the capsid. The high stability of the capsid of Qβ coat protein is an advantageous feature, in particular, for its use in immunization and vaccination of mammals and humans in accordance of the present invention.

Upon expression in *E. coli*, the N-terminal methionine of Qβ coat protein is usually removed, as we observed by N-terminal Edman sequencing as described in Stoll, E. et al. J. Biol. Chem. 252:990-993 (1977). VLP composed from Qβ coat proteins where the N-terminal methionine has not been removed, or VLPs comprising a mixture of Qβ coat proteins where the N-terminal methionine is either cleaved or present are also within the scope of the present invention.

Further RNA phage coat proteins have also been shown to self-assemble upon expression in a bacterial host (Kastelein, R A. et al., *Gene* 23: 245-254 (1983), Kozlovskaya, T M. et al., *Dokl. Akad. Nauk SSSR* 287: 452-455 (1986), Adhin, M R. et al., *Virology* 170: 238-242 (1989), Ni, C Z., et al., *Protein Sci.* 5: 2485-2493 (1996), Priano, C. et al., J. Mol. Biol. 249: 283-297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. *Biochemistry* 28: 71-76 (1989); Lim F. et al., *J. Biol. Chem.* 271: 31839-31845 (1996)). The stem loop and RNA in general are known to be involved in the virus assembly (Golmohammadi, R. et al., *Structure* 4: 543-5554 (1996)).

In a further preferred embodiment of the present invention, the virus-like particle comprises, or alternatively consists essentially of, or alternatively consists of recombinant proteins, or fragments thereof, of a RNA-phage, wherein the recombinant proteins comprise, consist essentially of or alternatively consist of mutant coat proteins of a RNA phage, preferably of mutant coat proteins of the RNA phages mentioned above. In another preferred embodiment, the mutant coat proteins of the RNA phage have been modified by removal of at least one lysine residue by way of substitution, or by addition of at least one lysine residue by way of substitution; alternatively, the mutant coat proteins of the RNA phage have been modified by deletion of at least one lysine residue, or by addition of at least one lysine residue by way of insertion.

In another preferred embodiment, the virus-like particle comprises, or alternatively consists essentially of, or alternatively consists of recombinant proteins, or fragments thereof, of the RNA-bacteriophage Qβ, wherein the recombinant proteins comprise, or alternatively consist essentially of, or alternatively consist of coat proteins having an amino acid sequence of SEQ ID NO:10, or a mixture of coat proteins having amino acid sequences of SEQ ID NO:10 and of SEQ ID NO: 11 or mutants of SEQ ID NO: 11 and wherein the N-terminal methionine is preferably cleaved.

In a further preferred embodiment of the present invention, the virus-like particle comprises, consists essentially of or alternatively consists of recombinant proteins of Qβ, or fragments thereof, wherein the recombinant proteins comprise, or alternatively consist essentially of, or alternatively consist of mutant Qβ coat proteins. In another preferred embodiment, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLPs can, thus, be used in the practice of the invention: "Qβ-240" (Lys13-Arg; SEQ ID NO:23), "Qβ-243" (Asn 10-Lys; SEQ ID NO:24), "Qβ-250" (Lys 2-Arg, Lys13-Arg; SEQ ID NO:25), "Qβ-251" (SEQ ID NO:26) and "Qβ-259" (Lys 2-Arg, Lys16-Arg; SEQ ID NO:27). Thus, in further preferred embodiment of the present invention, the virus-like particle comprises, consists essentially of or alternatively consists of recombinant proteins of mutant Qβ coat proteins, which comprise proteins having an amino acid sequence selected from the group of a) the amino acid sequence of SEQ ID NO: 23; b) the amino acid sequence of SEQ ID NO:24; c) the amino acid sequence of SEQ ID NO: 25; d) the amino acid sequence of SEQ ID NO:26; and e) the amino acid sequence of SEQ ID NO: 27. The construction, expression and purification of the above indicated Qβ coat proteins, mutant Qβ coat protein VLPs and capsids, respectively, are disclosed in pending U.S. application Ser. No. 10/050,902 filed on Jan. 18, 2002. In particular is hereby referred to Example 18 of above mentioned application.

In a further preferred embodiment of the present invention, the virus-like particle comprises, or alternatively consists essentially of, or alternatively consists of recombinant proteins of Qβ, or fragments thereof, wherein the recombinant proteins comprise, consist essentially of or alternatively consist of a mixture of either one of the foregoing Qβ mutants and the corresponding A1 protein.

In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., *J. Gen. Virol.* 83: 1523-33 (2002)). AP205 coat protein can be expressed from plasmid pAP283-58 (SEQ ID NO: 79), which is a derivative of pQb10 (Kozlovska, T. M. et al., *Gene* 137:133-37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in the co-pending U.S. provisional patent application with the title "Molecular Antigen Arrays" (Application No. 60/396,126) and having been filed on Jul. 17, 2002, which is incorporated by reference in its entirety. Vectors pQb10 and pQb185 are vectors derived from pGEM vector, and expression of the cloned genes in these vectors is controlled by the trp promoter (Kozlovska, T. M. et al., *Gene* 137:133-37 (1993)). Plasmid pAP283-58 (SEQ ID NO:79) comprises a putative AP205 ribosomal binding site in the following sequence, which is downstream of the XbaI site, and immediately upstream of the ATG start codon of the AP205 coat protein: tctagaATTTTCTGCGCACCCATC-CCGGGTGGCGCCCAAAGTGAGGAAAATCAC atg (SEQ ID NO:5). The vector pQb185 comprises a Shine Delagarno sequence downstream from the XbaI site and upstream of the start codon (tctagaTTAACCCAACGCGT AGGAGTCAGGCCatg, Shine Delagarno sequence underlined, SEQ ID NO:6).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 80) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the substitution of proline at amino acid 5 to threonine (SEQ ID NO: 81), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 82), which is derived directly from pQb185, and which contains the mutant AP205 coat protein gene instead of the Qβ coat protein gene. Vectors for expression of the AP205 coat protein are transfected into *E. coli* for expression of the AP205 coat protein.

Methods for expression of the coat protein and the mutant coat protein, respectively, leading to self-assembly into VLPs are described in co-pending U.S. provisional patent application with the title "Molecular Antigen Arrays" (Application No. 60/396,126) and having been filed on Jul. 17, 2002, which is incorporated by reference in its entirety. Suitable *E. coli* strains include, but are not limited to, *E. coli* K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., *Gene* 137:133-37 (1993)).

AP205 coat proteins expressed from the vectors pAP283-58 and pAP281-32 may be devoid of the initial Methionine amino-acid, due to processing in the cytoplasm of *E. coli*. Cleaved, uncleaved forms of AP205 VLP, or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or alternatively consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof as described in the co-pending U.S. provisional patent application with the title "Molecular Antigen Arrays (Application No. 60/396,126) and having been filed on Jul. 17, 2002, which is incorporated by reference in its entirety. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

The crystal structure of several RNA bacteriophages has been determined (Golmohammadi, R. et al., *Structure* 4:543-554 (1996)). Using such information, surface exposed residues can be identified and, thus, RNA-phage coat proteins can be modified such that one or more reactive amino acid residues can be inserted by way of insertion or substitution. As a consequence, those modified forms of bacteriophage coat proteins can also be used for the present invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2, bacteriophage AP 205) can also be used to prepare compositions of the present invention.

Although the sequence of the variants proteins discussed above will differ from their wild-type counterparts, these variant proteins will generally retain the ability to form capsids or capsid-like structures. Thus, the invention further includes compositions and vaccine compositions, respectively, which further includes variants of proteins which form capsids or capsid-like structures, as well as methods for preparing such compositions and vaccine compositions, respectively, individual protein subunits used to prepare such compositions, and nucleic acid molecules which encode these protein subunits. Thus, included within the scope of the invention are variant forms of wild-type proteins which form capsids or capsid-like structures and retain the ability to associate and form capsids or capsid-like structures.

As a result, the invention further includes compositions and vaccine compositions, respectively, comprising proteins, which comprise, or alternatively consist essentially of, or alternatively consist of amino acid sequences which are at least 80%, 85%, 90%, 95%, 97%, or 99% identical to wild-type proteins which form ordered arrays and have an inherent repetitive structure, respectively.

Further included within the scope of the invention are nucleic acid molecules which encode proteins used to prepare compositions of the present invention.

In other embodiments, the invention further includes compositions comprising proteins, which comprise, or alternatively consist essentially of, or alternatively consist of amino acid sequences which are at least 80%, 85%, 90%, 95%, 97%, or 99% identical to any of the amino acid sequences shown in SEQ ID NOs:10-27.

Proteins suitable for use in the present invention also include C-terminal truncation mutants of proteins which form capsids or capsid-like structures, or VLPs. Specific examples of such truncation mutants include proteins having an amino acid sequence shown in any of SEQ ID NOs:10-27 where 1, 2, 5, 7, 9, 10, 12, 14, 15, or 17 amino acids have been removed from the C-terminus. Typically, theses C-terminal truncation mutants will retain the ability to form capsids or capsid-like structures.

Further proteins suitable for use in the present invention also include N-terminal truncation mutants of proteins which form capsids or capsid-like structures. Specific examples of such truncation mutants include proteins having an amino acid sequence shown in any of SEQ ID NOs:10-27 where 1, 2, 5, 7, 9, 10, 12, 14, 15, or 17 amino acids have been removed from the N-terminus. Typically, these N-terminal truncation mutants will retain the ability to form capsids or capsid-like structures.

Additional proteins suitable for use in the present invention include N- and C-terminal truncation mutants which form capsids or capsid-like structures. Suitable truncation mutants include proteins having an amino acid sequence shown in any of SEQ ID NOs:10-27 where 1, 2, 5, 7, 9, 10, 12, 14, 15, or 17 amino acids have been removed from the N-terminus and 1, 2, 5, 7, 9, 10, 12, 14, 15, or 17 amino acids have been removed from the C-terminus. Typically, these N-terminal and C-terminal truncation mutants will retain the ability to form capsids or capsid-like structures.

The invention further includes compositions comprising proteins which comprise, or alternatively consist essentially of, or alternatively consist of, amino acid sequences which are at least 80%, 85%, 90%, 95%, 97%, or 99% identical to the above described truncation mutants.

The invention thus includes compositions and vaccine compositions prepared from proteins which form capsids or VLPs, methods for preparing these compositions from individual protein subunits and VLPs or capsids, methods for preparing these individual protein subunits, nucleic acid molecules which encode these subunits, and methods for vaccinating and/or eliciting immunological responses in individuals using these compositions of the present invention.

Fragments of VLPs which retain the ability to induce an immune response can comprise, or alternatively consist of, polypeptides which are about 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450 or 500 amino acids in length, but will obviously depend on the length of the sequence of the subunit composing the VLP. Examples of such fragments include fragments of proteins discussed herein which are suitable for the preparation of the immune response enhancing composition.

In another preferred embodiment of the invention, the VLP's are free of a lipoprotein envelope or a lipoprotein-containing envelope. In a further preferred embodiment, the VLP's are free of an envelope altogether.

The lack of a lipoprotein envelope or lipoprotein-containing envelope and, in particular, the complete lack of an envelope leads to a more defined virus-like particle in its structure and composition. Such more defined virus-like particles, therefore, may minimize side-effects. Moreover, the lack of a lipoprotein-containing envelope or, in particular, the complete lack of an envelope avoids or minimizes incorporation of potentially toxic molecules and pyrogens within the virus-like particle.

As previously stated, the invention includes virus-like particles or recombinant forms thereof. Skilled artisans have the knowledge to produce such particles and attach antigens thereto. By way of providing other examples, the invention provides herein for the production of Hepatitis B virus-like particles as virus-like particles (Example 1).

In one embodiment, the particles used in compositions of the invention are composed of a Hepatitis B capsid (core) protein (HBcAg) or a fragment of a HBcAg which has been modified to either eliminate or reduce the number of free cysteine residues. Zhou et al. (*J. Virol.* 66:5393-5398 (1992)) demonstrated that HBcAgs which have been modified to remove the naturally resident cysteine residues retain the ability to associate and form multimeric structures. Thus, core particles suitable for use in compositions of the invention include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified and their amino acids sequences are readily available to those skilled in the art. For example, the HBcAg protein having the amino acid sequence shown in FIG. 1 is 185 amino acids in length and is generated by the processing of a 212 amino acid Hepatitis B core antigen precursor protein. This processing results in the removal of 29 amino acids from the N-terminus of the Hepatitis B core antigen precursor protein. Similarly, the HBcAg protein that is 185 amino acids in length is generated by the processing of a 214 amino acid Hepatitis B core antigen precursor protein.

In preferred embodiments, vaccine compositions of the invention will be prepared using the processed form of a HBcAg (i.e., a HBcAg from which the N-terminal leader sequence of the Hepatitis B core antigen precursor protein have been removed).

Further, when HBcAgs are produced under conditions where processing will not occur, the HBcAgs will generally be expressed in "processed" form. For example, bacterial systems, such as *E. coli*, generally do not remove the leader sequences, also referred to as "signal peptides," of proteins which are normally expressed in eukaryotic cells. Thus, when an K coli expression system directing expression of the protein to the cytoplasm is used to produce HBcAgs of the invention, these proteins will generally be expressed such that the N-terminal leader sequence of the Hepatitis B core antigen precursor protein is not present.

The preparation of Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in pending U.S. application Ser. No. 10/050,902 filed on Jan. 18, 2002. For the latter application, it is in particular referred to Example 23, 24, 31 and 51. All three documents are explicitly incorporated herein by reference.

The present invention also includes HBcAg variants which have been modified to delete or substitute one or more additional cysteine residues. Thus, the vaccine compositions of the invention include compositions comprising HBcAgs in which cysteine residues not present in the amino acid sequence shown in FIG. 1 have been deleted.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether.

A number of naturally occurring HBcAg variants suitable for use in the practice of the present invention have been identified. Yuan et al., (*J. Virol.* 73:10122-10128 (1999)), for example, describe variants in which the isoleucine residue at position corresponding to position 97 in SEQ ID NO:28 is replaced with either a leucine residue or a phenylalanine residue. The amino acid sequences of a number of HBcAg variants, as well as several Hepatitis B core antigen precursor variants, are disclosed in GenBank reports AAF121240 (SEQ ID NO:29), AF121239 (SEQ ID NO:30), X85297 (SEQ ID NO:31), X02496 (SEQ ID NO:32), X85305 (SEQ ID NO:33), X85303 (SEQ ID NO:34), AF151735 (SEQ ID NO:35), X85259 (SEQ ID NO:36), X85286 (SEQ ID NO:37), X85260 (SEQ ID NO:38), X85317 (SEQ ID NO:39), X85298 (SEQ ID NO:40), AF043593 (SEQ ID NO:41), M20706 (SEQ ID NO:42), X85295 (SEQ ID NO:43), X80925 (SEQ ID NO:44), X85284 (SEQ ID NO:45), X85275 (SEQ ID NO:46), X72702 (SEQ ID NO:47), X85291 (SEQ ID NO:48), X65258 (SEQ ID NO:49), X85302 (SEQ ID NO:50), M32138 (SEQ ID NO:51), X85293 (SEQ ID NO:52), X85315 (SEQ ID NO:53), U95551 (SEQ ID NO:54), X85256 (SEQ ID NO:55), X85316 (SEQ ID NO:56), X85296 (SEQ ID NO:57), AB033559 (SEQ ID NO:58), X59795 (SEQ ID NO:59), X85299 (SEQ ID NO:60), X85307 (SEQ ID NO:61), X65257 (SEQ ID NO:62), X85311 (SEQ ID NO:63), X85301 (SEQ ID NO:64), X85314 (SEQ ID NO:65), X85287 (SEQ ID NO:66), X85272 (SEQ ID NO:67), X85319 (SEQ ID NO:68), AB010289 (SEQ ID NO:69), X85285 (SEQ ID NO:70), AB010289 (SEQ ID NO:71), AF121242 (SEQ ID NO:72), M90520 (SEQ ID NO:73), P03153 (SEQ ID NO:74), AF110999 (SEQ ID NO:75), and M95589 (SEQ ID NO:76), the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:77. Further HBcAg variants suitable for use in the compositions of the invention, and which may be further modified according to the disclosure of this specification are described in WO 00/198333, WO 00/177158 and WO 00/214478.

HBcAgs suitable for use in the present invention can be derived from any organism so long as they are able to enclose or to be coupled or otherwise attached to, in particular as long as they are capable of packaging, an unmethylated CpG-containing oligonucleotide and induce an immune response.

As noted above, generally processed HBcAgs (i.e., those which lack leader sequences) will be used in the vaccine compositions of the invention. The present invention includes vaccine compositions, as well as methods for using these compositions, which employ the above described variant HBcAgs.

Further included within the scope of the invention are additional HBcAg variants which are capable of associating to form dimeric or multimeric structures. Thus, the invention further includes vaccine compositions comprising HBcAg polypeptides comprising, or alternatively consisting of, amino acid sequences which are at least 80%, 85%, 90%, 95%, 97% or 99% identical to any of the wild-type amino acid sequences, and forms of these proteins which have been processed, where appropriate, to remove the N-terminal leader sequence.

Whether the amino acid sequence of a polypeptide has an amino acid sequence that is at least 80%, 85%, 90%, 95%, 97% or 99% identical to one of the wild-type amino acid sequences, or a subportion thereof, can be determined conventionally using known computer programs such the Bestfit program. When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed.

The HBcAg variants and precursors having the amino acid sequences set out in SEQ ID NOs: 29-72 and 73-76 are relatively similar to each other. Thus, reference to an amino acid residue of a HBcAg variant located at a position which corresponds to a particular position in SEQ ID NO:77, refers to the amino acid residue which is present at that position in the amino acid sequence shown in SEQ ID NO:77. The homology between these HBcAg variants is for the most part high enough among Hepatitis B viruses that infect mammals so that one skilled in the art would have little difficulty reviewing both the amino acid sequence shown in SEQ ID NO:77 and in FIG. 1, respectively, and that of a particular HBcAg variant and identifying "corresponding" amino acid residues. Furthermore, the HBcAg amino acid sequence shown in SEQ ID NO:73, which shows the amino acid sequence of a HBcAg derived from a virus which infect woodchucks, has enough homology to the HBcAg having the amino acid sequence shown in SEQ ID NO:77 that it is readily apparent that a three amino acid residue insert is present in SEQ ID NO:73 between amino acid residues 155 and 156 of SEQ ID NO:77.

The invention also includes vaccine compositions which comprise HBcAg variants of Hepatitis B viruses which infect birds, as wells as vaccine compositions which comprise fragments of these HBcAg variants. As one skilled in the art would recognize, one, two, three or more of the cysteine residues naturally present in these polypeptides could be either substituted with another amino acid residue or deleted prior to their inclusion in vaccine compositions of the invention.

As discussed above, the elimination of free cysteine residues reduces the number of sites where toxic components can bind to the HBcAg, and also eliminates sites where cross-linking of lysine and cysteine residues of the same or of neighboring HBcAg molecules can occur. Therefore, in another embodiment of the present invention, one or more cysteine residues of the Hepatitis B virus capsid protein have been either deleted or substituted with another amino acid residue.

In other embodiments, compositions and vaccine compositions, respectively, of the invention will contain HBcAgs from which the C-terminal region (e.g., amino acid residues 145-185 or 150-185 of SEQ ID NO: 77) has been removed. Thus, additional modified HBcAgs suitable for use in the practice of the present invention include C-terminal truncation mutants. Suitable truncation mutants include HBcAgs where 1, 5, 10, 15, 20, 25, 30, 34, 35, amino acids have been removed from the C-terminus.

HBcAgs suitable for use in the practice of the present invention also include N-terminal truncation mutants. Suitable truncation mutants include modified HBcAgs where 1, 2, 5, 7, 9, 10, 12, 14, 15, or 17 amino acids have been removed from the N-terminus.

Further HBcAgs suitable for use in the practice of the present invention include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, amino acids have been removed from the C-terminus.

The invention further includes compositions and vaccine compositions, respectively, comprising HBcAg polypeptides comprising, or alternatively essentially consisting of, or alternatively consisting of, amino acid sequences which are at least 80%, 85%, 90%, 95%, 97%, or 99% identical to the above described truncation mutants.

In certain embodiments of the invention, a lysine residue is introduced into a HBcAg polypeptide, to mediate the binding of the antigen or antigenic determinant to the VLP of HBcAg. In preferred embodiments, compositions of the invention are prepared using a HBcAg comprising, or alternatively consisting of, amino acids 1-144, or 1-149, 1-185 of SEQ ID NO:77, which is modified so that the amino acids corresponding to positions 79 and 80 are replaced with a peptide having the amino acid sequence of Gly-Gly-Lys-Gly-Gly (SEQ ID NO:78). These compositions are particularly useful in those embodiments where an antigenic determinant is coupled to a VLP of HBcAg. In further preferred embodiments, the cysteine residues at positions 48 and 107 of SEQ ID NO:77 are mutated to serine. The invention further includes compositions comprising the corresponding polypeptides having amino acid sequences shown in any of SEQ ID NOs:29-74 which also have above noted amino acid alterations. Further included within the scope of the invention are additional HBcAg variants which are capable of associating to form a capsid or VLP and have the above noted amino acid alterations. Thus, the invention further includes compositions and vaccine compositions, respectively, comprising HBcAg polypeptides which comprise, or alternatively consist of, amino acid sequences which are at least 80%, 85%, 90%, 95%, 97% or 99% identical to any of the wild-type amino acid sequences, and forms of these proteins which have been processed, where appropriate, to remove the N-terminal leader sequence and modified with above noted alterations.

Compositions or vaccine compositions of the invention may comprise mixtures of different HBcAgs. Thus, these vaccine compositions may be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). Further, preferred vaccine compositions of the invention are those which present highly ordered and repetitive antigen arrays.

As previously disclosed, the invention is based on the surprising finding that immunostimulatory substances, preferably immunostimulatory nucleic acids and even more preferably DNA oligonucleotides can be packaged into VLPs. Unexpectedly, the nucleic acids present in VLPs can be replaced specifically by the immunostimulatory substances, preferably by the immunostimulatory nucleic acids and even more preferably by the DNA-oligonucleotides containing CpG motifs. As an example, the CpG-VLPs are dramatically more immunogenic and elicit more specific effects than their CpG-free counterparts and induce enhanced B and T cell responses. The immune response against antigens coupled, fused or attached otherwise to the VLPs is similarly enhanced as the immune response against the VLP itself. In addition, the T cell responses against both the VLPs and antigens are especially directed to the Th1 type. Furthermore, the packaged nucleic acids and CpGs, respectively, are protected from degradation, i.e., they are more stable. Moreover, non-specific activation of cells from the innate immune system is dramatically reduced.

The innate immune system has the capacity to recognize invariant molecular pattern shared by microbial pathogens. Recent studies have revealed that this recognition is a crucial step in inducing effective immune responses. The main mechanism by which microbial products augment immune responses is to stimulate APC, especially dendritic cells to produce proinflammatory cytokines and to express high levels costimulatory molecules for T cells. These activated dendritic cells subsequently initiate primary T cell responses and dictate the type of T cell-mediated effector function.

Two classes of nucleic acids, namely 1) bacterial DNA that contains immunostimulatory sequences, in particular unmethylated CpG dinucleotides within specific flanking bases (referred to as CpG motifs) and 2) double-stranded RNA synthesized by various types of viruses represent important members of the microbial components that enhance immune responses. Synthetic double stranded (ds) RNA such as polyinosinic-polycytidylic acid (poly I:C) are capable of inducing dendritic cells to produce proinflammatory cytokines and to express high levels of costimulatory molecules.

A series of studies by Tokunaga and Yamamoto et al. has shown that bacterial DNA or synthetic oligodeoxynucleotides induce human PBMC and mouse spleen cells to produce type I interferon (IFN) (reviewed in Yamamoto et al., Springer Semin Immunopathol. 22:11-19). Poly (I:C) was originally synthesized as a potent inducer of type I IFN but also induces other cytokines such as IL-12.

Preferred ribonucleic acid encompass polyinosinic-polycytidylic acid double-stranded RNA (poly I:C). Ribonucleic acids and modifications thereof as well as methods for their production have been described by Levy, H. B (Methods Enzymol. 1981, 78:242-251), DeClercq, E (Methods Enzymol. 1981, 78:227-236) and Torrence, P. F. (Methods Enzymol 1981; 78:326-331) and references therein. Ribonucleic acids can be isolated from organisms. Ribonucleic acids also encompass further synthetic ribonucleic acids, in particular synthetic poly (I:C) oligonucleotides that have been rendered nuclease resistant by modification of the phosphodiester backbone, in particular by phosphorothioate modifications. In a further embodiment the ribose backbone of poly (I:C) is replaced by a deoxyribose. Those skilled in the art know procedures how to synthesize synthetic oligonucleotides.

In another preferred embodiment of the invention molecules that active toll-like receptors (TLR) are enclosed. Ten human toll-like receptors are known uptodate. They are activated by a variety of ligands. TLR2 is activated by peptidoglycans, lipoproteins, lipoteichonic acid and Zymosan; TLR3 is activated by double-stranded RNA such as poly (I:C); TLR4 is activated by lipopolysaccharide, lipoteichoic acids and taxol; TLR5 is activated by bacterial flagella, especially the flagellin protein; TLR6 is activated by peptidoglycans, TLR7 is activated by imiquimoid and imidazoquinoline compounds, such as R418 and TLR9 is activated by bacterial DNA, in particular CpG DNA. Ligands for TLR1, TLR8 and TLR10 are not known so far. However, recent reports indicate that same receptors can react with different ligands and that further receptors are present. The above list of ligands is not exhaustive and further ligands are within the knowledge of the person skilled in the art.

Preferably, the unmethylated CpG-containing oligonucleotide comprises the sequence:

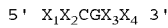

$$5' \ X_1X_2CGX_3X_4 \ 3'$$

wherein $X_1$, $X_2$, $X_3$ and $X_4$ are any nucleotide. In addition, the oligonucleotide can comprise about 6 to about 100,000 nucleotides, preferably about 6 to about 2000 nucleotides, more preferably about 20 to about 2000 nucleotides, and even more preferably comprises about 20 to about 300 nucleotides. In addition, the oligonucleotide can comprise more than 100 to about 2000 nucleotides, preferably more than 100 to about 1000 nucleotides, and more preferably more than 100 to about 500 nucleotides.

In a preferred embodiment, the CpG-containing oligonucleotide contains one or more phosphorothioate modifications of the phosphate backbone. For example, a CpG-containing oligonucleotide having one or more phosphate backbone modifications or having all of the phosphate backbone modified and a CpG-containing oligonucleotide wherein one, some or all of the nucleotide phosphate backbone modifications are phosphorothioate modifications are included within the scope of the present invention.

The CpG-containing oligonucleotide can also be recombinant, genomic, synthetic, cDNA, plasmid-derived and single or double stranded. For use in the instant invention, the nucleic acids can be synthesized de novo using any of a number of procedures well known in the art. For example, the b-cyanoethyl phosphoramidite method (Beaucage, S. L., and Caruthers, M. H., Tet. Let. 22:1859 (1981); nucleoside H-phosphonate method (Garegg et al., Tet. Let. 27:4051-4054 (1986); Froehler et al., Nucl. Acid. Res. 14:5399-5407 (1986); Garegg et al., Tet. Let. 27:4055-4058 (1986), Gaffney et al., Tet. Let. 29:2619-2622 (1988)). These chemistries can be performed by a variety of automated oligonucleotide synthesizers available in the market. Alternatively, CpGs can be produced on a large scale in plasmids, (see Sambrook, T., et al., "Molecular Cloning: A Laboratory Manual," Cold Spring Harbor laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases.

The immunostimulatory substances, the immunostimulatory nucleic acids as well as the unmethylated CpG-containing oligonucleotide can be bound to the VLP by any way known is the art provided the composition enhances an immune response in an animal. For example, the oligonucleotide can be bound either covalently or non-covalently. In addition, the VLP can enclose, fully or partially, the immunostimulatory substances, the immunostimulatory nucleic acids as well as the unmethylated CpG-containing oligonucleotide. Preferably, the immunostimulatory nucleic acid as well as the unmethylated CpG-containing oligonucleotide can be bound to a VLP site such as an oligonucleotide binding site (either naturally or non-naturally occurring), a DNA binding site or a RNA binding site. In another embodiment, the VLP site comprises an arginine-rich repeat.

One specific use for the compositions of the invention is to activate dendritic cells for the purpose of enhancing a specific immune response against antigens. The immune response can be enhanced using ex vivo or in vivo techniques. The ex vivo procedure can be used on autologous or heterologous cells, but is preferably used on autologous cells. In preferred embodiments, the dendritic cells are isolated from peripheral blood or bone marrow, but can be isolated from any source of dendritic cells. Ex vivo manipulation of dendritic cells for the purposes of cancer immunotherapy have been described in several references in the art, including Engleman, E. G., *Cytotechnology* 25:1 (1997); Van Schooten, W., et al., *Molecular Medicine Today*, June, 255 (1997); Steinman, R. M., *Experimental Hematology* 24:849 (1996); and Gluckman, J. C., *Cytokines, Cellular and Molecular Therapy* 3:187 (1997).

The dendritic cells can also be contacted with the inventive compositions using in vivo methods. In order to accomplish this, the CpGs are administered in combination with the VLP optionally coupled, fused or otherwise attached to an antigen directly to a subject in need of immunotherapy. In some embodiments, it is preferred that the VLPs/CpGs be administered in the local region of the tumor, which can be accomplished in any way known in the art, e.g., direct injection into the tumor.

The inventive composition can further comprise an antigen or antigenic determinant bound to the virus-like particle. The invention provides for compositions that vary according to the antigen or antigenic determinant selected in consideration of the desired therapeutic effect. Very preferred antigens or antigenic determinants suitable for use in the present invention are disclosed in WO 00/32227, in WO 01/85208 and in WO 02/056905, the disclosures of which are herewith incorporated by reference in their entireties.

The antigen can be any antigen of known or yet unknown provenance. It can be isolated from bacteria, viruses or other pathogens or can be a recombinant antigen obtained from expression of suitable nucleic acid coding therefor. It can also be isolated from prions, tumors, self-molecules, non-peptidic hapten molecules, allergens and hormones. In a preferred embodiment, the antigen is a recombinant antigen. The selection of the antigen is, of course, dependent upon the immunological response desired and the host.

In one embodiment of the immune enhancing composition of the present invention, the immune response is induced against the VLP itself. In another embodiment of the invention a virus-like particle is coupled, fused or otherwise attached to an antigen/immunogen against which an enhanced immune response is desired.

In a further preferred embodiment of the invention, the at least one antigen or antigenic determinant is fused to the virus-like particle. As outlined above, a VLP is typically composed of at least one subunit assembling into a VLP. Thus, in again a further preferred embodiment of the invention, the antigen or antigenic determinant is fused to at least one subunit of the virus-like particle or of a protein capable of being incorporated into a VLP generating a chimeric VLP-subunit-antigen fusion.

Fusion of the antigen or antigenic determinant can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting antigen or antigenic determinant sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. Fusion of antigens or antigenic determinants to either the N- or C-terminus of the truncation mutants VLP-subunits also lead to embodiments of the invention. Likewise, fusion of an epitope into the sequence of the VLP subunit may also be effected by substitution, where for example for the specific VLP HBcAg, amino acids 79-81 are replaced with a foreign epitope. Thus, fusion, as referred to hereinafter, may be effected by insertion of the antigen or antigenic determinant sequence in the sequence of a VLP subunit, by substitution of part of the sequence of the VLP subunit with the antigen or antigenic determinant, or by a combination of deletion, substitution or insertions.

The chimeric antigen or antigenic determinant-VLP subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In a further embodiment of the invention, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of, and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In a specific embodiment of the invention, the VLP is a Hepatitis B core antigen VLP. Fusion proteins of the antigen or antigenic determinant to either the N-terminus of a HBcAg (Neyrinck, S. et al., *Nature Med.* 5:1157-1163 (1999)) or insertions in the so called major immunodominant region (MIR) have been described (Pumpens, P. and Grens, E., *Intervirology* 44:98-114 (2001)), WO 01/98333), and are preferred embodiments of the invention. Naturally occurring variants of HBcAg with deletions in the MIR have also been described (Pumpens, P. and Grens, E., *Intervirology* 44:98-114 (2001), which is expressly incorporated by reference in its entirety), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., *Intervirology* 44:98-114 (2001)). One skilled in the art will easily find guidance on how to construct fusion proteins using classical molecular biology techniques (Sambrook, J. et al., eds., *Molecular Cloning, A Laboratory Manual,* 2nd. edition, Cold Spring Harbor Laboratory Press, Cold Spring Harbor, N.Y. (1989), Ho et al., *Gene* 77:51 (1989)). Vectors and plasmids encoding HBcAg and HBcAg fusion proteins and useful for the expression of a HBcAg and HBcAg fusion proteins have been described (Pumpens, P. & Grens, E. Intervirology 44: 98-114 (2001), Neyrinck, S. et al., *Nature Med.* 5:1157-1163 (1999)) and can be used in the practice of the invention. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., *Intervirology* 44:98-114 (2001); EP 0 421 635; U.S. Pat. No. 6,231,864) upon insertion, or in other words, which amino acids form HBcAg are to be substituted with the new epitope. For example, substitution of HBcAg amino acids 76-80, 79-81, 79-80, 75-85 or 80-81 with foreign epitopes has been described (Pumpens, P. and Grens, E., *Intervirology* 44:98-114 (2001); EP0421635; U.S. Pat. No. 6,231,864). HBcAg contains a long arginine tail (Pumpens, P. and Grens, E., *Intervirology* 44:98-114 (2001)) which is dispensable for capsid assembly and capable of binding nucleic acids (Pumpens, P. and Grens, E., *Intervirology* 44:98-114 (2001)). HBcAg either comprising or lacking this arginine tail are both embodiments of the invention.

In a further preferred embodiment of the invention, the VLP is a VLP of a RNA phage. The major coat proteins of RNA phages spontaneously assemble into VLPs upon expression in bacteria, and in particular in *E. coli*. Specific examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein) and bacteriophage fr (SEQ ID NO: 13; PIR Accession No. VCBPFR).

In a more preferred embodiment, the at least one antigen or antigenic determinant is fused to a Qβ coat protein. Fusion protein constructs wherein epitopes have been fused to the C-terminus of a truncated form of the A1 protein of Qβ, or inserted within the A1 protein have been described (Kozlovska, T. M., et al., *Intervirology*, 39:9-15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in *E. coli*, and such is the case for N-termini of the Qβ coat proteins. The part of the A1 gene, 3' of the UGA amber codon encodes the CP extension, which has a length of 195 amino acids. Insertion of the at least one antigen or antigenic determinant between position 72 and 73 of the CP extension leads to further embodiments of the invention (Kozlovska, T. M., et al., *Intervirology* 39:9-15 (1996)). Fusion of an antigen or antigenic determinant at the C-terminus of a C-terminally truncated Qβ A1 protein leads to further preferred embodiments of the invention. For example, Kozlovska et al., (*Intervirology*, 39: 9-15 (1996)) describe Qβ A1 protein fusions where the epitope is fused at the C-terminus of the Qβ CP extension truncated at position 19.

As described by Kozlovska et al. (*Intervirology*, 39: 9-15 (1996)), assembly of the particles displaying the fused epitopes typically requires the presence of both the A1 protein-antigen fusion and the wt CP to form a mosaic particle. However, embodiments comprising virus-like particles, and hereby in particular the VLPs of the RNA phage Qβ coat protein, which are exclusively composed of VLP subunits having at least one antigen or antigenic determinant fused thereto, are also within the scope of the present invention.

The production of mosaic particles may be effected in a number of ways. Kozlovska et al., *Intervirology*, 39:9-15 (1996), describe three methods, which all can be used in the practice of the invention. In the first approach, efficient display of the fused epitope on the VLPs is mediated by the expression of the plasmid encoding the Qβ A1 protein fusion having a UGA stop codong between CP and CP extension in a *E. coli* strain harboring a plasmid encoding a cloned UGA suppressor tRNA which leads to translation of the UGA codon into Trp (pISM3001 plasmid (Smiley B. K., et al., *Gene* 134:33-40 (1993))). In another approach, the CP gene stop codon is modified into UAA, and a second plasmid expressing the A1 protein-antigen fusion is cotransformed. The second plasmid encodes a different antibiotic resistance and the origin of replication is compatible with the first plasmid (Kozlovska, T. M., et al., *Intervirology* 39:9-15 (1996)). In a third approach, CP and the A1 protein-antigen fusion are encoded in a bicistronic manner, operatively linked to a promoter such as the Trp promoter, as described in FIG. 1 of Kozlovska et al., *Intervirology*, 39:9-15 (1996).

In a further embodiment, the antigen or antigenic determinant is inserted between amino acid 2 and 3 (numbering of the cleaved CP, that is wherein the N-terminal methionine is cleaved) of the fr CP, thus leading to an antigen or antigenic determinant-fr CP fusion protein. Vectors and expression systems for construction and expression of fr CP fusion proteins self-assembling to VLP and useful in the practice of the invention have been described (Pushko P. et al., *Prot. Eng.* 6:883-891 (1993)). In a specific embodiment, the antigen or antigenic determinant sequence is inserted into a deletion variant of the fr CP after amino acid 2, wherein residues 3 and 4 of the fr CP have been deleted (Pushko P. et al., *Prot. Eng.* 6:883-891 (1993)).

Fusion of epitopes in the N-terminal protuberant β-hairpin of the coat protein of RNA phage MS-2 and subsequent presentation of the fused epitope on the self-assembled VLP of RNA phage MS-2 has also been described (WO 92/13081), and fusion of an antigen or antigenic determinant by insertion or substitution into the coat protein of MS-2 RNA phage is also falling under the scope of the invention.

In another embodiment of the invention, the antigen or antigenic determinant is fused to a capsid protein of papillomavirus. In a more specific embodiment, the antigen or antigenic determinant is fused to the major capsid protein L1 of bovine papillomavirus type 1 (BPV-1). Vectors and expression systems for construction and expression of BPV-1 fusion proteins in a baculovirus/insect cells systems have been described (Chackerian, B. et al., *Proc. Natl. Acad. Sci. USA* 96:2373-2378 (1999), WO 00/23955). Substitution of amino acids 130-136 of BPV-1 L1 with an antigen or antigenic determinant leads to a BPV-1 L1-antigen fusion protein, which is a preferred embodiment of the invention. Cloning in a baculovirus vector and expression in baculovirus infected Sf9 cells has been described, and can be used in the practice of the invention (Chackerian, B. et al., *Proc. Natl. Acad. Sci. USA* 96:2373-2378 (1999), WO 00/23955). Purification of the assembled particles displaying the fused antigen or antigenic determinant can be performed in a number of ways, such as for example gel filtration or sucrose gradient ultracentrifugation (Chackerian, B. et al., *Proc. Natl. Acad. Sci. USA* 96:2373-2378 (1999), WO 00/23955).

In a further embodiment of the invention, the antigen or antigenic determinant is fused to a Ty protein capable of being incorporated into a Ty VLP. In a more specific embodiment, the antigen or antigenic determinant is fused to the p1 or capsid protein encoded by the TYA gene (Roth, J. F., *Yeast* 16:785-795 (2000)). The yeast retrotransposons Ty1, 2, 3 and 4 have been isolated from *Saccharomyces Serevisiae*, while the retrotransposon Tf1 has been isolated from *Schizosaccharomyces Pombae* (Boeke, J. D. and Sandmeyer, S. B., "Yeast Transposable elements," in *The molecular and Cellular Biology of the Yeast Saccharomyces: Genome dynamics, Protein Synthesis, and Energetics*, p. 193, Cold Spring Harbor Laboratory Press (1991)). The retrotransposons Ty1 and 2 are related to the copia class of plant and animal elements, while Ty3 belongs to the gypsy family of retrotransposons, which is related to plants and animal retroviruses. In the Ty1 retrotransposon, the p1 protein, also referred to as Gag or capsid protein, has a length of 440 amino acids. P1 is cleaved during maturation of the VLP at position 408, leading to the p2 protein, the essential component of the VLP.

Fusion proteins to p1 and vectors for the expression of said fusion proteins in Yeast have been described (Adams, S. E., et al., *Nature* 329:68-70 (1987)). So, for example, an antigen or antigenic determinant may be fused to p1 by inserting a sequence coding for the antigen or antigenic determinant into the BamH1 site of the pMA5620 plasmid (Adams, S. E., et al., *Nature* 329:68-70 (1987)). The cloning of sequences coding for foreign epitopes into the pMA5620 vector leads to expression of fusion proteins comprising amino acids 1-381 of p1 of Ty1-15, fused C-terminally to the N-terminus of the foreign epitope. Likewise, N-terminal fusion of an antigen or antigenic determinant, or internal insertion into the p1 sequence, or substitution of part of the p1 sequence are also meant to fall within the scope of the invention. In particular, insertion of an antigen or antigenic determinant into the Ty sequence between amino acids 30-31, 67-68, 113-114 and 132-133 of the Ty protein p1 (EP0677111) leads to preferred embodiments of the invention.

Further VLPs suitable for fusion of antigens or antigenic determinants are, for example, Retrovirus-like-particles (WO9630523), HIV2 Gag (Kang, Y. C., et al, *Biol. Chem.* 380:353-364 (1999)), Cowpea Mosaic Virus (Taylor, K. M. et al., *Biol. Chem.* 380:387-392 (1999)), parvovirus VP2 VLP (Rueda, P. et al., *Virology* 263:89-99 (1999)), HBsAg (U.S. Pat. No. 4,722,840, EP0020416B1).

Examples of chimeric VLPs suitable for the practice of the invention are also those described in *Intervirology* 39:1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus have also been made, and chimeric VLPs of those VLPs comprising an antigen or antigenic determinant are also within the scope of the present invention.

As indicated, embodiments comprising antigens fused to the virus-like particle by insertion within the sequence of the virus-like particle building monomer are also within the scope of the present invention. In some cases, antigens can be inserted in a form of the virus-like particle building monomer containing deletions. In these cases, the virus-like particle building monomer may not be able to form virus-like structures in the absence of the inserted antigen.

In some instances, recombinant DNA technology can be utilized to fuse a heterologous protein to a VLP protein (Kratz, P. A., et al., *Proc. Natl. Acad. Sci. USA* 96:1915 (1999)). For example, the present invention encompasses VLPs recombinantly fused or chemically conjugated (including both covalently and non-covalently conjugations) to an antigen (or portion thereof, preferably at least 10, 20 or 50 amino acids) of the present invention to generate fusion proteins or conjugates. The fusion does not necessarily need to be direct, but can occur through linker sequences. More generally, in the case that epitopes, either fused, conjugated or otherwise attached to the virus-like particle, are used as antigens in accordance with the invention, spacer or linker sequences are typically added at one or both ends of the epitopes. Such linker sequences preferably comprise sequences recognized by the proteasome, proteases of the endosomes or other vesicular compartment of the cell.

One way of coupling is by a peptide bond, in which the conjugate can be a contiguous polypeptide, i.e. a fusion protein. In a fusion protein according to the present invention, different peptides or polypeptides are linked in frame to each other to form a contiguous polypeptide. Thus a first portion of the fusion protein comprises an antigen or immunogen and a second portion of the fusion protein, either N-terminal or C-terminal to the first portion, comprises a VLP. Alternatively, internal insertion into the VLP, with optional linking sequences on both ends of the antigen, can also be used in accordance with the present invention.

When HBcAg is used as the VLP, it is preferred that the antigen is linked to the C-terminal end of the HBcAg particle. The hepatitis B core antigen (HBcAg) exhibiting a C-terminal fusion of the MHC class I restricted peptide p33 derived from lymphocytic choriomeningitis virus (LCMV) glycoprotein was used as a model antigen (HBcAg-p33). The 185 amino acids long wild type HBc protein assembles into highly structured particles composed of 180 subunits assuming icosahedral geometry. The flexibility of the HBcAg and other VLPs in accepting relatively large insertions of foreign sequences at different positions while retaining the capacity to form structured capsids is well documented in the literature. This makes the HBc VLPs attractive candidates for the design of non-replicating vaccines.

A flexible linker sequence (e.g. a polyglycine/polyserine-containing sequence such as [Gly$_4$ Ser]$_2$ (Huston et al., *Meth. Enzymol* 203:46-88 (1991), (SEQ ID NO:129)) can be inserted into the fusion protein between the antigen and ligand. Also, the fusion protein can be constructed to contain an "epitope tag", which allows the fusion protein to bind an antibody (e.g. monoclonal antibody) for example for labeling or purification purposes. An example of an epitope tag is a Glu-Glu-Phe tripeptide which is recognized by the monoclonal antibody YL1/2.

The invention also relates to the chimeric DNA which contains a sequence coding for the VLP and a sequence coding for the antigen/immunogen. The DNA can be expressed, for example, in insect cells transformed with Baculoviruses, in yeast or in bacteria. There are no restrictions regarding the expression system, of which a large selection is available for routine use. Preferably, a system is used which allows expression of the proteins in large amounts. In general, bacterial expression systems are preferred on account of their efficiency. One example of a bacterial expression system suitable for use within the scope of the present invention is the one described by Clarke et al., *J. Gen. Virol.* 71: 1109-1117 (1990); Borisova et al., *J. Virol.* 67: 3696-3701 (1993); and Studier et al., *Methods Enzymol.* 185:60-89 (1990). An example of a suitable yeast expression system is the one described by Emr, *Methods Enzymol.* 185:231-3 (1990); Baculovirus systems, which have previously been used for preparing capsid proteins, are also suitable. Constitutive or inducible expression systems can be used. By the choice and possible modification of available expression systems it is possible to control the form in which the proteins are obtained.

In a specific embodiment of the invention, the antigen to which an enhanced immune response is desired is coupled, fused or otherwise attached in frame to the Hepatitis B virus capsid (core) protein (HBcAg). However, it will be clear to all individuals in the art that other virus-like particles can be utilized in the fusion protein construct of the invention.

In a further preferred embodiment of the present invention, the at least one antigen or antigenic determinant is bound to the virus-like particle by at least one covalent bond. Preferably, the least one antigen or antigenic determinant is bound to the virus-like particle by at least one covalent bond, said covalent bond being a non-peptide bond leading to an antigen or antigenic determinant array and antigen or antigenic determinant-VLP conjugate, respectively. This antigen or antigenic determinant array and conjugate, respectively, has typically and preferably a repetitive and ordered structure since the at least one antigen or antigenic determinant is bound to the VLP in an oriented manner. The formation of a repetitive and ordered antigen or antigenic determinant-VLP array and conjugate, respectively, is ensured by an oriented and directed as well as defined binding and attachment, respectively, of the at least one antigen or antigenic determinant to the VLP as will become apparent in the following. Furthermore, the typical inherent highly repetitive and organized structure of the VLPs advantageously contributes to the display of the antigen or antigenic determinant in a highly ordered and repetitive fashion leading to a highly organized and repetitive antigen or antigenic determinant-VLP array and conjugate, respectively.

Therefore, the preferred inventive conjugates and arrays, respectively, differ from prior art conjugates in their highly organized structure, dimensions, and in the repetitiveness of the antigen on the surface of the array. The preferred embodiment of this invention, furthermore, allows expression of the particle in an expression host guaranteeing proper folding and assembly of the VLP, to which the antigen is then further coupled The present invention discloses methods of binding of antigen or antigenic determinant to VLPs. As indicated, in one aspect of the invention, the at least one antigen or antigenic determinant is bound to the VLP by way of chemical cross-linking, typically and preferably by using a heterobifunctional cross-linker. Several hetero-bifunctional cross-linkers are known to the art. In preferred embodiments, the hetero-bifunctional cross-linker contains a functional group which can react with preferred first attachment sites, i.e. with the side-chain amino group of lysine residues of the VLP or at least one VLP subunit, and a further functional group which can react with a preferred second attachment site, i.e. a cysteine residue fused to the antigen or antigenic determinant and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigen or antigenic determinant is reacted with the activated VLP, and this step is typically called the coupling step. Unreacted antigen or antigenic determinant may be optionally removed in a fourth step, for example by dialysis. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage. Another class of cross-linkers suitable in the practice of the invention is characterized by the introduction of a disulfide linkage between the antigen or antigenic determinant and the VLP upon coupling. Preferred cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i.e. the amount of antigens or antigenic determinants per subunits of the VLP can be adjusted by varying the experimental conditions described above to match the requirements of the vaccine.

A particularly favored method of binding of antigens or antigenic determinants to the VLP, is the linking of a lysine residue on the surface of the VLP with a cysteine residue on the antigen or antigenic determinant. In some embodiments, fusion of an amino acid linker containing a cysteine residue, as a second attachment site or as a part thereof, to the antigen or antigenic determinant for coupling to the VLP may be required.

In general, flexible amino acid linkers are favored. Examples of the amino acid linker are selected from the group consisting of: (a) CGG (SEQ ID NO:130); (b) N-terminal gamma 1-linker; (c) N-terminal gamma 3-linker; (d) Ig hinge regions; (e) N-terminal glycine linkers; (f) $(G)_kC(G)_n$ with n=0-12 and k=0-5 (SEQ ID NO:131); (g) N-terminal glycine-serine linkers; (h) $(G)_kC(G)_m(S)_l(GGGGS)_n$ (SEQ ID NO:127) with n=0-3, k=0-5, m=0-10, l=0-2; (i) GGC (SEQ ID NO:135); (k) GGC-NH2 (SEQ ID NO:136); (l) C-terminal gamma 1-linker; (m) C-terminal gamma 3-linker; (n) C-terminal glycine linkers; (o) $(G)_nC(G)_k$ with n=0-12 and k=0-5 (SEQ ID NO:132); (p) C-terminal glycine-serine linkers; (q) $(G)_m(S)_l(GGGGS)_n(G)_oC(G)_k$ with n=0-3, k=0-5, m=0-10, l=0-2, and o=0-8 (SEQ ID NO:128).

Further examples of amino acid linkers are the hinge region of Immunoglobulins, glycine serine linkers $(GGGGS)_n$ (SEQ ID NO:133), and glycine linkers $(G)_n$ all further containing a cysteine residue as second attachment site and optionally further glycine residues. Typically preferred examples of said amino acid linkers are N-terminal gamma1: CGDKTHTSPP (SEQ ID NO:7); C-terminal gamma 1: DKTHTSPPCG (SEQ ID NO:8); N-terminal gamma 3: CGGPKPSTPPGSSGGAP (SEQ ID NO:9); C-terminal gamma 3: PKPSTPPGSSG-GAPGGCG (SEQ ID NO:83); N-terminal glycine linker: GCGGG (SEQ ID NO:84) and C-terminal glycine linker: GGGGCG (SEQ ID NO:85).

Other amino acid linkers particularly suitable in the practice of the invention, when a hydrophobic antigen or antigenic determinant is bound to a VLP, are CGKKGG (SEQ ID NO:86), or CGDEGG (SEQ ID NO:87) for N-terminal linkers, or GGKKGC (SEQ ID NO:88) and GGEDGC (SEQ ID NO:89), for the C-terminal linkers. For the C-terminal linkers, the terminal cysteine is optionally C-terminally amidated.

In preferred embodiments of the present invention, GGCG (SEQ ID NO:134), GGC (SEQ ID NO:135) or GGC-NH2 (SEQ ID NO:136, "NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction. In the most preferred embodiment of the invention, the amino acid linker GGC-NH2 (SEQ ID NO:136) is fused to the C-terminus of the antigen or antigenic determinant.

The cysteine residue present on the antigen or antigenic determinant has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or β-mercaptoethanol is required. Low concentrations of reducing agent are compatible with coupling as described in WO 02/05690, higher concentrations inhibit the coupling reaction, as a skilled artisan would know, in which case the reductand has to be removed or its concentration decreased prior to coupling, e.g. by dialysis, gel filtration or reverse phase HPLC.

Binding of the antigen or antigenic determinant to the VLP by using a hetero-bifunctional cross-linker according to the preferred methods described above, allows coupling of the antigen or antigenic determinant to the VLP in an oriented fashion. Other methods of binding the antigen or antigenic determinant to the VLP include methods wherein the antigen or antigenic determinant is cross-linked to the VLP using the carbodiimide EDC, and NHS. In further methods, the antigen or antigenic determinant is attached to the VLP using a homo-bifunctional cross-linker such as glutaraldehyde, DSG, BM[PEO]$_4$, BS$^3$, (Pierce Chemical Company, Rockford, Ill., USA) or other known homo-bifunctional cross-linkers with functional groups reactive towards amine groups or carboxyl groups of the VLP.

Other methods of binding the VLP to an antigen or antigenic determinant include methods where the VLP is biotinylated, and the antigen or antigenic determinant expressed as a streptavidin-fusion protein, or methods wherein both the antigen or antigenic determinant and the VLP are biotinylated, for example as described in WO 00/23955. In this case, the antigen or antigenic determinant may be first bound to streptavidin or avidin by adjusting the ratio of antigen or antigenic determinant to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the antigen or antigenic determinant, may be used as binding agents for binding antigen or antigenic determinant to the VLP. Alternatively, either the ligand or the receptor may be fused to the antigen or antigenic determinant, and so mediate binding to the VLP chemically bound or fused either to the receptor, or the ligand respectively. Fusion may also be effected by insertion or substitution.

As already indicated, in a favored embodiment of the present invention, the VLP is the VLP of a RNA phage, and in a more preferred embodiment, the VLP is the VLP of RNA phage Qβ coat protein.

One or several antigen molecules, i.e. one or several antigens or antigenic determinants, can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the Qβ coat protein VLP is thus the possibility to couple several antigens per subunit. This allows for the generation of a dense antigen array.

In a preferred embodiment of the invention, the binding and attachment, respectively, of the at least one antigen or antigenic determinant to the virus-like particle is by way of interaction and association, respectively, between at least one first attachment site of the virus-like particle and at least one second attachment of the antigen or antigenic determinant.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In further preferred embodiments of the present invention, the first attachment site is a lysine residue and/or the second attachment comprises sulfhydryl group or a cysteine residue. In a very preferred embodiment of the present invention, the first attachment site is a lysine residue and the second attachment is a cysteine residue.

In very preferred embodiments of the invention, the antigen or antigenic determinant is bound via a cysteine residue, to lysine residues of the VLP of RNA phage coat protein, and in particular to the VLP of Qβ coat protein.

Another advantage of the VLPs derived from RNA phages is their high expression yield in bacteria that allows production of large quantities of material at affordable cost.

As indicated, the inventive conjugates and arrays, respectively, differ from prior art conjugates in their highly organized structure, dimensions, and in the repetitiveness of the antigen on the surface of the array. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qβ coat protein allows to achieve very high epitope density. In particular, a density of more than 1.5 epitopes per subunit could be reached by coupling the human Aβ1-6 peptide to the VLP of Qβ coat protein. The preparation of compositions of VLPs of RNA phage coat proteins with a high epitope density can be effected using the teaching of this application. In preferred embodiment of the invention, when an antigen or antigenic determinant is coupled to the VLP of Qβ coat protein, an average number of antigen or antigenic determinant per subunit of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 2.5, 2.6, 2.7, 2.8, 2.9, or higher is preferred.

The second attachment site, as defined herein, may be either naturally or non-naturally present with the antigen or the antigenic determinant. In the case of the absence of a suitable natural occurring second attachment site on the antigen or antigenic determinant, such a, then non-natural second attachment has to be engineered to the antigen.

As described above, four lysine residues are exposed on the surface of the VLP of Qβ coat protein. Typically these residues are derivatized upon reaction with a cross-linker molecule. In the instance where not all of the exposed lysine residues can be coupled to an antigen, the lysine residues which have reacted with the cross-linker are left with a cross-linker molecule attached to the ε-amino group after the derivatization step. This leads to disappearance of one or several positive charges, which may be detrimental to the solubility and stability of the VLP. By replacing some of the lysine residues with arginines, as in the disclosed Qβ coat protein mutants described below, we prevent the excessive disappearance of positive charges since the arginine residues do not react with the cross-linker. Moreover, replacement of lysine residues by arginines may lead to more defined antigen arrays, as fewer sites are available for reaction to the antigen.

Accordingly, exposed lysine residues were replaced by arginines in the following Qβ coat protein mutants and mutant Qβ VLPs disclosed in this application: Qβ-240 (Lys13-Arg; SEQ ID NO:23), Qβ-250 (Lys 2-Arg, Lys13-Arg; SEQ ID NO: 25) and Qβ-259 (Lys 2-Arg, Lys16-Arg; SEQ ID NO:27). The constructs were cloned, the proteins expressed, the VLPs purified and used for coupling to peptide and protein antigens. Qβ-251; (SEQ ID NO: 26) was also constructed, and guidance on how to express, purify and couple the VLP of Qβ-251 coat protein can be found throughout the application.

In a further embodiment, we disclose a Qβ mutant coat protein with one additional lysine residue, suitable for obtaining even higher density arrays of antigens. This mutant Qβ coat protein, Qβ-243 (Asn 10-Lys; SEQ ID NO: 24), was cloned, the protein expressed, and the capsid or VLP isolated and purified, showing that introduction of the additional lysine residue is compatible with self-assembly of the subunits to a capsid or VLP. Thus, antigen or antigenic determinant arrays and conjugates, respectively, may be prepared using VLP of Qβ coat protein mutants. A particularly favored method of attachment of antigens to VLPs, and in particular to VLPs of RNA phage coat proteins is the linking of a lysine residue present on the surface of the VLP of RNA phage coat proteins with a cysteine residue added to the antigen. In order for a cysteine residue to be effective as second attachment site, a sulfhydryl group must be available for coupling. Thus, a cysteine residue has to be in its reduced state, that is, a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or β-mercaptoethanol is required. The concentration of reductand, and the molar excess of reductand over antigen has to be adjusted for each antigen. A titration range, starting from concentrations as low as 10 μM or lower, up to 10 to 20 mM or higher reductand if required is tested, and coupling of the antigen to the carrier assessed. Although low concentrations of reductand are compatible with the coupling reaction as described in WO 02/056905, higher concentrations inhibit the coupling reaction, as a skilled artisan would know, in which case the reductand has to be removed or its concentration decreased, e.g. by dialysis, gel filtration or reverse phase HPLC. Advantageously, the pH of the dialysis or equilibration buffer is lower than 7, preferably 6. The compatibility of the low pH buffer with antigen activity or stability has to be tested.

Epitope density on the VLP of RNA phage coat proteins can be modulated by the choice of cross-linker and other reaction conditions. For example, the cross-linkers Sulfo-GMBS and SMPH typically allow reaching high epitope density. Derivatization is positively influenced by high concentration of reactands, and manipulation of the reaction conditions can be used to control the number of antigens coupled to VLPs of RNA phage coat proteins, and in particular to VLPs of Qβ coat protein.

Prior to the design of a non-natural second attachment site the position at which it should be fused, inserted or generally engineered has to be chosen. The selection of the position of the second attachment site may, by way of example, be based on a crystal structure of the antigen. Such a crystal structure of the antigen may provide information on the availability of the C- or N-termini of the molecule (determined for example from their accessibility to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction, with e.g. 2-mercaptoethylamine, TCEP, β-mercaptoethanol or DTT. Mild reduction conditions not affecting the immunogenicity of the antigen will be chosen. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will be selected such that steric hindrance from the second attachment site or any amino acid linker containing the same is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In very preferred embodiments, the antigen or antigenic determinant comprises a single second attachment site or a single reactive attachment site capable of association with the first attachment sites on the core particle and the VLPs or VLP subunits, respectively. This further ensures a defined and uniform binding and association, respectively, of the at least one, but typically more than one, preferably more than 10, 20, 40, 80, 120 antigens to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine—(as the first attachment site) and cysteine—(as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the VLP and the first attachment site of the core particle, respectively.

In some embodiments, engineering of a second attachment site onto the antigen require the fusion of an amino acid linker containing an amino acid suitable as second attachment site according to the disclosures of this invention. Therefore, in a preferred embodiment of the present invention, an amino acid linker is bound to the antigen or the antigenic determinant by way of at least one covalent bond. Preferably, the amino acid linker comprises, or alternatively consists of, the second attachment site. In a further preferred embodiment, the amino acid linker comprises a sulfhydryl group or a cysteine residue. In another preferred embodiment, the amino acid linker is cysteine. Some criteria of selection of the amino acid linker as well as further preferred embodiments of the amino acid linker according to the invention have already been mentioned above.

In another specific embodiment of the invention, the attachment site is selected to be a lysine or cysteine residue that is fused in frame to the HBcAg. In a preferred embodiment, the antigen is fused to the C-terminus of HBcAg via a three leucine linker.

When an antigen or antigenic determinant is linked to the VLP through a lysine residue, it may be advantageous to either substitute or delete one or more of the naturally resident lysine residues, as well as other lysine residues present in HBcAg variants.

In many instances, when the naturally resident lysine residues are eliminated, another lysine will be introduced into the HBcAg as an attachment site for an antigen or antigenic determinant. Methods for inserting such a lysine residue are known in the art. Lysine residues may also be added without removing existing lysine residues.

The C-terminus of the HBcAg has been shown to direct nuclear localization of this protein. (Eckhardt et al., *J. Virol.* 65:575-582 (1991)). Further, this region of the protein is also believed to confer upon the HBcAg the ability to bind nucleic acids.

As indicated, HBcAgs suitable for use in the practice of the present invention also include N-terminal truncation mutants. Suitable truncation mutants include modified HBcAgs where 1, 2, 5, 7, 9, 10, 12, 14, 15, or 17 amino acids have been removed from the N-terminus. However, variants of virus-like particles containing internal deletions within the sequence of the subunit composing the virus-like particle are also suitable in accordance with the present invention, provided their compatibility with the ordered or particulate structure of the virus-like particle. For example, internal deletions within the sequence of the HBcAg are suitable (Preikschat, P., et al., *J. Gen. Virol.* 80:1777-1788 (1999)).

Further HBcAgs suitable for use in the practice of the present invention include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, 35, 36, 37, 38, 39 40, 41, 42 or 48 amino acids have been removed from the C-terminus.

Vaccine compositions of the invention can comprise mixtures of different HBcAgs. Thus, these vaccine compositions can be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). In most applications, however, only one type of a HBcAg will be used.

The present invention is applicable to a wide variety of antigens. In a preferred embodiment, the antigen is a protein, polypeptide or peptide. In another embodiment the antigen is DNA. The antigen can also be a lipid, a carbohydrate, or an organic molecule, in particular a small organic molecule such as nicotine.

Antigens of the invention can be selected from the group consisting of the following: (a) polypeptides suited to induce an immune response against cancer cells; (b) polypeptides suited to induce an immune response against infectious diseases; (c) polypeptides suited to induce an immune response against allergens; (d) polypeptides suited to induce an immune response in farm animals or pets; and (e) fragments (e.g., a domain) of any of the polypeptides set out in (a)-(d).

Preferred antigens include those from a pathogen (e.g. virus, bacterium, parasite, fungus) and tumors (especially tumor-associated antigens or "tumor markers"). Other preferred antigens are autoantigens.

In the specific embodiments described in the Examples, the antigen is the peptide p33 derived from lymphocytic choriomeningitis virus (LCMV). The p33 peptide represents one of the best studied CTL epitopes (Pircher et al., "Tolerance induction in double specific T-cell receptor transgenic mice varies with antigen," *Nature* 342:559 (1989); Tissot et al., "Characterizing the functionality of recombinant T-cell receptors in vitro: a pMHC tetramer based approach," *J Immunol Methods* 236:147 (2000); Bachmann et al., "Four types of Ca2+-signals after stimulation of naive T cells with T cell agonists, partial agonists and antagonists," *Eur. J. Immunol.* 27:3414 (1997); Bachmann et al., "Functional maturation of an anti-viral cytotoxic T cell response," *J. Virol.* 71:5764 (1997); Bachmann et al., "Peptide induced TCR-down regulation on naive T cell predicts agonist/partial agonist properties and strictly correlates with T cell activation," *Eur. J. Immunol.* 27:2195 (1997); Bachmann et al., "Distinct roles for LFA-1 and CD28 during activation of naive T cells: adhesion versus costimulation," *Immunity* 7:549 (1997)). p33-specific T cells have been shown to induce lethal diabetic disease in transgenic mice (Ohashi et al., "Ablation of 'tolerance' and induction of diabetes by virus infection in viral antigen transgenic mice," *Cell* 65:305 (1991)) as well as to be able to prevent growth of tumor cells expressing p33 (Kündig et al., "Fibroblasts act as efficient antigen-presenting cells in lymphoid organs," *Science* 268:1343 (1995); Speiser et al., "CTL tumor therapy specific for an endogenous antigen does not cause autoimmune disease," *J. Exp. Med.* 186:645 (1997)). This specific epitope, therefore, is particularly well suited to study autoimmunity, tumor immunology as well as viral diseases.

In one specific embodiment of the invention, the antigen or antigenic determinant is one that is useful for the prevention of infectious disease. Such treatment will be useful to treat a wide variety of infectious diseases affecting a wide range of hosts, e.g., human, cow, sheep, pig, dog, cat, other mammalian species and non-mammalian species as well. Treatable infectious diseases are well known to those skilled in the art, and examples include infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc. Thus, antigens or antigenic determinants selected for the compositions of the invention will be well known to those in the medical art; examples of antigens or antigenic determinants include the following: the HIV antigens gp140 and gp160; the influenza antigens hemagglutinin, M2 protein and neuraminidase, Hepatitis B surface antigen or core and circumsporozoite protein of malaria or fragments thereof.

As discussed above, antigens include infectious microbes such as viruses, bacteria and fungi and fragments thereof, derived from natural sources or synthetically. Infectious viruses of both human and non-human vertebrates include retroviruses, RNA viruses and DNA viruses. The group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian mycloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A, C, D, E and G viruses, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukunicmi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses and filoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxyiridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D and E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses which do not fit into the above families such as Kuru and Creutzfeldt-Jacob disease viruses and chronic infectious neuropathic agents (CHINA virus).

Each of the foregoing lists is illustrative, and is not intended to be limiting.

In a specific embodiment of the invention, the antigen comprises one or more cytotoxic T cell epitopes, Th cell epitopes, or a combination of the two epitopes.

In addition to enhancing an antigen specific immune response in humans, the methods of the preferred embodiments are particularly well suited for treatment of other mammals or other animals, e.g., birds such as hens, chickens, turkeys, ducks, geese, quail and pheasant. Birds are prime targets for many types of infections.

An example of a common infection in chickens is chicken infectious anemia virus (CIAV). CIAV was first isolated in Japan in 1979 during an investigation of a Marek's disease vaccination break (Yuasa et al., *Avian Dis.* 23:366-385 (1979)). Since that time, CIAV has been detected in commercial poultry in all major poultry producing countries (van Bulow et al., pp. 690-699 in "Diseases of Poultry", 9th edition, Iowa State University Press 1991).

Vaccination of birds, like other vertebrate animals can be performed at any age. Normally, vaccinations are performed at up to 12 weeks of age for a live microorganism and between 14-18 weeks for an inactivated microorganism or other type of vaccine. For in ovo vaccination, vaccination can be performed in the last quarter of embryo development. The vaccine can be administered subcutaneously, by spray, orally, intraocularly, intratracheally, nasally, in ovo or by other methods described herein.

Cattle and livestock are also susceptible to infection. Disease which affect these animals can produce severe economic losses, especially amongst cattle. The methods of the invention can be used to protect against infection in livestock, such as cows, horses, pigs, sheep and goats.

Cows can be infected by bovine viruses. Bovine viral diarrhea virus (BVDV) is a small enveloped positive-stranded RNA virus and is classified, along with hog cholera virus (HOCV) and sheep border disease virus (BDV), in the pestivirus genus. Although Pestiviruses were previously classified in the Togaviridae family, some studies have suggested their reclassification within the Flaviviridae family along with the flavivirus and hepatitis C virus (HCV) groups.

Equine herpesviruses (EHV) comprise a group of antigenically distinct biological agents which cause a variety of infections in horses ranging from subclinical to fatal disease. These include Equine herpesvirus-1 (EHV-1), a ubiquitous pathogen in horses. EHV-1 is associated with epidemics of abortion, respiratory tract disease, and central nervous system disorders. Other EHV's include EHV-2, or equine cytomegalovirus, EHV-3, equine coital exanthema virus, and EHV-4, previously classified as EHV-1 subtype 2.

Sheep and goats can be infected by a variety of dangerous microorganisms including visna-maedi.

Primates such as monkeys, apes and macaques can be infected by simian immunodeficiency virus. Inactivated cell-virus and cell-free whole simian immunodeficiency vaccines have been reported to afford protection in macaques (Stott et al., Lancet 36:1538-1541 (1990); Desrosiers et al., PNAS USA 86:6353-6357 (1989); Murphey-Corb et al., Science 246:1293-1297 (1989); and Carlson et al., AIDS Res. Human Retroviruses 6:1239-1246 (1990)). A recombinant HIV gp120 vaccine has been reported to afford Protection in chimpanzees (Berman et al., Nature 345:622-625 (1990)).

Cats, both domestic and wild, are susceptible to infection with a variety of microorganisms. For instance, feline infectious peritonitis is a disease which occurs in both domestic and wild cats, such as lions, leopards, cheetahs, and jaguars. When it is desirable to prevent infection with this and other types of pathogenic organisms in cats, the methods of the invention can be used to vaccinate cats to prevent them against infection.

Domestic cats may become infected with several retroviruses, including but not limited to feline leukemia virus (FeLV), feline sarcoma virus (FeSV), endogenous type C oncomavirus (RD-114), and feline syncytia-forming virus (FeSFV). The discovery of feline T-lymphotropic lentivirus (also referred to as feline immunodeficiency) was first reported in Pedersen et al., Science 235:790-793 (1987). Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat and pallas cat.

Viral and bacterial diseases in fin-fish, shellfish or other aquatic life forms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic life forms facility. Prevention of disease is a more desired remedy to these threats to fish than intervention once the disease is in progress. Vaccination of fish is the only preventative method which may offer long-term protection through immunity. Nucleic acid based vaccinations of fish are described, for example, in U.S. Pat. No. 5,780,448.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Vaccines can be administered orally or by immersion or injection.

Aquaculture species include but are not limited to fin-fish, shellfish, and other aquatic animals. Fin-fish include all vertebrate fish, which may be bony or cartilaginous fish, such as, for example, salmonids, carp, catfish, yellowtail, seabream and seabass. Salmonids are a family of fin-fish which include trout (including rainbow trout), salmon and Arctic char. Examples of shellfish include, but are not limited to, clams, lobster, shrimp, crab and oysters. Other cultured aquatic animals include, but are not limited to, eels, squid and octopi.

Polypeptides of viral aquaculture pathogens include but are not limited to glycoprotein or nucleoprotein of viral hemorrhagic septicemia virus (VHSV); G or N proteins of infectious hematopoietic necrosis virus (IHNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

Polypeptides of bacterial pathogens include but are not limited to an iron-regulated outer membrane protein, (TROMP), an outer membrane protein (OMP), and an A-protein of Aeromonis salmonicida which causes furunculosis, p57 protein of Renibacterium salmoninarum which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (TROMP), and a structural protein of Pasteurellosis; an OMP and a flagellar protein of Vibrosis anguillarum and V. ordalii; a flagellar protein, an OMP protein, aroA, and purA of Edwardsiellosis ictaluri and E. tarda; and surface antigen of Ichthyophthirius; and a structural and regulatory protein of Cytophaga columnari; and a structural and regulatory protein of Rickettsia.

Polypeptides of a parasitic pathogen include but are not limited to the surface antigens of Ichthyophthirius.

In another aspect of the invention, there is provided vaccine compositions suitable for use in methods for preventing and/or attenuating diseases or conditions which are caused or exacerbated by "self" gene products (e.g., tumor necrosis factors). Thus, vaccine compositions of the invention include compositions which lead to the production of antibodies that prevent and/or attenuate diseases or conditions caused or exacerbated by "self" gene products. Examples of such diseases or conditions include graft versus host disease, IgE-mediated allergic reactions, anaphylaxis, adult respiratory distress syndrome, Crohn's disease, allergic asthma, acute lymphoblastic leukemia (ALL), non-Hodgkin's lymphoma (NHL), Graves' disease, systemic lupus erythematosus (SLE), inflammatory autoimmune diseases, myasthenia gravis, immunoproliferative disease lymphadenopathy (IPL), angioimmunoproliferative lymphadenopathy (AIL), immunoblastive lymphadenopathy (IBL), rheumatoid arthritis, diabetes, prion diseases, multiple sclerosis, Alzheimer disease and osteoporosis.

In related specific embodiments, compositions of the invention are an immunotherapeutic that can be used for the treatment and/or prevention of allergies, cancer or drug addiction.

The selection of antigens or antigenic determinants for the preparation of compositions and for use in methods of treatment for allergies would be known to those skilled in the medical arts treating such disorders. Representative examples of such antigens or antigenic determinants include the following: bee venom phospholipase $A_2$, Bet v I (birch pollen allergen), 5 Dol m V (white-faced hornet venom allergen), and Der p I (House dust mite allergen), as well as fragments of each which can be used to elicit immunological responses.

The selection of antigens or antigenic determinants for compositions and methods of treatment for cancer would be known to those skilled in the medical arts treating such disorders (see Renkvist et al., *Cancer. Immunol. Immunother.* 50:3-15 (2001) which is incorporated by reference), and such antigens or antigenic determinants are included within the scope of the present invention. Representative examples of such types of antigens or antigenic determinants include the following: Her2 (breast cancer); GD2 (neuroblastoma); EGF-R (malignant glioblastoma); CEA (medullary thyroid cancer); CD52 (leukemia); human melanoma protein gp100; human melanoma protein gp100 epitopes such as amino acids 154-162 (sequence: KTWGQYWQV, SEQ ID NO:90), 209-217 (ITDQVPFSV, SEQ ID NO:91), 280-288 (YLEPG-PVTA, SEQ ID NO:92), 457-466 (LLDGTATLRL, SEQ ID NO:93) and 476-485 (VLYRYGSFSV, SEQ ID NO:94); human melanoma protein melan-A/MART-1; human melanoma protein melan-A/MART-1 epitopes such as amino acids 27-35 (AAGIGILTV, SEQ ID NO:95) and 32-40 (IL-TVILGVL, SEQ ID NO:96); tyrosinase and tyrosinase related proteins (e.g., TRP-1 and TRP-2); tyrosinase epitopes such as amino acids 1-9 (MLLAVLYCL, SEQ ID NO:97) and 369-377 (YMDGTMSQV, SEQ ID NO:98); NA17-A nt protein; NA17-A nt protein epitopes such as amino acids 38-64 (VLPDVFIRC, SEQ ID NO:99); MAGE-3 protein; MAGE-3 protein epitopes such as amino acids 271-279 (FLWG-PRALV, SEQ ID NO:100); other human tumors antigens, e.g. CEA epitopes such as amino acids 571-579 (YLSGANLNL, SEQ ID NO:101); p53 protein; p53 protein epitopes such as amino acids 65-73 (RMPEAAPPV, SEQ ID NO:102), 149-157 (STPPPGTRV, SEQ ID NO:103) and 264-272 (LLGRNSFEV, SEQ ID NO:104); Her2/neu epitopes such as amino acids 369-377 (KIFGSLAFL, SEQ ID NO:104) and 654-662 (IISAVVGIL, SEQ ID NO:105); NY-ESO-1 peptides 157-165 and 157-167, 159-167; HPV16 E7 protein; HPV16 E7 protein epitopes such as amino acids 86-93 (TL-GIVCPI, SEQ ID NO:106); as well as fragments of each which can be used to elicit immunological responses.

The selection of antigens or antigenic determinants for compositions and methods of treatment for drug addiction, in particular recreational drug addiction, would be known to those skilled in the medical arts treating such disorders. Representative examples of such antigens or antigenic determinants include, for example, opioids and morphine derivatives such as codeine, fentanyl, heroin, morphium and opium; stimulants such as amphetamine, cocaine, MDMA (methylenedioxymethamphetamine), methamphetamine, methylphenidate and nicotine; hallucinogens such as LSD, mescaline and psilocybin; as well as cannabinoids such as hashish and marijuana.

The selection of antigens or antigenic determinants for compositions and methods of treatment for other diseases or conditions associated with self antigens would be also known to those skilled in the medical arts treating such disorders. Representative examples of such antigens or antigenic determinants are, for example, lymphotoxins (e.g. Lymphotoxin α (LT α), Lymphotoxin β (LT β)), and lymphotoxin receptors, Receptor activator of nuclear factor kappaB ligand (RANKL), vascular endothelial growth factor (VEGF) and vascular endothelial growth factor receptor (VEGF-R), Interleukin 17 and amyloid beta peptide ($A\beta_{1-42}$), TNFα, MIF, MCP-1, SDF-1, Rank-L, M-CSF, Angiotensin II, Endoglin, Eotaxin, Grehlin, BLC, CCL21, IL-13, IL-17, IL-5, IL-8, IL-15, Bradykinin, Resistin, LHRH, GHRH, GIH, CRH, TRH and Gastrin, as well as fragments of each which can be used to elicit immunological responses.

In a particular embodiment of the invention, the antigen or antigenic determinant is selected from the group consisting of: (a) a recombinant polypeptide of HIV; (b) a recombinant polypeptide of Influenza virus (e.g., an Influenza virus M2 polypeptide or a fragment thereof); (c) a recombinant polypeptide of Hepatitis C virus; (d) a recombinant polypeptide of Hepatitis B virus (e) a recombinant polypeptide of *Toxoplasma*; (f) a recombinant polypeptide of *Plasmodium falciparum*; (g) a recombinant polypeptide of *Plasmodium vivax*; (h) a recombinant polypeptide of *Plasmodium ovale*; (i) a recombinant polypeptide of *Plasmodium malariae*; (j) a recombinant polypeptide of breast cancer cells; (k) a recombinant polypeptide of kidney cancer cells; (l) a recombinant polypeptide of prostate cancer cells; (m) a recombinant polypeptide of skin cancer cells; (n) a recombinant polypeptide of brain cancer cells; (o) a recombinant polypeptide of leukemia cells; (p) a recombinant profiling; (q) a recombinant polypeptide of bee sting allergy; (r) a recombinant polypeptide of nut allergy; (s) a recombinant polypeptide of pollen; (t) a recombinant polypeptide of house-dust; (u) a recombinant polypeptide of cat or cat hair allergy; (v) a recombinant protein of food allergies; (w) a recombinant protein of asthma; (x) a recombinant protein of *Chlamydia*; and (y) a fragment of any of the proteins set out in (a)-(x).

In another embodiment of the present invention, the antigen, being coupled, fused or otherwise attached to the virus-like particle, is a T cell epitope, either a cytotoxic or a Th cell epitope. In a further preferred embodiment, the antigen is a combination of at least two, preferably different, epitopes, wherein the at least two epitopes are linked directly or by way of a linking sequence. These epitopes are preferably selected from the group consisting of cytotoxic and Th cell epitopes.

It should also be understood that a mosaic virus-like particle, e.g. a virus-like particle composed of subunits attached to different antigens and epitopes, respectively, is within the scope of the present invention. Such a composition of the present invention can be, for example, obtained by transforming *E. coli* with two compatible plasmids encoding the subunits composing the virus-like particle fused to different antigens and epitopes, respectively. In this instance, the mosaic virus-like particle is assembled either directly in the cell or after cell lysis. Moreover, such an inventive composition can also be obtained by attaching a mixture of different antigens and epitopes, respectively, to the isolated virus-like particle.

The antigen of the present invention, and in particular the indicated epitope or epitopes, can be synthesized or recombinantly expressed and coupled to the virus-like particle, or fused to the virus-like particle using recombinant DNA techniques. Exemplary procedures describing the attachment of antigens to virus-like particles are disclosed in WO 00/32227, in WO 01/85208 and in WO 02/056905, the disclosures of which are herewith incorporated by reference in its entirety The invention also provides a method of producing a composition for enhancing an immune response in an animal comprising a VLP and an immunostimulatory substance, preferably an unmethylated CpG-containing oligonucleotide bound to the VLP which comprises incubating the VLP with the immunostimulatory substance and oligonucleotide, respectively, adding RNase and purifying said composition. In an equally preferred embodiment, the method comprises incubating the VLP with RNase, adding the immunostimulatory substance and oligonucleotide, respectively, and purifying the composition. In one embodiment, the VLP is produced in a bacterial expression system. In another embodiment, the RNase is RNase A.

The invention further provides a method of producing a composition for enhancing an immune response in an animal comprising a VLP bound to an immunostimulatory substance, preferably to an unmethylated CpG-containing oligonucleotide which comprises disassembling the VLP, adding the immunostimulatory substance and oligonucleotide, respectively, and reassembling the VLP. The method can further comprise removing nucleic acids of the disassembled VLP and/or purifying the composition after reassembly.

The invention also provides vaccine compositions which can be used for preventing and/or attenuating diseases or conditions. Vaccine compositions of the invention comprise, or alternatively consist of, an immunologically effective amount of the inventive immune enhancing composition together with a pharmaceutically acceptable diluent, carrier or excipient. The vaccine can also optionally comprise an adjuvant.

The invention further provides vaccination methods for preventing and/or attenuating diseases or conditions in animals. In one embodiment, the invention provides vaccines for the prevention of infectious diseases in a wide range of animal species, particularly mammalian species such as human, monkey, cow, dog, cat, horse, pig, etc. Vaccines can be designed to treat infections of viral etiology such as HIV, influenza, Herpes, viral hepatitis, Epstein Bar, polio, viral encephalitis, measles, chicken pox, etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

In another embodiment, the invention provides vaccines for the prevention of cancer in a wide range of species, particularly mammalian species such as human, monkey, cow, dog, cat, horse, pig, etc. Vaccines can be designed to treat all types of cancer including, but not limited to, lymphomas, carcinomas, sarcomas and melanomas.

As would be understood by one of ordinary skill in the art, when compositions of the invention are administered to an animal, they can be in a composition which contains salts, buffers, adjuvants or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1990)).

Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts, MF-59, and Virosomal adjuvant technology. The adjuvants can also comprise a mixture of these substances.

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention can be administered by various methods known in the art. The particular mode selected will depend of course, upon the particular composition selected, the severity of the condition being treated and the dosage required for therapeutic efficacy. The methods of the invention, generally speaking, can be practiced using any mode of administration that is medically acceptable, meaning any mode that produces effective levels of the active compounds without causing clinically unacceptable adverse effects. Such modes of administration include oral, rectal, parenteral, intracistemal, intravaginal, intraperitoneal, topical (as by powders, ointments, drops or transdermal patch), bucal, or as an oral or nasal spray. The term "parenteral" as used herein refers to modes of administration which include intravenous, intramuscular, intraperitoneal, intrasternal, subcutaneous and intraarticular injection and infusion. The composition of the invention can also be injected directly in a lymph node.

Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Combinations can be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Dosage levels depend on the mode of administration, the nature of the subject, and the quality of the carrier/adjuvant formulation. Typical amounts are in the range of about 0.1 μg to about 20 mg per subject. Preferred amounts are at least about 1 μg to about 100 μg per subject. Multiple administration to immunize the subject is preferred, and protocols are those standard in the art adapted to the subject in question.

The compositions can conveniently be presented in unit dosage form and can be prepared by any of the methods well-known in the art of pharmacy. Methods include the step of bringing the compositions of the invention into association with a carrier which constitutes one or more accessory ingredients. In general, the compositions are prepared by uniformly and intimately bringing the compositions of the invention into association with a liquid carrier, a finely divided solid carrier, or both, and then, if necessary, shaping the product.

Compositions suitable for oral administration can be presented as discrete units, such as capsules, tablets or lozenges, each containing a predetermined amount of the compositions of the invention. Other compositions include suspensions in aqueous liquids or non-aqueous liquids such as a syrup, an elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art.

Other embodiments of the invention include processes for the production of the compositions of the invention and methods of medical treatment for cancer and allergies using said compositions.

Further aspects and embodiments of the present invention will become apparent in the following examples and the appended claims.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference in their entirety.

EXAMPLE 1

Generation of p33-HBcAg VLPs

The DNA sequence of HBcAg containing peptide p33 from LCMV is given in FIG. 1B. The p33-HBcAg VLPs (p33-VLPs) were generated as follows: Hepatitis B clone pEco63 containing the complete viral genome of Hepatitis B virus was purchased from ATCC. The gene encoding HBcAg was introduced into the EcoRI/HindIII restriction sites of expression vector pkk223.3 (Pharmacia) under the control of a strong tac promoter. The p33 peptide (KAVYNFATM, SEQ ID NO:107) derived from lymphocytic choriomeningitis virus (LCMV) was fused to the C-terminus of HBcAg (1-185) via a three leucine-linker by standard PCR methods. A clone of $E.\ coli$ K802 selected for good expression was transfected with the plasmid, and cells were grown and resuspended in 5 ml lysis buffer (10 mM $Na_2HPO_4$, 30 mM NaCl, 10 mM EDTA, 0.25% Tween-20, pH 7.0). 200 μl of lysozyme solution (20 mg/ml) was added. After sonication, 4 μl Benzonase and 10 mM $MgCl_2$ was added and the suspension was incubation for 30 minutes at RT, centrifuged for 15 minutes at 15,000 rpm at 4° C. and the supernatant was retained.

Figure 2B:
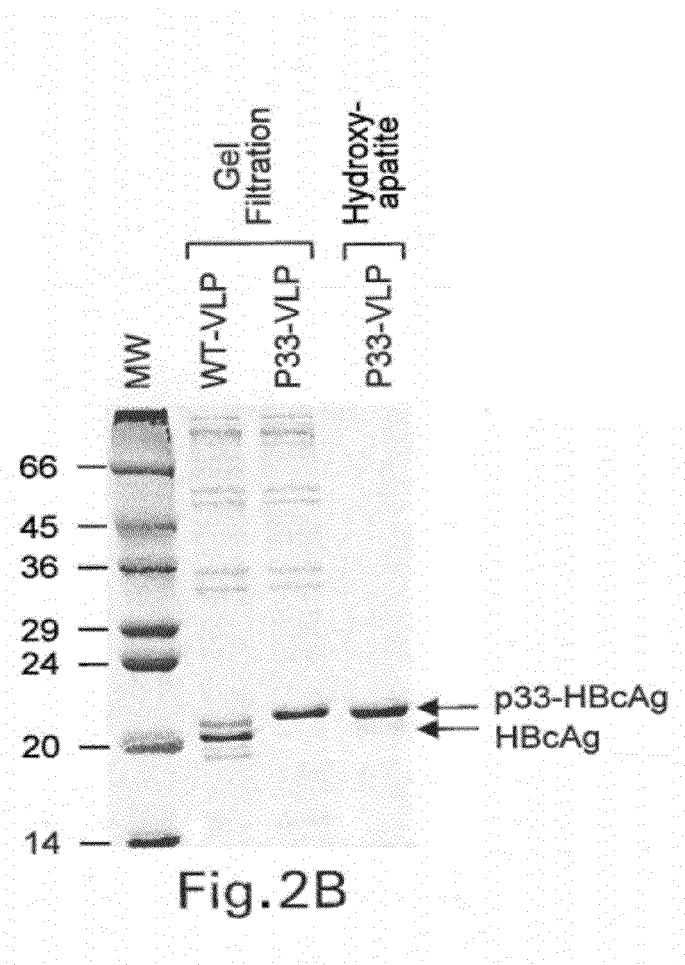

Next, 20% (w/v) (0.2 g/ml lysate) ammonium sulfate was added to the supernatant. After incubation for 30 minutes on ice and centrifugation for 15 minutes at 20,000 rpm at 4° C. the supernatant was discarded and the pellet resuspended in 2-3 ml PBS. 20 ml of the PBS-solution was loaded onto a Sephacryl S-400 gel filtration column (Amersham Pharmacia Biotechnology AG), fractions were loaded onto a SDS-Page gel and fractions with purified p33-VLP capsids were pooled. Pooled fractions were loaded onto a Hydroxyappatite column. Flow through (which contains purified p33-VLP capsids) was collected (FIG. 2B). Electron microscopy was performed according to standard protocols. A representative example is shown in FIG. 2A.

EXAMPLE 2

CpG-Containing Oligonucleotides can be Packaged into HBcAg VLPs

Recombinant p33-VLPs were run on a native agarose (1%) gel electrophoresis and stained with ethidium bromide or Coomassie blue for the detection of RNA/DNA or protein (FIG. 3). Bacterial produced VLPs contain high levels of single stranded RNA, which is presumably binding to the arginine repeats appearing near the C-terminus of the HBcAg protein and being geographically located inside the VLPs as shown by X-ray crystallography. The contaminating RNA can be easily digested and so eliminated by incubating the VLPs with RNase A. The highly active RNase A enzyme has a molecular weight of about 14 kDa and is presumably small enough to enter the VLPs to eliminate the undesired ribonucleic acids.

Figure 4A:
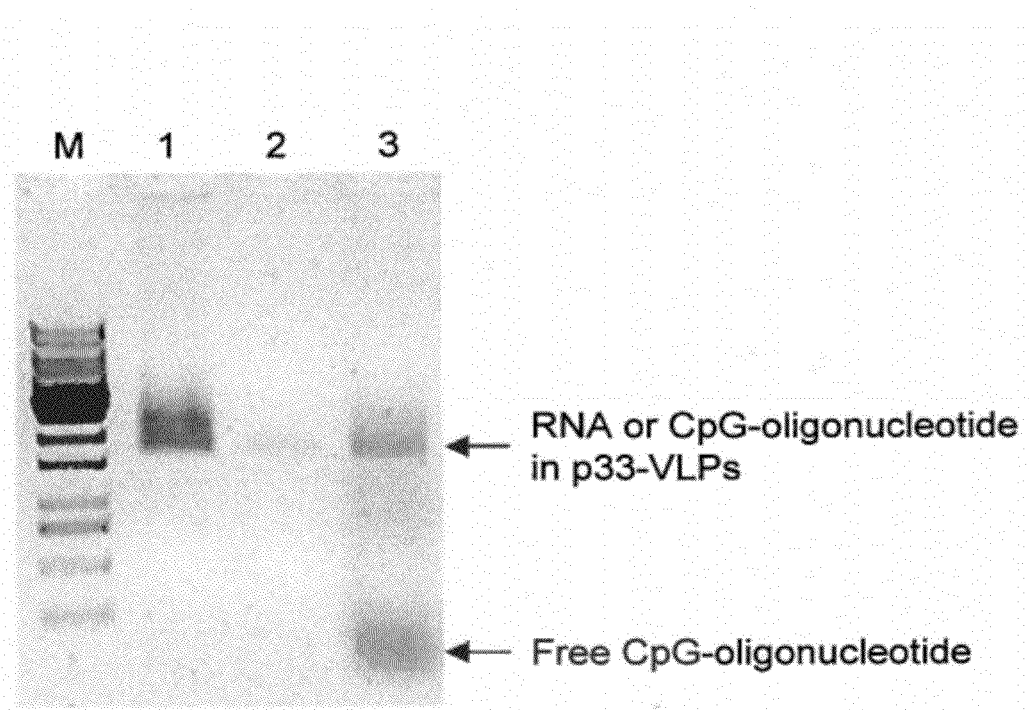
Figure 4B:
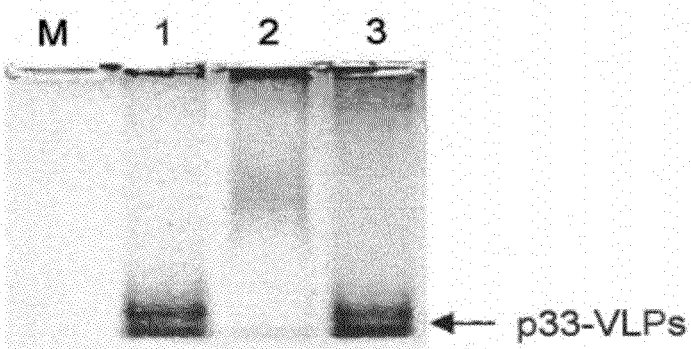
Figure 5A:
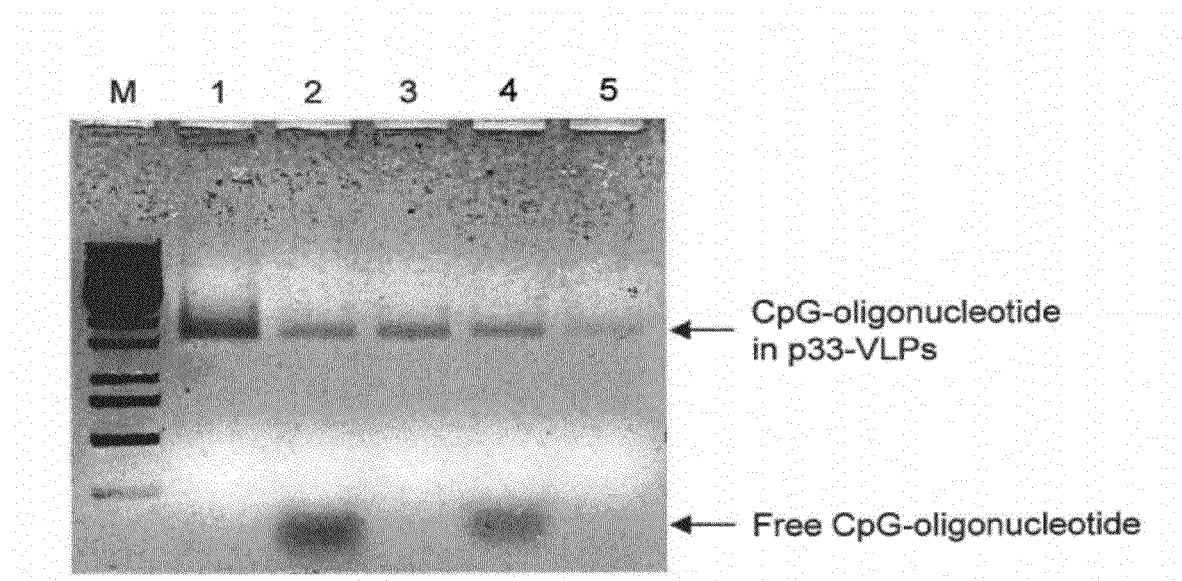
Figure 5B:
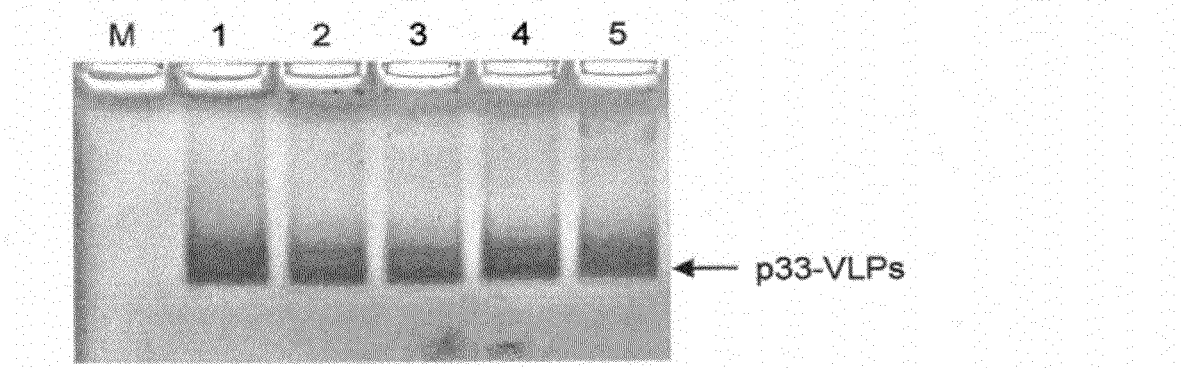

The recombinant p33-VLPs were supplemented with CpG-oligonucleotides (FIG. 1A) before digestion with RNase A. As shown in FIG. 4 the presence of CpG-oligonucleotides preserved the capsid structure as shown by similar migration compared to untreated p33-VLPs. The CpG-oligonucleotide-containing VLPs were purified from unbound oligonucleotides via dialysis (4500-fold dilution in PBS for 24 hours using a 300 kDa MWCO dialysis membrane) (FIG. 5).

EXAMPLE 3

Figure 6A:
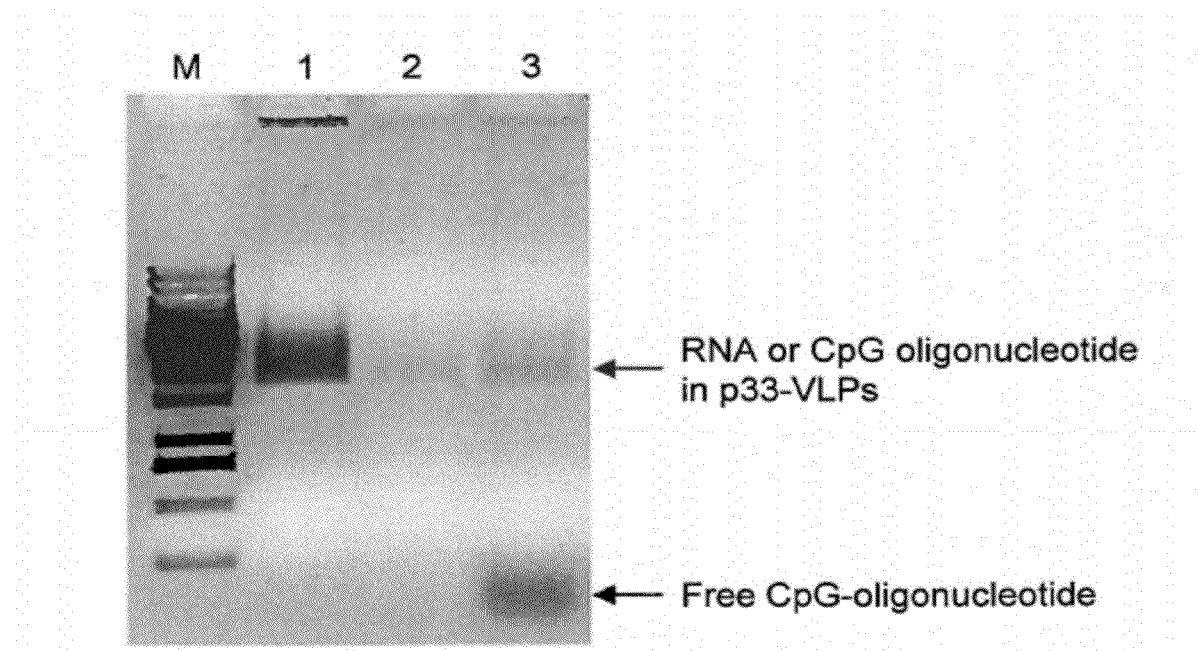
Figure 6B:
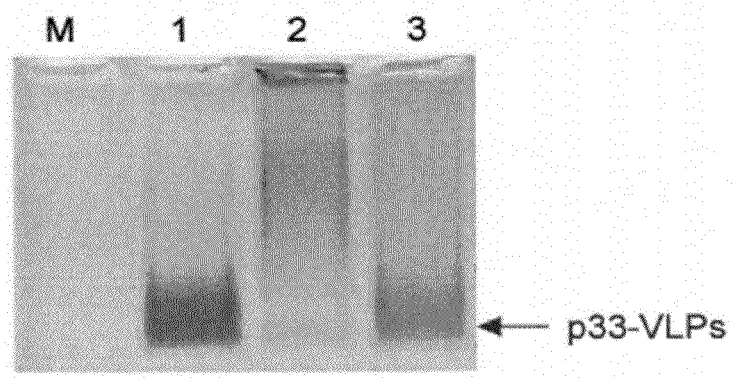

CpG-Oligonucleotides can be Packaged into VLPs by Removal of the RNA with RNAse and Subsequent Packaging of Oligonucleotides into VLPs The p33-VLPs (containing bacterial single-stranded RNA) were first incubated with RNase A to remove the RNA and in a second step the immunostimulating CpG-oligonucleotides (with normal phosphodiester bonds but also with phosphorothioate modification of the phosphate backbone) was supplemented to the samples (FIG. 6). This experiment clearly shows that the CpG-oligonucleotides are not absolutely required simultaneously during the RNA degradation reaction but can be added at a later time.

EXAMPLE 4

Figure 7:
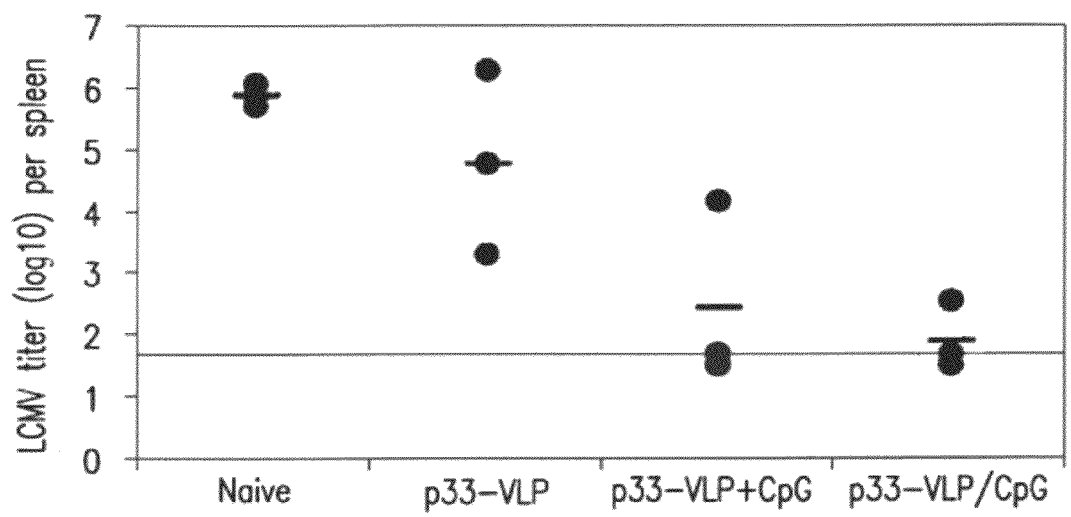
Figure 8:
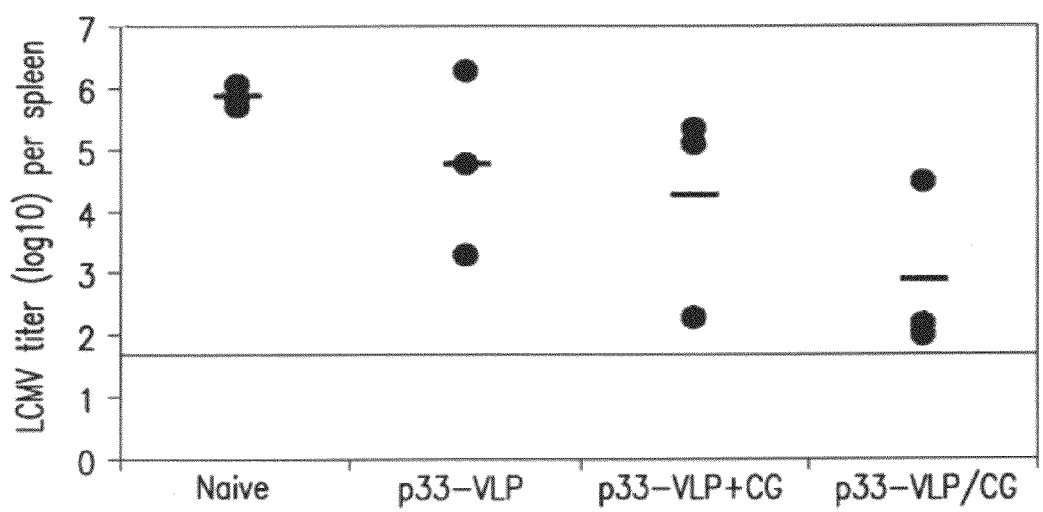
Figure 9:
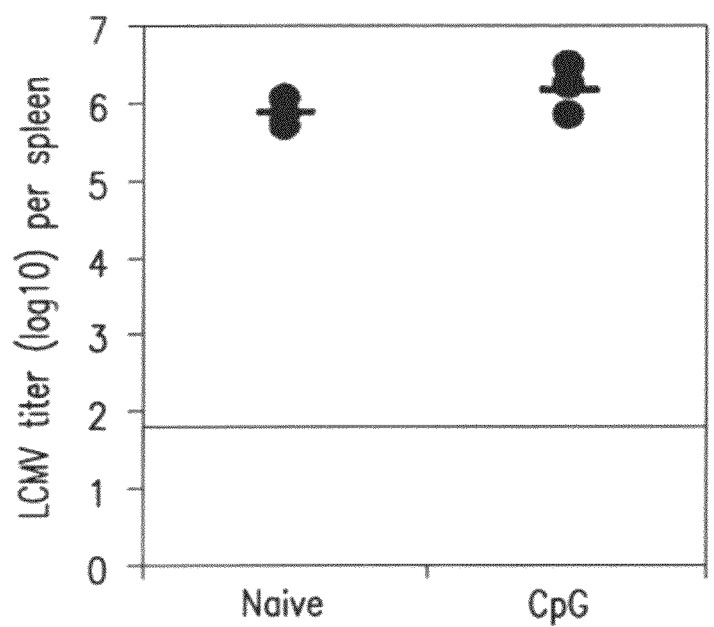

VLPs containing CpG-Oligonucleotides (with Phosphorothioate Modification of the Phosphate Backbone or Normal Phosphodiester Bonds) Induce Enhanced Anti-Viral Protection Mice were subcutaneously primed with 100 μg CpG-oligonucleotide containing p33-VLPs. Before immunization, p33-VLP preparations were extensively purified from unbound CpG-oligonucleotides via dialysis (see Example 2 and FIG. 5). As controls mice were subcutaneously primed with 100 μg p33-VLP alone, mixed with 20 nmol CpG-oligonucleotide, with 20 nmol CpG-oligonucleotide alone or left untreated. Twenty-one days later, mice were challenged with LCMV (200 pfu, intravenously) and viral titers were assessed in the spleens 5 days later as described in Bachmann, M. F., "Evaluation of lymphocytic choriomeningitis virus-specific cytotoxic T cell responses," in Immunology Methods Manual, Lefkowitz, I., ed., Academic Press Ltd., New York, N.Y. (1997) p. 1921. The results are shown in FIGS. 7, 8 and 9.

EXAMPLE 5

Generation of BKV Polyoma Capsids

BK virus (BKV) is a non-enveloped double stranded DNA virus belonging to the polyoma virus subfamily of the papovaviridae. VP1 is the major capsid protein. VP1 has 362 amino acids (FIG. 10, SEQ ID NO:3) and is 42 kDa in size. When produced in $E.\ coli$, insect cells or yeast VP1 spontaneously forms capsid structures (Salunke D. M., et al., Cell 46(6):895-904 (1986); Sasnauskas, K., et al., Biol. Chem. 380(3):381-6 (1999); Sasnauskas, K., et al., 3$^{rd}$ International Workshop "Virus-like particles as vaccines" Berlin, Sep. 26-29, 2001; Touze, A., et al., J Gen Virol. 82(Pt 12):3005-9 (2001). The capsid is organized in 72 VP1 pentamers forming an icosahedral structure. The capsids have a diameter of approximately 45 nm.

EXAMPLE 6

Fluorescein Labeled CpG-Containing Oligonucleotides can be Packaged into BKV VLPs VLPs produced in yeast contain small amounts of RNA which can be easily digested and so eliminated by incubating the VLPs with RNase A. The highly active RNase A enzyme has a molecular weight of about 14 kDa and is small enough to enter the VLPs to eliminate the undesired ribonucleic acids. Recombinantly produced BKV VLPs were concentrated to 1 mg/ml in PBS buffer pH7.2 and incubated in the absence or presence of RNase A (200 µg/ml, Roche Diagnostics Ltd, Switzerland) for 3 h at 37° C. After RNase A digestion BKV VLPs were supplemented with 75 nmol/ml fluorescein labeled phosphorothioate CpG-FAM oligonucleotide and incubated for 3 h at 37° C. Subsequently BKV VLPs were subjected to DNaseI digestion for 3 h at 37° C. (40 u/ml AMPD1, Sigma, Division of Fluka AG, Switzerland) or loaded without DNaseI digestion. The samples were complemented with 6-fold concentrated DNA-loading buffer (10 mM Tris pH7.5, 10% v/v glycerol, 0.4% orange G) and run for 1 h at 65 volts in a 0.8% native tris-acetate pH 7.5 agarose gel.

Figure 12A:
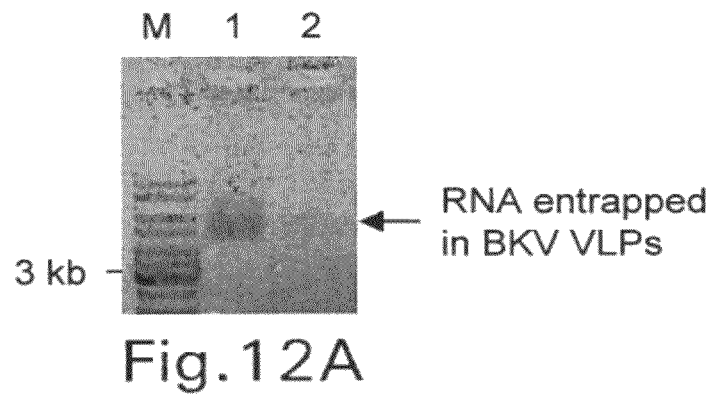
Figure 12B:
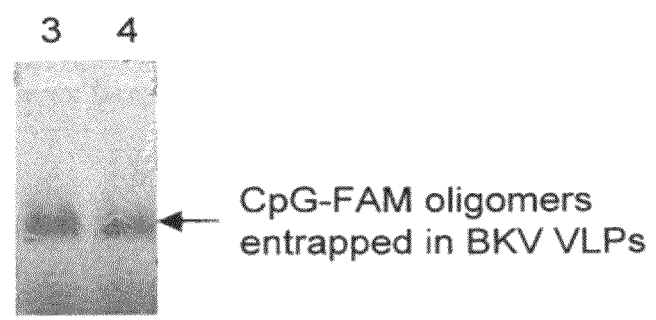

FIG. 12 shows BKV VLPs in a native 0.8% agarose gel electrophoresis after control incubation or after digestion with RNase A and subsequent incubation with fluorescent CpG-FAM oligonucleotides (oligonucleotide from FIG. 1A with a 5'-fluorescein-label) upon staining with ethidium bromide or without ethidium bromide staining. In the presence of ethidium bromide nucleic acids are detected, while in its absence UV excitation leads to fluorescence of the fluorescein-label in the CpG-FAM.

Figure 13A:
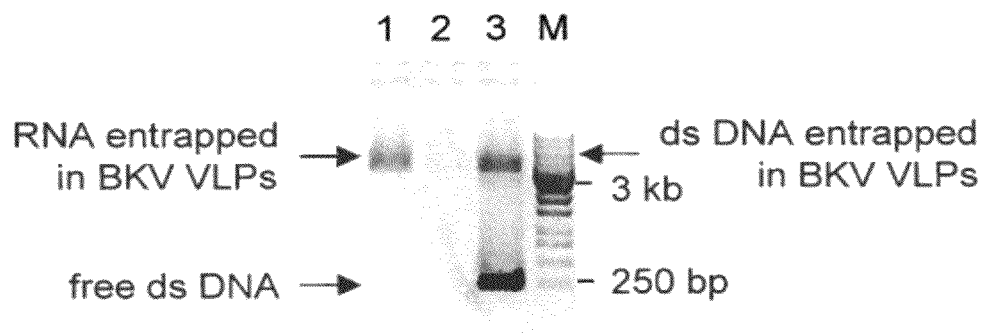
Figure 13B:
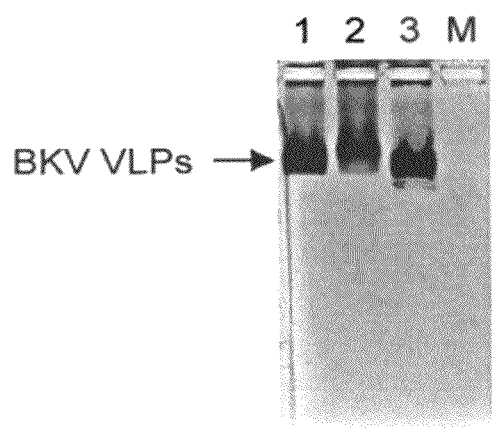
Figure 14A:
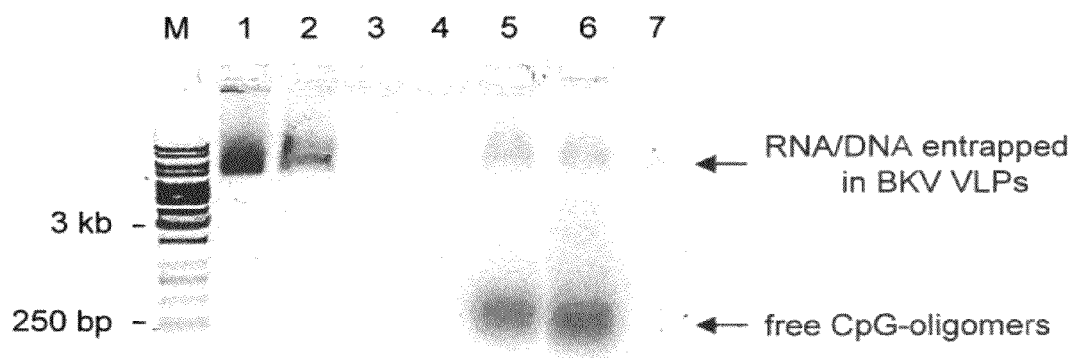
Figure 14B:
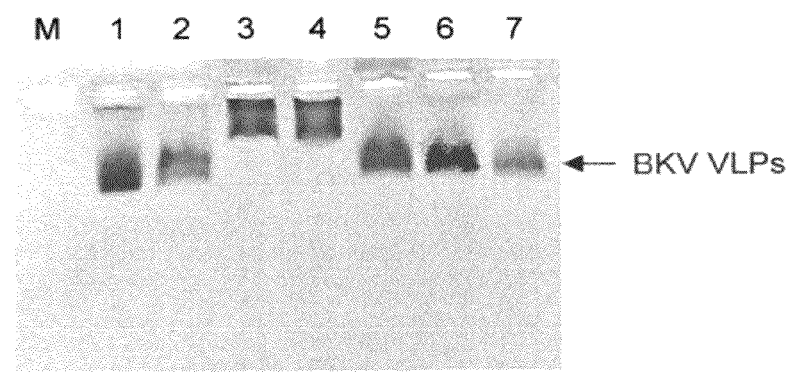

The RNase A digestion leads to a change in migration of the VLP, visible on Coomassie stained agarose gel, presumably due to the lack of negative charges from the RNA (FIGS. 13 and 14). Addition of CpG-oligonucleotide restores the migration of BKV VLPs and results in a fluorescent band with the same migration as the RNA band present in untreated VLPs. This clearly shows that CpG-FAM oligonucleotides have been packaged into VLPs.

EXAMPLE 7

Large Double Stranded Oligonucleotides can be Packaged into BKV VLPs

To introduce double stranded (ds) nucleotide sequences, the RNase A treated recombinant BKV VLPs (Example 6) were supplemented with 50 µg/ml (ds) DNA fragments (246 bp in length, FIG. 11, SEQ ID NO:4) and incubated for 3 h at 37° C. The samples were complemented with 6-fold concentrated DNA-loading buffer (10 mM Tris pH8.0, 10% v/v glycerol, 0.4% orange G) and run for 1 h at 65 volts in a 0.8% native tris-acetate pH 8.0 agarose gel.

FIG. 13 shows BKV VLPs (15 µg) in a native 0.8% agarose gel electrophoresis after control incubation or after digestion with RNase A and subsequent incubation with (ds) DNA upon staining with ethidium bromide or Coomassie Blue in order to assess the presence of RNA/DNA or protein. Packaged DNA molecules are visible in the presence of ethidium bromide as a band with the same migration as the VLP band visualized with Coomassie Blue.

Addition of (ds) DNA restores the migration of BKV VLPs and results in a DNA band with the same migration as the Coomassie Blue stained VLPs. This clearly shows that (ds) DNA has been packaged into BKV VLPs.

EXAMPLE 8

CpG-Containing Oligonucleotides can be Packaged into BKV VLPs

To introduce immunostimulatory CpG-oligonucleotides, the RNase A treated recombinant BKV VLPs (Example 6) were supplemented with 150 mmol/ml CpG-oligonucleotides with phosphodiester backbone or with phosphorothioate backbone and incubated for 3 h at 37° C. VLP preparations for mouse immunization were extensively dialysed (10.000-fold diluted) for 24 h against PBS pH7.2 with a 300 kDa MWCO dialysis membrane (Spectrum Medical industries Inc., Houston, USA) to eliminate RNase A and the excess of CpG-oligonucleotides. The samples were complemented with 6-fold concentrated DNA-loading buffer (10 mM Tris pH7.5, 10% v/v glycerol, 0.4% orange G) and run for 1 h at 65 volts in a 0.8% native tris-acetate pH7.5 agarose gel.

FIG. 14 shows BKV VLPs (15 µg) in a native 0.8% agarose gel electrophoresis after control incubation or after digestion with RNase A and subsequent incubation with CpG-oligonucleotides (with phosphodiester- or with phosphorothioate backbone) upon staining with ethidium bromide (A) or Coomassie Blue (B) in order to assess the presence of RNA/DNA or protein and the reduction of unbound CpG-oligonucleotides after dialysis. Unbound CpG-oligonucleotides are visible as a low molecular weight ethidium bromide stained band.

Addition of CpG-oligonucleotides restores the migration of BKV VLPs and results in a DNA band with the same migration as the Coomassie Blue stained VLPs. This clearly shows that CpG-oligonucleotides are packaged into BKV VLPs.

EXAMPLE 9

VLPs Containing CpG-Oligonucleotides (with Phosphorothioate Modification of the Phosphate Backbone) Induce Enhanced Th1 Directed Immune Response Female BALB/c mice (three mice per group) were subcutaneously injected with 10 µg BKV VLPs containing phosphorothioate CpG-oligonucleotide (FIG. 1A, SEQ ID NO:109). As controls mice were subcutaneously injected with either 10 µg of RNase treated BKV VLPs alone or BKV VLPs mixed with 0.3 nmol or 20 nmol phosphorothioate CpG-oligonucleotides in 200 µl PBS pH7.2 or were left untreated. BKV VLPs were prepared as described in Example 8 and before immunization extensively purified from unbound CpG-oligonucleotide by dialysis. On day 14 after immunization blood was taken and IgG1 and IgG2a antibody response to BKV VLPs was determined.

Figure 15:
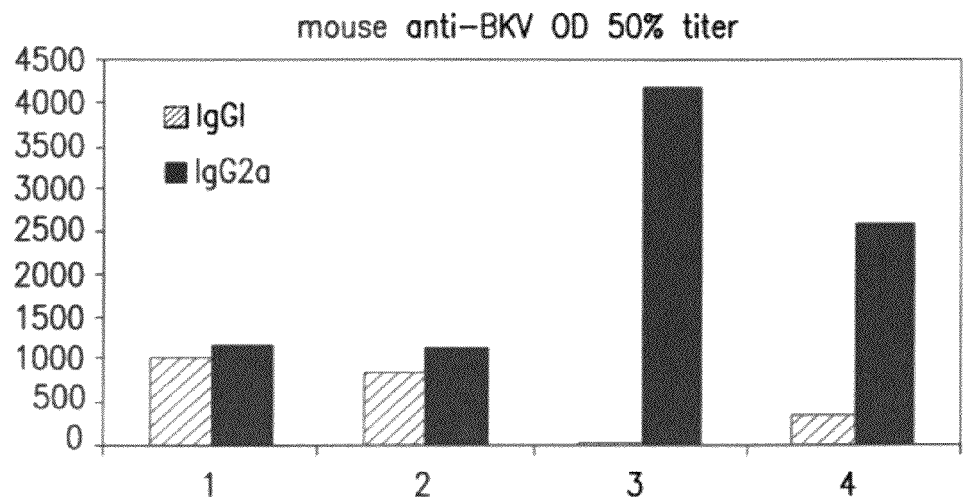

FIG. 15 shows IgG1 and IgG2a antibody response to BKV VLPs on day 14 after immunization. Immunization with RNase A treated BKV VLPs containing phosphorothioate CpG-oligonucleotides results in a decreased IgG1 and an increased anti-BKV VLP IgG2a titer as compared to immunization with the same amount (0.3 nmol) of CpG-oligonucleotides mixed with BKV VLPs or BKV VLPs alone. Mice immunized with BKV VLPs mixed with 20 nmol phosphorothioate CpG-oligonucleotides show very low IgG1 and high IgG2a titers. The decrease in IgG1 titer and the increase in IgG2a titer as compared to controls demonstrates a Th1 cell directed immune response induced by phosphorothioate CpG-oligonucleotides packaged in BKV VLPs. FIG. 15 clearly demonstrates the higher potency of BKV VLPs containing CpG-oligonucleotides packaged within the particles as compared to BKV VLPs simply mixed with CpG-oligonucleotides.

EXAMPLE 10

Figure 16A:
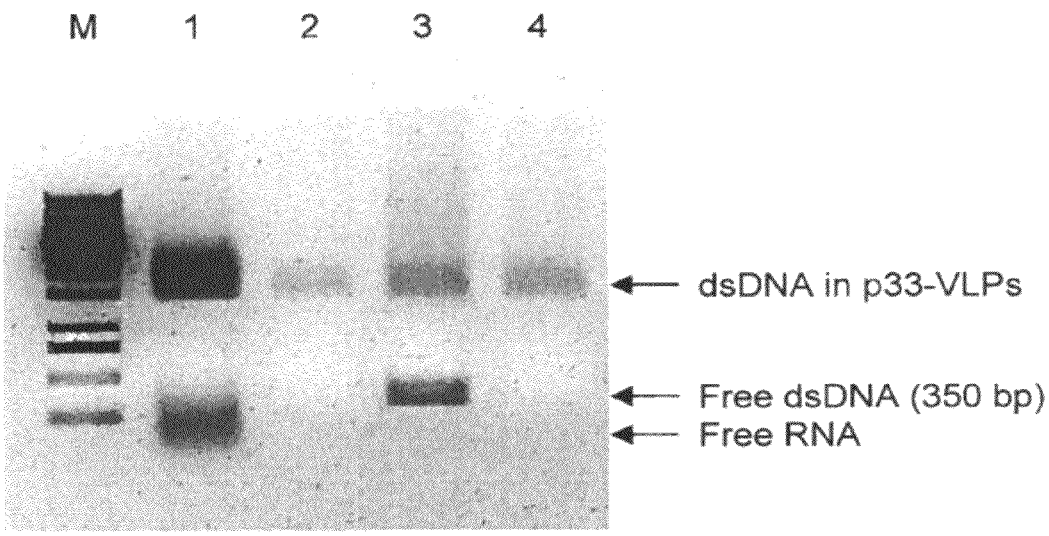
Figure 16B:
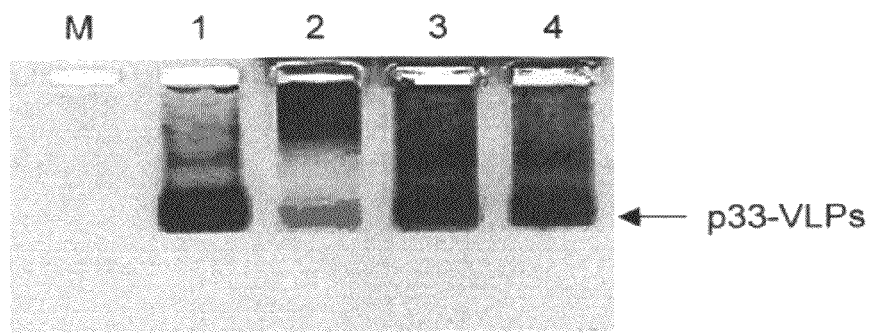

Linear Double-Stranded DNA (dsDNA) can be Packaged into VLPs by First RNAse Digestion and Subsequently Addition of dsDNA The p33-VLPs preparations (containing bacterial RNA) (EXAMPLE 1) were first incubated with RNaseA to remove the RNA and in a second step the linear dsDNA (350 bp long) was supplemented to the samples (FIG. 16). The migration of the p33-VLPs packaged with the dsDNA was similar to the one of p33-VLP containing RNA. This experiment shows that linear dsDNA of at least 350 base pairs in length can be packaged into the virus-like particles.

EXAMPLE 11

Immunostimulatory Nucleic Acids can be Packaged into HBcAg VLPs Comprising Fusion Proteins with Antigens HBcAg VLPs, when produced in *E. coli* by expressing the Hepatitis B core antigen fusion protein HBc33 (Example 1) or the fusion protein to the peptide P1A (HBcP1A), contain RNA which can be digested and so eliminated by incubating the VLPs with RNase A.

The gene P1A codes for a protein that is expressed by the mastocytoma tumor cell line P815. The dominant CTL epitope, termed P1A peptide, binds to MHC class I (Ld) and the complex is recognized by specific CTL clones (Brändle et al., 1998, Eur. J. Immunol. 28: 4010-4019). Fusion of peptide P1A-1 (LPYLGWLVF, SEQ ID NO:108) to the C-terminus of HBcAg (aa 185, see Example 1) was performed by PCR using appropriate primers using standard molecular biology techniques. A three leucine linker was cloned between the HBcAg and the peptide sequence. Expression was performed as described in Example 1. The fusion protein of HBcAg with P1A, termed HBcP1A, formed capsids when expressed in *E. coli* which could be purified similar to the procedure described in Example 1.

Enzymatic RNA Hydrolysis:

Recombinantly produced HBcAg-p33 (HBc33) and HBcAg-P1A (HBcP1A) VLPs at a concentration of 1.0 mg/ml in 1×PBS buffer (KCl 0.2 g/L, KH2PO4 0.2 g/L, NaCl 8 g/L, Na$_2$HPO4 1.15 g/L) pH 7.4, were incubated in the presence of 300 µg/ml RNase A (Qiagen AG, Switzerland) for 3 h at 37° C. in a thermomixer at 650 rpm.

Packaging of Immunostimulatory Nucleic Acids:

After RNA digestion with RNAse A HBcAg-p33 VLPs were supplemented with 130 nmol/ml CpG-oligonucleotides B-CpG (SEQ ID NO:112), NKCpG (SEQ ID NO:114), G10-PO (SEQ ID NO:116) (Table I). Similarly, the 150 mer single-stranded Cy150-1 (SEQ ID NO:123) and 253mer double stranded dsCyCpG-253 (SEQ ID NO:124), both containing multiple copies of CpG motifs, were added at 130 nmol/ml or 1.2 nmol/ml, respectively, and incubated in a thermomixer for 3 h at 37° C. Double stranded CyCpG-253 DNA was produced by cloning a double stranded multimer of CyCpG into the EcoRV site of pBluescript KS-. The resulting plasmid, produced in *E. coli* XL1-blue and isolated using the Qiagen Endofree plasmid Giga Kit, was digested with restriction endonucleases XhoI and XbaI and resulting restriction products were separated by agarose electrophoresis. The 253 bp insert was isolated by electro-elution and ethanol precipitation. Sequence was verified by sequencing of both strands.

TABLE I

Sequences of immunostimulatory nucleic acids used in the Examples.
Small letters indicate deoxynucleotides connected via phosphorothioate bonds while larger letters indicate deoxynucleotides connected via phosphodiester bonds

| | | |
|---|---|---|
| CyCpGpt | tccatgacgttcctgaataat | (SEQ ID NO: 109) |
| CyCpG | TCCATGACGTTCCTGAATAAT | (SEQ ID NO: 110) |
| B-CpGpt | tccatgacgttcctgacgtt | (SEQ ID NO: 111) |
| B-CpG | TCCATGACGTTCCTGACGTT | (SEQ ID NO: 112) |
| NKCpGpt | ggGGTCAACGTTGAggggg | (SEQ ID NO: 113) |
| NKCpG | GGGGTCAACGTTGAGGGGG | (SEQ ID NO: 114) |
| CyCpG-rev-pt | attattcaggaacgtcatgga | (SEQ ID NO: 115) |
| g10gacga-PO (G10-PO) | GGGGGGGGGGGACGATCGTCGGGGGGGGGG | (SEQ ID NO: 116) |
| g10gacga-PS (G10-PS) | ggggggggggggacgatcgtcgggggggggg | (SEQ ID NO: 117) |

TABLE I-continued

Sequences of immunostimulatory nucleic acids used in the Examples. Small letters indicate deoxynucleotides connected via phosphorothioate bonds while larger letters indicate deoxynucleotides connected via phosphodiester bonds

| | |
|---|---|
| (CpG) 20OpA | (SEQ ID NO: 118)<br>CGCGCGCGCGCGCGCGCGCGCGCGCGCGCGCGC<br>GCGCGCGAAATGCATGTCAAAGACAGCAT |
| Cy (CpG) 20 | (SEQ ID NO: 119)<br>TCCATGACGTTCCTGAATAATCGCGCGCGCGCG<br>CGCGCGCGCGCGCGCGCGCGCGCGCGCG |
| Cy (CpG) 20-OpA | (SEQ ID NO: 120)<br>TCCATGACGTTCCTGAATAATCGCGCGCGCGCG<br>CGCGCGCGCGCGCGCGCGCGCGCGCGAAATG<br>CATGTCAAAGACAGCAT |
| CyOpA | (SEQ ID NO: 121)<br>TCCATGACGTTCCTGAATAATAAATGCATGTCA<br>AAGACAGCAT |
| CyCyCy | (SEQ ID NO: 122)<br>TCCATGACGTTCCTGAATAATTCCATGACGTTC<br>CTGAATAATTCCATGACGTTCCTGAATAAT |
| Cy150-1 | (SEQ ID NO: 123)<br>TCCATGACGTTCCTGAATAATTCCATGACGTTC<br>CTGAATAATTCCATGACGTTCCTGAATAATTGG<br>ATGACGTTGGTGAATAATTCCATGACGTTCCTG<br>AATAATTCCATGACGTTCCTGAATAATTCCATG<br>ACGTTCCTGAATAATTCC |
| dsCyCpG-253<br>(complementary strand not shown) | (SEQ ID NO: 124)<br>CTAGAACTAGTGGATCCCCCGGGCTGCAGGAAT<br>TCGATTCATGACTTCCTGAATAATTCCATGACG<br>TTGGTGAATAATTCCATGACGTTCCTGAATAAT<br>TCCATGACGTTCCTGAATAATTCCATGACGTTC<br>CTGAATAATTCCATGACGTTCCTGAATAATTCC<br>ATGACGTTCCTGAATAATTCCATGACGTTCCTG<br>AATAATTCCATGACGTTCCTGAAAATTCCAATC<br>AAGCTTATCGATACCGTCGACC |

DNAse I Treatment:

Packaged HBcAg-p33 VLPs were subsequently subjected to DNaseI digestion (5 U/ml) for 3 h at 37° C. (DNaseI, RNase free Fluka AG, Switzerland) and were extensively dialysed (2× against 200-fold volume) for 24 h against PBS pH 7.4 with a 300 kDa MWCO dialysis membrane (Spectrum Medical industries Inc., Houston, USA) to eliminate RNAse A and the excess of CpG-oligonucleotides.

Benzonase Treatment:

Since some single stranded oligodeoxynucleotides were partially resistant to DNaseI treatment, Benzonase treatment was used to eliminate free oligonucleotides from the preparation. 100-120 U/ml Benzonase (Merck KGaA, Darmstadt, Germany) and 5 mM $MgCl_2$ were added and incubated for 3 h at 37° C. before dialysis.

Dialysis:

VLP preparations packaged with immunostimulatory nucleic acids used in mouse immunization experiments were extensively dialysed (2× against 200 fold volume) for 24 h against PBS pH 7A with a 300 kDa MWCO dialysis membrane (Spectrum Medical Industries, Houston, US) to eliminate added enzymes and free nucleic acids.

Analytics of Packaging: Release of Packaged Immunostimulatory Nucleic Acids:

To 50 µl capsid solution 1 µl of proteinase K (600 U/ml, Roche, Mannheim, Germany), 3 µl 10% SDS-solution and 6 µl 10 fold proteinase buffer (0.5 M NaCl, 50 mM EDTA, 0.1 M Tris pH 7.4) were added and subsequently incubated overnight at 37° C. VLPs are completed hydrolysed under these conditions. Proteinase K was inactivated by heating for 20 min at 65° C. 1 µl RNAse A (Qiagen, 100 µg/ml, diluted 250 fold) was added to 25 µl of capsid. 2-30 µg of capsid were mixed with 1 volume of 2× loading buffer (1×TBE, 42% w/v urea, 12% w/v Ficoll, 0.01% Bromphenolblue), heated for 3 min at 95° C. and loaded on a 10% (for oligonucleotides of about 20 nt length) or 15% (for >than 40 mer nucleic acids) TBE/urea polyacrylamid gel (Invitrogen). Alternatively samples were loaded on a 1% agarose gel with 6× loading dye (10 mM Tris pH 7.5, 50 mM EDTA, 10% v/v glycerol, 0.4% orange G). TBE/urea gels were stained with CYBRGold and agarose gels with stained with ethidium bromide.

Figure 17A:
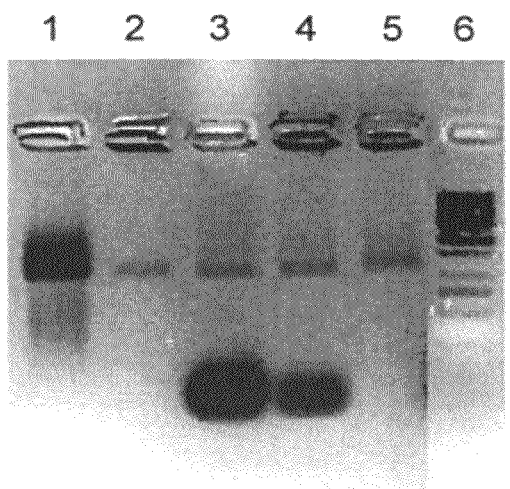
FIG. 17 shows packaging of B-CpG (SEQ ID NO:112) into HBc33 VLPs.
Figure 17B:
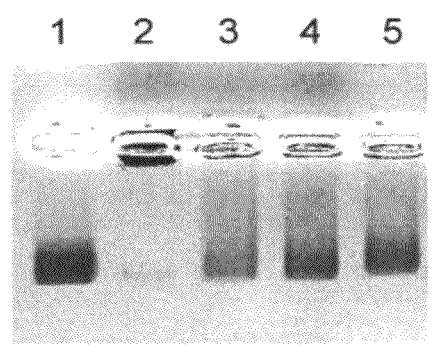
Figure 17C:
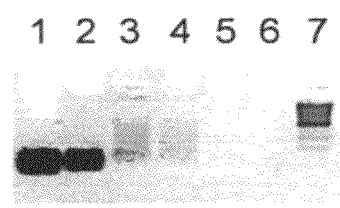
Figure 18A:
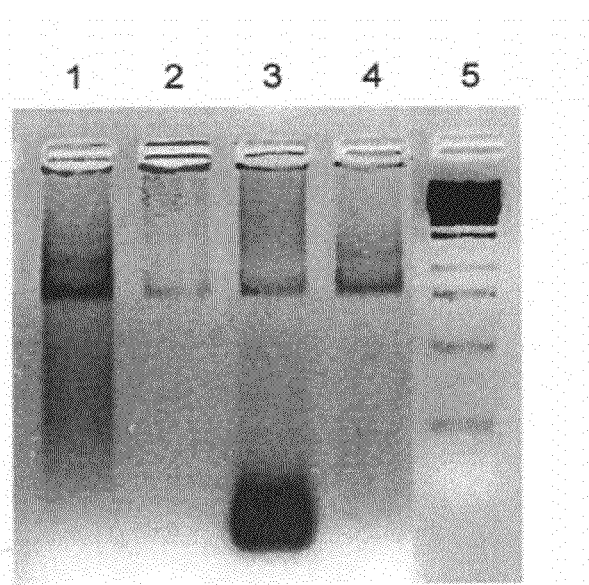
FIG. 18 shows packaging of NKCpG (SEQ ID NO:114) into HBc33 VLPs.
Figure 18B:
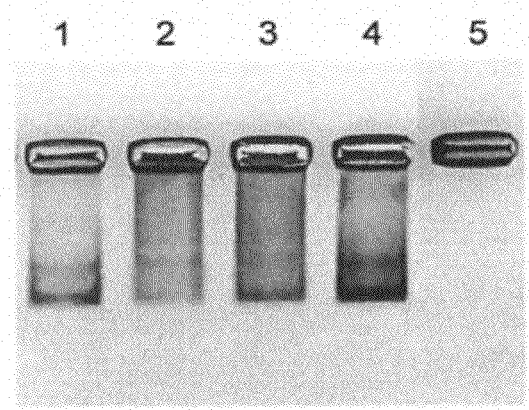
Figure 18C:
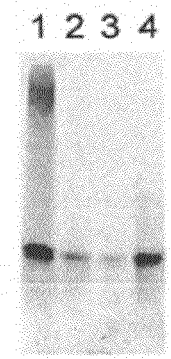
Figure 19A:
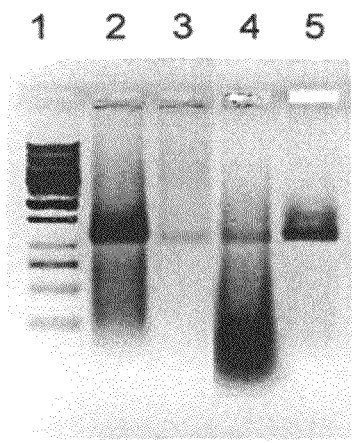
FIG. 19 shows packaging of g10gacga-PO (SEQ ID NO:116) into HBc33 VLPs.
Figure 19B:
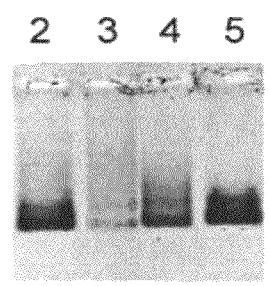

FIGS. 17, 18 and 19 show the packaging of B-CpG (SEQ ID NO:112), NKCpG (SEQ ID NO:114) and G10-PO (SEQ ID NO:116) oligonucleotides into HBc33. RNA content in the VLPs was strongly reduced after RNaseA treatment (FIG. 17A, 18A, 19A) while most of the capsid migrated as a a slow migrating smear presumably due to the removal of the negatively charged RNA (FIG. 17B, 18B, 19B). After incubation with an excess of oligonucleotide the capsids contained a higher amount of nucleic acid than the RNAseA treated capsids and therefore migrated at similar velocity as the untreated capsids. Additional treatment with DNAse I or Benzonase degraded the free oligonucleotides while oligonucleotides packaged in the capsids did not degrade, clearly showing packaging of oligonucleotides. In some cases packaging of oligonucleotides was confirmed by proteinase K digestion (as described in Examples 15 and 16) after DNAseI/Benzonase treatment and dialysis. The finding that oligonucleotides released from the capsid with the procedure described above were of the same size than the oligonucleotide used for packaging clearly demonstrated packaging of oligonucleotides (FIG. 17C, 18C).

Figure 20A:
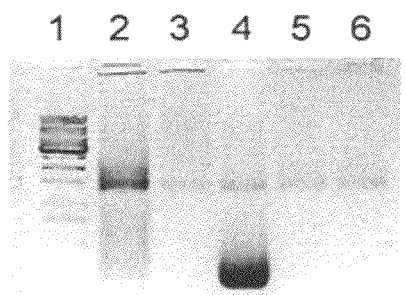
FIG. 20 shows packaging of Cy-150-1 (SEQ ID NO:123) into HBc33 VLPs.
Figure 20B:
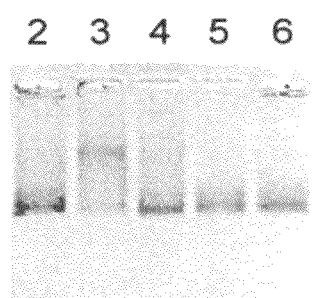
Figure 20C:
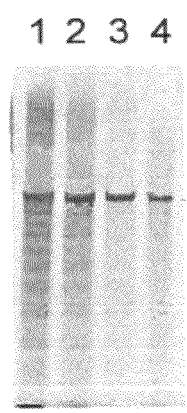

FIG. 20 shows packaging of a large single-stranded oligonucleotide Cy150-1 (SEQ ID NO:123) into HBc33. Cy150-1 contains 7.5 repeats of CyCpG and was synthesized according standard oligonucleotide synthesis methods (IBA, Göttingen, Germany). RNA content in the capsid was strongly reduced after RNaseA treatment while most of the capsid migrated as a slow migrating smear (FIG. 20A, B). Capsid were diluted with 4 volumes of water and concentrated to 1 mg/ml. After incubation with an excess of Cy150-1 the capsid contained a bigger amount of nucleic acid and thus migrated at similar velocity as the untreated capsids. Additional treatment with DNaseI degraded the free, not packaged oligonucleotides while oligonucleotides in capsids were not degraded (FIG. 20A). Release of the DNaseI-resistant nucleic acid from the packaged VLPs by heating for 3 min at 95° C. in TBE/urea loading buffer revealed the presence of the 150 mer (FIG. 20 C).

Figure 21A:
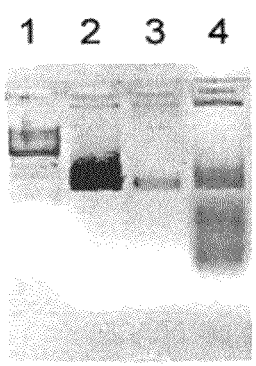
FIG. 21 shows packaging of NKCpGpt (SEQ ID NO: 113) into HBcP1A VLPs.
Figure 21B:
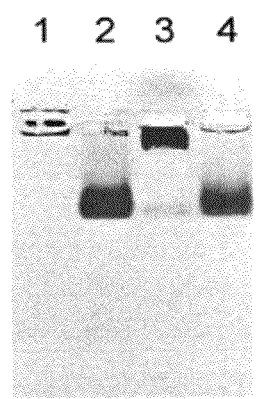

FIG. 21 shows packaging of oligonucleotide NKCpGpt (SEQ ID NO:113) in HBcP1A. Treatment with RNAse reduced nucleic acid content and slowed migration of the capsids. Addition of NKCpGpt restored nucleic acid content in capsids and fast migration.

FIG. 17 depicts the analysis of B-CpG (SEQ ID NO:112) packaging into HBc33 VLPs on a 1% agarose gel stained with ethidium bromide (A) and Coomassie Blue (B). Loaded on the gel are 50 μg of the following samples: 1. HBc33 VLP untreated; 2. HBc33 VLP treated with RNase A; 3. HBc33 VLP treated with RNase A and packaged with B-CpG; 4. HBc33 VLP treated with RNase A, packaged with B-CpG and treated with DNaseI; 5. HBc33 VLP treated with RNase A, packaged with B-CpG, treated with DNaseI and dialysed; 6. 1 kb MBI Fermentas DNA ladder. (C) depicts the analysis of the amount of packaged oligo extracted from the VLP on a 1.5% agarose gel stained with ethidium bromide: Loaded on gel are the following samples: 1. 0.5 nmol B-CpG control; 2. 0.5 mmol B-CpG control; 3. B-CpG oligo content HBc33 after phenol/chloroform extraction; 4. B-CpG oligo content HBc33 after phenol/chloroform extraction and RNase A treatment; 5. B-CpG oligo content HBc33 after phenol/chloroform extraction and DNaseI treatment; 6. empty; 7. MBI Fermentas 100 bp DNA ladder FIG. 18 depicts the analysis of NKCpG (SEQ ID NO:114) packaging into HBc33 VLPs on a 1% agarose gel stained with ethidium bromide (A) and Coomassie Blue (B). Loaded on the gel are 15 μg of the following samples: 1. HBc33 VLP untreated; 2. HBc33 VLP treated with RNase A; 3. HBc33 VLP treated with RNase A and packaged with NKCpG; 4. HBc33 VLP treated with RNase A, packaged with NKCpG, treated with DNaseI and dialysed; 5. 1 kb MBI Fermentas DNA ladder. (C) depicts the analysis of the amount of packaged oligo extracted from the VLP on a 15% TBE/urea gel stained with CYBR Gold. Loaded on gel are the following samples: 1. NKCpG oligo content HBc33 after proteinase K digestion and RNase A treatment; 2. 20 pmol NKCpG control; 3. 10 pmol NKCpG control; 4. 40 pmol NKCpG control.

FIG. 19 depicts the analysis of g10gacga-PO SEQ ID NO:116) packaging into HBc33 VLPs on a 1% agarose gel stained with ethidium bromide (A) and Coomassie Blue (B). Loaded on the gel are 15 μg of the following samples: 1. 1 kb MBI Fermentas DNA ladder; 2. HBc33 VLP untreated; 3. HBc33 VLP treated with RNase A; 4. HBc33 VLP treated with RNase A and packaged with g10gacga-PO; 5. HBc33 VLP treated with RNase A, packaged with g10gacga-PO, treated with Benzonase and dialysed.

FIG. 20 depicts the analysis of CyCpG-150 (SEQ ID NO:123) packaging into HBc33 VLPs on a 1% agarose gel stained with ethidium bromide (A) and Coomassie Blue (B). Loaded on the gel are 15 μg of the following samples: 1. 1 kb MBI Fermentas DNA ladder; 2. HBc33 VLP untreated; 3. HBc33 VLP treated with RNase A; 4. HBc33 VLP treated with RNase A and packaged with CyCpG-150; 5. HBc33 VLP treated with RNase A, packaged with CyCpG-150, treated with DNaseI and dialysed; 6. HBc33 VLP treated with RNase A, packaged with CyCpG-150, treated with DNaseI and dialysed. (C) depicts the analysis of the amount of packaged oligo extracted from the VLP on a 10% TBE/urea gel stained with CYBR Gold. Loaded on gel are the following samples: 1. 20 pmol CyCpG-150 control; 2. 10 pmol CyCpG-150 control; 3. 4 pmol CyCpG-150 control; 4. CyCpG-150 oligo content of 4 μg HBc33 after 3 min at 95° C. with 1 volume TBE/urea sample buffer.

FIG. 21 depicts the analysis of NKCpGpt (SEQ ID NO:1131 packaging into HBcP1A VLPs on a 1% agarose gel stained with ethidium bromide (A) and Coomassie Blue (B). Loaded on the gel are 15 μg of the following samples: 1. 1 kb MBI Fermentas DNA ladder; 2. HBcP1A VLP untreated; 3. HBcP1A VLP treated with RNase A; 4. HBcP1A VLP treated with RNase A and packaged with NKCpGpt.

EXAMPLE 12

Immunostimulatory Nucleic Acids can be Packaged in HBcAg-Wt Coupled with Antigens Recombinantly produced HBcAg-wt VLPs were packaged after coupling with peptide p33 (CGG-KAVYNFATM, SEQ ID NO:125), derived from lymphocytic choriomeningitis virus (LCMV). For coupling HBcAg-wt VLPs (2 mg/ml) were derivatized with 25× molar excess of SMPH (Succinimidyl-6-[(β-maleimidopropionamido)hexanoate], Pierce) for 1 h at 25° C. in a thermomixer. The derivatized VLPs were dialyzed to Mes buffer (2-(N-morpholino) ethanesulphonic acid) pH 7.4 for 2×2 h using MWCO 10.000 kD dialysis membranes at 4° C. VLPs (50 μM) were subsequently coupled to the N-terminal cysteine of the p33 peptide (250 μM) during a 2 h incubation in a thermomixer at 25° C. Samples were dialyzed (MWCO 300.000) extensively to 1×PBS pH 7.4 to eliminate undesired free peptide.

Figure 22:
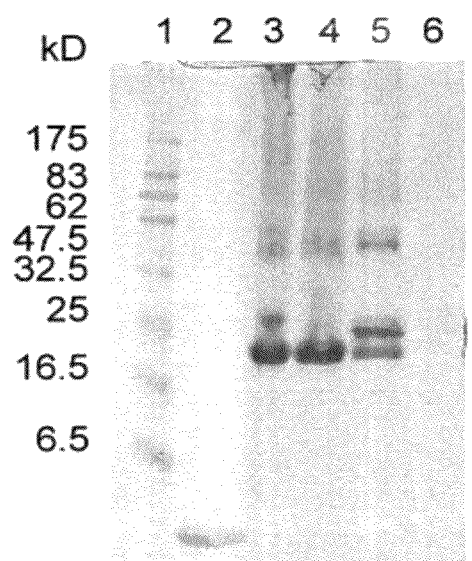
FIG. 22 shows coupling of p33 to HBcAg VLPs.

FIG. 22 shows SDS-PAGE analysis of HBcAg wt VLPs derivatization with SMPH and coupling to p33 peptide. Samples were analysed by 16% SDS PAGE and stained with Coomassie Blue. HBcAg-wt was visible as a 21 kD protein band. Due to the low molecular weight of SMPH is the derivatised product only slightly larger and can not be distinguished by SDS-PAGE. Peptide alone was visible as a 3 kD band and coupled product, termed HBx33, showed a strong secondary band at approximately 24 kD accounting for more than 50% of total HBcAg-wt.

Enzymatic RNA Hydrolysis:
HBx33 VLPs (0.5-1.0 mg/ml, 1×PBS buffer pH7.4) in the presence of RNase A (300 μg/ml, Qiagen AG, Switzerland) were diluted with 4 volumes H$_2$O to decrease salt concentration to a final 0.2×PBS concentration and incubated for 3 h at 37° C. in a thermomixer at 650 rpm.

Figure 23A:
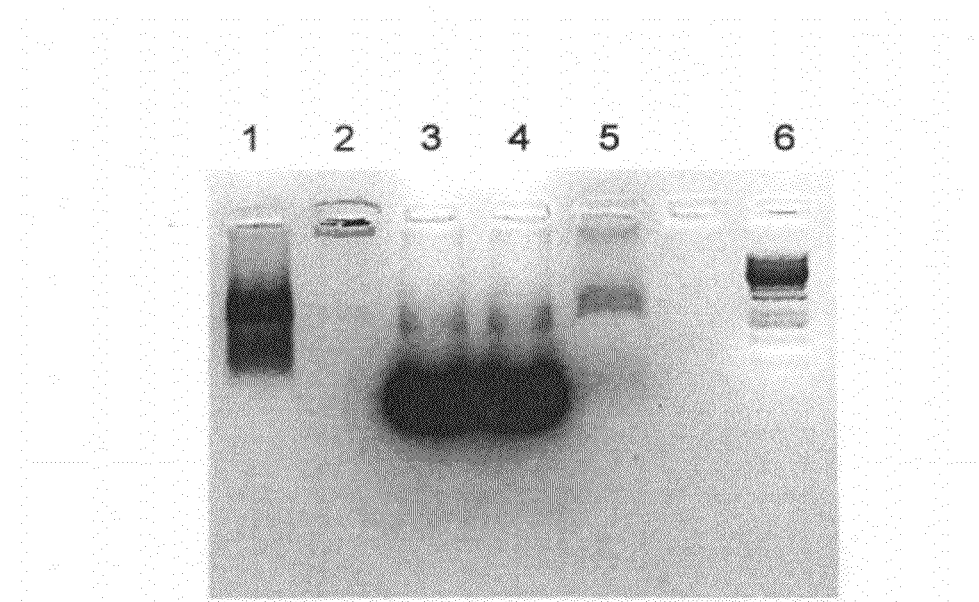
FIG. 23 shows packaging of B-CpGpt (SEQ ID NO:111) into HBx33 VLPs.
Figure 23B:
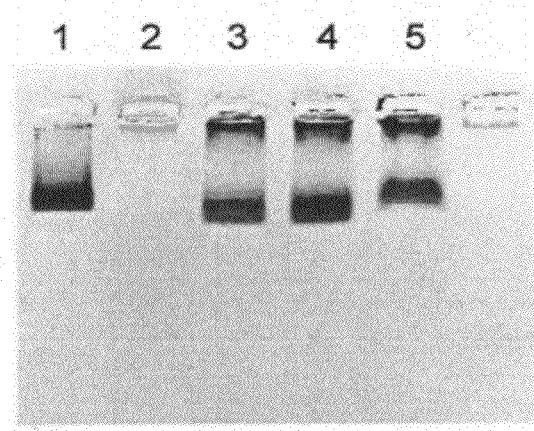

Packaging of Immunostimulatory Nucleic Acids:

After RNase A digestion HBx33 VLPs were concentrated using Millipore Microcon or Centriplus concentrators, then supplemented with 130 nmol/ml CpG-oligonucleotide B-CpGpt (SEQ ID NO:111) and incubated in a thermomixer for 3 h at 37° C. in 0.2×PBS pH 7.4. Subsequently, reaction mixtures were subjected to DNaseI digestion (5 U/ml) for 3 h at 37° C. (DNaseI, RNase free Fluka AG, Switzerland). VLP preparations for mouse immunization were extensively dialysed (2× against 200-fold volume) for 24 h against PBS pH 7.4 with a 300 kDa MWCO dialysis membrane (Spectrum Medical industries Inc., Houston, USA) to eliminate RNase A and the excess of CpG-oligonucleotides. FIG. 23 shows that RNAse treatment reduced the nucleic acid content of the capsids and slowed their migration. Addition of B-CpGpt restored nucleic acid content and fast migration of capsids. DNAse I only digested the free oligonucleotides while the packaged oligonucleotides remained in the VLP also after dialysis (FIG. 23).

FIG. 22 depicts the SDS-PAGE analysis of the p33 coupling to HBc VLPs after Coomassie Blue staining. Loaded on the gel are the following samples: 1. NEB Prestained Protein Marker, Broad Range (#7708S), 10 µl; 2. CGG-p33 peptide (SEQ ID NO:125); 3. HBc VLP derivatized with SMPH, before dialysis; 4. HBc VLP derivatized with SMPH, after dialysis; 5. HBc VLP coupled with CGG-p33, supernatant; 6. HBc VLP coupled with CGG-p33, pellet.

FIG. 23 depicts the analysis of B-CpGpt (SEQ ID NO:111) packaging into HBx33 VLPs on a 1% agarose gel stained with ethidium bromide (A) and Coomassie Blue (B). Loaded on the gel are 50 µg of the following samples: 1. HBx33 VLP untreated; 2. HBx33 VLP treated with RNase A; 3. HBx33 VLP treated with RNase A and packaged with B-CpGpt; 4. HBx33 VLP treated with RNase A, packaged with B-CpGpt and treated with DNaseI; 5. HBx33 VLP treated with RNase A, packaged with B-CpGpt, treated with DNaseI and dialysed; 6. 1 kb MBI Fermentas DNA ladder.

EXAMPLE 13

Figure 24A:
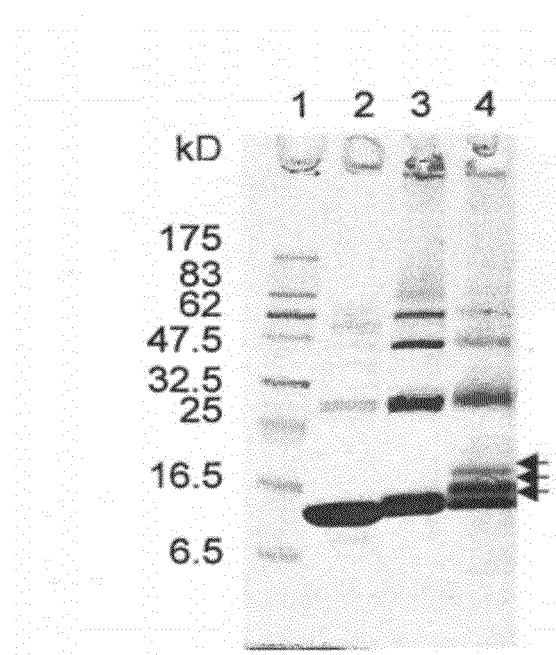
FIG. 24 shows coupling of p33 to Qβ VLPs.
Figure 24B:
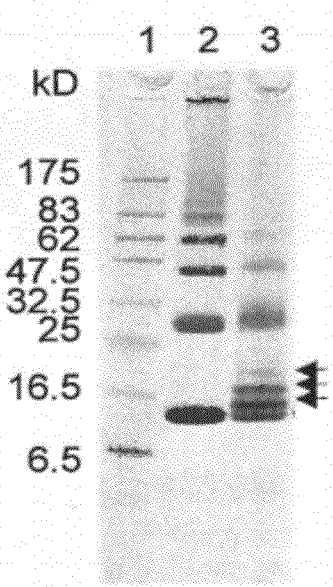
Figure 25A:
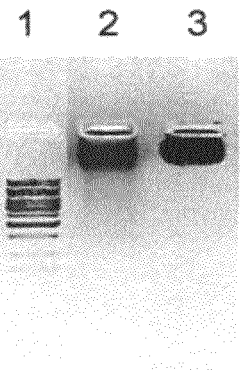
FIG. 25 shows ionic strength and low protein concentration allow RNA hydrolysis by RNase A in Qβ VLPs.
Figure 25B:
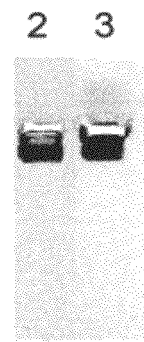
Figure 25C:
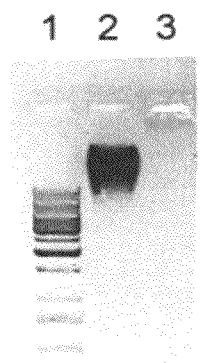
Figure 25D:
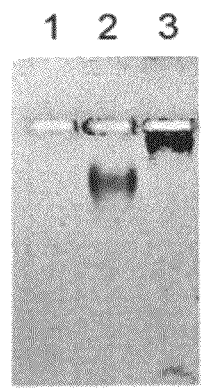

Immunostimulatory Nucleic Acids can be Packaged into Qβ VLPs Coupled with Antigens Coupling of p33 Peptides to Qβ VLPs:

Recombinantly produced Qβ VLPs were used after coupling to p33 peptides containing an N-terminal CGG or and C-terminal GGC extension (COG-KAVYNFATM (SEQ ID NO:125) and KAVYNFATM-GGC (SEQ ID NO:1261). Recombinantly produced Qβ VLPs were derivatized with a 10 molar excess of SMPH (Pierce) for 0.5 h at 25° C., followed by dialysis against 20 mM HEPES, 150 mM NaCl, pH 7.2 at 4° C. to remove unreacted SMPH. Peptides were added in a 5 fold molar excess and allowed to react for 2 h in a thermomixer at 25° C. in the presence of 30% acetonitrile. FIG. 24 shows the SDS-PAGE analysis demonstrating multiple coupling bands consisting of one, two or three peptides coupled to the Qβ monomer (Arrows, FIG. 24 A,B).

Qβ VLPs, when produced in *E. coli* by expressing the bacteriophage Qβ capsid protein, contain RNA which can be digested and so eliminated by incubating the VLPs with RNase A.

Low Ionic Strength and Low Qβ Concentration Allow RNA Hydrolysis of Qβ VLPs by RNAse A:

Qβ VLPs at a concentration of 1.0 mg/ml in 20 mM Hepes/150 mM NaCl buffer (HBS) pH 7.4 were either digested directly by addition of RNase A (300 µg/ml, Qiagen AG, Switzerland) or were diluted with 4 volumes $H_2O$ to a final 0.2×HBS concentration and then incubated with RNase A (60 µg/ml, Qiagen AG, Switzerland). Incubation was allowed for 3 h at 37° C. in a thermomixer at 650 rpm. FIG. 25 demonstrates that in 1×HBS only a very weak reduction of RNA content was observed, while in 0.2×HBS most of the RNA were hydrolysed. In agreement, capsid migration was unchanged after addition of RNAse A in 1×HBS, while migration was slower after addition of RNAse in 0.2×HBS (FIG. 25 B,D).

Figure 26A:
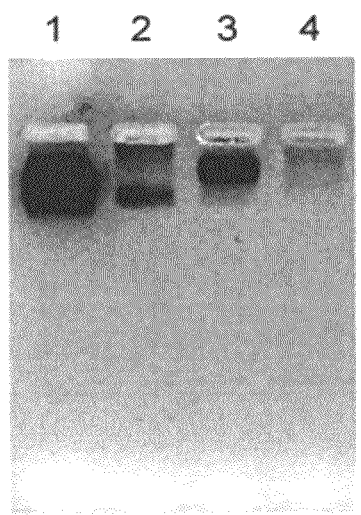
FIG. 26 shows ionic strength increases immunostimulatory nucleic acid packaging into Qβ VLPs.
Figure 26B:

Low Ionic Strength Increases Nucleic Acid Packaging in Qβ VLPs:

After RNase A digestion in 0.2×FIBS the Qβ VLPs were concentrated, to 1 mg/ml using Millipore Microcon or Centriplus concentrators and aliquots were dialysed against 1×HBS or 0.2×HBS. Qβ VLPs were supplemented with 130 nmol/ml CpG-oligonucleotide B-CpG (SEQ ID NO:112) and incubated in a thermomixer for 3 h at 37° C. Subsequently Qβ VLPs were subjected to Benzonase digestion (100 U/ml) for 3 h at 37° C. Samples were analysed on 1% agarose gels after staining with ethidium bromide or Coomassie Blue. FIG. 26 shows that in 1×FIBS only a very low amount of oligonucleotides could be packaged, while in 0.2×HBS a strong ethidium bromide stained band was detectable, which colocalized with the Coomassie blue stain of the capsids.

Figure 27A:
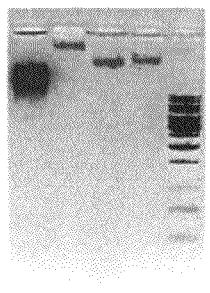
FIG. 27 shows packaging of B-CpGpt (SEQ ID NO:111), g10gacga-PO (SEQ ID NO:116) and dsCyCpG (SEQ ID NO:124) into Qbx33 VLPs.
Figure 27B:
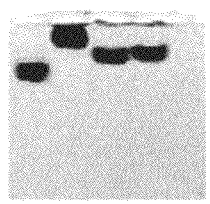
Figure 27C:
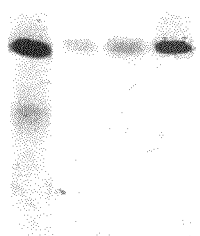
Figure 27D:
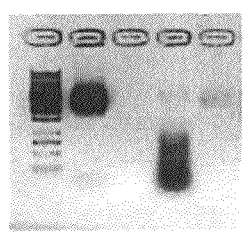
Figure 27E:
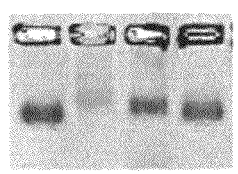
Figure 27F:
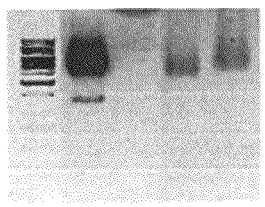
Figure 27G:
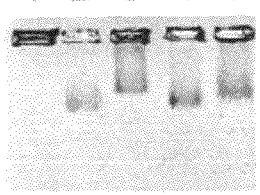

Different Immunostimulatory Nucleic Acids can be Packaged in Qβ VLPs:

After RNase A digestion in 0.2×HBS the Qβ VLPs were concentrated to 1 mg/ml using Millipore Microcon or Centriplus concentrators and supplemented with 130 nmol/ml CpG-oligonucleotides B-CpGpt (SEQ ID NO:111), g10gacga and the 253mer dsCyCpG-253 (SEQ ID NO:124) (Table I) and incubated in a thermomixer for 3 h at 37° C. Subsequently Qβ VLPs were subjected to DNAse I digestion (5 U/ml) or Benzonase digestion (100 U/ml) for 3 h at 37° C. Samples were analysed on 1% agarose gels after staining with ethidium bromide or Coomassie Blue. FIG. 27 shows that the different nucleic acids B-CpGpt, g10gacga and the 253mer dsDNA could be packaged into Qbx33. Packaged nucleic acids were resistant to DNAse I digestion and remained packaged during dialysis (FIG. 27). Packaging of B-CpGpt was confirmed by release of the nucleic acid by proteinase K digestion followed by agarose electrophoresis and ethidium bromide staining (FIG. 27C).

FIG. 24 depicts the SDS-PAGE analysis of the p33 coupling to Qβ VLPs after Coomassie Blue staining. Loaded are the following samples: (A) 1. NEB Prestained Protein Marker, Broad Range (#7708S), 10 µl; 2. Qβ VLP, 14 µg; 3. Qβ VLP derivatized with SMPH, after dialysis; 4. Qβ VLP coupled with CGG-p33, supernatant. (B) 1. NEB Prestained Protein Marker, Broad Range (#7708S), 10 µA 2. Qβ VLP, 10 µg; 3. Qβ VLP coupled with GGC-p33, supernatant.

FIG. 25 depicts the analysis of RNA hydrolysis from Qβ VLPs by RNase A under low and high ionic strength on a 1% agarose gel stained with ethidium bromide (A, C) and Coomassie Blue (B, D). Loaded on the gel are the following samples: (A, B) 1. MBI Fermentas 1 kb DNA ladder; 2. Qβ VLP untreated; 3. Qβ VLP treated with RNase A mix HBS buffer pH7.2. (C, D) 1. MBI Fermentas 1 kb DNA ladder; 2. Qβ VLP untreated; 3. Qβ VLP treated with RNase A in 0.2×HBS buffer pH7.2.

FIG. 26 depicts the analysis of B-CpG (SEQ ID NO:112) packaging into Qβ VLPs under low and high ionic strength on a 1% agarose gel stained with ethidium bromide (A) and Coomassie Blue (B). Loaded on the gel are the following samples: 1. Qβ VLP untreated; 2. Qβ VLP treated with RNase A; 3. Qβ VLP treated with RNase A and packaged with B-CpG in 0.2×HBS buffer pH7.2 and treated with Benzonase; 4. HBx33 VLP treated with RNase A, packaged with B-CpG in 1×HBS buffer pH7.2 and treated with Benzonase.

FIG. 27 depicts the analysis of B-CpGpt (SEQ ID NO:113) packaging into Qbx33 VLPs on a 1% agarose gel stained with ethidium bromide (A) and Coomassie Blue (B). Loaded on the gel are 50 μg of the following samples: 1. Qbx33 VLP untreated; 2. Qbx33 VLP treated with RNase A; 3. Qbx33 VLP treated with RNase A and packaged with B-CpGpt; 4. Qbx33 VLP treated with RNase A, packaged with B-CpGpt, treated with DNaseI and dialysed; 5. 1 kb MBI Fermentas DNA ladder. (C) depicts the analysis of the amount of packaged oligo extracted from the VLP on a 15% TBE/urea stained with CYBR Gold. Loaded on gel are the following samples: 1. B-CpGpt oligo content of 2 μg Qbx33 VLP after proteinase K digestion and RNase A treatment; 2. 20 pmol B-CpGpt control; 3. 10 pmol B-CpGpt control; 4. 5 pmol B-CpGpt control.

FIGS. 27 D and E depict the analysis of g10gacga-PO (SEQ ID NO:116) packaging into Qbx33 VLPs on a 1% agarose gel stained with ethidium bromide (D) and Coomassie Blue (E). Loaded on the gel are 15 μg of the following samples: 1. MBI Fermentas 1 kb DNA ladder; 2. Qbx33 VLP untreated; 3. Qbx33 VLP treated with RNase A; 4. Qbx33 VLP treated with RNase A and packaged with g10gacga-PO; 5. Qbx33 VLP treated with RNase A, packaged with g10gacga-PO, treated with Benzonase and dialysed.

FIGS. 27 E and F depict the analysis of dsCyCpG-253 (SEQ ID NO:124) packaging into Qbx33 VLPs on a 1% agarose gel stained with ethidium bromide (E) and Coomassie Blue (F). Loaded on gel are 15 μg of the following samples: 1. MBI Fermentas 1 kb DNA ladder; 2. Qbx33 VLP untreated; 3. Qbx33 VLP treated with RNase A; 4. Qbx33 VLP treated with RNase A, packaged with dsCyCpG-253 and treated with DNaseI; 5. Qbx33 VLP treated with RNase A, packaged with dsCyCpG-253, treated with DNaseI and dialysed.

EXAMPLE 14

Qβ Disassembly Reassembly and Packaging of Immunostimulatory Nucleic Acids

Disassembly and Reassembly of VLP
Disassembly:

70 mg of pure lyophilized Qβ VLP gave a protein content of about 35 mg, according to spectrophotometric determination using the average result obtained with the following three formulae: 1. $(183*OD^{230\,nm}-75.8*OD^{260\,nm})*$volume (ml)- 2. $(OD^{235\,nm}-OD^{280\,nm})/2.51)\times$volume-3. $((OD^{228.5\,nm}-OD^{234.5\,nm})*0.37)\times$volume. The pure lyophilized Qβ VLP was solubilized in 7 ml of 6 M GuHCl and incubated overnight at 4° C. The solution was clarified for 15 minutes, at 6000 rpm (Eppendorf 5810 R, in fixed angle rotor F34-6-38, used in all the following steps). A negligible sediment was discarded, and the supernatant was dialysed 5× against 200-300 ml NET buffer (20 mM Tris-HCl, pH 7.8 with 5 mM EDTA and 150 mM NaCl) over 3 days. Alternatively, the supernatant was dialyzed in a continuous mode against 1.5 l NET buffer over 3-4 days. The resulting suspension was centrifuged at 12000 rpm for 20 minutes. The pellet was resolubilized in 2-3 ml 8 M urea, while the supernatant was precipitated with solid ammonium sulphate at 60% saturation. A saturated ammonium sulphate solution was added to the pellet previously resolubilized in urea to 60% saturation, and the solution was left to precipitate 4 days at 4° C., with subsequent centrifugation at 12000 rpm for 20 minutes. This pellet, and the pellet of the initial supernatant were resolubilized and joined in a total volume of 3 ml of 7 M urea, 10 mM DTT. This material was loaded on a Sephadex G75 column, eluted at 2 ml/h with 7 M urea, 10 mM DTT. Two peaks were isolated. A high molecular weight peak preceded a peak of lower apparent molecular weight. Calibration of the column with chymotrypsin in the same elution buffer revealed that the apparent molecular weight of the second peak is consistent with Qβ coat protein being in a dimeric form. Fractions containing this dimer material were pooled and precipitated with ammonium sulphate (2 days, at 4° C.). The pellet was washed with a few droplets of water, centrifuged again, and solubilized in 2 ml of 7 M urea, 10 mM DTT. This material was then purified on a short (1.5×27 cm) Sepharose 4B column. One peak eluted from the column and the fractions were pooled, leading to a protein preparation with a volume of 10 ml, and a ratio of absorbance at 280 nm vs. 260 nm of 0.68/0.5, yielding about 450 nmol of Qβ coat protein (giving a maximum of 2.5 nmol VLP after reassembly, considering that there are 180 subunits in the VLP) and a protein concentration of 630 μg/ml (calculated using the spectrophotometric methods described above).

Reassembly:

β-mercaptoethanol was added to the 10 ml dimer fraction to a final concentration of 10%, and 300 μl of a solution of $(CpG)_{20}OpA$ oligodeoxynucleotide (SEQ ID NO:118), containing 12.3 nmol of oligonucleotide, were added. The reassembly mixture was first dialyzed against 30 ml NET buffer containing 10% beta-mercaptoethanol for 2 hours at 4° C., and then dialyzed in a continuous mode, with a flow of NET buffer of 8 ml/h over 4 days at 4° C. The reassembly mixture was then desalted against water by dialysis, with 6 buffer exchanges (4×100 ml, 2×1 liter).

The ratio of absorbance at 280 nm vs. 260 nm was of 0.167/0.24. The protein was dried by lyophilization. The dried protein was resolubilized in water and purified by ultracentrifugation on a sucrose gradient in a Beckman L 8-80 centrifuge, with the SW 50.1 rotor at 22000 rpm, for 17 h at +4° C. The sucrose gradient purification was performed as follows. 5 layers of 1 ml of the following sucrose concentrations (w/v) were dispensed into a centrifuge tube: 50%, 43%, 36%, 29% and 22%. The so formed succession of layers was left standing overnight at 4° C. 0.5 ml of the protein sample was layered on the gradient, and centrifuged for 17 h as indicated above. The gradient was eluted from the bottom of the centrifuge tube, and the 5 ml of the gradient were divided in 16 fractions of approximately 300 μl. The fractions in the gradient were analyzed by SDS-PAGE (FIG. 28) and Ouchterlony assay. Fractions 6-9 contained Qβ coat protein and gave the precipitation band typical of Qβ VLP in an Ouchterlony assay. Fractions 11-15, with a lower apparent density and containing Qβ protein gave no capsid band in the Ouchterlony assay. The reassembled Qβ had the same apparent density as wt Qβ within experimental error. The fractions 6-9 of the sucrose gradient were pooled, dialyzed against water and lyophilized. This material was then resolubilized for electron microscopy (EM) analysis (FIG. 29) and Ouchterlony assay (FIGS. 30 A and B). The EM procedure was as follows: A suspension of the proteins was absorbed on carbon-formvar coated grids and stained with 2% phosphotungstic acid (pH 6,8). The grids were examined with a JEM 100C (JEOL, Japan) electron microscope at an accelerating voltage of 80 kV. Photographic records (negatives) were performed on Kodak electron image film and electron micrographs were obtained by printing of negatives on Kodak Polymax paper. Both methods indicate that the reassembled VLPs have the same macromolecular properties as intact Qβ VLP.

Figure 31A:
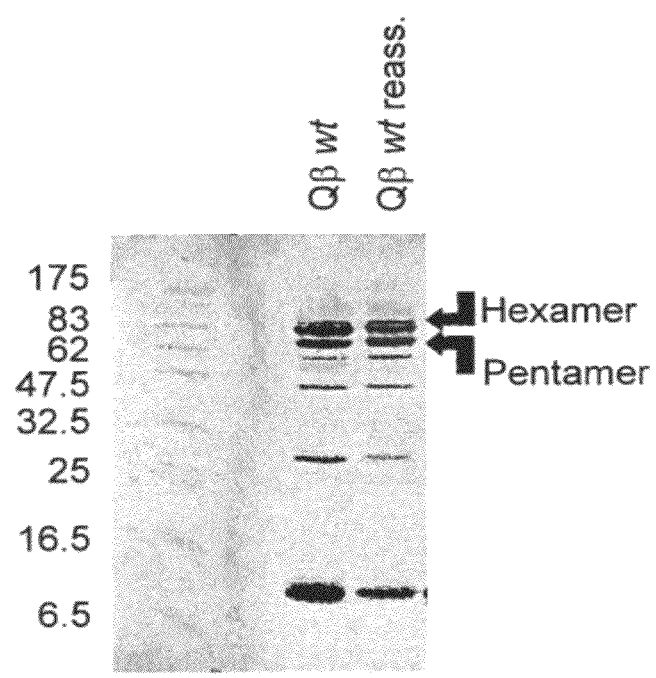
FIG. 31 shows gelelectrophoretic analysis of dissassembled and reassembled Qβ VLP.

In addition, the pattern of disulfide bonds displayed by the purified reassembled Qβ VLP is indistinguishable from the disulfide bond pattern displayed by the untreated Qβ VLP, with the typical pattern of pentamers and hexamers (FIG. 31A).

Figure 31B:
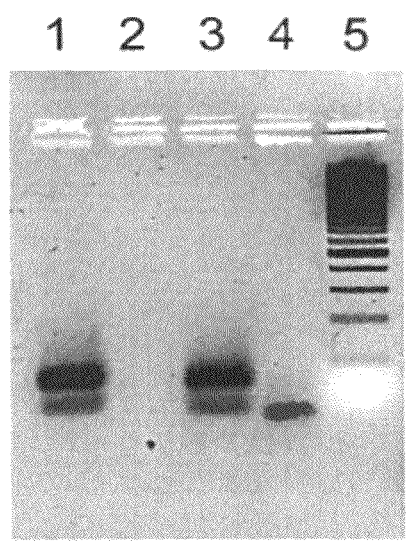

Analysis of Nucleic Acid Content:

Reassembled Qβ VLP was digested with pancreatic DNAse I as follows. To 200 μl of a 0.5 mg/ml solution of Qβ VLP reassembled with $(CpG)_{20}OpA$ oligodeoxynucleotide were added 20 μl of a 1 U/μl DNAse I (Fluka) solution, and 22 μl of DNAse I buffer (20 mM $MgCl_2$, 200 mM Tris, pH 8.3). The reaction mixture was incubated for 2 h 30 min. at 37° C. The nucleic acid content of the sample was subsequently isolated by phenol/chloroform extraction, and loaded on a 2% agarose gel stained with ethidium bromide (FIG. 31B). A band of the size of the packaged oligodeoxynucleotide was detected on the gel. A band migrating at a higher apparent molecular weight was also visible. We cannot exclude the presence of multimers of the $(CpG)_{20}OpA$ oligodeoxynucleotide which would lead to a band at this height. The gel thus shows that DNAse I protected oligodeoxynucleotides of the right size were present in the reassembled Qβ VLP, since the oligodeoxynucleotides could subsequently be digested by DNAse I, but not by RNAse A. Oligodeoxynucleotides could thus be successfully packaged in Qβ VLP after initial disassembly of the VLP, purification of the disassembled coat protein from nucleic acids and subsequent reassembly of the VLP in the presence of oligodeoxynucleotide.

Figure 28:
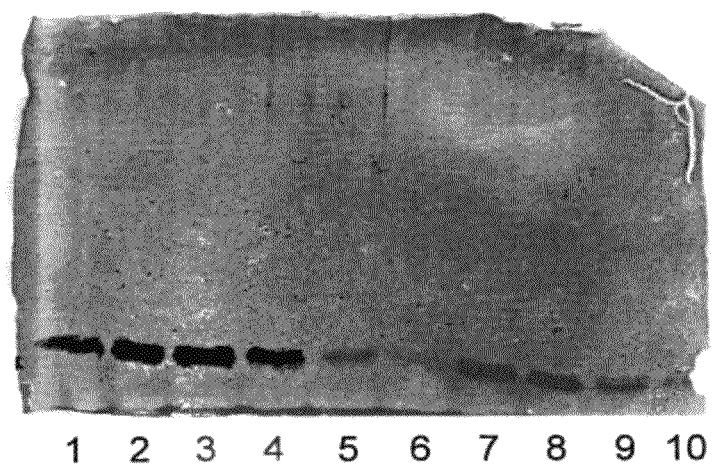
FIG. 28 shows SDS-PAGE analysis of the fractions from the sucrose gradient centrifugation after Qβ VLP disassembly and reassembly in the presence of immunostimulatory nucleic acids.

FIG. 28 shows the SDS-PAGE analysis of the fractions from the sucrose gradient centrifugation. Loaded on the gels were the following samples. Lane 1-10: fractions 6-15 of the sucrose gradient ultracentrifugation.

Figure 29A:
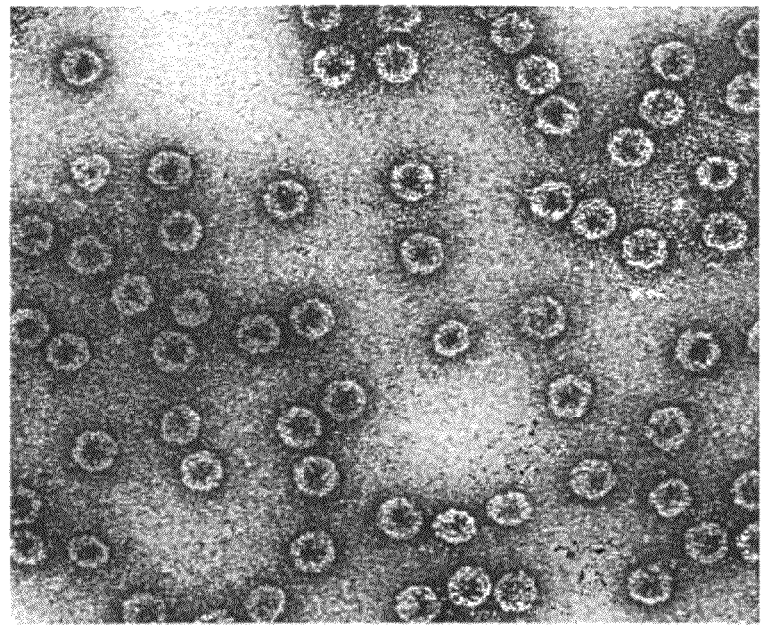
FIG. 29 shows electron micrographs of Qβ VLP after disassembly and reassembly in the presence of oligonucleotide (CpG)$_{20}$OpA (SEQ ID NO:120).
Figure 29B:
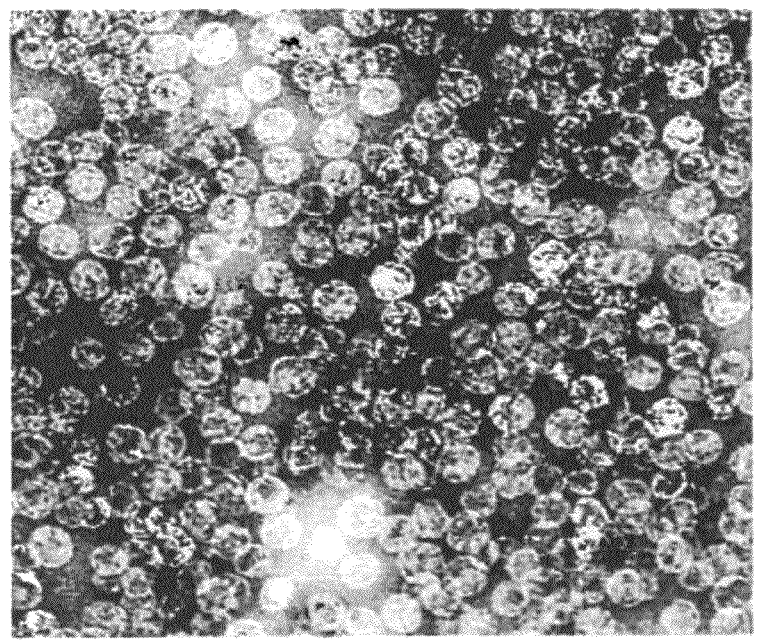
Figure 30A:
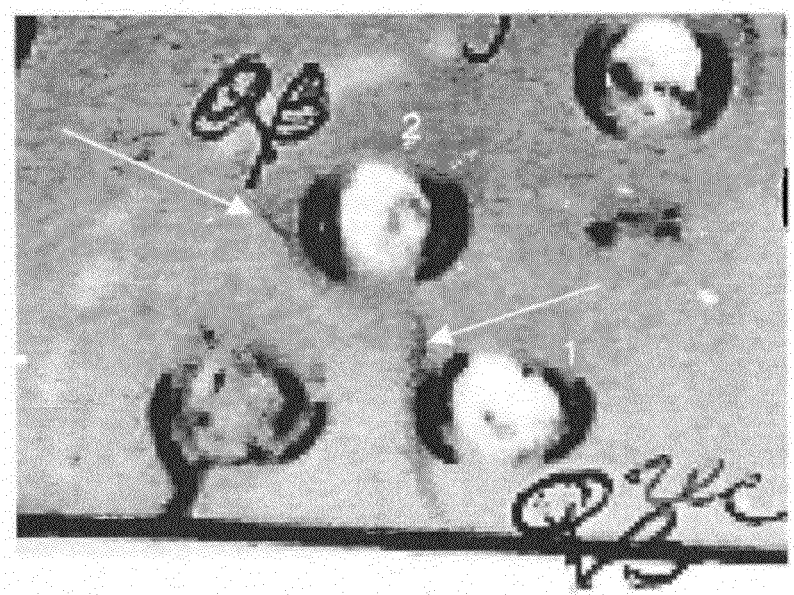
FIG. 30 shows ouchterlony analysis (immunodiffusion) of the disassembled and reassembled Qβ VLP.
Figure 30B:
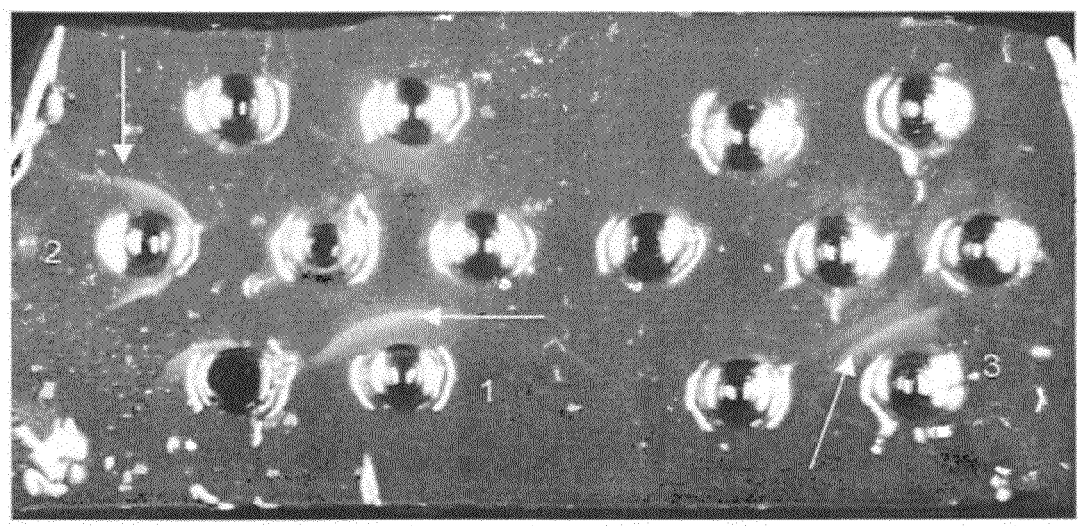

FIG. 29 shows the EM pictures of (A) intact Qβ VLP and (B) Qβ VLP after disassembly and reassembly in the presence of oligonucleotide $(CpG)_{20}OpA$, and subsequent purification by sucrose gradient ultracentrifugation. A dense overlay of capsids is observed, and those capsids display the same structural features and properties as the intact Qβ VLPs.

FIG. 30 shows the Ouchterlony analysis (immunodiffusion) of the reconstructed Qβ VLP. In FIG. 30 A, Qβ VLP reassembled with oligonucleotide (CpG)20OpA was loaded next to intact Qβ VLP. The two characteristic precipitation bands are indicated by black arrows. The two precipitation bands are concurrent, indicating that the reassembled Qβ VLP diffuse as the intact Qβ VLP. In FIG. 30 B, sample 1 is Qβ VLP reassembled in the presence of ribosomal RNA, while sample 2 is intact Qβ VLP and sample 3 is Qβ VLP reassembled with oligonucleotide (CpG)20OpA. The precipitation bands are indicated by white arrows.

FIG. 31A shows the analysis of the untreated and reassembled Qβ VLP by non-reducing SDS-PAGE. The pentamers and hexamers of Qβ VLP are indicated by arrows.

FIG. 31B shows the agarose gel electrophoresis analysis of the nucleotide content extracted after DNAse I digestion of Qβ VLP reassembled with oligonucleotide (CpG)20OpA. The nucleic acid content was either untreated (lane 1), or subsequently digested with DNAse I (lane2) or RNAse A (lane 3); 33 μg of reassembled VLP were loaded on each lane. 300 ng of a 50 bp oligonucleotide were loaded on lane 4, while 10 μl of the GeneRuler 100 bp DNA ladder+marker (MBI Fermentas) was loaded on lane 5.

EXAMPLE 15

Qβ Disassembly Reassembly with Different Immunostimulatory Nucleic Acids

Disassembly and Reassembly of Qβ VLP with Oligodeoxynucleotides of Various Sequences The disassembly of Qβ VLP was performed essentially as described in Example 1, but for the use of 8 M urea instead of 7 M urea to resuspend the ammonium sulphate pellets.

The reassembly of Qβ VLP with the oligos CyOpA (SEQ ID NO:121), CyCyCy (SEQ ID NO:122), (CpG)20-OpA (SEQ ID NO:118) and CyCpG (SEQ ID NO:110) was performed essentially as described in Example 1, but for the following variations. A dialysis step against 10% β-mercaptoethanol in NET buffer (20 mM Tris-HCl, pH 7.8 with 5 mM EDTA and 150 mM NaCl) for 1 hour at 4° C. was added to the procedure before addition of the oligodeoxynucleotide solution to the dimer solution in the dialysis bag. The oligodeoxynucleotides were then added to the dimer solutions, resulting approx. in a ten-fold molar excess of oligonucleotide to capsid (180 subunits) as described previously. The reassembly mixture was first dialyzed against 30 ml NET buffer containing 10% β-mercaptoethanol for 1 hours at 4° C., and then dialyzed in a continuous mode, with a flow of NET buffer of 8 ml/h over 4 days at 4° C. A sample of the reassembly reaction of Qβ VLP with oligodeoxynucleotide CyOpA was taken for EM analysis (FIG. 32) at the end of the reassembly reaction. The EM procedure using phosphotungstic acid and described above was used. The reassembly mixtures were then desalted against water by dialysis and dried.

The dried protein was resolubilized in water and purified by ultracentrifugation on a sucrose gradient. The purified reassembled Qβ VLPs were also analyzed by EM (FIG. 33 A-D). The electron micrographs indicate that the reassembled VLPs have the same macromolecular properties as intact Qβ VLP. Purification notably enriches the preparations for reassembled particles. Thus, Qβ VLP was successfully reassembled with oligodeoxynucleotides of various lengths and sequences.

Coupling of the p33 Peptide to Reassembled Qβ VLP:

Qβ VLP reassembled with the oligodeoxynucleotide CyOpA was reacted at a concentration of 1.5 mg/ml, with the cross-linker SMPH diluted from a stock solution in DMSO at a final concentration of cross-linker of 536 μM for 35 minutes at 26° C. in 20 mM Hepes pH 7.4. The derivatized Qβ VLP was dialyzed 2×2 hours against a thousand volumes of 20 mM Hepes, 150 mM NaCl, pH 7.4. The dialysed derivatized Qβ VLP at a concentration of 1.4 mg/ml was subsequently reacted with the p33GGC peptide (sequence: KAVYNFAT-MGGC, SEQ ID NO:126) at a final concentration of peptide of 250 μM for 2 hours at 15° C. in 20 mM Hepes, 150 mM NaCl, pH 7.4. The gel of FIG. 34 indicates successful coupling of the p33 peptide to Qβ VLP. Coupling bands corresponding to one, respectively two peptides coupled per subunit are indicated by an arrow in the Figure.

Analysis of Nucleic Acid Content:

The nucleic acid content of reassembled and coupled Qβ VLP was analysed by proteinase K digestion, phenol chloroform extraction and subsequent loading of the extracted oligonucleotide on a TBE/Urea PAGE gel. The analysis procedure was as follows. 25 μl reassembled Qβ VLP (0.5-1 mg/ml) were supplemented with 0.5 μl proteinase K, 1.5 μl 10% SDS and 3 μl 10× proteinase buffer (0.5 M NaCl, 50 mM EDTA, 0.1 M Tris pH7.4). After incubation overnight at 37° C., proteinase K was inactivated by heating 20 min at 65° C. and the nucleic acid content was extracted from the samples by 1× phenol and 1× chloroform extraction. Subsequently the samples were incubated 2 h at 37° C. with 1 μl RNAseA (Qiagen, 100 μg/ml, diluted 250×). The equivalent of 2 μg starting protein was heated 3 min at 95° C. with 1 volume of 2× loading buffer (1 ml 10×TBE, 4.2 g Urea, 1.2 g Ficoll, 1 ml 0.1% Bromophenolblue, $H_2O$ up to 10 ml) and loaded on a 15% TBE/Urea polyacrylamide gel (Invitrogen). The gel was run for 1.5 h at 180 V, and fixed in 10% acetic acid/20% ethanol and stained with CYBR Gold (Molecular Probes, Eugene, Oreg., USA). For quantification, 10 and 20 pmol of the oligonucleotide used for the reassembly were applied on the gel as a reference. Resistance of the nucleic acid content to RNAse and its size proved that the packaged nucleic acid was the oligonucleotide used for reassembly. Quantification of the packaged oligodeoxynucleotide was performed by comparison of the band intensity of the extracted oligonucleotide with the band intensity of a reference amount of the same oligonucleotide loaded on the same gel. A figure of 1.75 nmol CyOpA/100 µg Qβ VLP was obtained, giving a ratio of 44 oligonucleotides per VLP on average.

Figure 32:
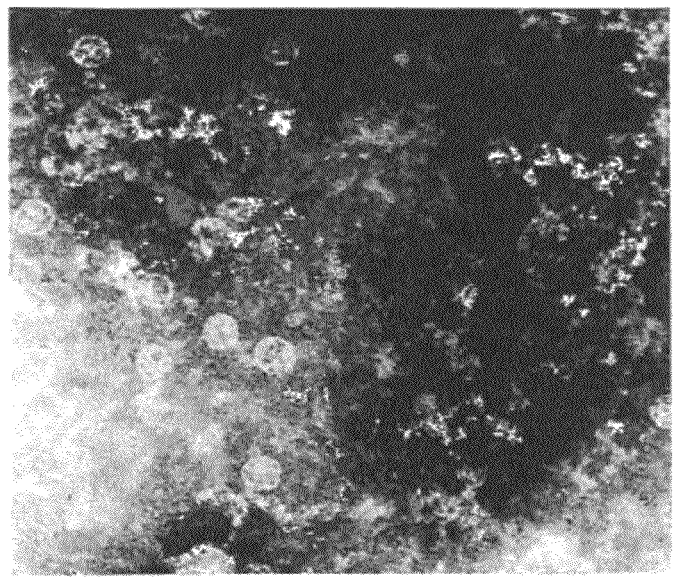
FIG. 32 shows electron micrographs of the disassembled and reassembled Qβ VLP with the oligonucleotide CyOpA (SEQ ID NO:121).
Figure 33A:
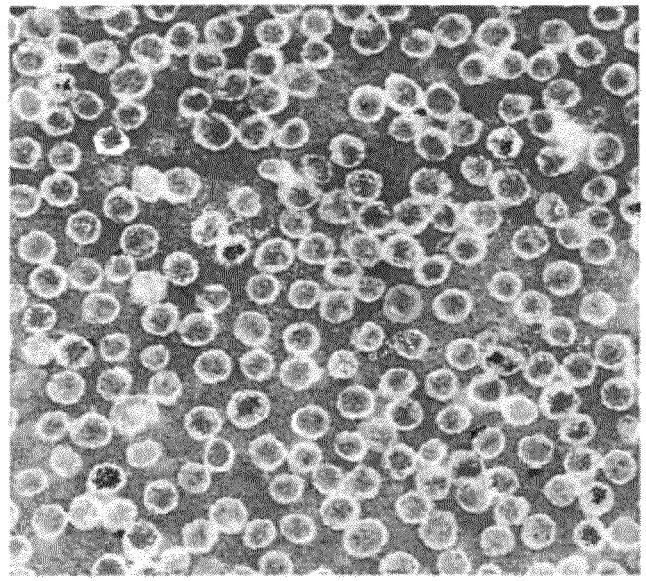
FIG. 33 shows electron micrographs of the purified dissassembled and reassembled Qβ VLP with the different immunostimulatory nucleic acids.
Figure 33B:
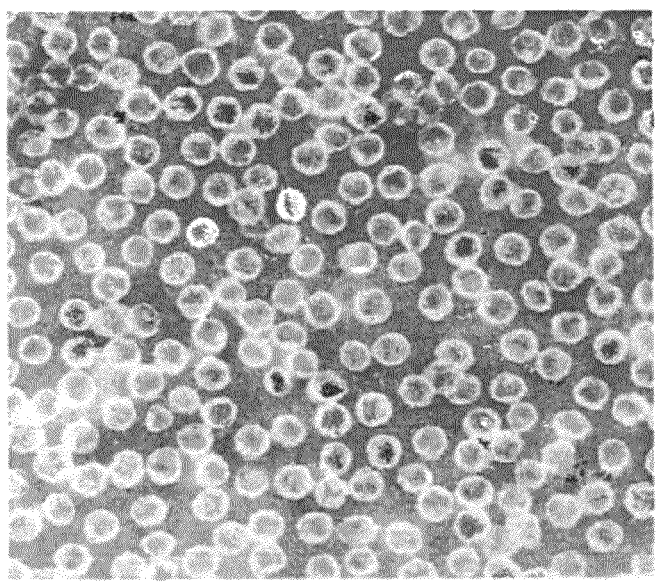
Figure 33C:
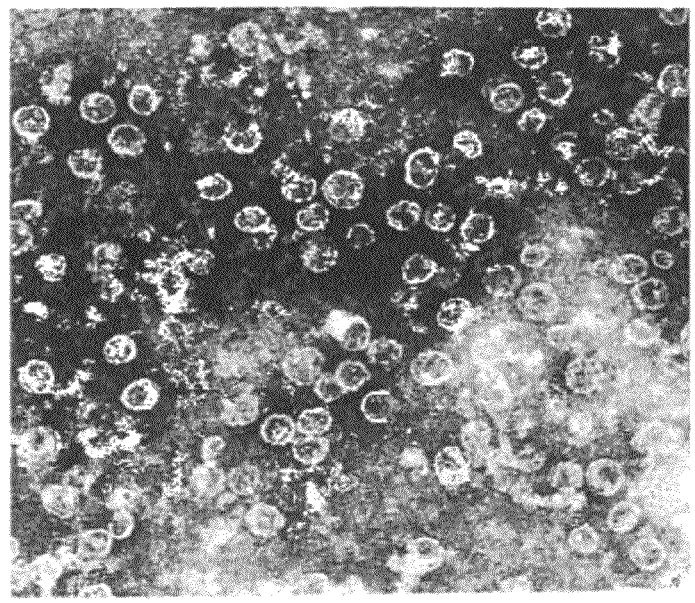
Figure 33D:
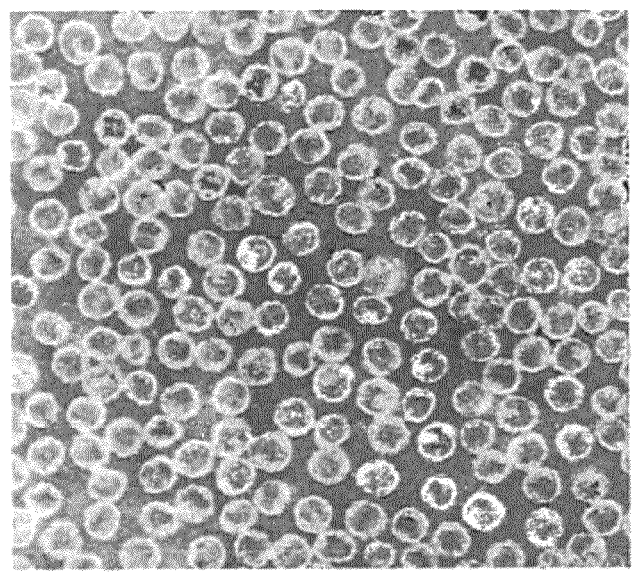

FIG. 32 depicts the electron micrographs of the reassembly reaction of Qβ VLP with the oligonucleotide CyOpA (SEQ ID NO:121) before purification. The magnification was 200000 fold.

FIG. 33 A-D show the electron micrographs of the purified reassembly reactions of Qβ VLP with the oligodeoxynucleotides Cy(CpG)20 (SEQ ID NO:119) (A), CyCyCy (SEQ ID NO:122) (B), CyCpG (SEQ ID NO:110) (C) and CyOpA (SEQ ID NO:121) (D). The magnification was 200000 fold.

Figure 34:
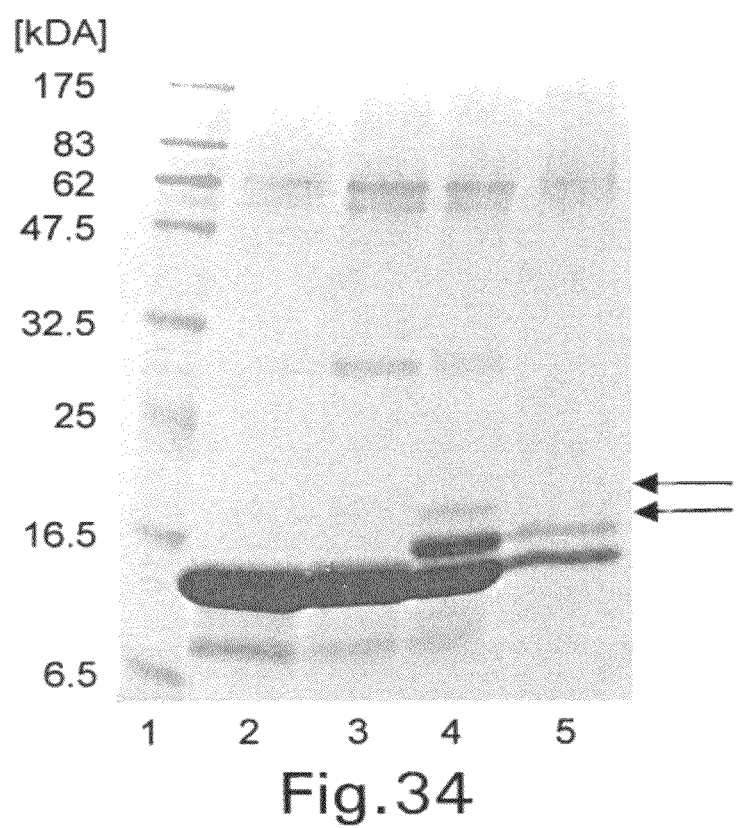
FIG. 34 shows SDS-PAGE analysis of the coupling of Qβ VLP reassembled with the oligodeoxynucleotide CyOpA (SEQ ID NO:121) to the p33GGC peptide.

FIG. 34 depicts the SDS-PAGE analysis of the coupling of Qβ VLP reassembled with the oligodeoxynucleotide CyOpA (SEQ ID NO:121) to the p33GGC peptide. Loaded on the gel were the following samples: 1. Prestained Protein Marker, Broad Range (#7708S) 10 µl; 2. Qβ VLP reassembled with CyOpA [1.5 mg/ml] 10 µl; 3. Qβ VLP reassembled with CyOpA [1.5 mg/ml] and derivatized with SMPH 10 µl; 4. Qβ VLP reassembled with CyOpA [1.5 mg/ml], derivatized with SMPH and coupled with p33-peptide 10 µA; 5. Qβ VLP reassembled with CyOpA [1.5 mg/ml], derivatized with SMPH and coupled with p33-peptide, $\frac{1}{5}^{th}$ vol of the pellet.

Figure 35:
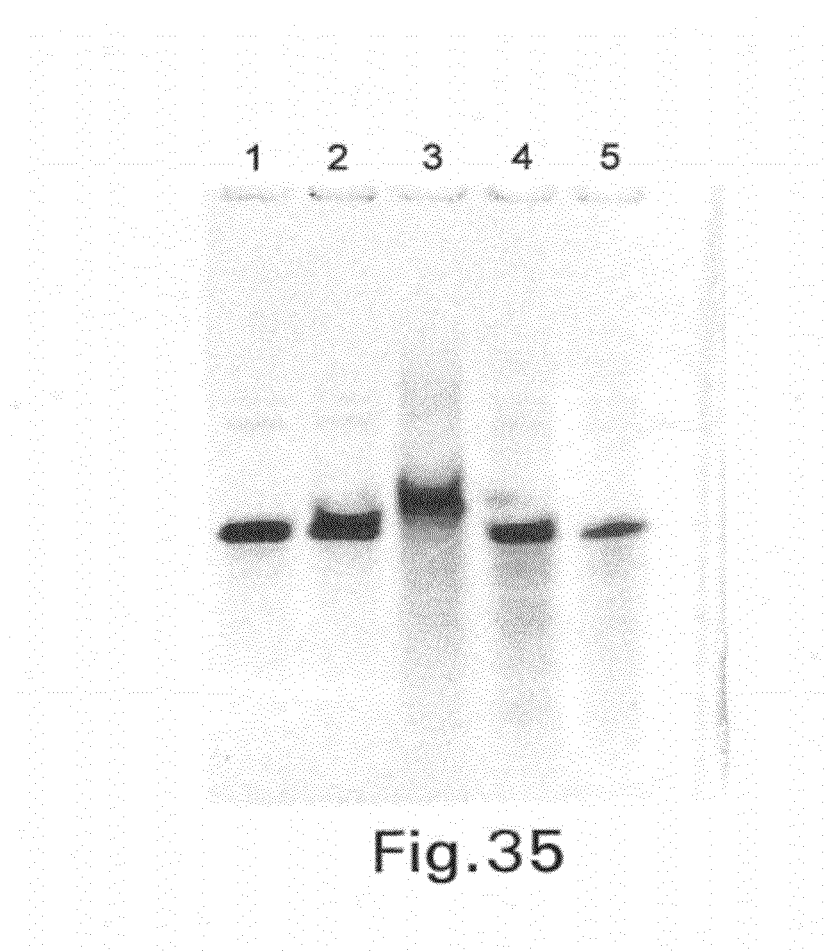
FIG. 35 shows packaged oligodeoxynucleotides after disassembly and reassembly of Qβ VLPs and subsequent coupling to p33 GGC peptide.
Figure 36A:
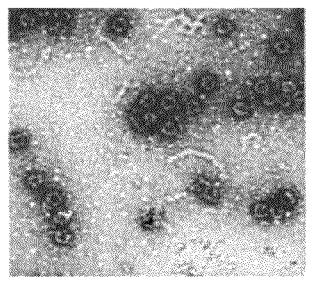
FIG. 36 shows purification of disassembled Qβ coat protein by size exclusion chromatography.
Figure 36B:
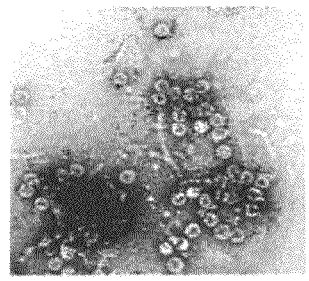
Figure 36C:
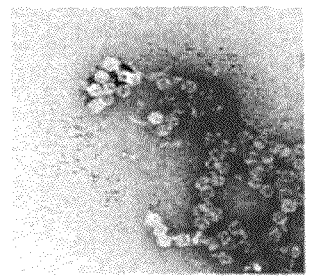
Figure 36D:
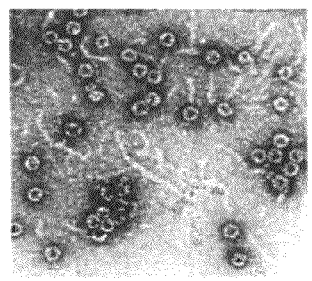
Figure 36E:
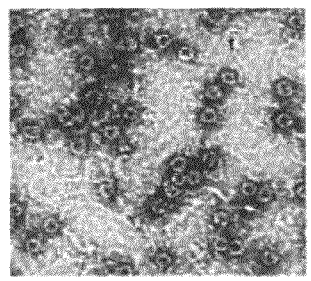
Figure 36F:
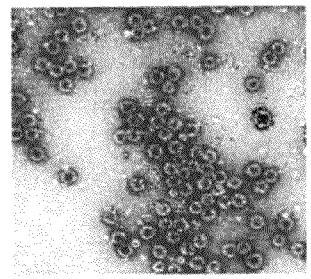
Figure 36G:
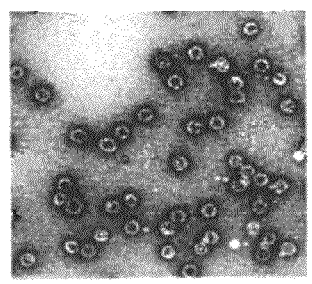
Figure 36H:
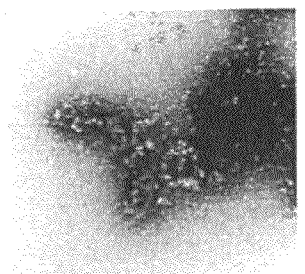

FIG. 35 depicts the analysis of the extracted packaged oligodeoxynucleotides by Urea Polyacrylamide gel electrophoresis, stained with CYBR Gold. The following samples were loaded on the gel: 1. Qβ VLP reassembled with oligonucleotide CyOpA (SEQ ID NO:1211 and coupled to p33 GGC peptide, 2 µg protein loaded on the gel. 2. Qβ VLP reassembled with oligonucleotide CyOpA and coupled to p33GGC peptide, frozen and thawed before loading on the gel, 2 µg protein. 3. Qβ VLP reassembled with oligonucleotide Cy(CpG)$_{20}$ and coupled to p33GGC peptide, frozen and thawed before loading on the gel; 2 µg protein. 4. CyOpA oligonucleotide, 20 pmol. 5. CyOpA oligonucleotide, 10 pmol.

EXAMPLE 16

Qβ Disassembly Reassembly and Packaging

Disassembly and Reassembly of Qβ VLP

Disassembly:

10 mg Qβ VLP (as determined by Bradford analysis) in 20 mM HEPES, pH 7.4, 150 mM NaCl was precipitated with solid ammonium sulfate at a final saturation of 60%. Precipitation was performed over night at 4° C. and precipitated VLPs were sedimented by centrifugation for 60 minutes at 4° C. (SS-34 rotor). Pellets were resuspended in 1 ml of 6 M Guanidine hydrochloride (GuHCl) containing 100 mM DTT (final concentration) and incubated for 8 h at 4° C.

Purification of Qβ Coat Protein by Size Exclusion Chromatography:

The solution was clarified for 10 minutes at 14000 rpm (Eppendorf 5417 R, in fixed angle rotor F45-30-11, used in all the following steps) and dialysed against a buffer containing 7 M urea, 100 mM TrisHCl, pH 8.0, 10 mM DTT (2000 ml) over night. Dialysis buffer was exchanged once and dialysis continued for another 2 h. The resulting suspension was centrifuged at 14000 rpm for 10 minutes at 4° C. A negligible sediment was discarded, and the supernatant was kept as "load fraction" containing disassembled coat protein and RNA. Protein concentration was determined by Bradford analysis and 5 mg total protein was applied onto a HiLoad™ Superdex™ 75 prep grade column (26/60, Amersham Biosciences) equilibrated with 7 M urea, 100 mM TrisHCl and 10 mM DTT. Size exclusion chromatography was performed with the equilibration buffer (7 M urea, 100 mM TrisHCl pH 8.0, 10 mM DTT) at 12° C. with a flow-rate of 0.5 ml/min. During the elution absorbance at 254 nm and 280 nm was monitored. Two peaks were isolated. A high molecular weight peak preceded a peak of lower apparent molecular weight. Peaks were collected in fractions of 1.5 ml and aliquots were analysed by SDS-PAGE followed by Coomassie staining as well as SYBR®Gold staining (FIG. 36 A-H).

Purification of Qβ Coat Protein by Ion Exchange Chromatography:

Alternatively, the clearified supernatant was dialysed against a buffer containing 7 M urea, 20 mM MES, 10 mM DTT, pH 6.0 (2000 ml) over night. Dialysis buffer was exchanged once and dialysis continued for another 2 h. The resulting suspension was centrifuged at 14000 rpm for 10 minutes at 4° C. A negligible sediment was discarded, and the supernatant was kept as "load fraction" containing disassembled coat protein and RNA. Protein concentration was determined by Bradford analysis and 10 mg total protein was diluted to a final volume of 10 ml with buffer A (see below) and applied with a flowrate of 1 ml/min to a 1 ml HiTrap™ SP HP column (Amersham Biosciences, Cat. No. 17-1151-01) equilibrated with buffer A: 7 M urea, 20 mM MES, 10 mM DTT, pH 6.0. The flowthrough which contained the RNA was collected as one fraction. After the column was extensively washed with buffer A (30 CV) the bound Qβ coat protein was eluted in a linear gradient from 0%-100% buffer B (gradient length was 5 CV; buffer A: see above, buffer B: 7 M urea, 20 mM MES, 10 mM DTT, 2 M NaCl, pH 6.0). During the loading, wash and elution the absorbance at 254 nm and 280 nm was monitored. Peak fractions of 1 ml were collected and analysed by SDS-PAGE followed by Coomassie staining as well as SYBR®Gold staining. Fractions containing the Qβ coat protein but not the RNA were identified and the pH was adjusted by addition of 100 µl 1 M TrisHCl, pH 8.0.

Samples containing the Qβ coat protein but no RNA were pooled and dialysed against 0.87 M urea, 100 mM TrisHCl, 10 mM DTT (2000 ml) over night and buffer was exchanged once and dialysis continued for another 2 h. The resulting suspension was centrifuged at 14000 rpm for 10 minutes at 4° C. A negligible sediment was discarded, and the supernatant was kept as "disassembled coat protein". Protein concentration was determined by Bradford analysis.

Reassembly:

Purified Qβ coat protein with a concentration of 0.5 mg/ml was used for the reassembly of VLPs in the presence of an oligodeoxynucleotide. For the reassembly reaction the oligodeoxynucleotide was used in a tenfold excess over the calculated theoretical amount of Qβ-VLP capsids (monomer concentration divided by 180). After the Qβ coat protein was mixed with the oligodeoxynucleotide to be packaged during the reassembly reaction, this solution (volume up to 5 ml) was first dialysed for 2 h against 500 ml NET buffer containing 10% β-mercaptoethanol at 4° C., then dialyzed in a continuous mode, with a flow of NET buffer of 8 ml/h over 72 h at 4° C., and finally for another 72 h with the same continuous mode with a buffer composed of 20 mM TrisHCl pH 8.0, 150 mM NaCl. The resulting suspension was centrifuged at 14000 rpm for 10 minutes at 4° C. A negligible sediment was discarded, and the supernatant contained the reassembled and packaged VLPs. Protein concentration was determined by Bradford analysis and if needed reassembled and packaged VLPs were concentrated with centrifugal filter devices (Millipore, UFV4BCC25, 5K NMWL) to a final protein concentration of 3 mg/ml.

Figure 37A:
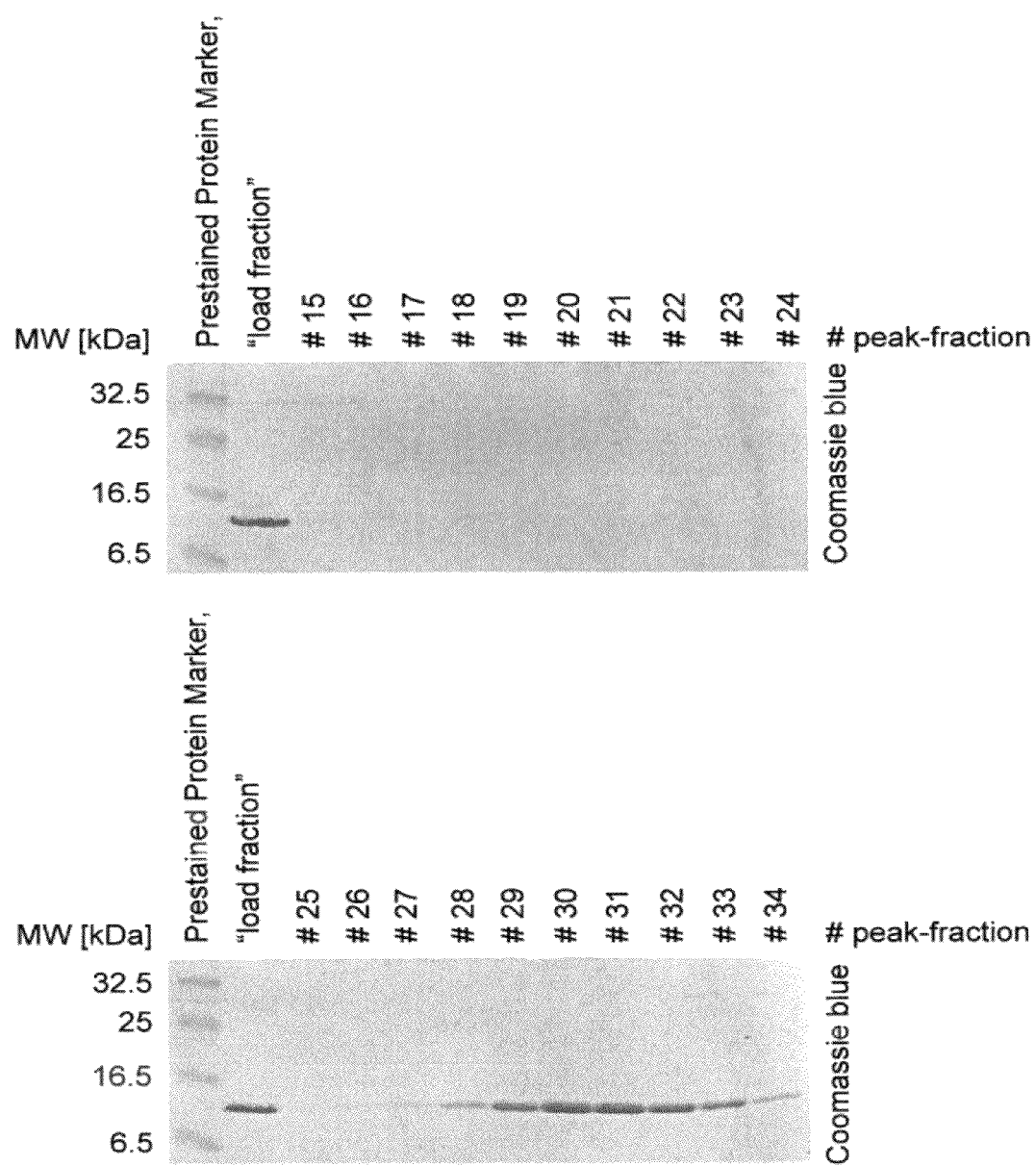
FIG. 37 shows purification of reassembled Qβ VLPs by size exclusion chromatography.
Figure 37B:
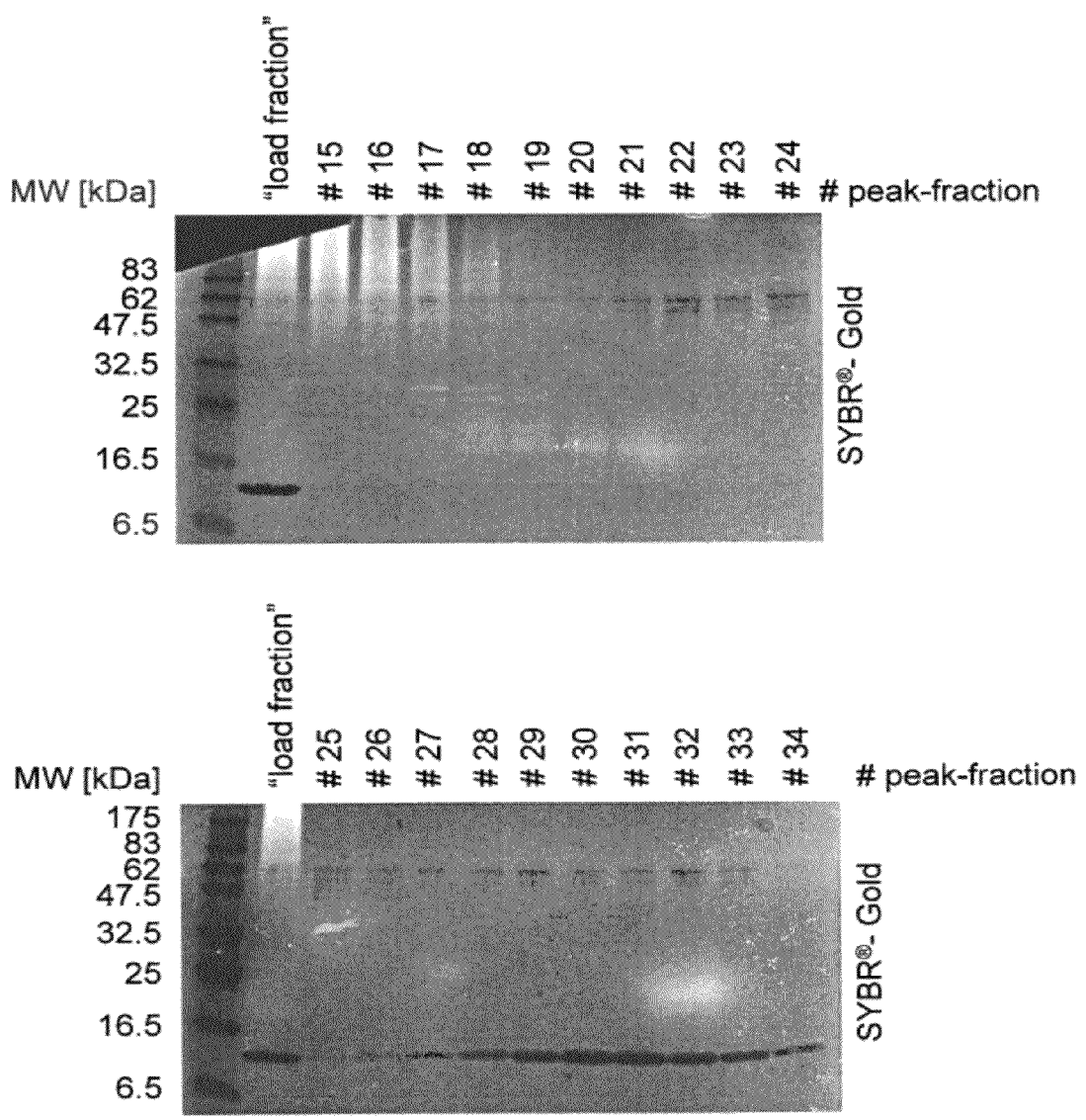

Purification of Reassembled and Packaged VLPs:

Up to 10 mg total protein was loaded onto a Sepharose™ CL-4B column (16/70, Amersham Biosciences) equilibrated with 20 mM HEPES pH 7.4, 150 mM NaCl. Size exclusion chromatography was performed with the equilibration buffer (20 mM HEPES pH 7.4, 150 mM NaCl) at room temperature with a flow-rate of 0.4 ml/min. During the elution absorbance at 254 nm and 280 nm was monitored. Two peaks were isolated. A high molecular weight peak preceded a peak of lower apparent molecular weight. Fractions of 0.5 ml were collected and analysed by SDS-PAGE followed by Coomassie blue staining (FIG. 37). Calibration of the column with intact and highly purified Qβ capsids from E. coli revealed that the apparent molecular weight of the major first peak was consistent with Qβ capsids.

Figure 38:
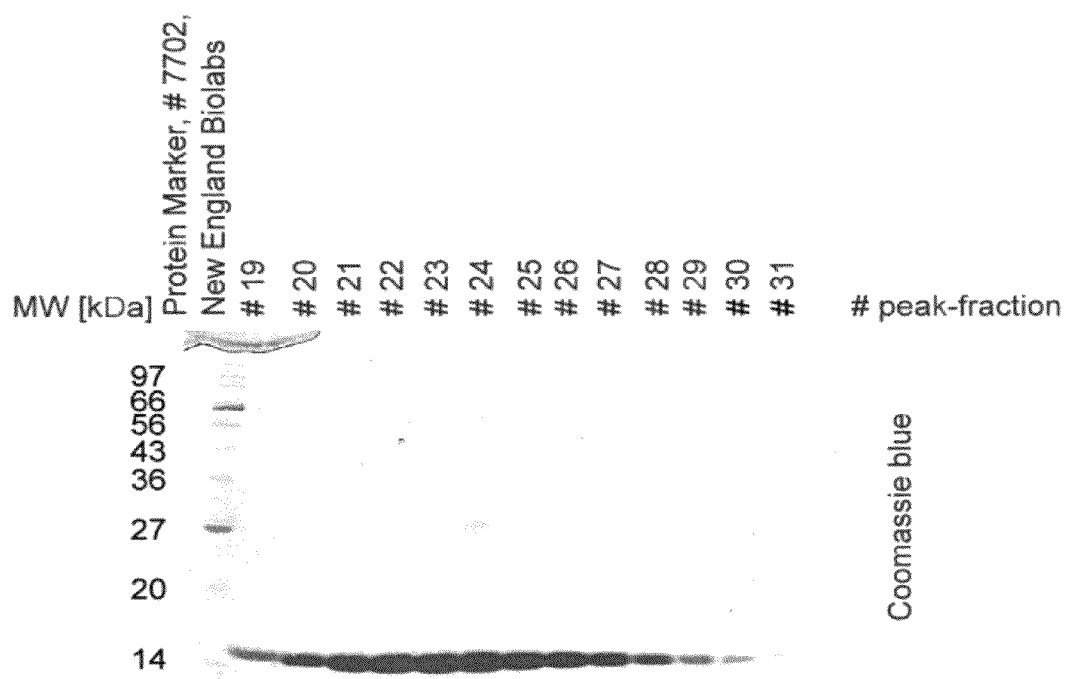
FIG. 38 shows electron micrographs of Qβ VLPs that were reassembled in the presence of different oligodeoxynucleotides.

Analysis of Qβ VLPs which had been reassembled in the presence of oligodeoxynucleotides:

A) Overall structure of the capsids: Qβ VLPs that were reassembled either in the presence of one of the following oligodeoxynucleotides (CyOpA (SEQ ID NO:121), Cy(CpG)20OpA (SEQ ID NO:120), Cy(CpG)20 (SEQ ID NO:119), CyCyCy (SEQ ID NO:122), (CpG)20OpA) (SEQ ID NO:118), or in the presence of tRNA from E. coli (Roche Molecular Biochemicals, Cat. No. 109541) were analyzed by electron microscopy (negative staining with uranylacetate pH 4.5) and compared to intact Qβ VLPs purified from E. coli. As a negative control served a reassembly reaction where nucleic acid was omitted. Reassembled capsids display the same structural features and properties as the intact Qβ VLPs (FIG. 38).

B) Hydrodynamic size of reassembled capsids: Qβ capsids which had been reassembled in the presence of oligodeoxynucleotides were analyzed by dynamic light scattering (DLS) and compared to intact Qβ VLPs which had been purified from E. coli. Reassembled capsids showed the same hydrodynamic size (which depends both on mass and conformation) as the intact Qβ VLPs.

Figure 39:
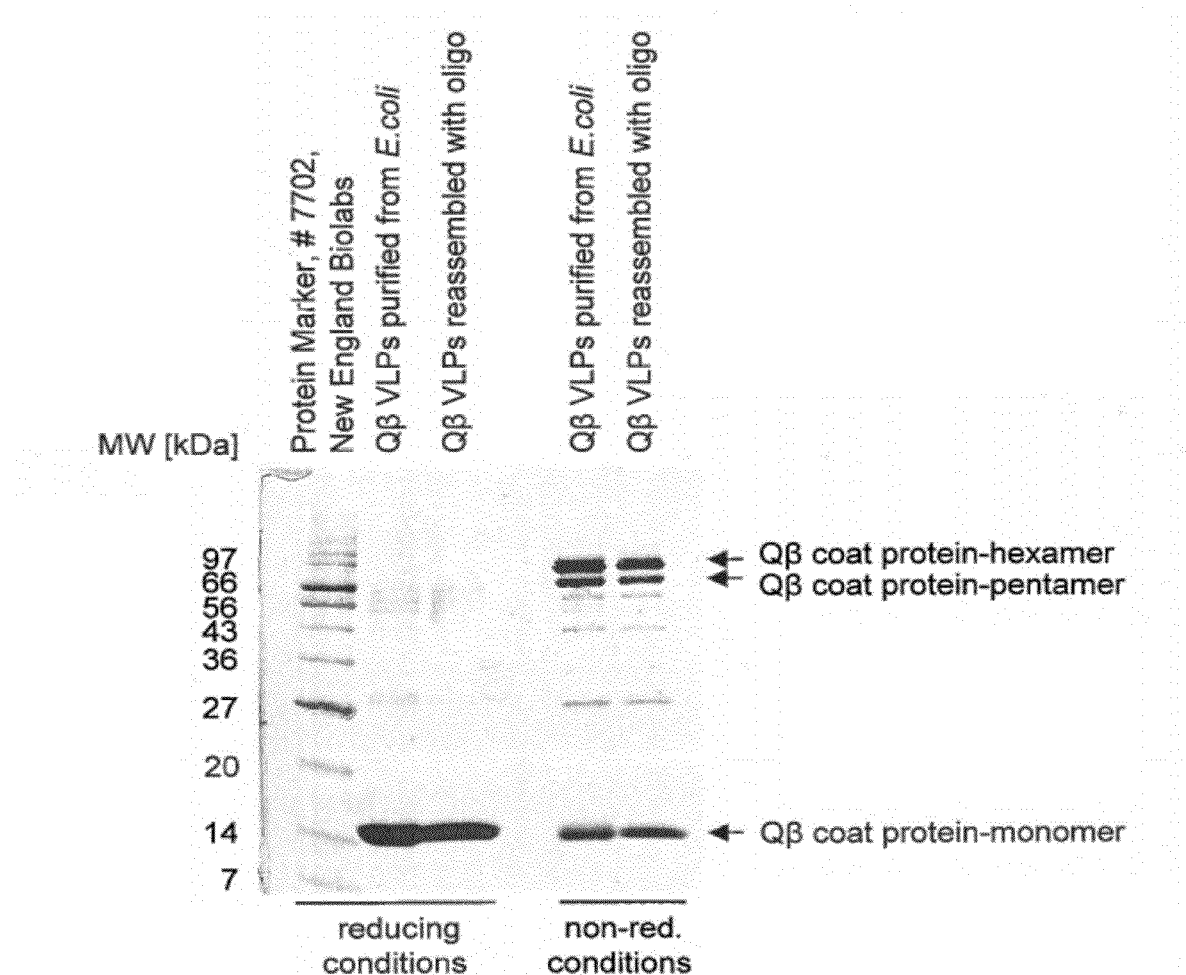
FIG. 39 shows analysis of the disulfide-bond pattern in reassembled and purified Qβ capsids.

C) Disulfide-bond formation in reassembled capsids: Reassembled Qβ VLPs were analyzed by native polyacrylamid gelelectrophoresis and compared to intact Qβ VLPs which had been purified from E. coli. Reassembled capsids displayed the same disulfide-bond pattern as the intact Qβ VLPs (FIG. 39).

Figure 40A:
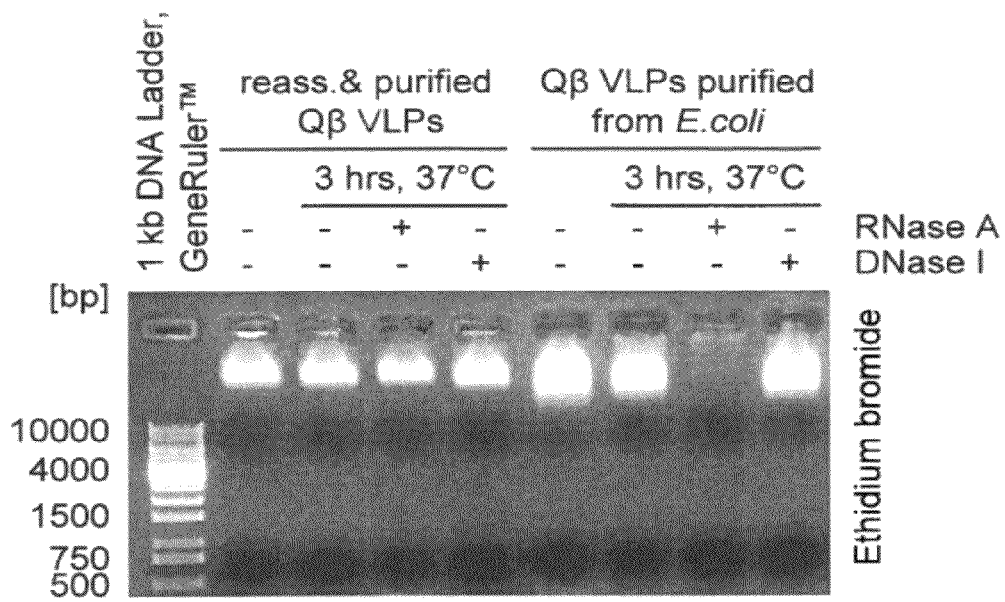
FIG. 40 shows analysis of nucleic acid content of the reassembled Qβ VLPs by nuclease treatment and agarose gelelectrophoresis.
Figure 40B:
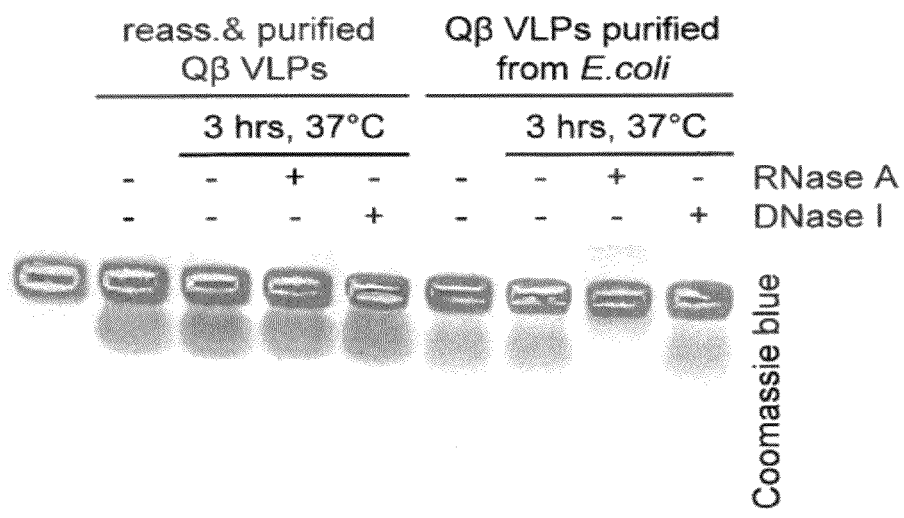

D) Analysis of nucleic acid content of the Qβ VLPs which had been reassembled in the presence of oligodeoxynucleotides by agarose gelelectrophoresis: 5 μg reassembled Qβ VLPs were incubated in total reaction volume of 25 μl either with 0.35 units RNase A (Qiagen, Cat. No. 19101), 15 units DNAse I (Fluka, Cat. No. 31136), or without any further addition of enzymes for 3 h at 37° C. Intact Qβ VLPs which had been purified from E. coli served as control and were incubated under the same conditions as described for the capsids which had been reassembled in the presence of oligodeoxynucleotides. The reactions were then loaded on a 0.8% agarose gel that was first stained with ethidumbromide (FIG. 40A) and subsequently with Coomassie blue (FIG. 40B). The ethidium bromide stain shows, that none of the added enzymes could digest the nucleic acid content in the reassembled Qβ capsids showing that the nucleic acid content (i.e. the oligodeoxynucleotides) is protected. This result indicates that the added oligodeoxynucleotides were packaged into the newly formed capsids during the reassembly reaction. In contrast, the nucleic acid content in the intact Qβ VLPs which had been purified from E. coli was degraded upon addition of RNase A, indicating that the nucleic acid content in this VLPs consists of RNA. In addition, both the ethidium bromide stain and the Coomasie blue stain of the agarose gel shows that the nucleic acid containing Qβ VLPs (reassembled and purified from E. coli, respectively) are migrating at about the same size, which indicates that the reassembly reaction led to Qβ VLPs of comparable size to intact Qβ VLPs which had been purified from E. coli.

The gel thus shows that DNAse I protected oligodeoxynucleotides were present in the reassembled Qβ VLP. Furthermore, after the packaged oligodeoxynucleotides had been extracted by phenol/chloroform they were digestable by DNAse I, but not by RNAse A. Oligodeoxynucleotides could thus be successfully packaged into Qβ VLPs after initial disassembly of the VLP, purification of the disassembled coat protein from nucleic acids and subsequent reassembly of the VLPs in the presence of oligodeoxynucleotides.

E) Analysis of nucleic acid content of the Qβ VLPs which had been reassembled in the presence of oligodeoxynucleotides by denaturing polyacrylamide TBE-Urea gelelectrophoresis: 40 μg reassembled Qβ VLPs (0.8 mg/ml) were incubated in a total reaction volume of 60 μl with 0.5 mg/ml proteinase K (PCR-grade, Roche Molecular Biochemicals, Cat. No. 1964364) and a reaction buffer according to the manufacturers instructions for 3 h at 37° C. Intact Qβ VLPs which had been purified from E. coli served as control and were incubated with proteinase K under the same conditions as described for the capsids which had been reassembled in the presence of oligodeoxynucleotides. The reactions were then mixed with a TBE-Urea sample buffer and loaded on a 15% polyacrylamide TBE-Urea gel (Novex®, Invitrogen Cat. No. EC6885). As a qualitative as well as quantitative standard, 1 pmol, 5 pmol and 10 pmol of the oligodeoxynucleotide which was used for the reassembling reaction, were loaded onto the same gel. This gel was fixed with 10% acetic acid, 20% methanol, equilibrated to neutral pH and stained with SYBR®-Gold (Molecular Probes Cat. No. S-11494). The SYBR®-Gold stain showed (FIG. 41), that the reassembled Qβ capsids contained nucleic acid comigrating with the oligodeoxynucleotides which were used in the reassembly reaction. Note that intact Qβ VLPs (which had been purified from E. coli) did not contain a nucleic acid of similar size. Taken together, analysis of the nucleic acid content of the Qβ VLPs which had been reassembled in the presence of oligodeoxynucleotides showed that oligodeoxynucleotides were protected from DNase I digestion, meaning that they were packaged) and that the added oligodeoxynucleotides could be reisolated by proper means (e.g. proteinase K digestion of the Qβ VLP).

FIG. 37 A-B shows the purification of disassembled Qβ coat protein by size exclusion chromatography. 5 μl of the indicated fractions (#) were mixed with sample buffer and loaded onto 16% Tris-Glycine gels (Novex® by Invitrogen, Cat. No. EC64952). After the run was completed the gels were stained first with Coomassie blue (A) and after documentation the same gels were stained with SYBR®-Gold (B). Note that the first high molecular weight peak (fractions #15-#20) contained no protein but nucleic acids. On the other hand, the second peak of lower apparent molecular weight contained disassembled coat protein which was thereby separated from the nucleic acids.

FIG. 38 shows the purification of reassembled Qβ VLPs by size exclusion chromatography. 10 μl of the indicated fractions (#) were mixed with sample buffer and loaded onto a 16% Tris-Glycine gel (Novex® by Invitrogen, Cat. No. EC64952). After the run was completed the gel was stained with Coomassie blue. Due to the reducing conditions, disulfide bonds were reduced and the proteinaceous monomer of the reassembled VLPs is visible as 14 kDa coat protein.

FIG. 36 A-H shows electron micrographs of Qβ VLPs that were reassembled in the presence of different oligodeoxynucleotides. The VLPs had been reassembled in the presence of the indicated oligodeoxynucleotides or in the presence of tRNA but had not been purified to a homogenous suspension by size exclusion chromatography. As positive control served preparation of "intact" Qβ VLPs which had been purified from E. coli. Importantly, by adding any of the indicated nucleic acids during the reassembly reaction, VLPs of the correct size and conformation could be formed, when compared to the "positive" control. This implicates that the reassembly process in general is independent of the nucleotide sequence and the length of the used oligodeoxynucleotides. Note that adding of nucleic acids during the reassembly reaction is required for the formation of Qβ VLPs, since no particles had been formed if nucleic acids were omitted from the reassembly reaction.

FIG. 39 shows the analysis of the disulfide-bond pattern in reassembled and purified Qβ capsids. 5 μg of the indicated capsids were mixed with sample buffer that either contained a reducing agent or not and loaded onto a 16% Tris-Glycine gel. After the run was completed the gel was stained with Coomassie blue. When compared to "intact" capsids purified from E. coli, the reassembled Qβ VLPs displayed the same disulfide bond pattern.

FIG. 40 shows the analysis of nucleic acid content of the reassembled Qβ VLPs by nuclease treatment and agarose gelelectrophoresis: 5 μg of reassembled and purified Qβ VLPs and 5 μg of Qβ VLPs which had been purified from E. coli, respectively, were treated as indicated. After this treatment, samples were mixed with loading dye and loaded onto a 0.8% agarose gel. After the run the gel was stained first with ethidum bromide (A) and after documentation the same gel was stained with Coomassie blue (B). Note that the nucleic acid content of the reassembled and purified Qβ VLPs were resistant towards RNase A digestion while the nucleic acid content of Qβ VLPs purified from E. coli was digested upon incubation with RNase A. This indicates that the nucleic acid content of the reassembled Qβ capsids consists out of deoxynucleotides which of course are protected from RNase A digestion. Hence, oligodeoxynucleotides were packaged into Qβ VLPs during the reassembly reaction.

Figure 41:
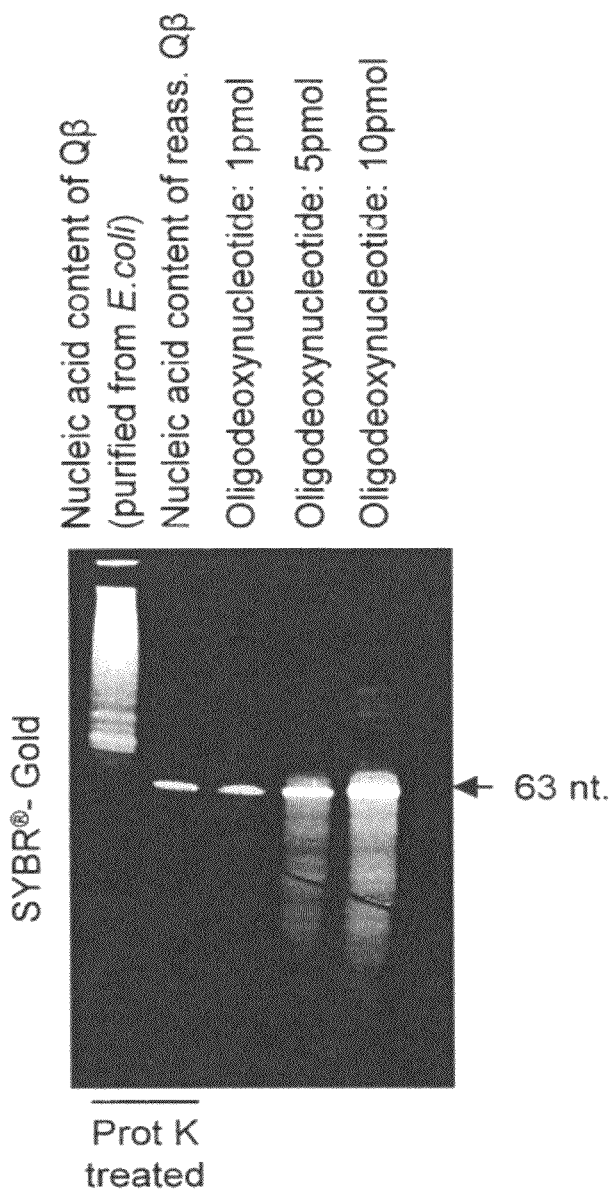
FIG. 41 shows analysis of nucleic acid content of the reassembled Qβ VLPs by proteinase K treatment and polyacrylamide TBE/Urea gelelectrophoresis.

FIG. 41 shows the analysis of nucleic acid content of the reassembled Qβ VLPs by proteinase K treatment and polyacrylamide TBE/Urea gelelectrophoresis: The equivalent of 1 ug Qβ VLPs which had been digested by proteinase K-treatment was mixed with a TBE-Urea sample buffer and loaded on a 15% polyacrylamide TBE-Urea gel (Novex®, Invitrogen Cat. No. EC6885). As qualitative as well as quantitative standard, 1 pmol, 5 pmol and 10 pmol of the oligodeoxynucleotide which was used for the reassembly reaction, was loaded onto the same gel. After the run was completed, the gel was fixed, equilibrated to neutral pH and stained with SYBR®-Gold (Molecular Probes Cat. No. S-11494). Note that intact Qβ VLPs (which had been purified from E. coli) did not contain nucleic acids of similar size than those which had been extracted from reassembled Qβ capsids. In addition, nucleic acids isolated from reassembled VLPs were comigrating with the oligodeoxynucleotides which had been used in the reassembly reaction. This results confirmed that the used oligodeoxynucleotides were packaged into reassembled Qβ capsids.

EXAMPLE 17

AP205 Disassembly-Purification-Reassembly and Packaging of Immunostimulatory Nucleic Acids A. Disassembly and Reassembly of AP205 VLP from Material Able to Reassemble without Addition of Oligonucleotide Disassembly:

40 mg of lyophilized purified AP205 VLP were resolubilized in 4 ml 6 M GuHCl, and incubated overnight at 4° C. The disassembly mixture was centrifuged at 8000 rpm (Eppendorf 5810 R, in fixed angle rotor F34-6-38, used in all the following steps). The pellet was resolubilized in 7 M urea, while the supernatant was dialyzed 3 days against NET buffer (20 mM Tris-HCl, pH 7.8 with 5 mM EDTA and 150 mM NaCl) with 3 changes of buffer. Alternatively, dialysis was conducted in continuous mode over 4 days. The dialyzed solution was centrifuged at 8000 rpm for 20 minutes, and the pellet was resolubilized in 7 M urea, while the supernatant was pelletted with ammonium sulphate (60% saturation), and resolubilized in a 7 M urea buffer containing 10 mM DTT. The previous pellets all resolubilized in 7 M urea were joined, and precipitated with ammonium sulphate (60% saturation), and resolubilized in a 7 M urea buffer containing 10 mM DTT. The materials resolubilized in the 7 M urea buffer containing 10 mM DTT were joined and loaded on a Sephadex G75 column equilibrated and eluted with the 7 M urea buffer containing 10 mM DTT at 2 ml/h. One peak eluted from the column. Fractions of 3 ml were collected. The peak fractions containing AP205 coat protein were pooled and precipitated with ammonium sulphate (60% saturation). The pellet was isolated by centrifugation at 8000 rpm, for 20 minutes. It was resolubilized in 7 M urea, 10 mM DTT, and loaded on a short Sepharose 4B column (1.5×27 cm Sepharose 4B, 2 ml/h, 7 M urea, 10 mM DTT as elution buffer). Mainly one peak, with a small shoulder eluted from the column. The fractions containing the AP205 coat protein were identified by SDS-PAGE, and pooled, excluding the shoulder. This yielded a sample of 10.3 ml. The protein concentration was estimated spectrophotometrically by measuring an aliquot of protein diluted 25-fold for the measurement, using the following formula: (1.55×OD280−0.76×OD260)×volume. The average concentration was of 1 nmol/ml of VLP (2.6 mg/ml). The ratio of absorbance at 280 nm vs. 260 nm was of 0.12/0.105.

Reassembly:

1.1 ml beta-mercaptoethanol was added to the sample, and the following reassembly reactions were set up:

1. 1 ml of AP205 coat protein, no nucleic acids
2. 1 ml of AP205 coat protein, rRNA (approx. 200 OD260 units, 10 nmol)
3. 9 ml of AP205 coat protein, CyCpG (SEQ ID NO:110) (370 ul of 225 pmol/μl solution, i.e. 83 nmol).

Figure 42B:
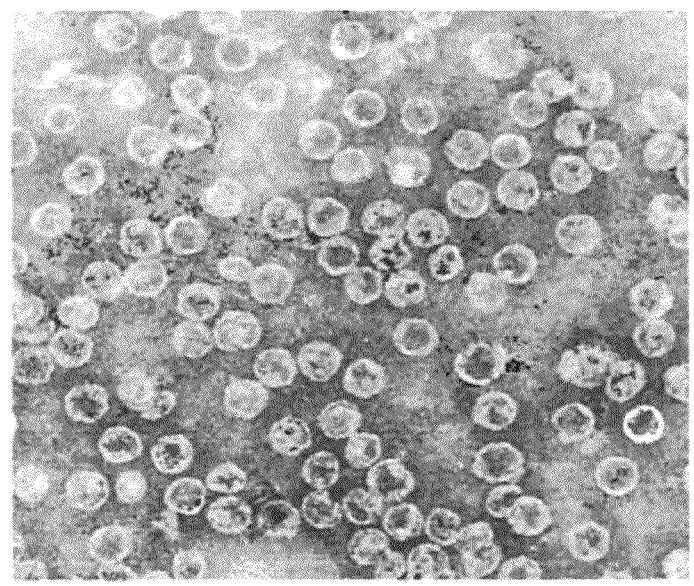
Figure 43A:
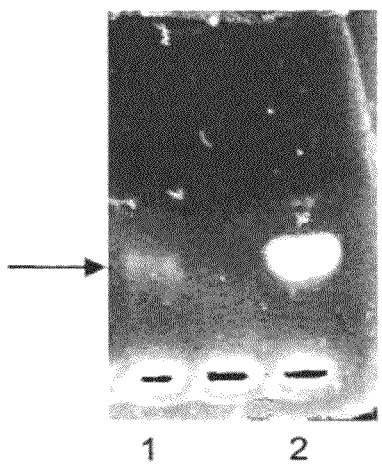
FIG. 43 shows agarose gel-electrophoresis analysis of AP205 VLPs disassembled and reassembled in the presence of CyCpG (SEQ ID NO:110).

These mixtures were dialyzed 1 hour against 30 ml of NET buffer containing 10% beta-mercaptoethanol. The mixture containing no nucleic acids was dialyzed separately. The dialysis was then pursued in a continuous mode, and 1 l of NET buffer was exchanged over 3 days. The reaction mixtures were subsequently extensively dialyzed against water (5 changes of buffer), and lyophilized. They were resolubilized in water, and analyzed by EM. All mixtures contained capsids, showing that AP205 VLP reassembly is independent of the presence of detectable nucleic acids, as measured by agarose gel electrophoresis using ethidium bromide staining. The EM analysis of AP205 reassembled with CyCpG is shown on FIG. 42B. The EM procedure was as follows: A suspension of the proteins was absorbed on carbon-formvar coated grids and stained with 2% phosphotungstic acid (pH 6,8). The grids were examined with a JEM 100C (JEOL, Japan) electron microscope at an accelerating voltage of 80 kV. Photographic records (negatives) were performed on Kodak electron image film and electron micrographs were obtained by printing of negatives on Kodak Polymax paper. The VLP reassembled in the presence of the CyCpG was purified over a Sepharose 4B column (1×50 cm), eluted with NET buffer (1 ml/h). The fractions were analyzed by Ouchterlony assay, and the fractions containing VLP were pooled. This resulted in a sample of 8 ml, which was desalted against water by dialysis, and dried. The yield of capsid was of 10 mg. Analysis of resolubilized material in a 0.6% agarose gel stained with ethidium-bromide showed that the capsids were empty of nucleic acids. Samples of the reassembly reaction containing CyCpG taken after the reassembly step and before extensive dialysis were analysed on a 0.6% agarose gel and are shown in FIGS. 43A and B. A band migrating at the same height than intact AP205 VLP and staining both for ethidium-bromide and Coomassie blue staining could be obtained, showing that AP205 VLP containing oligodeoxynucleotide had been reassembled. The extensive dialysis steps following the reassembly procedure are likely to have led to diffusion of the oligodeoxynucleotide outside of the VLPs. Significantly, the AP205 VLPs could also be reassembled in the absence of detectable oligodeoxynucleotide, as measured by agarose gel electrophoresis using ethidium bromide staining. Oligodeoxynucleotides could thus be successfully bound to AP205 VLP after initial disassembly of the VLP, purification of the disassembled coat protein from nucleic acids and subsequent reassembly of the VLP in the presence of oligodeoxynucleotide.

Figure 42A:
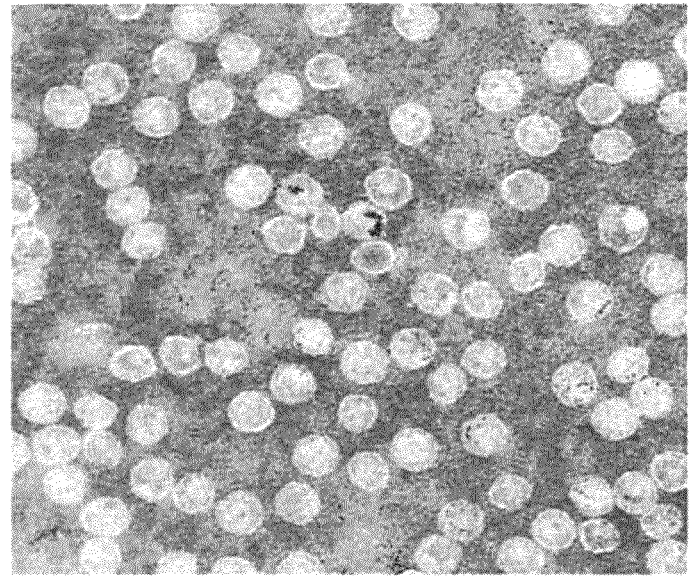
FIG. 42 shows electron micrographs AP205 VLP disassembled and subsequently reassembled in the presence of CyCpG (SEQ ID NO:110).

FIG. 42 shows electron micrographs of either intact recombinant AP205 VLP used for the disassembly step (A), or AP205 VLP disassembled, and subsequently reassembled in the presence of CyCpG (SEQ ID NO:110) (B).

Figure 43B:
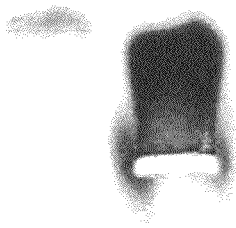

FIG. 43 shows the agarose gel-electrophoresis analysis of the AP205 VLP sample reassembled in the presence of CyCpG (SEQ ID NO:110), and taken directly after the reassembly step before dialysis. The gel on FIG. 43A was stained with ethidium-bromide. AP205 VLP reassembled with CyCpG was loaded on land, while untreated pure AP205 VLP was loaded on lane 2. The arrow indicates the band of the reassembled AP205 VLP. The gel on FIG. 43 B was stained with Coomassie-brilliant blue. Untreated AP205 VLP was loaded on lane 1, while AP205 VLP reassembled with CyCpG was loaded on on lane 2.

B. Reassembly of AP205 VLP Using Disassembled Material which does not Reassemble in the Absence of Added Oligonucleotide Disassembly:

100 mg of purified and dried recombinant AP205 VLP (Cytos patent) were used for disassembly as described above. All steps were performed essentially as described under disassembly in part A, but for the use of 8 M urea to solubilize the pellets of the ammonium sulphate precipitation steps and the omission of the gel filtration step using a CL-4B column prior to reassembly. The pooled fractions of the Sephadex G-75 column contained 21 mg of protein as determined by spectroscopy using the formula described in part A. The ratio of absorbance at 280 nm to the absorbance at 260 nm of the sample was of 0.16 to 0.125. The sample was diluted 50 times for the measurement.

Figure 44A:
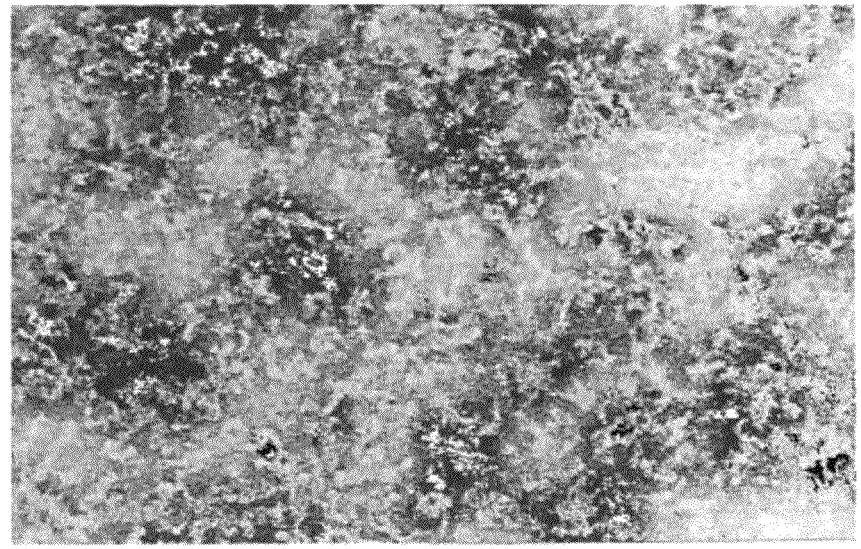
FIG. 44 shows electron micrograph of disassembled and reassembled AP205.

Reassembly:

The protein preparation resulting from the Sephadex G-75 gel filtration purification step was precipitated with ammonium sulphate at 60% saturation, and the resulting pellet solubilized in 2 ml 7 M urea, 10 mM DTT. The sample was diluted with 8 ml of 10% 2-mercaptoethanol in NET buffer, and dialyzed for 1 hour against 40 ml of 10% 2-mercaptoethanol in NET buffer. Reassembly was initiated by adding 0.4 ml of a CyCpG solution (109 nmol/ml) to the protein sample in the dialysis bag. Dialysis in continuous mode was set up, and NET buffer used as eluting buffer. Dialysis was pursued for two days and a sample was taken for EM analysis after completion of this dialysis step (FIG. 44 B). The dialyzed reassembly solution was subsequently dialyzed against 50% v/v Glycerol in NET buffer, to achieve concentration. One change of buffer was effected after one day of dialysis. The dialysis was pursued over a total of three days.

The dialyzed and concentrated reassembly solution was purified by gel filtration over a Sepharose 4-B column (1×60 cm) at a flow rate of 1 ml/hour, in NET buffer. Fractions were tested in an Ouchterlony assay, and fractions containing capsids were dried, resuspended in water, and rechromatographed on the 4-B column equilibrated in 20 mM Hepes pH 7.6. Using each of the following three formula:

1. $(183*OD^{230\,nm} - 75.8*OD^{260\,nm})*\text{volume (ml)} - 2$.
$(OD^{235\,nm} - OD^{280\,nm})/2.51) \times \text{volume} - 3$.
$((OD^{228.5\,nm} - OD^{234.5\,nm})*0.37) \times \text{volume}$ protein amounts of 6 26 mg of reassembled VLP were determined.

The reassembled AP205 VLPs were analyzed by EM as described above, agarose gel electrophoresis and SDS-PAGE under non-reducing conditions.

Figure 44B:
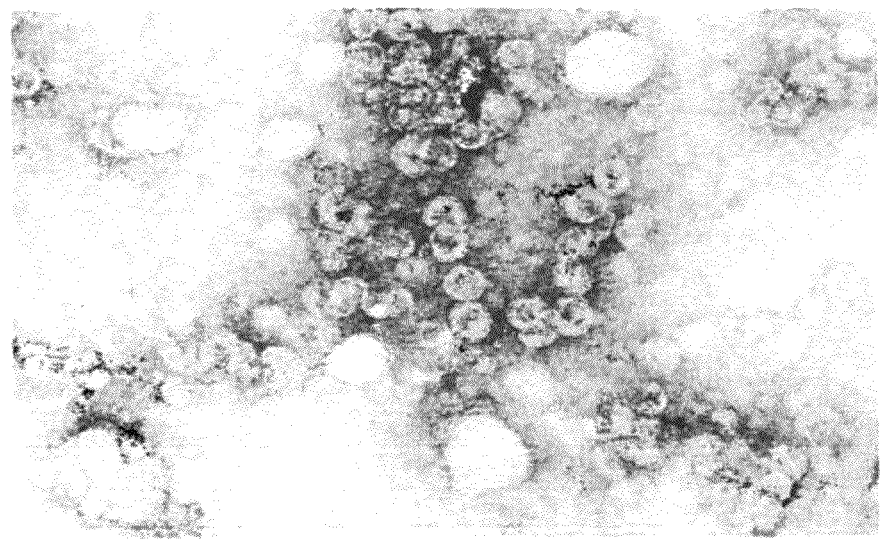
Figure 44C:
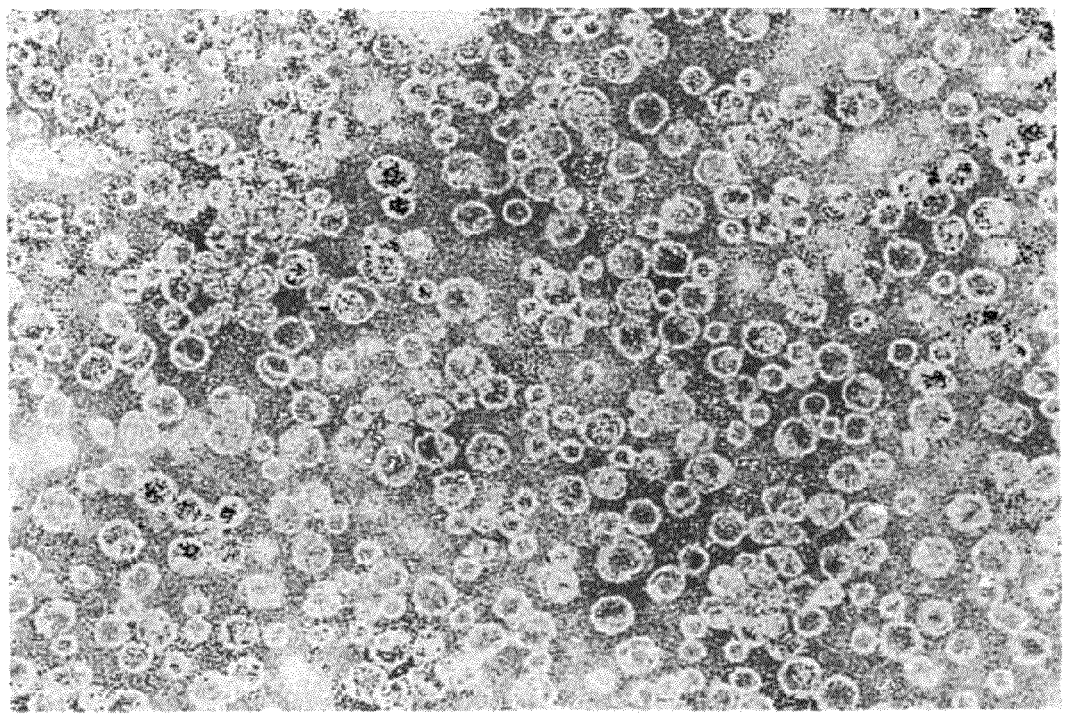
Figure 45A:
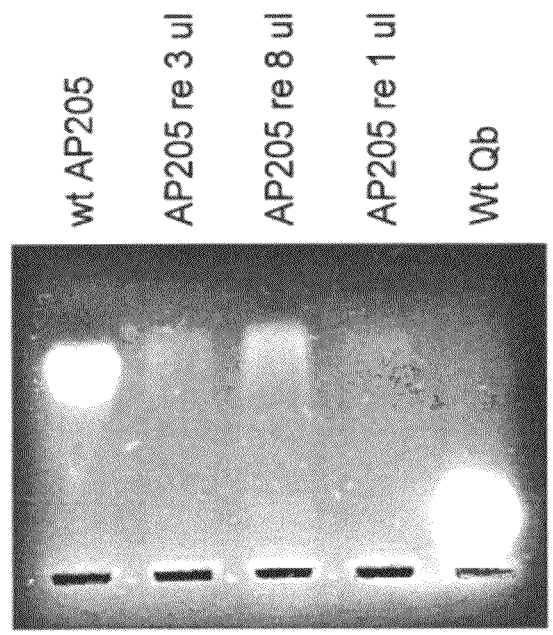
FIG. 45 shows Agarose gel-electrophoresis analysis of AP205 VLPs disassembled and reassembled in the presence of CyCpG (SEQ ID NO:110).
Figure 45B:
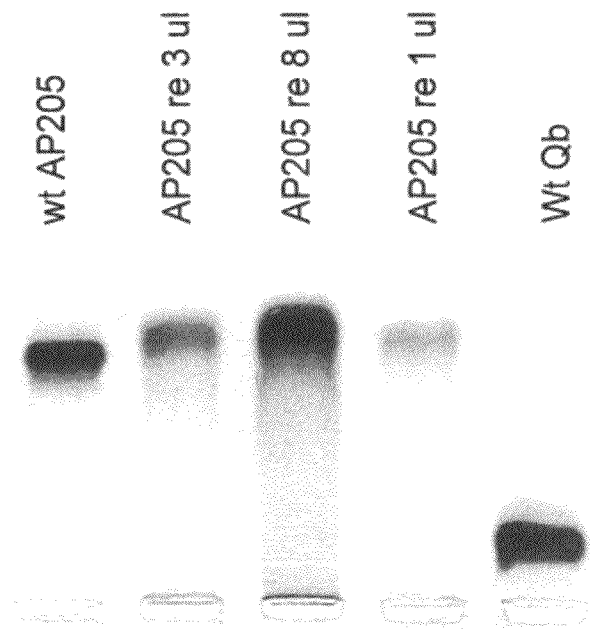

The EM analysis of disassembled material shows that the treatment of AP205 VLP with guanidinium-chloride essentially disrupts the capsid assembly of the VLP. Reassembly of this disassembled material with an oligonucleotide yielded capsids (FIG. 44B), which were purified and further enriched by gel filtration (FIG. 44 C). Two sizes of particles were obtained; particles of about 25 nm diameter and smaller particles are visible in the electron micrograph of FIG. 44C. No reassembly was obtained in the absence of oligonucleotides. Loading of the reassembled particles on agarose electrophoresis showed that the reassembled particles contained nucleic acids. Extraction of the nucleic acid content by phenol extraction and subsequent loading on an agarose gel stained with ethidium bromide revealed that the particles contained the oligonucleotide used for reassembly (FIG. 45A). Identity of the packaged oligonucleotide was controlled by loading a sample of this oligonucleotide side to side to the nucleic acid material extracted from the particles. The agarose gel where the reassembled AP205 VLP had been loaded and previously stained with ethidium bromide was subsequently stained with Coomassie blue, revealing comigration of the oligonucleotide content with the protein content of the particles (FIG. 45B), showing that the oligonucleotide had been packaged in the particles.

Loading of the reassembled AP205 VLP on an SDS-PAGE gel, run in the absence of reducing agent (FIG. 46) demonstrated that the reassembled particles have formed disulfide bridges, as is the case for the untreated AP205 VLP. Moreover, the disulfide bridge pattern is identical to the untreated particles.

Figure 3A:
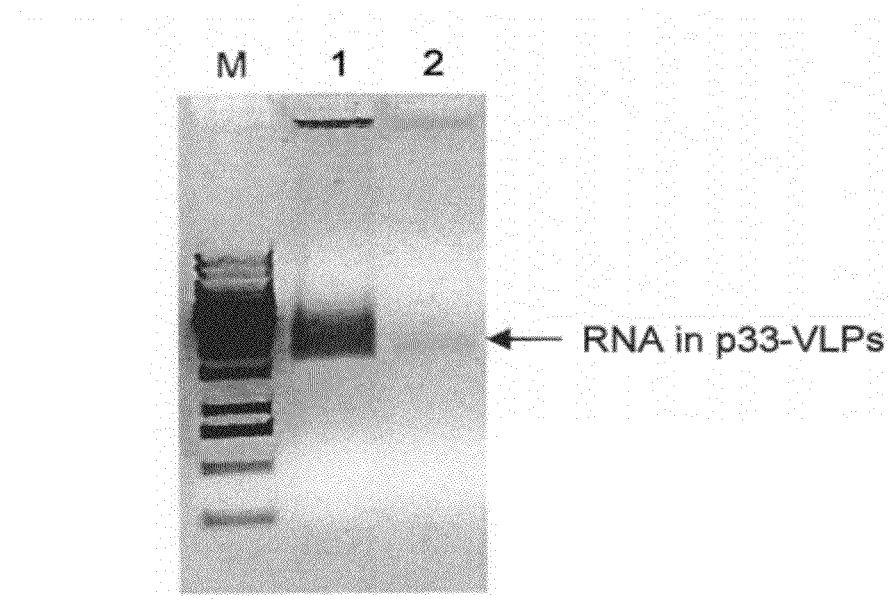
Figure 3B:
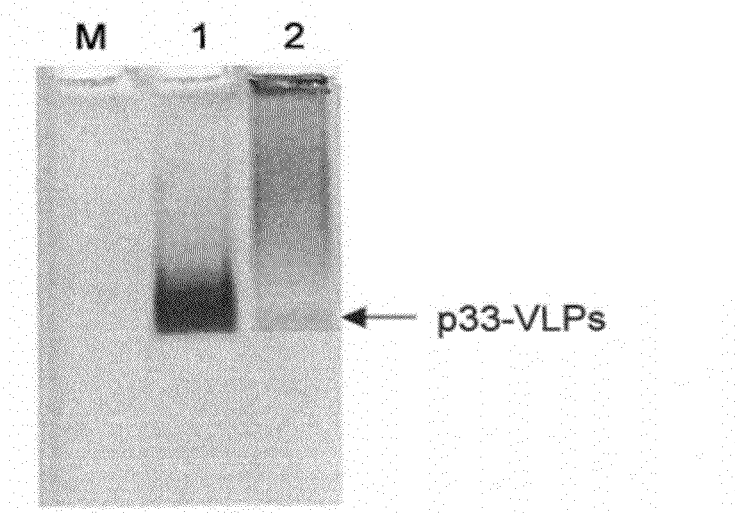

Depicted on FIG. 44 A is an electron micrograph of the disassembled AP205 VLP protein, while FIG. 44 B shows the reassembled particles before purification. FIG. 3 C shows an electron micrograph of the purified reassembled AP205 VLPs. The magnification of FIG. 3A-C is 200 000×.

FIGS. 45 A and B show the reassembled AP205 VLPs analyzed by agarose gel electrophoresis. The samples loaded on the gel from both figures were, from left to right: untreated AP205 VLP, 3 samples with differing amount of AP205 VLP reassembled with CyCpG and purified, and untreated Qβ VLP. The gel on FIG. 45A was stained with ethidium bromide, while the same gel was stained with Coomassie blue in FIG. 45 B.

Figure 46:
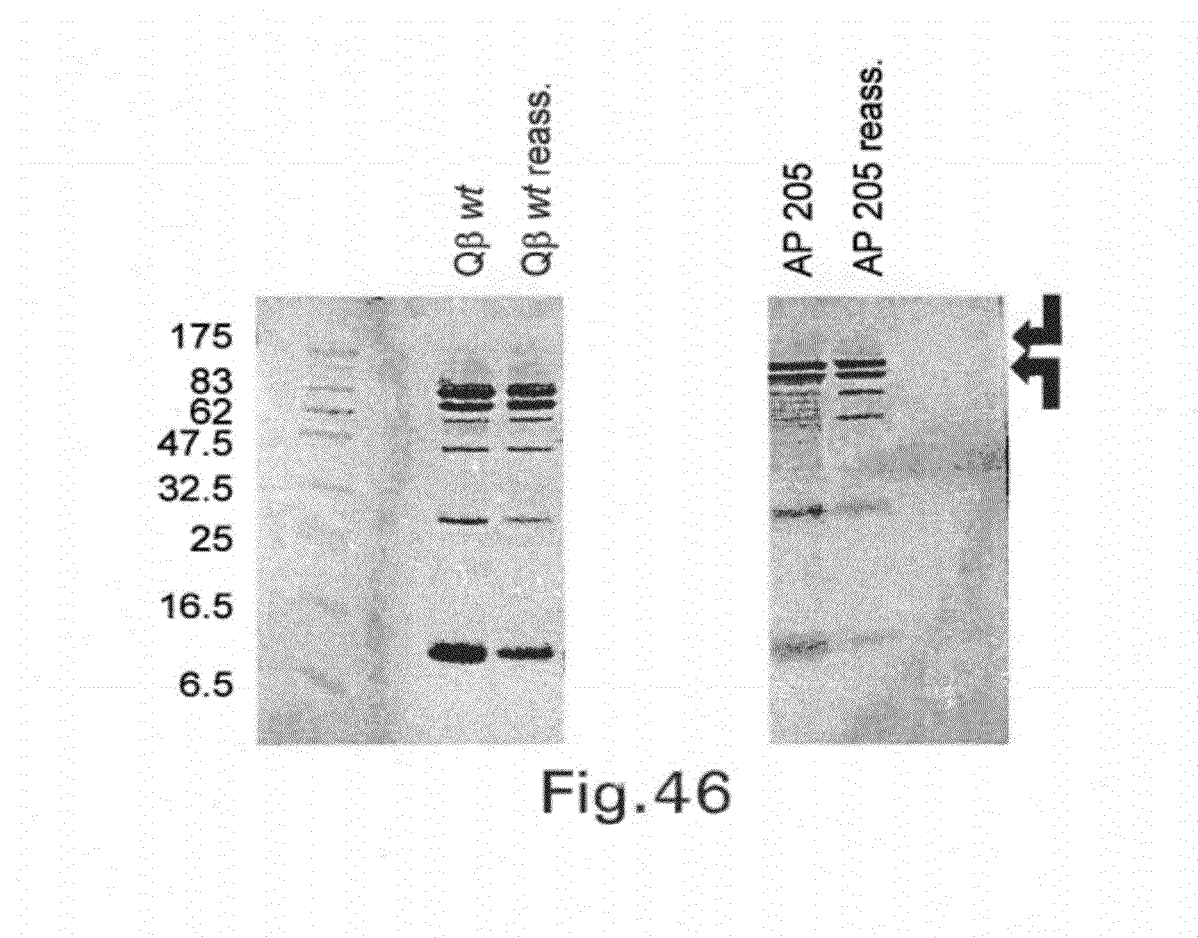
FIG. 46 shows SDS-PAGE analysis, of disassembled and reassembled AP205 VLPs.

FIG. 46 depicts an SDS-PAGE analysis of reassembled AP205 VLP, loaded under non-reducing conditions. 5 samples were loaded on the gel. The samples loaded on the gel are, from left to right: Protein Marker, untreated wt Qβ, reassembled wt Qβ, untreated AP205 VLP, reassembled AP205 VLP. The Molecular Weight of the AP205 VLP subunit is 14.0 kDa, while the molecular weight of the Qβ subunit is 14.3 kDa (both molecular weights calculated with the N-terminal methionine). The disulfide linked multimers are each indicated by an arrow on the figure.

C. Coupling of p33 Epitope (Sequence: H2N-KAVYN-FATMGGC-COOH (SEQ ID NO: 126), with Free N- and C-Termini) to AP205 VLPs Reassembled with CyCpG (SEQ ID NO: 110)

Reassembled AP205 VLP obtained as described in part B, and in 20 mM Hepes, 150 mM NaCl, pH 7.4 was reacted at a concentration of 1.4 mg/ml with a 5-fold excess of the crosslinker SMPH diluted from a 50 mM stock in DMSO for 30 minutes at 15° C. The obtained so-called derivatized AP205 VLP was dialyzed 2×2 hours against at least a 1000-fold volume of 20 mM Hepes, 150 mM NaCl, pH 7.4 buffer. The derivatized AP205 was reacted at a concentration of 1 mg/ml with either a 2.5-fold, or with a 5-fold excess of peptide, diluted from a 20 mM stock in DMSO, for 2 hours at 15° C. The sample was subsequently flash frozen in liquid nitrogen for storage.

The result of the coupling reaction is shown in FIG. 6. A higher degree of coupling could be achieved by using a 5-fold excess of peptide rather than with a 2.5 fold excess of peptide in the coupling reaction.

Figure 47:
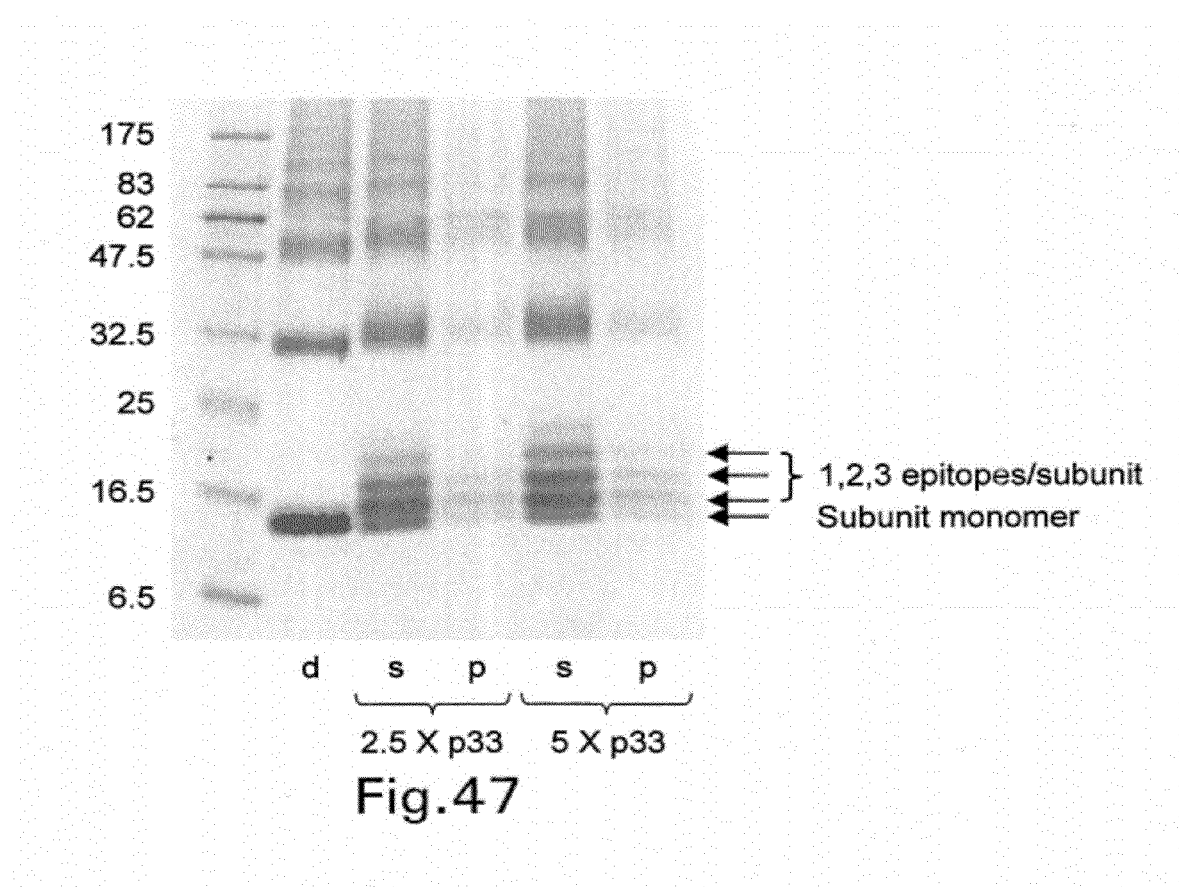
FIG. 47 shows SDS-PAGE analysis of the peptide coupling to disassembled and reassembled AP205 VLPs.

Depicted on FIG. 47 is the SDS-PAGE analysis of the coupling reaction. The following samples (from left to right) were loaded on the gel: protein marker; derivatized AP205 VLP (d); AP205 VLP coupled with a 2.5-fold excess of peptide, supernatant (s); AP205 VLP coupled with a 2.5-fold excess of peptide, pellet (p); AP205 VLP coupled with a 5-fold excess of peptide, supernatant (s); AP205 VLP coupled with a 5-fold excess of peptide, pellet (p).

EXAMPLE 18

Figure 48A:
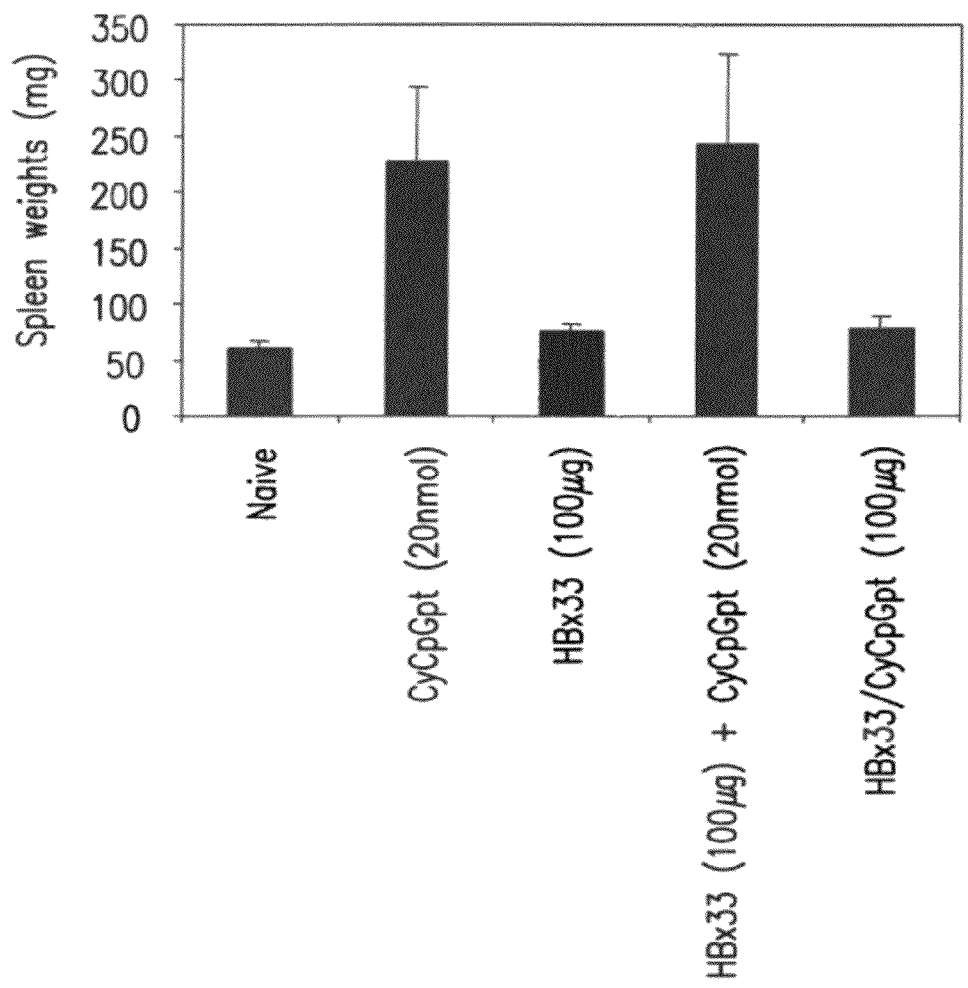
FIG. 48 shows free immunostimulatory nucleic acids but not immunostimulatory nucleic acids packaged in VLPs induce splenomegaly.
Figure 48B:
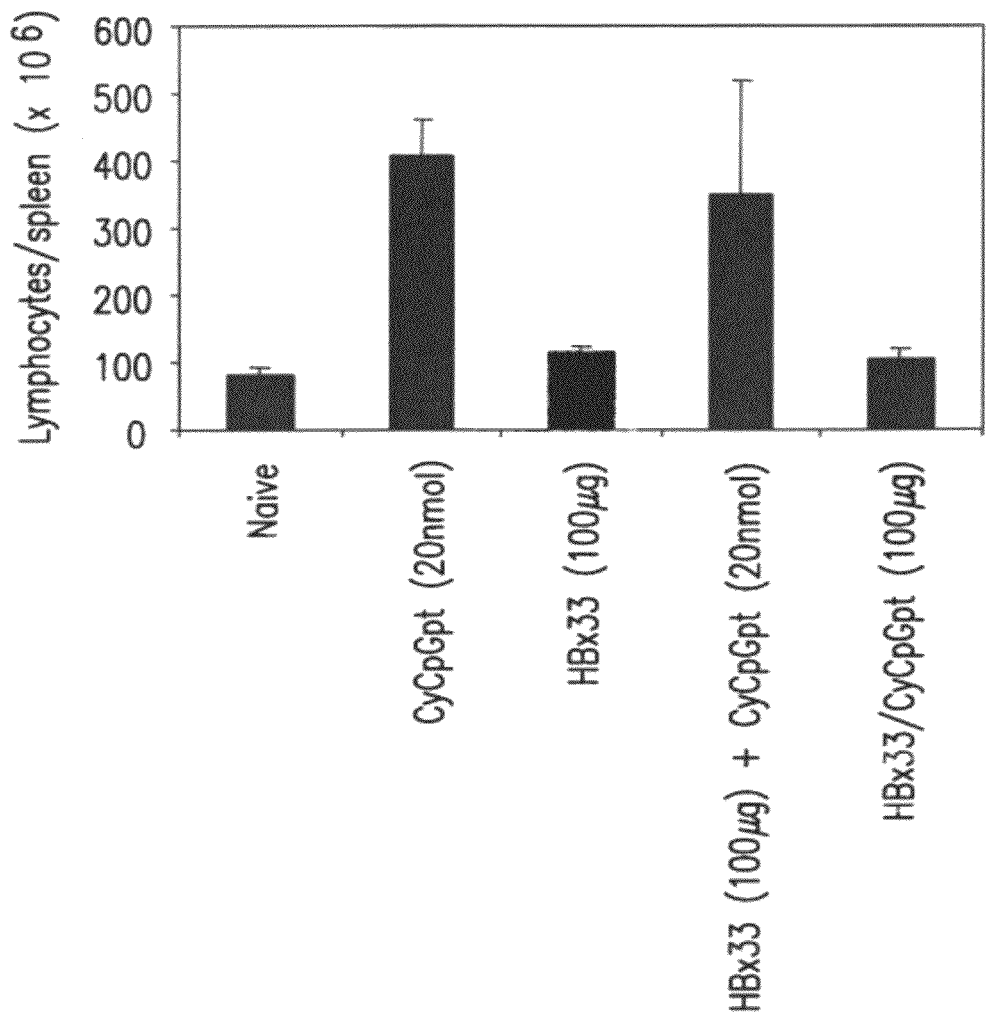

Free Immunostimulatory Nucleic Acids but not Immunostimulatory Nucleic Acids Packaged in VLPs Induce Splenomegaly Mice were left untreated or immunized s.c. with 100 μg HBc33 alone, 20 nmol CyCpGpt, 100 μg HBc33 mixed with 20 nmol CyCpGpt (SEQ ID NO:109), or 100 μg HBc33 packaged with CyCpGpt. Twelve days later, spleens were isolated and spleen weights and splenic cellularity were assessed. CyCpGpt induced a massive increase in spleen weight and number of cells when given alone (FIG. 48 A B). No such effect was seen with CyCpGpt packaged in HBc33 although this composition was able to induce protection against viral challenge (see EXAMPLE 4).

EXAMPLE 19

In-Vivo Virus Protection Assays

Vaccinia Protection Assay

Groups of three female C57Bl/6 mice were immunized s.c. with 100 μg VLP coupled or fused to p33 alone, mixed with 20 nmol immunostimulatory nucleic acid or packaged with immunostimulatory nucleic acid. To assess antiviral immunity in peripheral tissues, mice were infected 7-9 days later, i.p., with $1.5 \times 10^6$ pfu recombinant vaccinia virus expressing the LCMV-glycoprotein (inclusive of the p33 peptide). Five days later the ovaries were collected and viral titers determined. Therefore, ovaries were ground with a homogenizer in Minimum Essential Medium (Gibco) containing 5% fetal bovine serum and supplemented with glutamine, Earls's salts and antibiotics (penicillin/streptomycin/amphotericin). The suspension was titrated in tenfold dilution steps onto BSC40 cells. After overnight incubation at 37° C., the adherent cell layer was stained with a solution consisting of 50% ethanol, 2% crystal violet and 150 mM NaCl for visualization of viral plaques. Non-immunized naïve mice were used as control.

LCMV Protection Assay

Groups of three female C57Bl/6 mice were immunized s.c. with 100 μg VLP coupled or fused to p33 alone or mixed with adjuvant/20 nmol CpG oligonucleotide. To examine systemic antiviral immunity mice were infected i.p. 11-13 days later with 200 pfu LCMV-WE. Four days later spleens were isolated and viral titers determined. The spleens were ground with a homogenizer in Minimum Essential Medium (Gibco) containing 2% fetal bovine serum and supplemented with glutamine, earls's salts and antibiotics (penicillin/streptomycin/amphotericin). The suspension was titrated in tenfold dilution steps onto MC57 cells. After incubation for one hour the cells were overlayed with DMEM containing 5% Fetal bovine serum, 1% methyl cellulose, and antibiotics (penicillin/streptomycin/amphotericin). Following incubation for 2 days at 37° C. the cells were assessed for LCMV infection by the intracellular staining procedure (which stains the viral nucleoprotein): Cells were fixed with 4% Formaldehyde for 30 min followed by a 20 min lysing step with 1% Triton X-100. Incubation for 1 hour with 10% fetal bovine serum blocked unspecific binding. Cells were stained with a rat anti-LCMV-antibody (VL-4) for 1 hour. A peroxidase-conjugated goat anti-rat-IgG (Jackson ImmunoResearch Laboratories, Inc) was used as secondary antibody followed by a colour reaction with ODP substrate according to standard procedures.

EXAMPLE 20

Different Immunostimulatory Nucleic Acids Packaged in VLP Fused to Antigen Result in a Potent Antigen-Specific CTL Response and Virus Protection The fusion protein of HBcAg with the peptide p33 (HBc33) was produced as described in EXAMPLE 1 and packaged with different CpG nucleic acids as described in EXAMPLE 11.

100 μg of vaccines were injected into mice and vaccina titers in the ovaries after recombinant vaccinia challenge were detected as described in EXAMPLE 19. Double stranded CyCpGpt (dsCyCpGpt) (SEQ ID NO:109) was produced by annealing 0.5 mM of DNA oligonucleotides CyCpGpt and CyCpG-rev-pt (Table I) in 15 mM Tris pH7.5 by a 10 min heating step at 80° C. and subsequent cooling to RT. Oligonucleotide hybridization was checked on a 20% TBE polyacrylamid gel (Novex).

Figure 49:
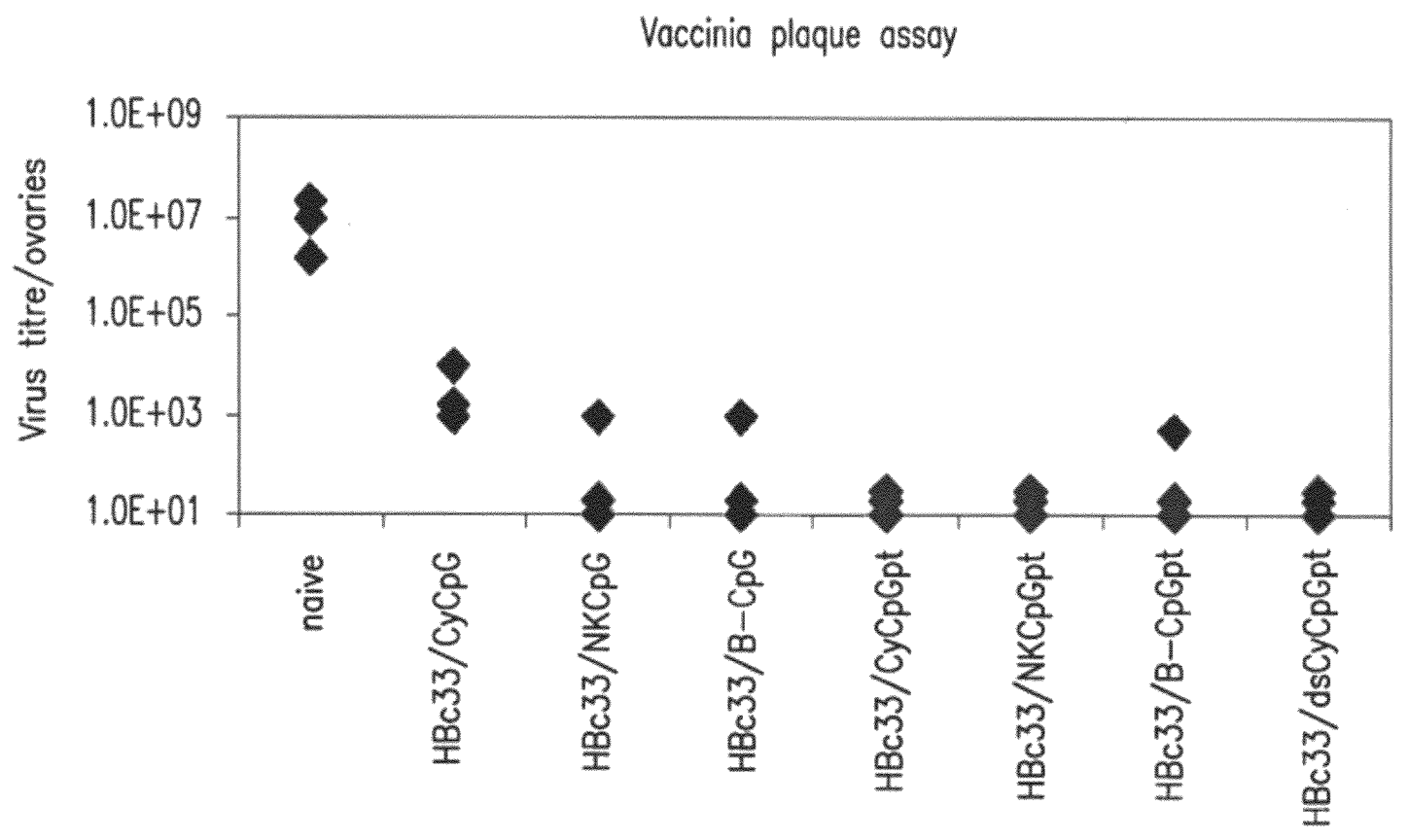
Figure 50:
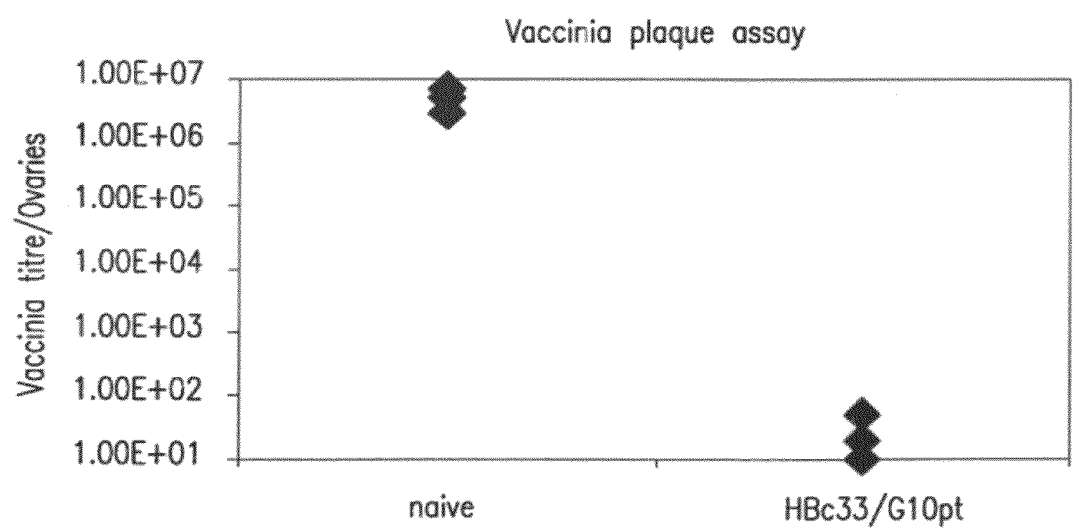
FIG. 50 shows the immunostimulatory nucleic acid g10gacga-PS (SEQ ID NO:117) packaged in VLP fused to antigen result in a potent antigen-specific CTL response and virus protection.

HBc33 capsids containing CyCpG (SEQ ID NO:110), NKCpG (SEQ ID NO:114), B-CpG (SEQ ID NO:112) and g10gacga-PS (SEQ ID NO:117) did induce CTL responses capable of completely inhibition viral infection (FIG. 49, FIG. 50). Protection was observed with nucleic acids contained phosphodiester or phosphothioate bonds (pt or PS). Even a double stranded oligonucleotide dsCyCpGpt was inducing protection against vaccinia challenge (FIG. 49).

EXAMPLE 21

Figure 51:
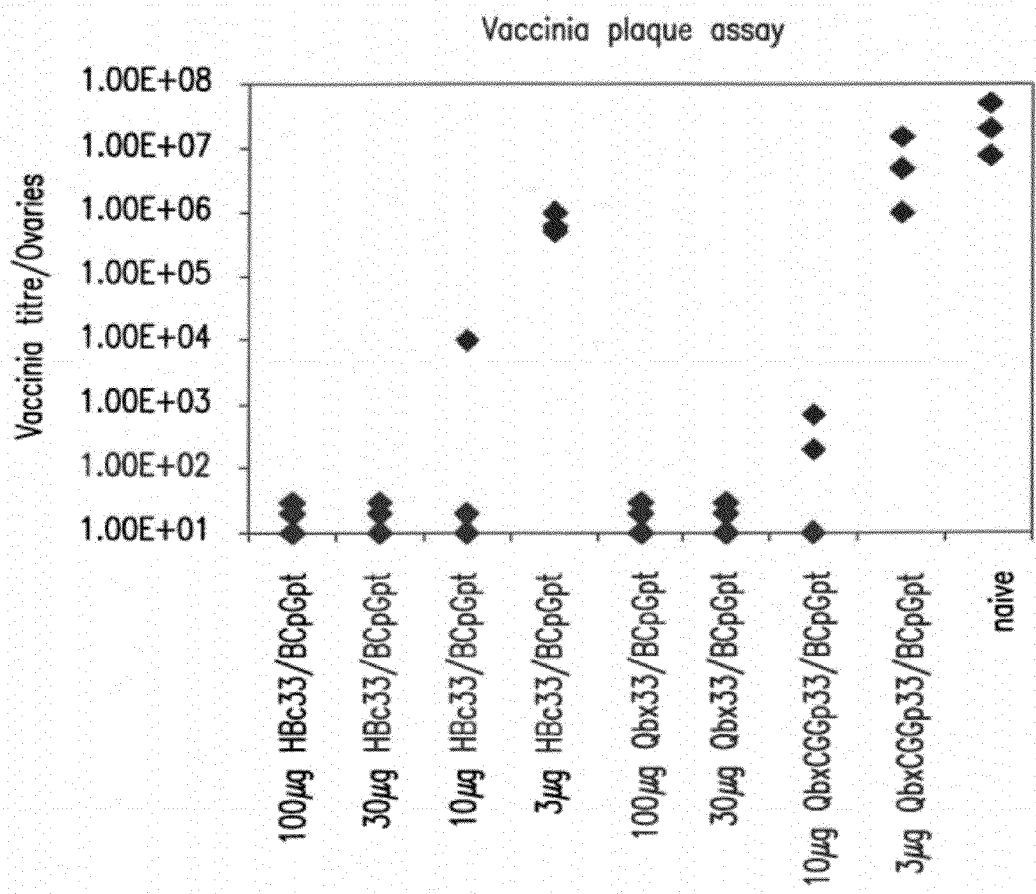
FIG. 51 shows immunostimulatory nucleic acids packaged in HBcAg and Qβ VLPs result in a potent antigen-specific CTL response and virus protection.

Immunostimulatory Nucleic Acids Packaged in HBcAg and Qβ VLPs Result in a Potent Antigen-Specific CTL Response and Virus Protection The fusion protein of HBcAg with the peptide p33 (HBc33) was produced as described in EXAMPLE 1 and packaged with oligonucleotide B-CpGpt (SEQ ID NO:112) as described in EXAMPLE 11. Peptide p33 was coupled to the RNA phage Qβ and oligonucleotide B-CpGpt were packaged as described in EXAMPLE 13. 100 µg, 30 µg, 10 µg or 3 µg of each vaccine was injected into mice and vaccina titers in the ovaries after recombinant vaccinia challenge were detected as described in EXAMPLE 19. 100 µg and 30 µg HBc33 and Qbx33 with packaged B-CpG did induce full protection against viral challenge while at lower concentrations partial or no protection was observed (FIG. 51).

EXAMPLE 22

Immunostimulatory Nucleic Acids Packaged in VLPs which are Coupled to Selfantigens can Overcome Tolerance to Self-Antigens Transgenic mice expressing LCMV glycoprotein in pancreatic islet cells (Ohasi et al., Cell 65, 305-317 (1991)) were immunized with 200 pfu LCMV, 100 µg HBc33 mixed with 20 nmol CyCpGpt, 100 µg HBc33 packaged with CyCpGpt or 100 µg p33 peptide mixed with 20 nmol CyCpGpt as control. Blood glucose levels were measured every four days with the Glucotrend Plus Glucose test kit (Roche). Mice with blood glucose levels larger 12 mM were considered diabetic. Immunization with LCMV induced diabetes in 4/4 animals at day 12. CyCpGpt mixed with HBc33 only caused diabetes in ⅓ mice. Two of three mice immunized with HBc33 in which CyCpGpt was packaged develop diabetes at day 12, the third mouse at day 16. Immunization with peptide p33 mixed with CyCpGpt did not induce diabetes in three mice. This clearly shows that immunostimulatory nucleic acid packaged into VLP to which antigens are fused are much more efficient in enhancing a strong CTL response than a mixture of nucleic acid and antigen. They even induced a stronger response than antigen fused to VLP and mixed with the immunostimulatory nucleic acid.

EXAMPLE 23

Immunostimulatory Nucleic Acids Packaged in VLPs-Coupled to Antigens are Even More Efficient in Inducing Antigen-Specific CD8+ T Cells than VLPs Mixed with Immunostimulatory Nucleic Acids C57BL/6 mice were subcutaneously immunized with 100 µg HBc33 alone, mixed with CyCpGpt or, alternatively, packaged with CyCpGpt. Untreated mice served as controls.

8 days after immunization blood lymphocytes were double-stained with PE-labeled p33-tetramers and FITC-coupled monoclonal anti-CD8 antibodies for p33-specific CD8+ T cell detection and percentage of p33-specific cells on the total CD8+ T cell population were determined by FACS analysis.

TABLE II

| Immunization | Frequencies of p33-specific CD8+ T cells | Mice per group |
|---|---|---|
| Untreated | 0.2 | 2 |
| HBc33 | 0.3 ± 0.1 | 4 |
| HBc33 + CyCpGpt (SEQ ID NO: 109) (mixed) | 2.1 ± 0.9 | 5 |
| HBc33/CyCpGpt (SEQ ID NO: 109) (packaged) | 4.3 ± 1.1 | 5 |

HBc33 with packaged CyCpGpt induced a higher frequence of p33-specific CD8+ T cells than HBc33 mixed with CyCpGpt (SEQ ID NO:109) (Table II). As the amount of packaged oligonucleotide is much lower (about ¹/₂₀) of the amount of oligonucleotide used in the mixed setting this clearly demonstrates that VLPs with packaged immunostimulatory nucleic acids are even more efficient in inducing high numbers of antigen-specific CD8+ T cells.

EXAMPLE 24

Immunostimulatory Nucleic Acids Packaged in VLPs are Even More Efficient in Inducing CTL Responses than VLPs Mixed with Immunostimulatory Nucleic Acids Groups of C57BL/6 mice were subcutaneously primed with 100 µg p33-VLP given alone, mixed with 20 nmol CyCpGpt (SEQ ID NO:109), or, alternatively, packaged with CyCpGpt. For detection of primary ex vivo cytotoxicity, effector cell suspensions were prepared from spleens of vaccinated mice 9 days after priming. EL-4 cells were pulsed with p33 peptide ($10^{-6}$ M, 2 h at 37° C. in 2% FCS MEM medium) and used in a 5 h $^{51}$Cr release assay.

Figure 52C:
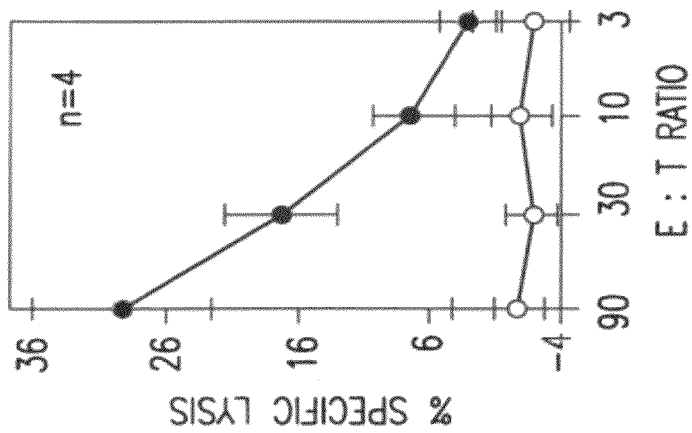
FIG. 52 shows immunostimulatory nucleic acids packaged in VLPs are even more efficient in inducing CTL responses than VLPs mixed with immunostimulatory nucleic acids.
Figure 52B:
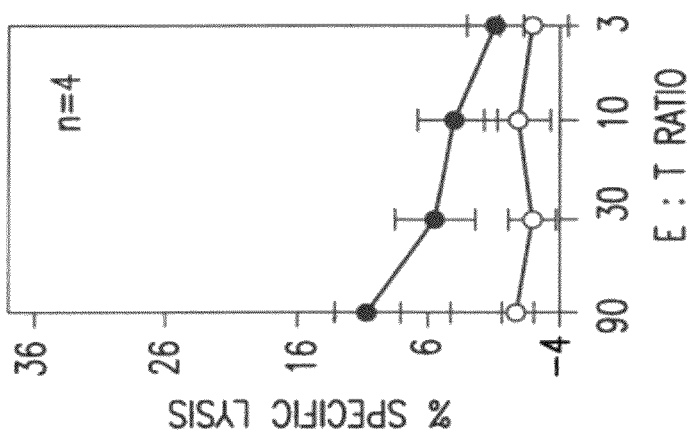
Figure 52A:
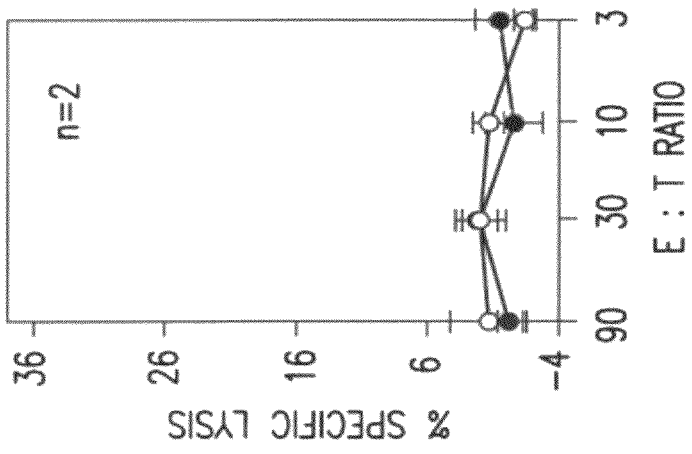

FIG. 52 shows the primary ex vivo cytotoxicity of groups of C57BL/6 mice that were subcutaneously primed with 100 µg p33-VLP given alone (A), mixed with 20 nmol CyCpGpt (SEQ ID NO:109) (B), or, alternatively, packaged with CyCpGpt (C). Nine days later spleen cells were tested for direct ex vivo CTL activity in a 5-h $^{51}$Cr-release assay on p33-pulsed (filled symbols) or on unpulsed (open symbols) EL-4 target cells at the indicated effector to target cell ratios. Radioactivity in cell culture supernatants was measured in a Cobra II Counter (Canberra Packard, Downers Growe, Ill.). Spontaneous release was always <10%. Two dilution series of effector cells per mouse were performed. In (A) two mice per group were used, whereas in (B) and (C) data from four mice per group are shown.

FIG. 52 clearly demonstrates that 100 µg HBc33 alone did not induce primary in vivo CTL response while the same amount HBc33 mixed with 20 nmol CyCpGpt (SEQ ID NO:109) did induce a significant cytotoxicity. However, although the amount of packaged oligonucleotide was much lower (about ¹/₂₀) of the amount of oligonucleotide used in the mixed setting cytotoxicity was enhanced when 100 µg HBc33 with packaged CyCpGpt were used for immunization (FIG. 52).

EXAMPLE 25

Figure 53:
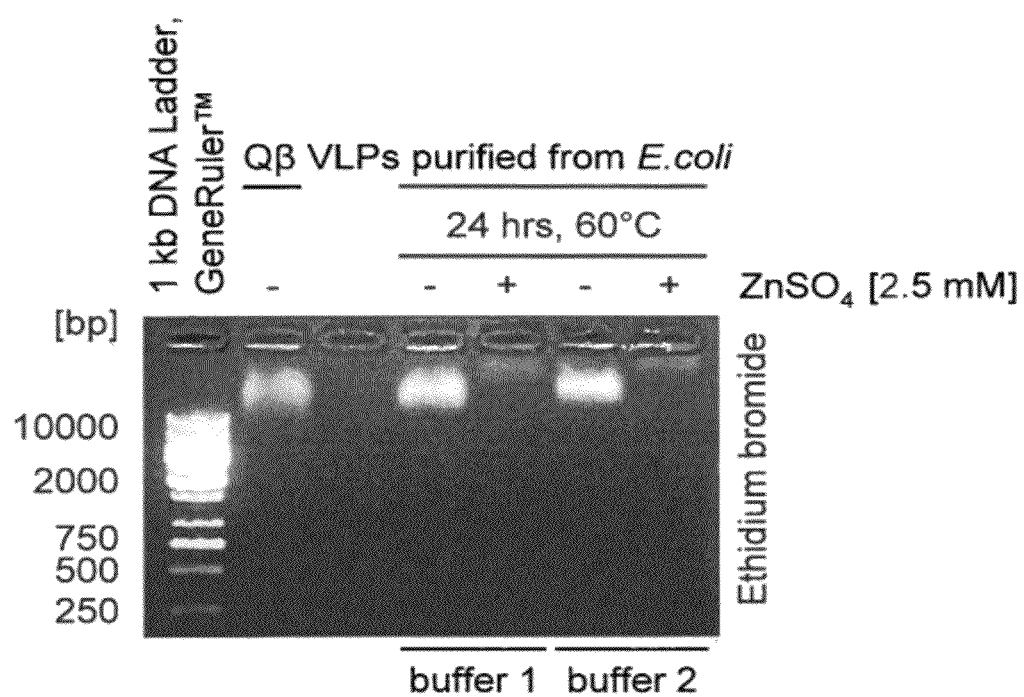
FIG. 53 shows analysis of non-enzymatic RNA hydrolysis of the RNA in Qβ VLPs.

Non-Enzymatic Hydrolysis of the RNA Content of VLPs and Packaging of Immunostimulatory Nucleic Acids $ZnSO_4$ Dependent Degradation of the Nucleic Acid Content of a VLP:

5 mg Qβ VLP (as determined by Bradford analysis) in 20 mM HEPES, pH 7.4, 150 mM NaCl was dialysed either against 2000 ml of 50 mM TrisHCl pH 8.0, 50 mM NaCl, 5% glycerol, 10 mM $MgCl_2$ or 2000 ml of 4 mM HEPES, pH 7.4, 30 mM NaCl for 2 h at 4° C. in SnakeSkin™ pleated dialysis tubing (Pierce, Cat. No. 68035). Each of the dialysis buffers was exchanged once and dialysis was allowed to continue for another 16 h at 4° C. The dialysed solution was clarified for 10 minutes at 14000 rpm (Eppendorf 5417 R, in fixed angle rotor F45-30-11, used in all the following steps) and protein concentration was again determined by Bradford analysis. Qβ VLPs in 50 mM TrisHCl pH 8.0, 50 mM NaCl, 5% glycerol, 10 mM $MgCl_2$ were diluted with the corresponding buffer to a final protein concentration of 1 mg/ml whereas Qβ VLPs in 4 mM HEPES pH 7.4, 30 mM NaCl were diluted with the corresponding buffer to a final protein concentration of 0.5 mg/ml. This capsid-containing solutions were centrifuged again for 10 minutes at 14000 rpm at 4° C. The supernatants were than incubated with $ZnSO_4$ which was added to a final concentration of 2.5 mM for 24 h at 60° C. in an Eppendorf Thermomixer comfort at 550 rpm. After 24 h the solutions were clarified for 10 minutes at 14000 rpm and the sediment was discarded. The efficiency of the $ZnSO_4$-dependent degradation of nucleic acids was confirmed by agarose gelelectrophoresis (FIG. 53). The supernatants were dialysed against 5000 ml of 4 mM HEPES pH 7.4, 30 mM NaCl for 2 h at 4° C. 5000 ml buffer was exchanged once and dialysis continued over night at 4° C. The dialysed solution was clarified for 10 minutes at 14000 rpm and 4° C., a negligible sediment was discarded and the protein concentration of the supernatants were determined by Bradford analysis.

Similar results were obtained with copper chloride/phenanthroline/hydrogen peroxide treatment of capsids. Those skilled in the art know alternative non-enzymatic procedures for hydrolysis or RNA.

Packaging of Oligodeoxynucleotides into $ZnSO_4$-Treated VLPs:

$ZnSO_4$-treated and dialysed Qβ capsids with a protein concentration (as determined by Bradford analysis) between 0.4 mg/ml and 0.9 mg/ml (which corresponds to a concentration of capsids of 159 nM and 357.5 nM, respectively) were used for the packaging of the oligodeoxynucleotides. The oligodeoxynucleotides were added at a 300-fold molar excess to the of Qβ-VLP capsids and incubated for 3 h at 37° C. in an Eppendorf Thermomixer comfort at 550 rpm. After 3 h the reactions were centrifuged for 10 minutes at 14000 rpm and 4° C. The supernatants were dialysed in Spectra/Por®CE DispoDialyzer with a MWCO 300'000 (Spectrum, Cat. No. 135 526) against 5000 ml of 20 mM HEPES pH 7.4, 150 mM NaCl for 8 h at 4° C. 5000 ml buffer was exchanged once and dialysis continued over night at 4° C. The protein concentration of the dialysed samples were determined by Bradford analysis. Qβ capsids and their nucleic acid contents were analyzed as described in Examples 11 and 13.

FIG. 53 shows the analysis of $ZnSO_4$-treated Qβ VLPs by agarose gelelectrophoresis: Qβ VLPs which had been purified from *E. coli* and dialysed either against buffer 1 (50 mM TrisHCl pH 8.0, 50 mM NaCl, 5% glycerol, 10 mM $MgCl_2$) or buffer 2 (4 mM HEPES, pH 7.4, 30 mM NaCl) were incubated either without or in the presence of 2.5 mM zinc sulfate ($ZnSO_4$) for 24 hrs at 60° C. After this treatment equal amounts of the indicated samples (5 μg protein) were mixed with loading dye and loaded onto a 0.8% agarose gel. After the run the gel was stained with ethidium bromide. Note that treatment of VLPs with $ZnSO_4$ causes degradation of the nucleic acid content, while the mock-treated controls were unaffected.

Figure 54:
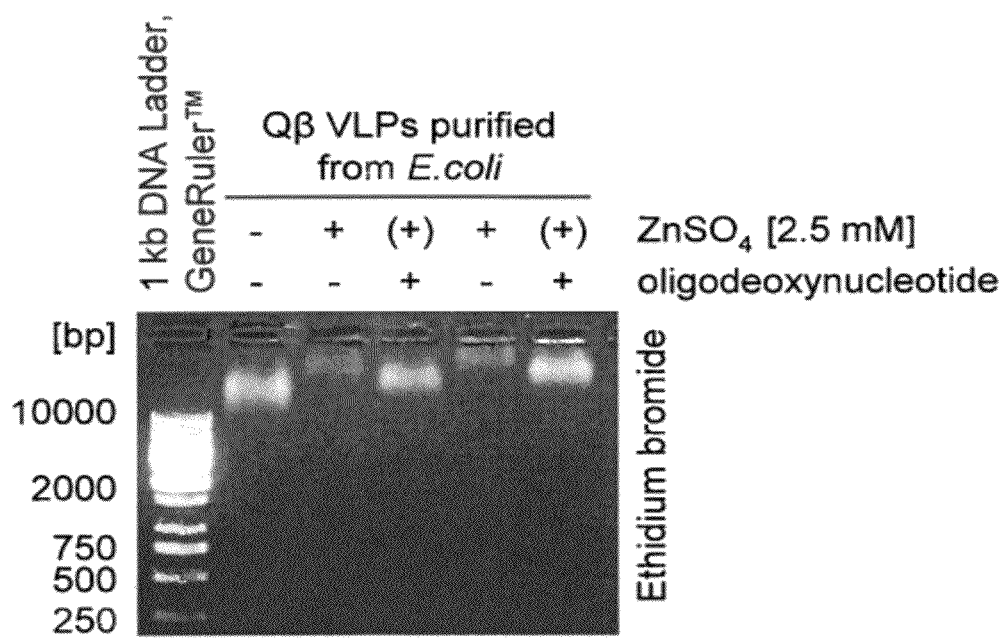
FIG. 54 shows packaging of oligodeoxynucleotides into Qβ VLPs after non-enzymatic RNA hydrolysis.

FIG. 54 shows the packaging of oligodeoxynucleotides into $ZnSO_4$-treated VLPs and analysis of them by agarose gelelectrophoresis. Qβ VLPs which had been treated with 2.5 mM zinc sulfate (+$ZnSO_4$) were dialysed against 4 mM HEPES pH 7.4, 30 mM NaCl and incubated for 3 hrs at 37° C. with an excess of oligodeoxynucleotides (due to the dialysis the concentration of $ZnSO_4$ was decreased by an order of $10^6$, therefore its indicated only in parenthesis) After this incubation in presence of oligodeoxynucleotides, equal amounts of the indicated samples (5 μg protein) were mixed with loading dye and loaded onto a 0.8% agarose gel. After the run the gel was stained with ethidium bromide. Note that adding of oligodeoxynucleotides to $ZnSO_4$-treated Qβ VLPs could restore the electrophoretical behaviour of the so treated capsids when compared to untreated Qβ capsids which had been purified from *E. coli*.

Figure 55:
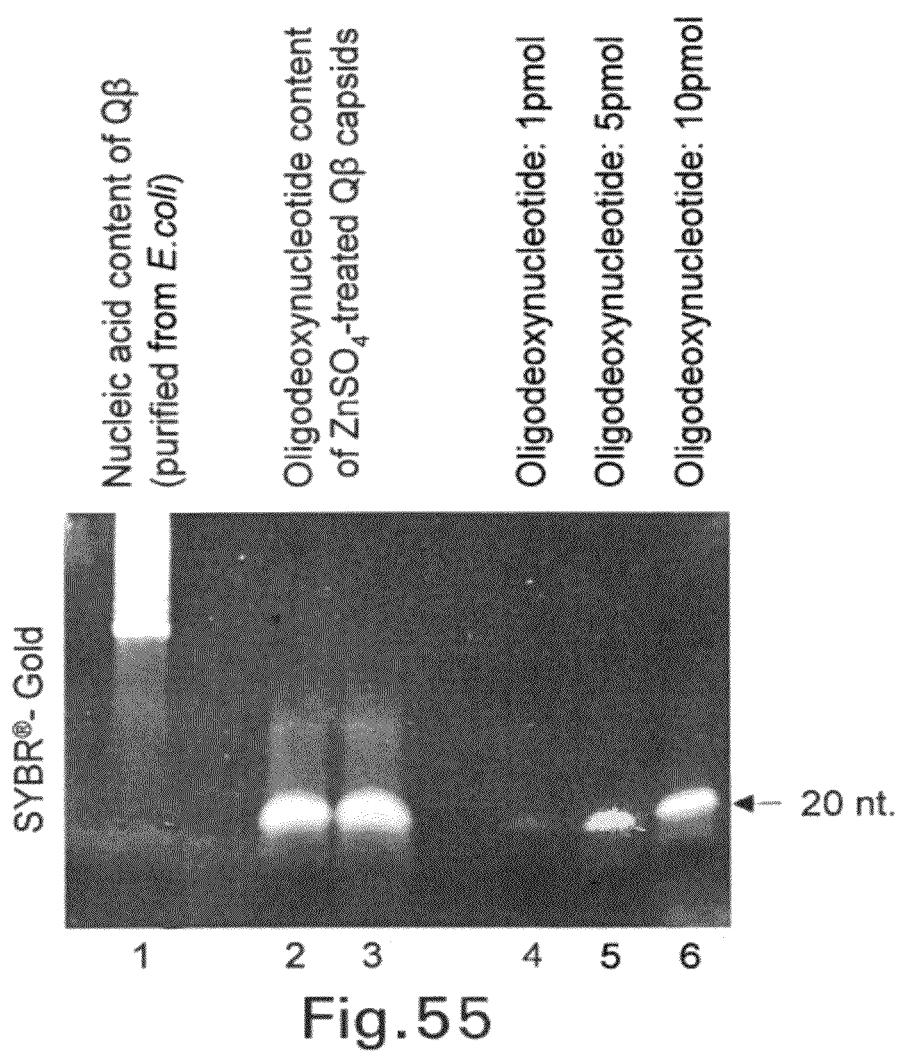
FIG. 55 shows analysis of packaging of oligodeoxynucleotides into Qβ VLPs after non-enzymatic RNA hydrolysis.

FIG. 55 shows the analysis of nucleic acid content of $ZnSO_4$— and oligodeoxynucleotide treated Qβ VLPs by Benzonase and proteinase K digestion and polyacrylamide TBE/Urea gelelectrophoresis: Oligodeoxynucleotides were packaged into $ZnSO_4$-treated Qβ VLPs as described above. 25 μg of these VLPs were digested with 25 μl Benzonase (Merck, Cat. No. 1.01694.0001) according to the manufactures instructions. After heat-inactivation of the nuclease (30 minutes at 80° C.) the VLPs were treated with Proteinase K (final enzyme concentration was 0.5 mg/ml) according to the manufactures instructions. After 3 hrs the equivalent of 2 ug VLPs which had been digested by Benzonase and proteinase K were mixed with TBE-Urea sample buffer and loaded on a 15% polyacrylamide TBE-Urea gel (Novex®, Invitrogen Cat. No. EC6885). The capsids loaded in lane 2 were treated with 2.5 mM $ZnSO_4$ in presence of buffer 1 (see above), while the capsids loaded in lane 3 were treated with 2.5 mM $ZnSO_4$ in presence of buffer 2 (see above). As qualitative as well as quantitative standard, 1 pmol, 5 pmol and 10 pmol of the oligodeoxynucleotide which was used for the reassembly reaction, was loaded onto the same gel (lanes 4-6). As control, Qβ capsids which had been purified from *E. coli* were treated exactly the same and analyzed on the same polyacrylamide TBE-Urea gel (lane 1). After the run was completed, the gel was fixed, equilibrated to neutral pH and stained with SYBR-Gold (Molecular Probes Cat. No. S-11494). Note that intact Qβ VLPs (which had been purified from *E. coli*) did not contain nucleic acids of similar size than those which had been extracted from $ZnSO_4$— and oligodeoxynucleotide treated Qβ capsids. In addition, nucleic acids isolated from the latter VLPs were comigrating with the oligodeoxynucleotides which had been used in the reassembly reaction. This results confirmed that the used oligodeoxynucleotides were packaged into $ZnSO_4$-treated Qβ capsids.

EXAMPLE 26

VLPs Containing Immunostimulatory Nucleic Acids Induce T Cell Responses that can be Boosted by Viral Vectors: LCMV Mice were subcutaneously primed with 20 μg p33-VLPs containing immunostimulatory nucleic acids. Before immu-

EXAMPLE 27

VLPs Containing Immunostimulatory Nucleic Acids Induce T Cell Responses that can be Boosted by Viral Vectors: Recombinant Vaccinia Virus Mice are subcutaneously primed with 20 μg p33-VLPs containing immunostimulatory nucleic acids. Before immunization, p33-VLP preparations are extensively purified from unbound CpG-oligonucleotides via dialysis (see Example 2 and FIG. 5). 12 days later, blood is taken and frequencies of p33-specific T cells are determined by tetramer staining. The mice are boosted with $10^6$ pfu of recombinant vaccina virus expressing LCMV-GP and frequencies of specific T cells are determined 5 days later.

EXAMPLE 28

VLPs Containing Immunostimulatory Nucleic Acids Induce T Cell Responses that can be Boosted by Viral Vectors: Recombinant Canary Pox Virus Mice are subcutaneously primed with 20 μg p33-VLPs containing immunostimulatory nucleic acids. Before immunization, p33-VLP preparations are extensively purified from unbound CpG-oligonucleotides via dialysis (see Example 2 and FIG. 5). 12 days later, blood is taken and frequencies of p33-specific T cells are determined by tetramer staining. The mice are boosted with $10^7$ pfu of recombinant canary pox virus expressing LCMV-GP and frequencies of specific T cells are determined 5 days later.

nization, p33-VLP preparations were extensively purified from unbound CpG-oligonucleotides via dialysis (sec Example 2 and FIG. 5). 12 days later, blood was taken and frequencies of p33-specific T cells were determined by tetramer staining. The mice were boosted with 200 pfu of live LCMV strain WE and frequencies of specific T cells were determined 5 days later. Frequencies before boost were 3.5%+/−1.8% and after boost 15.5%+/−1.9%.

EXAMPLE 29

VLPs Containing Immunostimulatory Nucleic Acids can Boost T Cell Responses

Mice are infected intravenously with recombinant vaccina virus expressing LCMV-GP. 20 days later, blood is taken and frequencies of p33-specific T cells are determined by tetramer staining. The mice are boosted the same day with p33-VLP preparations containing immunostimulatory nucleic acids (see Example 2 and FIG. 5) and frequencies of specific T cells are determined 5 days later.

EXAMPLE 30

Packaging of Immunostimulatory Ribonucleic Acids into VLPs

Immunostimulatory ribonucleic acids such as poly (I:C) (Sigma) or synthetic double-stranded 30 mer of polyinosinic acid and polycytidylic acid either with phosphodiester or phosphorothiate backbone are dissolved in water. Alternatively, polydeoxyinosinic acid and polydeoxyinosinic acid are used to prepare a double stranded poly(I:C) analogon. HBc33 VLPs and Qβ VLPs are treated with RNAse as described in Examples 11, 13 or 25 and nucleic acids are added at 1, 10 and 100 nmol/ml in 0.2×HBS and incubated for 3 h at 37° C. in a thermomixer. Excess nucleic acids are removed by enzymatic hydrolysis or dialysis and analysed as described in Example 11, 13 and 25.

Alternatively, immunostimulatory ribonucleic acids and their analoga are packaged during reassembly of Qβ coat proteins as described in Examples 14, 15, 16. Reassembly is performed by adding β-mercaptoethanol to the 10 ml dimer fraction to a final concentration of 10%, and 300 μl of a solution of nucleic acid, resulting in a 1, 10 and 100 molar excess over capsid concentration, are added. The reassembly mixtures are first dialyzed against 30 ml NET buffer containing 10% beta-mercaptoethanol for 2 hours at 4° C., and then dialyzed in a continuous mode, with a flow of NET buffer of 8 ml/h over 4 days at 4° C. The reassembly mixtures are then desalted against water by dialysis, with 6 buffer exchanges (4×100 ml, 2×1 liter). Reassembled Qβ VLPs are then isolated by sucrose gradient centrifugation as described in Example 14 or by gel filtration as described in Example 16.

What is claimed is:

1. A composition for enhancing an immune response in an animal comprising:
   (a) a virus-like particle, wherein said virus-like particle is a virus-like particle of an RNA-phage Qβ consisting of coat proteins with the amino acid sequence of SEQ ID NO:10; and
   (b) an immunostimulatory substance, wherein said immunostimulatory substance is an unmethylated CpG-containing oligonucleotide, wherein said unmethylated CpG-containing oligonucleotide consists of the sequence GGGGGGGGGGGGACGATCGTCGGGGGGGGGG (SEQ ID NO:116), and wherein said unmethylated CpG containing oligonucleotide exclusively consists of phosphodiester connected deoxynucleotides;
   wherein said immunostimulatory substance is packaged into said virus-like particle.

2. The composition of claim 1 further comprising at least one antigen, wherein said antigen is bound to said virus-like particle.

3. The composition of claim 2, wherein said virus-like particle comprises at least one first attachment site, and wherein said antigen further comprises at least one second attachment site being selected from the group consisting of:
   (a) an attachment site not naturally occurring with said antigen; and
   (b) an attachment site naturally occurring with said antigen;
   wherein said second attachment site associates with said first attachment site.

4. The composition of claim 3 further comprising an amino acid linker, wherein said amino acid linker comprises said second attachment site.

5. The composition of claim 2, wherein said antigen is selected from the group consisting of:
   (a) polypeptides;
   (b) carbohydrates;
   (c) steroid hormones; and
   (d) organic molecules.

6. The composition of claim 2, wherein said antigen is derived from the group consisting of:
   (a) viruses;
   (b) bacteria;
   (c) parasites;
   (d) prions;
   (e) tumors;
   (f) self-molecules;
   (g) non-peptidic hapten molecules
   (h) allergens; and
   (i) hormones.

7. The composition of claim 6, wherein said antigen is a tumor antigen.

8. The composition of claim 7, wherein said tumor antigen is selected from the group consisting of:
   (a) Her2;
   (b) GD2;
   (c) EGF-R;
   (d) CEA;
   (e) CD52;
   (f) CD21;
   (g) human melanoma protein gp100;
   (h) human melanoma protein melan-A/MART-1;
   (i) tyrosinase;
   (j) NA17-A nt protein;
   (k) MAGE-3 protein;
   (l) p53 protein;
   (m) HPV16 E7 protein; and
   (n) antigenic fragments of any of the tumor antigens from (a) to (m).

9. The composition of claim 2, wherein said antigen is bound to said virus-like particle by way of a linking sequence.

10. A method for enhancing an immune response in an animal comprising introducing into said animal a composition comprising:
    (a) a virus-like particle, wherein said virus-like particle is a virus-like particle of an RNA-phage Qβ consisting of coat proteins with the amino acid sequence of SEQ ID NO:10; and
    (b) an immunostimulatory substance, wherein said immunostimulatory substance is an unmethylated CpG-containing oligonucleotide, wherein said unmethylated CpG-containing oligonucleotide consists of the sequence GGGGGGGGGGGGACGATCGTCGGGGGGGGGG (SEQ ID NO:116), and wherein said unmethylated CpG containing oligonucleotide exclusively consists of phosphodiester connected deoxynucleotides;
    wherein said immunostimulatory substance is packaged into said virus-like particle.

11. The method of claim 10, wherein said composition further comprises an antigen, wherein said antigen is bound to said virus-like particle.

12. The method of claim 10, wherein said virus-like particle is produced in a bacterial expression system.

13. The method of claim 11, wherein said at least one antigen is bound to said virus-like particle by at least one non-peptide covalent bond.

14. The method of claim 11, wherein said virus-like particle comprises at least one first attachment site, and wherein said antigen further comprises at least one second attachment site selected from the group consisting of:
    (a) an attachment site not naturally occurring with said antigen; and
    (b) an attachment site naturally occurring with said antigen;
    wherein said second attachment site associates with said first attachment site.

15. The method of claim 11, wherein said antigen is selected from the group consisting of:
    (a) polypeptides;
    (b) carbohydrates;
    (c) steroid hormones; and
    (d) organic molecules.

16. The method of claim 10, wherein said immune response is an enhanced T cell response, wherein said T cell response is a Th cell response, and wherein said Th cell response is a Th1 cell response.

17. A method of producing a composition for enhancing an immune response in an animal comprising a virus-like particle and an immunostimulatory substance packaged into said virus-like particle which comprises:
    (a) incubating said virus-like particle with said immunostimulatory substance, wherein said virus-like particle is a virus-like particle of an RNA phage Qβ consisting of coat proteins with the amino acid sequence of SEQ ID NO:10, and wherein said immunostimulatory substance is an unmethylated CpG-containing oligonucleotide, wherein said unmethylated CpG-containing oligonucleotide consists of the sequence GGGGGGGGGGGGACGATCGTCGGGGGGGGGG (SEQ ID NO:116), and wherein said unmethylated CpG containing oligonucleotide exclusively consists of phosphodiester connected deoxynucleotides;

(b) adding RNase; and
(c) purifying said composition.

18. The method of claim 17, wherein said virus-like particle is produced in a bacterial expression system.

19. A method of producing a composition for enhancing an immune response in an animal comprising a virus-like particle and an immunostimulatory substance packaged into said virus-like particle which comprises:
   (a) incubating said virus-like particle with RNase, wherein said virus-like particle is a virus-like particle of an RNA-phage Qβ consisting of coat proteins with the amino acid sequence of SEQ ID NO 10;
   (b) adding said immunostimulatory substance, wherein said immunostimulatory substance is an unmethylated CpG-containing oligonucleotide, wherein said unmethylated CpG-containing oligonucleotide consists of the sequence GGGGGGGGGGGGAC-GATCGTCGGGGGGGGGG (SEQ ID NO 116), and wherein said unmethylated CpG containing oligonucleotide exclusively consists of phosphodiester connected deoxynucleotides; and
   (c) purifying said composition.

20. The method of claim 19, wherein said virus-like particle is produced in a bacterial expression system.

21. A method of producing a composition for enhancing an immune response in an animal comprising a virus-like particle and an immunostimulatory substance packaged into said virus-like particle which comprises:
   (a) disassembling said virus-like panicle, wherein said virus-like particle is a virus-like particle of an RNA-phage Qβ consisting of coat proteins with the amino acid sequence of SEQ ID NO:10;
   (b) adding said immunostimulatory substance, wherein said immunostimulatory substance is an unmethylated CpG-containing oligonucleotide, wherein said unmethylated CpG-containing oligonucleotide consists of the sequence GGGGGGGGGGGGAC-GATCGTCGGGGGGGGGG (SEQ ID NO:116), and wherein said unmethylated CpG containing oligonucleotide exclusively consists of phosphodiester connected deoxynucleotides; and
   (c) reassembling said virus-like particle.

22. The method of claim 21 further comprising removing nucleic acids of said disassembled virus-like particle.

23. The method of claim 21 further comprising purifying said composition after reassembly (c).

24. A method of producing a composition for enhancing an immune response in an animal comprising a virus-like particle and an immunostimulatory substance packaged into said virus-like particle which comprises:
   (a) incubating said virus-like particle with solutions comprising metal ions capable of hydrolyzing the nucleic acids of said virus-like particle, wherein said virus-like particle is a virus-like particle of an RNA-phage Qβ consisting of coat proteins with the amino acid sequence SEQ ID NO:10;
   (b) adding said immunostimulatory substance, wherein said immunostimulatory substance is an unmethylated CpG-containing oligonucleotide, wherein said unmethylated CpG-containing oligonucleotide consists of the sequence GGGGGGGGGGGGAC-GATCGTCGGGGGGGGGG (SEQ ID NO:116), and wherein said unmethylated CpG containing oligonucleotide exclusively consists of phosphodiester connected deoxynucleotides; and
   (c) purifying said composition.

25. The method of claim 24, wherein said metal ions are selected from the group consisting of:
   (a) zinc (Zn) ions;
   (b) copper (Cu) ions;
   (c) iron (Fe) ions; and
   (d) any mixtures of at least one ion of (a), (b) and/or (c).

26. An immunogenic composition comprising an immunologically effective amount of the composition of claim 1 together with a pharmaceutically acceptable diluent, carrier or excipient.

27. A method of immunizing an animal comprising administering to said animal an immunologically effective amount of the vaccine of claim 26.

28. An immunogenic composition comprising an immunologically effective amount of the composition of claim 2 together with a pharmaceutically acceptable diluent, carrier or excipient.

29. A method of immunizing an animal comprising administering to said animal an immunologically effective amount of the vaccine of claim 28.

30. The composition of claim 3, wherein said at least one antigen is bound to said virus-like particle by at least one non-peptide covalent bond.

31. The composition of claim 30, wherein said first attachment site is a lysine residue and said second attachment is a cysteine residue.

32. The composition of claim 31, wherein said at least one antigen is bound to said virus-like particle by way of a heterobifunctional cross-linker.

33. The composition of claim 32, wherein said heterobifunctional cross-linker is Succinimidyl-6-(β-maleimidopropionamido)hexanoate (SMPH).

* * * * *